US011401309B2

(12) United States Patent
Dela Cruz

(10) Patent No.: US 11,401,309 B2
(45) Date of Patent: Aug. 2, 2022

(54) PROTEIN M FUSION PROTEINS AND USES

(71) Applicant: Jay Dela Cruz, Moreno Valley, CA (US)

(72) Inventor: Jay Dela Cruz, Moreno Valley, CA (US)

( * ) Notice: Subject to any disclaimer, the term of this patent is extended or adjusted under 35 U.S.C. 154(b) by 0 days.

(21) Appl. No.: 17/469,708

(22) Filed: Sep. 8, 2021

(65) Prior Publication Data

US 2022/0089656 A1 Mar. 24, 2022

Related U.S. Application Data

(60) Provisional application No. 63/079,815, filed on Sep. 17, 2020.

(51) Int. Cl.

| | |
|---|---|
| ***A61P 31/12*** | (2006.01) |
| ***C07K 14/30*** | (2006.01) |
| ***C07K 14/005*** | (2006.01) |
| ***C07K 14/705*** | (2006.01) |
| ***A61K 38/00*** | (2006.01) |
| ***C12N 9/48*** | (2006.01) |
| ***C07K 14/73*** | (2006.01) |
| ***C07K 14/435*** | (2006.01) |
| ***A61P 31/14*** | (2006.01) |
| ***C07K 14/74*** | (2006.01) |
| ***C07K 14/725*** | (2006.01) |
| ***C07K 14/71*** | (2006.01) |
| ***C07K 14/32*** | (2006.01) |
| ***C12N 9/08*** | (2006.01) |
| ***A61K 47/68*** | (2017.01) |

(52) U.S. Cl.

CPC .......... *C07K 14/30* (2013.01); *A61K 47/6835* (2017.08); *A61P 31/14* (2018.01); *C07K 14/005* (2013.01); *C07K 14/32* (2013.01); *C07K 14/435* (2013.01); *C07K 14/7051* (2013.01); *C07K 14/7056* (2013.01); *C07K 14/70503* (2013.01); *C07K 14/70514* (2013.01); *C07K 14/70539* (2013.01); *C07K 14/70596* (2013.01); *C07K 14/71* (2013.01); *C12N 9/0065* (2013.01); *C12N 9/485* (2013.01); *C12Y 111/01007* (2013.01); *C12Y 304/17023* (2013.01); *A61K 38/00* (2013.01); *C07K 2319/00* (2013.01); *C12N 2770/32422* (2013.01)

(58) Field of Classification Search

None

See application file for complete search history.

(56) References Cited

PUBLICATIONS

Arfi et al. (2021) mBio 12(6)e0197421: 1-13.*
Blötz et al. (2020) Front. Microbiol. 11(685): 1-12.*
Grover et al. (2014) Science 343(6171): 656-661.*
Rentero et al. (2011) Chimia 65: 843-845.*

* cited by examiner

*Primary Examiner* — Ilia I Ouspenski

(57) ABSTRACT

Fusion proteins with immunoglobulin binding properties, their uses and related methods and compositions are disclosed. The fusion proteins are comprised of an antibody-binding fragment of protein M from *Mycoplasma* spp. conjugated to a receptor fragment. The receptor fragment is a protein fragment to which a pathogen, a toxin or a cancer cell can specifically bind. The fusion proteins can be used to neutralize or eradicate a wide group of pathogens, toxins or cancer cells.

30 Claims, 21 Drawing Sheets

Specification includes a Sequence Listing.

armY-ACE2 armed mAb binds to SARS-CoV-2 spike protein

Bar chart, ABS OD 650nm:
- mAb alone: ~0.03
- mAb + armY-ACE2: ~0.97
- armY-ACE2: ~0.05
- Buffer: ~0.03 mAb does not bind to natural antigen when armed with armY-ACE2

Bar chart, ABS OD 650nm:
- mAb alone: ~2.25
- mAb + armY-ACE2 (25X): ~0.10
- mAb + armY-ACE2 (50X): ~0.02
- Buffer: ~0.00

SEQUENCE LISTING

<160> NUMBER OF SEQ ID NOS: 101

<210> SEQ ID NO 1
<211> LENGTH: 520
<212> TYPE: PRT
<213> ORGANISM: Mycoplasma genitalium
<220> FEATURE:
<223> OTHER INFORMATION: The mature protein M sequence

<400> SEQUENCE: 1

Thr Asn Leu Val Asn Gln Ser Gly Tyr Ala Leu Val Ala Ser Gly Arg
1 5 10 15

Ser Gly Asn Leu Gly Phe Lys Leu Phe Ser Thr Gln Ser Pro Ser Ala
20 25 30

Glu Val Lys Leu Lys Ser Leu Ser Leu Asn Asp Gly Ser Tyr Gln Ser
35 40 45

Glu Ile Asp Leu Ser Gly Gly Ala Asn Phe Arg Glu Lys Phe Arg Asn
50 55 60

Phe Ala Asn Glu Leu Ser Glu Ala Ile Thr Asn Ser Pro Lys Gly Leu
65 70 75 80

Asp Arg Pro Val Pro Lys Thr Glu Ile Ser Gly Leu Ile Lys Thr Gly
85 90 95

Asp Asn Phe Ile Thr Pro Ser Phe Lys Ala Gly Tyr Tyr Asp His Val
100 105 110

Ala Ser Asp Gly Ser Leu Leu Ser Tyr Tyr Gln Ser Thr Glu Tyr Phe
115 120 125

Asn Asn Arg Val Leu Met Pro Ile Leu Gln Thr Thr Asn Gly Thr Leu
130 135 140

Met Ala Asn Asn Arg Gly Tyr Asp Asp Val Phe Arg Gln Val Pro Ser
145 150 155 160

Phe Ser Gly Trp Ser Asn Thr Lys Ala Thr Thr Val Ser Thr Ser Asn
165 170 175

Asn Leu Thr Tyr Asp Lys Trp Thr Tyr Phe Ala Ala Lys Gly Ser Pro
180 185 190

Leu Tyr Asp Ser Tyr Pro Asn His Phe Phe Glu Asp Val Lys Thr Leu
195 200 205

Ala Ile Asp Ala Lys Asp Ile Ser Ala Leu Lys Thr Thr Ile Asp Ser
210 215 220

Glu Lys Pro Thr Tyr Leu Ile Ile Arg Gly Leu Ser Gly Asn Gly Ser
225 230 235 240

Gln Leu Asn Glu Leu Gln Leu Pro Glu Ser Val Lys Lys Val Ser Leu
245 250 255

Tyr Gly Asp Tyr Thr Gly Val Asn Val Ala Lys Gln Ile Phe Ala Asn
260 265 270

Val Val Glu Leu Glu Phe Tyr Ser Thr Ser Lys Ala Asn Ser Phe Gly
275 280 285

Phe Asn Pro Leu Val Leu Gly Ser Lys Thr Asn Val Ile Tyr Asp Leu
290 295 300

Phe Ala Ser Lys Pro Phe Thr His Ile Asp Leu Thr Gln Val Thr Leu
305 310 315 320

Gln Asn Ser Asp Asn Ser Ala Ile Asp Ala Asn Lys Leu Lys Gln Ala
325 330 335

Val Gly Asp Ile Tyr Asn Tyr Arg Arg Phe Glu Arg Gln Phe Gln Gly
340 345 350

Tyr Phe Ala Gly Gly Tyr Ile Asp Lys Tyr Leu Val Lys Asn Val Asn

```
        355                 360                 365

Thr Asn Lys Asp Ser Asp Asp Asp Leu Val Tyr Arg Ser Leu Lys Glu
    370                 375                 380

Leu Asn Leu His Leu Glu Glu Ala Tyr Arg Glu Gly Asp Asn Thr Tyr
385                 390                 395                 400

Tyr Arg Val Asn Glu Asn Tyr Tyr Pro Gly Ala Ser Ile Tyr Glu Asn
                405                 410                 415

Glu Arg Ala Ser Arg Asp Ser Glu Phe Gln Asn Glu Ile Leu Lys Arg
            420                 425                 430

Ala Glu Gln Asn Gly Val Thr Phe Asp Glu Asn Ile Lys Arg Ile Thr
        435                 440                 445

Ala Ser Gly Lys Tyr Ser Val Gln Phe Gln Lys Leu Glu Asn Asp Thr
    450                 455                 460

Asp Ser Ser Leu Glu Arg Met Thr Lys Ala Val Glu Gly Leu Val Thr
465                 470                 475                 480

Val Ile Gly Glu Glu Lys Phe Glu Thr Val Asp Ile Thr Gly Val Ser
                485                 490                 495

Ser Asp Thr Asn Glu Val Lys Ser Leu Ala Lys Glu Leu Lys Thr Asn
            500                 505                 510

Ala Leu Gly Val Lys Leu Lys Leu
        515                 520


<210> SEQ ID NO 2
<211> LENGTH: 547
<212> TYPE: PRT
<213> ORGANISM: Mycoplasma pneumoniae
<220> FEATURE:
<223> OTHER INFORMATION: IgG-blocking mature protein M sequence

<400> SEQUENCE: 2

Ala Val Leu Ile Val Asn Glu Val Leu Arg Leu Gln Ser Gly Glu Thr
1               5                   10                  15

Leu Ile Ala Ser Gly Arg Ser Gly Asn Leu Ser Phe Gln Leu Tyr Ser
            20                  25                  30

Lys Val Asn Gln Asn Ala Lys Ser Lys Leu Asn Ser Ile Ser Leu Thr
        35                  40                  45

Asp Gly Gly Tyr Arg Ser Glu Ile Asp Leu Gly Asp Gly Ser Asn Phe
    50                  55                  60

Arg Glu Asp Phe Arg Asn Phe Ala Asn Asn Leu Ser Glu Ala Ile Thr
65                  70                  75                  80

Asp Ala Pro Lys Asp Leu Leu Arg Pro Val Pro Lys Val Glu Val Ser
                85                  90                  95

Gly Leu Ile Lys Thr Ser Ser Thr Phe Ile Thr Pro Asn Phe Lys Ala
            100                 105                 110

Gly Tyr Tyr Asp Gln Val Ala Ala Asp Gly Lys Thr Leu Lys Tyr Tyr
        115                 120                 125

Gln Ser Thr Glu Tyr Phe Asn Asn Arg Val Val Met Pro Ile Leu Gln
    130                 135                 140

Thr Thr Asn Gly Thr Leu Thr Ala Asn Asn Arg Ala Tyr Asp Asp Ile
145                 150                 155                 160

Phe Val Asp Gln Gly Val Pro Lys Phe Pro Gly Trp Phe His Asp Val
                165                 170                 175

Asp Lys Ala Tyr Tyr Ala Gly Ser Asn Gly Gln Ser Glu Tyr Leu Phe
            180                 185                 190

Lys Glu Trp Asn Tyr Tyr Val Ala Asn Gly Ser Pro Leu Tyr Asn Val
```

195 200 205

Tyr Pro Asn His His Phe Lys Gln Ile Lys Thr Ile Ala Phe Asp Ala
210 215 220

Pro Arg Ile Lys Gln Gly Asn Thr Asp Gly Ile Asn Leu Asn Leu Lys
225 230 235 240

Gln Arg Asn Pro Asp Tyr Val Ile Ile Asn Gly Leu Thr Gly Asp Gly
245 250 255

Ser Thr Leu Lys Asp Leu Glu Leu Pro Glu Ser Val Lys Lys Val Ser
260 265 270

Ile Tyr Gly Asp Tyr His Ser Ile Asn Val Ala Lys Gln Ile Phe Lys
275 280 285

Asn Val Leu Glu Leu Glu Phe Tyr Ser Thr Asn Gln Asp Asn Asn Phe
290 295 300

Gly Phe Asn Pro Leu Val Leu Gly Asp His Thr Asn Ile Ile Tyr Asp
305 310 315 320

Leu Phe Ala Ser Lys Pro Phe Asn Tyr Ile Asp Leu Thr Ser Leu Glu
325 330 335

Leu Lys Asp Asn Gln Asp Asn Ile Asp Ala Ser Lys Leu Lys Arg Ala
340 345 350

Val Ser Asp Ile Tyr Ile Arg Arg Arg Phe Glu Arg Gln Met Gln Gly
355 360 365

Tyr Trp Ala Gly Gly Tyr Ile Asp Arg Tyr Leu Val Lys Asn Thr Asn
370 375 380

Glu Lys Asn Val Asn Lys Asp Asn Asp Thr Val Tyr Ala Ala Leu Lys
385 390 395 400

Asp Ile Asn Leu His Leu Glu Glu Thr Tyr Thr His Gly Gly Asn Thr
405 410 415

Met Tyr Arg Val Asn Glu Asn Tyr Tyr Pro Gly Ala Ser Ala Tyr Glu
420 425 430

Ala Glu Arg Ala Thr Arg Asp Ser Glu Phe Gln Lys Glu Ile Val Gln
435 440 445

Arg Ala Glu Leu Ile Gly Val Val Phe Glu Tyr Gly Val Lys Asn Leu
450 455 460

Arg Pro Gly Leu Lys Tyr Thr Val Lys Phe Glu Ser Pro Gln Glu Gln
465 470 475 480

Val Ala Leu Lys Ser Thr Asp Lys Phe Gln Pro Val Ile Gly Ser Val
485 490 495

Thr Asp Met Ser Lys Ser Val Thr Asp Leu Ile Gly Val Leu Arg Asp
500 505 510

Asn Ala Glu Ile Leu Asn Ile Thr Asn Val Ser Lys Asp Glu Thr Val
515 520 525

Val Ala Glu Leu Lys Glu Lys Leu Asp Arg Glu Asn Val Phe Gln Glu
530 535 540

Ile Arg Thr
545

<210> SEQ ID NO 3
<211> LENGTH: 477
<212> TYPE: PRT
<213> ORGANISM: Mycoplasma iowae
<220> FEATURE:
<223> OTHER INFORMATION: IgG-blocking mature protein M sequence

<400> SEQUENCE: 3

Val Gly Val Tyr Val Ala Thr Thr Asn Thr Gln Asn Thr Ser Val Asn

-continued

```
1               5                   10                  15

Val Asn Asn Asn Glu Asn Ile Asn Tyr Lys Thr Asn Gly Thr Val Val
            20                  25                  30

Thr Gly Asp Lys Leu Thr Phe Ser Ala Val Val Gln Gln Asn Ser Asn
        35                  40                  45

Ile Ser Thr Gln Ala Phe Ile Asn Asp Gly Thr Lys Pro Val Gly Thr
    50                  55                  60

Tyr Asn Lys Glu Ile Asn Leu Gly Lys Asp Ser Ile Thr Pro Lys Tyr
65                  70                  75                  80

Thr Ser Gly Tyr Val Glu Thr Tyr Leu Glu Ser Gly Asp Thr Val Ser
                85                  90                  95

Arg Tyr Ser Ser Ser Glu Tyr His Asn Asn Arg Thr Leu Met Pro Ile
            100                 105                 110

Leu Asp Thr Lys Glu His Tyr Tyr Thr Ser Glu Arg Thr Tyr Ser Glu
        115                 120                 125

Ile Gln Lys Gly Ile Tyr Arg Gly Trp Glu Ile Ser Thr Lys Ser Ile
    130                 135                 140

Asn Tyr Gly Glu Gln Phe Ala Tyr Ser Ala Ser Pro Val Leu Lys Thr
145                 150                 155                 160

Val Phe Arg Asp Leu Lys Gln Glu Thr Ile Lys Ala Val Gln Phe Asn
                165                 170                 175

Leu Gly Leu Ser Asp Thr Ser Ile Glu Ser Ile Asn Ser Phe Leu Lys
            180                 185                 190

Thr Asn Thr Gly Ile Gln Phe Val Thr Ile Lys Gly Ile Ser Gln Asp
        195                 200                 205

Thr Asp Leu Ser Lys Leu Val Leu Pro Glu Ser Val Gln Lys Leu Thr
    210                 215                 220

Leu Leu Gly Gln Arg Asn Thr Ile Asn Asp Leu Lys Leu Pro Ser Glu
225                 230                 235                 240

Leu Gln Glu Ile Glu Ile Tyr Leu Gly Ser Ser Leu Lys Ser Ile Asp
                245                 250                 255

Pro Leu Ile Phe Pro Lys Ser Ala Asn Ile Ile Ser Asp Val Val Met
            260                 265                 270

Asn Asn Thr Ser Ser Val Phe Thr Glu Ile Lys Leu Ser Asp Ser Thr
        275                 280                 285

Ile Asp Asn Asn Ser Pro Lys Leu Gln Lys Ala Ile Asp Asp Val Tyr
    290                 295                 300

Thr Tyr Arg Ile Lys Glu Arg Ala Phe Gln Gly Leu Val Pro Gly Gly
305                 310                 315                 320

Tyr Ile Ala Ser Trp Asp Leu Thr Gly Thr Lys Val Thr Ser Phe Asn
                325                 330                 335

Asn Val Asn Ile Pro Pro Leu Asn Asp Gly Thr Gly Arg Phe Tyr Ile
            340                 345                 350

Ala His Val Glu Val Lys Thr Asp Gly Asn Phe Gly Asn Ser Gln Asn
        355                 360                 365

Glu Ser Ile Gly Ser Lys Pro Ser Asn Asp Ser Gln Ile Asn Asp Trp
    370                 375                 380

Phe Asp Trp Gly Gly Gly Trp Gln Lys Val Gln Glu Val Val Val Ser
385                 390                 395                 400

Ser Ser Glu Asn Val Ser Leu Glu Thr Ala Thr Gln Glu Ile Met Gly
                405                 410                 415

Phe Ile Ala Lys Tyr Pro Asn Val Lys Lys Ile Asn Ile Val Asn Val
            420                 425                 430
```

```
Lys Leu Thr Asp Gly Ser Thr His Glu Gln Leu Lys Asp Asn Val Ile
        435                 440                 445

Lys Ala Ile Thr Ala Lys Tyr Gly Glu Glu Ser Gln Tyr Lys Asp Ile
    450                 455                 460

Glu Phe Val Leu Pro Glu Thr Val Pro Ser Pro Val Ala
465                 470                 475


<210> SEQ ID NO 4
<211> LENGTH: 488
<212> TYPE: PRT
<213> ORGANISM: Mycoplasma tullyi
<220> FEATURE:
<223> OTHER INFORMATION: IgG-blocking mature protein M sequence

<400> SEQUENCE: 4

Ile Val Tyr Thr Ser Val Lys Ile Ser Asn Thr Leu Asn Gln Asp Lys
1               5                   10                  15

Gln Ile Ala Gly Ser Asn Leu Ser Pro Thr Gln Ser Asn Arg Leu Ile
            20                  25                  30

Gly Phe Gln Thr Leu Thr Lys Phe Lys Ile Gln Asp Leu Asp Phe Glu
        35                  40                  45

Leu Gln Arg Lys Ile Tyr Ser Ser Arg Leu Asn Ser Ala Glu Leu Ile
    50                  55                  60

Thr Lys Ser Ala Val Val Leu Asp Gln Ser Thr Leu Gln Asn His Asp
65                  70                  75                  80

Gly Glu Val Ala Ser Gly Gln Pro Ala Pro Gln Val Pro Pro Pro Val
                85                  90                  95

Arg Ile Pro Ala Lys Glu Gln Thr Gly His Thr Ser Asp Phe Ile Ser
            100                 105                 110

Gly Tyr Ser Glu Asn Asn Leu Tyr Tyr Gln Thr Pro Tyr Tyr Tyr Asn
        115                 120                 125

Asp Arg Val Tyr Met Pro Ile Leu Asp Ser Arg Lys Thr Tyr Leu Arg
    130                 135                 140

Asn Glu Arg Thr Thr Thr Asp Ile Gly Leu Asn Asn Tyr Glu Gly Trp
145                 150                 155                 160

Ile Thr Ser Asp His Ser Arg Val Asn Asn Arg Val Asn Val Phe Asn
                165                 170                 175

Tyr Arg Pro Ser Pro Glu Leu Leu Ala Lys Tyr Thr Asp Leu Ala Ala
            180                 185                 190

Asp Lys Leu Ile Phe Thr Met Thr Ile Asp Leu Tyr Gln Ala Asn Pro
        195                 200                 205

Glu Met Ile Asn Glu Ile Leu Lys Glu Tyr Ser Pro Asp Phe Val Ile
    210                 215                 220

Leu Ser Asn Ala Asp Ser Gln Val Met Lys Gln Leu Val Phe Pro Ser
225                 230                 235                 240

Ser Val Lys Lys Leu Thr Ile Lys Ser Asn Leu Leu Asp Arg Phe Asp
                245                 250                 255

Phe Ser Leu Ala Asn Thr Glu Ile Gln Glu Leu Glu Leu Tyr Thr Pro
            260                 265                 270

Arg Leu Thr Glu Tyr Asn Pro Phe Ala Leu Asn Pro Asn Thr His Leu
        275                 280                 285

Ile Phe Asp Ser Asn Tyr Ser Lys Pro Phe Thr Ser Ile Asn Leu Tyr
    290                 295                 300

Gly Val Pro Leu Thr His Gln Gln Val Leu Ser Ala Leu Glu Asp Val
305                 310                 315                 320
```

-continued

```
Phe Val Arg Arg His Tyr Glu Arg Ala Leu Gln Gly Ser Phe Ser Gly
                325                 330                 335

Gly Tyr Ile Ser Ser Leu Asp Leu Ser Asn Thr Gly Ile Thr Ser Leu
            340                 345                 350

Ser Asn Leu Met Ile Lys Asn Ile Asn Pro Tyr Tyr Asp Ser Tyr Thr
        355                 360                 365

Met Ser Val Lys Tyr Asn Ser Asn Lys Asn Gly Glu Ile Glu Leu Leu
    370                 375                 380

Lys Thr Asn Ser Trp Lys Asn Pro Asn Pro Ala Pro Val Ser Thr Pro
385                 390                 395                 400

Ala Ala Ser Ser Pro Thr Thr Pro Thr Val Pro Ser Thr Pro Gly Asp
                405                 410                 415

Ser Thr Ile Asn Val Gln Asp Lys Asp Leu Gly Leu Leu Val Ser Ser
            420                 425                 430

Glu Val Lys Val Asp Pro Gln Val Leu Ile Asn Val Val Ser Lys Tyr
        435                 440                 445

Leu His Asn Asn Pro Arg Val Asn Val Leu Asp Ile Ser Lys Val Ser
    450                 455                 460

Leu Lys Ser Gly Ser Leu Val Asp Val Ala Thr Asn Leu Lys Ala Lys
465                 470                 475                 480

Ile Asp Tyr Leu Asn Val Thr Ile
                485


<210> SEQ ID NO 5
<211> LENGTH: 479
<212> TYPE: PRT
<213> ORGANISM: Mycoplasma imitans
<220> FEATURE:
<223> OTHER INFORMATION: IgG-blocking mature protein M sequence

<400> SEQUENCE: 5

Gly Ile Ile Tyr Thr Ser Val Lys Ile Ser Ser Ser Gln Phe Asn Lys
1               5                   10                  15

Gln Ile Ser Asn Pro Ile Glu Val Pro Lys Arg Asn Asn Thr Leu Ile
            20                  25                  30

Gly Phe Gln Thr Leu Ala Arg Phe Lys Ile Glu Asn Leu Asp Phe Glu
        35                  40                  45

Leu Gln Lys Asn Ile Tyr Ser Gln Asn Glu Asn Ala Leu Val Asn Lys
    50                  55                  60

Ala Ala Val Val Gln Asp Asn Ser Ile Ile Asn His Asp Gly Glu Pro
65                  70                  75                  80

Thr Gly Gln Asn Glu Arg Gln Val Pro Ala Pro Val Lys Ile Leu Ala
                85                  90                  95

Lys Glu Gln Thr Gly His Thr Ser Asp Phe Ile Ser Gly Tyr Thr Asp
            100                 105                 110

Asn Asn Ser Tyr Tyr Gln Ser Pro Phe Tyr Tyr Asn Asp Arg Val Phe
        115                 120                 125

Met Pro Ile Leu Asp Ser His Ser Ile Tyr Leu Lys Asn Glu Arg Thr
    130                 135                 140

Ser Lys Glu Ile Gly Leu Asp Ser Tyr Glu Gly Trp Asp Lys Ile Gly
145                 150                 155                 160

Tyr Ser Thr Ile Asn Ser Arg Val Ser Phe Val Gln Tyr Arg Ala Thr
                165                 170                 175

Asp Gln Leu Ile Ala Lys Phe Asn Pro Ser Asn Lys Gln Ile Phe Ala
            180                 185                 190
```

```
Met Met Ile Asn Leu Tyr Gln Ala Asp Pro Ala Val Ile Asn Asn Thr
        195                 200                 205

Leu Arg Asn Tyr Leu Pro Asp Phe Val Ile Leu Ser Asn Ala Asp Asn
    210                 215                 220

Gln Ile Ile Lys Arg Leu Val Phe Pro Ser Ser Val Lys Lys Leu Thr
225                 230                 235                 240

Ile Lys Ser Asn Leu Leu Asp Arg Phe Asp Phe Ser Leu Ala Asn Ser
                245                 250                 255

Asn Ile Gln Glu Leu Glu Leu Tyr Thr Pro Asn Leu Thr Glu Tyr Asn
            260                 265                 270

Pro Leu Ala Leu Asn Pro Asp Thr His Leu Ile Phe Asp Thr Ala Tyr
        275                 280                 285

Ser Lys Pro Phe Thr Ser Ile Asn Leu Tyr Gly Ala Lys Leu Thr Thr
    290                 295                 300

Gln Glu Thr Gln Glu Ala Phe Asn Asp Ile Phe Val Arg Arg Tyr Tyr
305                 310                 315                 320

Glu Arg Tyr Leu Gln Gly Ala Phe Val Gly Gly Tyr Ile Ser Leu Leu
                325                 330                 335

Asp Leu Ser Asn Thr Gly Ile Asn Ser Val Asn Asp Tyr Val Val Lys
            340                 345                 350

Asn Ile Asn Pro Ala Tyr Ser Ser Tyr Thr Leu Ser Val Thr Tyr Asn
        355                 360                 365

Pro Gly Asp Pro Gly Gln Ile Ser Ile Leu Arg Thr Thr Thr Ser Ile
    370                 375                 380

Pro Ser Glu Thr Gln Pro Thr Asn Pro Ser Asn Asn Thr Pro Ser Gln
385                 390                 395                 400

Pro Thr Asp Pro Asn Ile Thr Thr Gln Ile Asp Ala Lys Glu Lys Asp
                405                 410                 415

Leu Lys Leu Val Val Ser Ser Thr Ile Gln Val Asp Thr Gln Val Val
            420                 425                 430

Ile Asn Val Val Gly Lys Tyr Leu Leu Asn Asn Pro Arg Val Asn Asn
        435                 440                 445

Val Asp Ile Ser Arg Ile Gln Leu Lys Ser Gly Thr Leu Val Asp Ile
    450                 455                 460

Ala Asn Asn Phe Lys Thr Lys Met Ser Tyr Leu Asn Val Ser Val
465                 470                 475


<210> SEQ ID NO 6
<211> LENGTH: 389
<212> TYPE: PRT
<213> ORGANISM: Mycoplasma gallisepticum
<220> FEATURE:
<223> OTHER INFORMATION: IgG-blocking mature protein M sequence

<400> SEQUENCE: 6

Gly Ile Ile Tyr Thr Ser Val Lys Ile Ser Asn Ser Leu Tyr Gln Asp
1               5                   10                  15

Lys Leu Ile Ser Gly Gln Asn Gln Pro Leu Ala Pro Val Asn Arg Leu
            20                  25                  30

Ile Gly Phe Gln Thr Leu Ala Lys Phe Arg Ile Glu Gly Leu Asp Phe
        35                  40                  45

Glu Leu Lys Lys Lys Ile Tyr Ser Ser Thr Val Glu Ser Val Glu Leu
    50                  55                  60

Val Asn Arg Ser Ala Val Leu Val Asp Asp Ser Val Leu Glu Asn His
65                  70                  75                  80
```

```
Asp Gly Glu Leu Thr Ser Val Gln Ser Asp Pro Gln Val Pro Ala Pro
                85                  90                  95

Val Lys Ile Leu Ala Lys Glu Gln Thr Gly His Thr Ser Asp Phe Val
            100                 105                 110

Ser Gly Tyr Ser Asp Asp Asn Lys Tyr Tyr Gln Ser Pro Tyr Tyr Tyr
        115                 120                 125

Asn Asp Arg Val Tyr Met Pro Ile Leu Asp Ser Pro Thr Ile Tyr Leu
    130                 135                 140

Lys Asn Glu Arg Thr Ser Ser Asp Ile Gly Leu Asn Asn Tyr Gln Gly
145                 150                 155                 160

Trp Ile Ala Val Gly His Ala Arg Val Asn Ser Arg Val Ser Val Phe
                165                 170                 175

Asn Tyr Arg Ala Thr Asp Glu Leu Leu Ala Lys Phe Asn Asn Leu Pro
            180                 185                 190

Asp Arg Leu Ile Phe Thr Met Ser Ile Asp Leu Tyr Gln Ala Asn Pro
        195                 200                 205

Ala Met Ile Asn Glu Thr Leu Lys Glu Tyr Ser Pro Asp Phe Val Ile
    210                 215                 220

Leu Ser Asn Ala Asp Ser Gln Thr Met Lys Gln Leu Val Phe Pro Ser
225                 230                 235                 240

Ser Val Lys Lys Leu Thr Ile Lys Ser Asn Ile Leu Asp Arg Phe Asp
                245                 250                 255

Phe Ser Leu Val Asn Ser Glu Ile Gln Glu Leu Glu Leu Tyr Thr Pro
            260                 265                 270

Asn Leu Thr Glu Tyr Asn Pro Leu Ala Leu Asn Pro Lys Thr His Leu
        275                 280                 285

Ile Phe Asp Ala Asp Tyr Ser Thr Arg Phe Leu Ser Ile Asn Leu Tyr
    290                 295                 300

Gly Ala Gln Leu Thr Asn Gln Gln Ala Leu Ala Ala Leu Glu Asp Val
305                 310                 315                 320

Phe Val His Arg Tyr Tyr Glu Arg Ala Leu Gln Gly Ser Phe Val Asp
                325                 330                 335

Gly Tyr Ile Ser Ser Leu Val Leu Ser Asp Thr Gly Ile Thr Ser Leu
            340                 345                 350

Asn Asn Leu Val Ile Lys Asn Ile Asn Pro Asn Tyr Asp Ser Tyr Ile
        355                 360                 365

Met Ser Val Lys Tyr His Ser Asn Asp Ser Gly Gln Ile Glu Leu Leu
    370                 375                 380

Lys Thr Thr Ala Trp
385
```

<210> SEQ ID NO 7
<211> LENGTH: 513
<212> TYPE: PRT
<213> ORGANISM: Mycoplasma alvi
<220> FEATURE:
<223> OTHER INFORMATION: IgG-blocking protein M sequence with signal peptide

<400> SEQUENCE: 7

```
Ile Ser Ile Pro Phe Ile Ile Gln Ser Thr His Thr Asn Asn Ala Asn
1               5                   10                  15

Ser Thr Ile Pro Asn Val Ser Lys Pro Ser Gly Ser Ser Leu Ala Pro
            20                  25                  30

Ile Asn Tyr Ser Tyr Asp Asn Phe Val Asn Asn Tyr Asp Gly Thr Leu
```

-continued

```
        35                  40                  45

Thr Ser Asn Ser Leu Val Phe Ser Ala Ser Gly Ser Lys Glu Val Lys
    50                  55                  60

Ser Ser Leu Gln Thr Arg Ala Ile Thr Val Asp Gly Leu Asn Asp Ile
65                  70                  75                  80

Asp Ser Ser Met Gly Leu Val Asp Ala Met Ser Gln Gly Leu Leu Asp
                85                  90                  95

Asn Ser Tyr Asp Pro Lys Tyr Asn Glu Val Arg Glu Val Ile Asp Met
            100                 105                 110

Asp Gly Ala His Arg Lys Ile Val Thr Thr Lys Cys Phe Asp Asn Asn
        115                 120                 125

Arg Lys Tyr Met Pro Ile Leu Thr Tyr Asn Asn Asp Thr Tyr Tyr Ser
    130                 135                 140

Tyr Ser Glu Ser Arg Thr Trp Asp Asp Val Asn Arg Ser Ile Tyr Pro
145                 150                 155                 160

Gly Trp Asn Leu Asn Arg Ser Asn Leu Ser Ser His Asn Gln Asn Lys
                165                 170                 175

Met Ile Gly Val Asp Ile Leu Val Tyr Thr Pro Thr Glu Val Leu Lys
            180                 185                 190

Thr Ala Tyr Pro Ser Val Thr Asp Lys Ile Ile Gly Leu Ser Ile Ser
        195                 200                 205

Leu Ser Asn Leu Ile Ser Thr Tyr Gly Asp Gln Thr Lys Gln Val Leu
    210                 215                 220

Ser Gln Leu Ile Asp Ala Val Asn Pro Ser Leu Val Asn Phe Trp Gly
225                 230                 235                 240

Val Ser Asp Ser Asn Leu Asp Lys Leu Pro Asp Leu Ser Ser Asn Thr
                245                 250                 255

Asn Ile Lys Lys Ile Ser Ile Arg Gly Asp Tyr Ser Asn Leu Asn Gly
            260                 265                 270

Phe Val Phe Pro Ser Ser Val Leu Glu Leu Glu Phe Ser Ser Gln Asn
        275                 280                 285

Tyr Lys Ala Val Asp Pro Leu Gln Ile Pro Glu Ser Ala Ala Ile Ile
    290                 295                 300

Tyr Glu Gln Gly Tyr Ser Ser Tyr Phe Thr Ser Ile Asp Leu Ser Thr
305                 310                 315                 320

His Lys Gly Met Ser Asn Glu Asp Leu Gln Lys Ala Val Asn Val Val
                325                 330                 335

Tyr Gln Gln Arg Ile His Glu Arg Ala Phe Gln Gly Asp Phe Ala Gly
            340                 345                 350

Gly Tyr Ile Tyr Ser Trp Asn Leu Arg Asn Thr Gly Ile Tyr Ser Phe
        355                 360                 365

Asn Asn Val Thr Ile Pro Met Leu Thr Asp Gly Thr Gly Arg Phe Tyr
    370                 375                 380

Ile Ala Tyr Val Ala Val Glu Thr Asp Gly Asn Gln Gly Pro Ile Ala
385                 390                 395                 400

Asn Glu Val Ile Ser Asp Asn Ser Ser Lys Pro Ser Asn Asp Ser Gln
                405                 410                 415

Ile Asn Glu Trp Phe Asp Trp Asn Gln Asn Gly Trp Ser Thr Ile Thr
            420                 425                 430

Glu Val Lys Ile Thr Ala Lys Asp Asn Val Lys Leu Asn Phe Asn Asn
        435                 440                 445

Thr Val Gln Glu Ile Leu Gly Phe Ile Asn Lys Tyr Pro Asn Ile Lys
    450                 455                 460
```

```
Val Val Asp Ile Ser Ala Leu Gln Phe Ser Asn Asp Glu Thr Leu Asp
465                 470                 475                 480

Glu Leu Ile Asp Ala Val Asn Lys Ala Ile Ala Asp Lys Tyr Thr Gly
                485                 490                 495

Met Asp Gly Thr Pro Thr Val Lys Leu Asp Phe Ile Lys Val Asn Tyr
            500                 505                 510

Leu


<210> SEQ ID NO 8
<211> LENGTH: 475
<212> TYPE: PRT
<213> ORGANISM: Mycoplasma penetrans
<220> FEATURE:
<223> OTHER INFORMATION: IgG-blocking mature protein M sequence

<400> SEQUENCE: 8

Leu Val Thr Ser Asn Asn Asn His Glu Asn Ser Leu Asn Asn Ser Ser
1               5                   10                  15

Ser Asn Asn Gly Ser Asn Leu Lys Val Asn Gly Ser Val Ile Ser Thr
            20                  25                  30

Asp Asn Leu Asn Ile Val Ala Thr Gly Leu Ser Ser Asn Val Ser Ser
        35                  40                  45

Gln Val Ser Arg Gln Ser Leu Ser Ser Ser Ser Ser Ser Glu Ser Thr
    50                  55                  60

Val Asp Ser Lys Tyr Thr Ala Lys Lys Lys Leu Thr Thr Val Ser Gly
65                  70                  75                  80

Gln Glu Lys Glu Tyr Leu Val Ser Thr Val Tyr Glu Asn Asn Arg Lys
                85                  90                  95

Phe Met Pro Ile Leu Ala Tyr Asp Glu Asp Ile Ser Tyr Asn Asn Tyr
            100                 105                 110

Gln Gln Ser Arg Glu Tyr Lys Asp Val Val Tyr Gly Asn Phe Pro Gly
        115                 120                 125

Trp Asp Lys Lys Val Ala Val Val His Gln Ile Asp Asn Val Asp Leu
    130                 135                 140

Ser Lys Ala Tyr Ala Ser Val Ala Glu Phe Thr Pro Thr Glu Ile Leu
145                 150                 155                 160

Lys Lys His Phe Gln Val Leu Gln Thr Ser Val Lys Gln Leu Tyr Val
                165                 170                 175

Ala Leu Asp Ser Lys Thr Met Thr Ala Asp Val Ile Thr Lys Leu Val
            180                 185                 190

Asp Arg Tyr Gln Pro Asp Tyr Leu Arg Ile Glu Ser Val Asp Asp Thr
        195                 200                 205

Ser Ile Lys Gln Leu Pro Asp Met Lys Tyr Phe Ser Thr Val Lys Lys
    210                 215                 220

Val Asp Leu Gly Gly Ala Phe Thr Thr Ile Lys Gly Val Ser Phe Pro
225                 230                 235                 240

Thr Thr Thr Gln Glu Leu Lys Ile Ser Ser Asp Asn Ile Lys Ser Ile
                245                 250                 255

Asp Pro Leu Gln Ile Pro Glu Ser Ala Ala Ile Ile Thr Glu Thr Val
            260                 265                 270

His Asp Ala Arg Phe Thr Glu Ile Asp Leu Ser Ser His Thr Asp Leu
        275                 280                 285

Thr Thr Asp Gln Leu Gln Lys Ala Val Asn Ile Val Tyr Lys Asp Arg
    290                 295                 300
```

```
Ile Lys Glu Arg Ala Phe Gln Gly Asn Phe Ala Gly Gly Tyr Ile Tyr
305                 310                 315                 320

Ser Trp Asn Leu Gln Asn Thr Gly Ile Thr Ser Phe Asn Asp Val Ser
                325                 330                 335

Ile Pro Lys Leu Asn Asp Gly Thr Asp Arg Phe Tyr Ile Ala Tyr Val
            340                 345                 350

Ala Val Ser Ser Gly Asn Ser Asn Gly Thr Ala Asn Glu Thr Ile Thr
        355                 360                 365

Gly Gly Lys Glu Pro Ser Asn Asp Ser Gln Ile Gly Glu Trp Trp Asp
    370                 375                 380

Ser Ser Ser Asp Gly Trp Ser Lys Val Ser Lys Val Thr Val Thr Ala
385                 390                 395                 400

Lys Asn Gly Ala Ser Leu Asp Tyr Asn Lys Thr Leu Thr Glu Ile Met
                405                 410                 415

Gly Phe Leu Ala Lys Tyr Pro Asn Val Lys Thr Ile Asp Ile Ser Leu
            420                 425                 430

Leu Lys Phe Glu Asp Ala Ser Lys Thr Leu Asp Gly Leu Lys Thr Glu
        435                 440                 445

Leu Thr Asn Gln Ile Lys Ser Lys Tyr Gly Glu Asp Ser Ser Tyr Ala
    450                 455                 460

Lys Ile Asp Phe Ile Ile Thr Ser Gln Ser Asn
465                 470                 475


<210> SEQ ID NO 9
<211> LENGTH: 1298
<212> TYPE: PRT
<213> ORGANISM: Artificial Sequence
<220> FEATURE:
<223> OTHER INFORMATION: armY-ACE2 fusion protein

<400> SEQUENCE: 9

Met Tyr Arg Met Gln Leu Leu Ser Cys Ile Ala Leu Ser Leu Ala Leu
1               5                   10                  15

Val Thr Asn Ser Glu Gln Lys Leu Ile Ser Glu Glu Asp Leu Leu Arg
            20                  25                  30

Lys Arg Gly Ser Pro Gly Gly Ala Gln Ser Thr Ile Glu Glu Gln Ala
        35                  40                  45

Lys Thr Phe Leu Asp Lys Phe Asn His Glu Ala Glu Asp Leu Phe Tyr
    50                  55                  60

Gln Ser Ser Leu Ala Ser Trp Asn Tyr Asn Thr Asn Ile Thr Glu Glu
65                  70                  75                  80

Asn Val Gln Asn Met Asn Asn Ala Gly Asp Lys Trp Ser Ala Phe Leu
                85                  90                  95

Lys Glu Gln Ser Thr Leu Ala Gln Met Tyr Pro Leu Gln Glu Ile Gln
            100                 105                 110

Asn Leu Thr Val Lys Leu Gln Leu Gln Ala Leu Gln Gln Asn Gly Ser
        115                 120                 125

Ser Val Leu Ser Glu Asp Lys Ser Lys Arg Leu Asn Thr Ile Leu Asn
    130                 135                 140

Thr Met Ser Thr Ile Tyr Ser Thr Gly Lys Val Cys Asn Pro Asp Asn
145                 150                 155                 160

Pro Gln Glu Cys Leu Leu Leu Glu Pro Gly Leu Asn Glu Ile Met Ala
                165                 170                 175

Asn Ser Leu Asp Tyr Asn Glu Arg Leu Trp Ala Trp Glu Ser Trp Arg
            180                 185                 190
```

-continued

```
Ser Glu Val Gly Lys Gln Leu Arg Pro Leu Tyr Glu Glu Tyr Val Val
        195                 200                 205

Leu Lys Asn Glu Met Ala Arg Ala Asn His Tyr Glu Asp Tyr Gly Asp
    210                 215                 220

Tyr Trp Arg Gly Asp Tyr Glu Val Asn Gly Val Asp Gly Tyr Asp Tyr
225                 230                 235                 240

Ser Arg Gly Gln Leu Ile Glu Asp Val Glu His Thr Phe Glu Glu Ile
                245                 250                 255

Lys Pro Leu Tyr Glu His Leu His Ala Tyr Val Arg Ala Lys Leu Met
            260                 265                 270

Asn Ala Tyr Pro Ser Tyr Ile Ser Pro Ile Gly Cys Leu Pro Ala His
        275                 280                 285

Leu Leu Gly Asp Met Trp Gly Arg Phe Trp Thr Asn Leu Tyr Ser Leu
    290                 295                 300

Thr Val Pro Phe Gly Gln Lys Pro Asn Ile Asp Val Thr Asp Ala Met
305                 310                 315                 320

Val Asp Gln Ala Trp Asp Ala Gln Arg Ile Phe Lys Glu Ala Glu Lys
                325                 330                 335

Phe Phe Val Ser Val Gly Leu Pro Asn Met Thr Gln Gly Phe Trp Glu
            340                 345                 350

Asn Ser Met Leu Thr Asp Pro Gly Asn Val Gln Lys Ala Val Cys His
        355                 360                 365

Pro Thr Ala Trp Asp Leu Gly Lys Gly Asp Phe Arg Ile Leu Met Cys
    370                 375                 380

Thr Lys Val Thr Met Asp Asp Phe Leu Thr Ala His His Glu Met Gly
385                 390                 395                 400

His Ile Gln Tyr Asp Met Ala Tyr Ala Ala Gln Pro Phe Leu Leu Arg
                405                 410                 415

Asn Gly Ala Asn Glu Gly Phe His Glu Ala Val Gly Glu Ile Met Ser
            420                 425                 430

Leu Ser Ala Ala Thr Pro Lys His Leu Lys Ser Ile Gly Leu Leu Ser
        435                 440                 445

Pro Asp Phe Gln Glu Asp Asn Glu Thr Glu Ile Asn Phe Leu Leu Lys
    450                 455                 460

Gln Ala Leu Thr Ile Val Gly Thr Leu Pro Phe Thr Tyr Met Leu Glu
465                 470                 475                 480

Lys Trp Arg Trp Met Val Phe Lys Gly Glu Ile Pro Lys Asp Gln Trp
                485                 490                 495

Met Lys Lys Trp Trp Glu Met Lys Arg Glu Ile Val Gly Val Val Glu
            500                 505                 510

Pro Val Pro His Asp Glu Thr Tyr Cys Asp Pro Ala Ser Leu Phe His
        515                 520                 525

Val Ser Asn Asp Tyr Ser Phe Ile Arg Tyr Tyr Thr Arg Thr Leu Tyr
    530                 535                 540

Gln Phe Gln Phe Gln Glu Ala Leu Cys Gln Ala Ala Lys His Glu Gly
545                 550                 555                 560

Pro Leu His Lys Cys Asp Ile Ser Asn Ser Thr Glu Ala Gly Gln Lys
                565                 570                 575

Leu Phe Asn Met Leu Arg Leu Gly Lys Ser Glu Pro Trp Thr Leu Ala
            580                 585                 590

Leu Glu Asn Val Val Gly Ala Lys Asn Met Asn Val Arg Pro Leu Leu
        595                 600                 605

Asn Tyr Phe Glu Pro Leu Phe Thr Trp Leu Lys Asp Gln Asn Lys Asn
```

```
    610                 615                 620

Ser Phe Val Gly Trp Ser Thr Asp Trp Ser Pro Tyr Ala Asp Gln Ser
625                 630                 635                 640

Ile Lys Val Arg Ile Ser Leu Lys Ser Ala Leu Gly Asp Lys Ala Tyr
                645                 650                 655

Glu Trp Asn Asp Asn Glu Met Tyr Leu Phe Arg Ser Ser Val Ala Tyr
            660                 665                 670

Ala Met Arg Gln Tyr Phe Leu Lys Val Lys Asn Gln Met Ile Leu Phe
        675                 680                 685

Gly Glu Glu Asp Val Arg Val Ala Asn Leu Lys Pro Arg Ile Ser Phe
    690                 695                 700

Asn Phe Phe Val Thr Ala Pro Lys Asn Val Ser Asp Ile Ile Pro Arg
705                 710                 715                 720

Thr Glu Val Glu Lys Ala Ile Arg Met Ser Arg Ser Arg Ile Asn Asp
                725                 730                 735

Ala Phe Arg Leu Asn Asp Asn Ser Leu Glu Phe Leu Gly Ile Gln Pro
            740                 745                 750

Thr Leu Gly Pro Pro Asn Gln Pro Pro Val Ser Gly Gly Gly Gly Ser
        755                 760                 765

Gly Gly Gly Gly Ser Gly Gly Gly Gly Ser Thr Asn Leu Val Asn Gln
    770                 775                 780

Ser Gly Tyr Ala Leu Val Ala Ser Gly Arg Ser Gly Asn Leu Gly Phe
785                 790                 795                 800

Lys Leu Phe Ser Thr Gln Ser Pro Ser Ala Glu Val Lys Leu Lys Ser
                805                 810                 815

Leu Ser Leu Asn Asp Gly Ser Tyr Gln Ser Glu Ile Asp Leu Ser Gly
            820                 825                 830

Gly Ala Asn Phe Arg Glu Lys Phe Arg Asn Phe Ala Asn Glu Leu Ser
        835                 840                 845

Glu Ala Ile Thr Asn Ser Pro Lys Gly Leu Asp Arg Pro Val Pro Lys
    850                 855                 860

Thr Glu Ile Ser Gly Leu Ile Lys Thr Gly Asp Asn Phe Ile Thr Pro
865                 870                 875                 880

Ser Phe Lys Ala Gly Tyr Tyr Asp His Val Ala Ser Asp Gly Ser Leu
                885                 890                 895

Leu Ser Tyr Tyr Gln Ser Thr Glu Tyr Phe Asn Asn Arg Val Leu Met
            900                 905                 910

Pro Ile Leu Gln Thr Thr Asn Gly Thr Leu Met Ala Asn Asn Arg Gly
        915                 920                 925

Tyr Asp Asp Val Phe Arg Gln Val Pro Ser Phe Ser Gly Trp Ser Asn
    930                 935                 940

Thr Lys Ala Thr Thr Val Ser Thr Ser Asn Asn Leu Thr Tyr Asp Lys
945                 950                 955                 960

Trp Thr Tyr Phe Ala Ala Lys Gly Ser Pro Leu Tyr Asp Ser Tyr Pro
                965                 970                 975

Asn His Phe Phe Glu Asp Val Lys Thr Leu Ala Ile Asp Ala Lys Asp
            980                 985                 990

Ile Ser Ala Leu Lys Thr Thr Ile Asp Ser Glu Lys Pro Thr Tyr Leu
        995                 1000                1005

Ile Ile Arg Gly Leu Ser Gly Asn Gly Ser Gln Leu Asn Glu Leu Gln
    1010                1015                1020

Leu Pro Glu Ser Val Lys Lys Val Ser Leu Tyr Gly Asp Tyr Thr Gly
1025                1030                1035                1040
```

Val Asn Val Ala Lys Gln Ile Phe Ala Asn Val Val Glu Leu Glu Phe
1045 1050 1055

Tyr Ser Thr Ser Lys Ala Asn Ser Phe Gly Phe Asn Pro Leu Val Leu
1060 1065 1070

Gly Ser Lys Thr Asn Val Ile Tyr Asp Leu Phe Ala Ser Lys Pro Phe
1075 1080 1085

Thr His Ile Asp Leu Thr Gln Val Thr Leu Gln Asn Ser Asp Asn Ser
1090 1095 1100

Ala Ile Asp Ala Asn Lys Leu Lys Gln Ala Val Gly Asp Ile Tyr Asn
1105 1110 1115 1120

Tyr Arg Arg Phe Glu Arg Gln Phe Gln Gly Tyr Phe Ala Gly Gly Tyr
1125 1130 1135

Ile Asp Lys Tyr Leu Val Lys Asn Val Asn Thr Asn Lys Asp Ser Asp
1140 1145 1150

Asp Asp Leu Val Tyr Arg Ser Leu Lys Glu Leu Asn Leu His Leu Glu
1155 1160 1165

Glu Ala Tyr Arg Glu Gly Asp Asn Thr Tyr Tyr Arg Val Asn Glu Asn
1170 1175 1180

Tyr Tyr Pro Gly Ala Ser Ile Tyr Glu Asn Glu Arg Ala Ser Arg Asp
1185 1190 1195 1200

Ser Glu Phe Gln Asn Glu Ile Leu Lys Arg Ala Glu Gln Asn Gly Val
1205 1210 1215

Thr Phe Asp Glu Asn Ile Lys Arg Ile Thr Ala Ser Gly Lys Tyr Ser
1220 1225 1230

Val Gln Phe Gln Lys Leu Glu Asn Asp Thr Asp Ser Ser Leu Glu Arg
1235 1240 1245

Met Thr Lys Ala Val Glu Gly Leu Val Thr Val Ile Gly Glu Glu Lys
1250 1255 1260

Phe Glu Thr Val Asp Ile Thr Gly Val Ser Ser Asp Thr Asn Glu Val
1265 1270 1275 1280

Lys Ser Leu Ala Lys Glu Leu Lys Thr Asn Ala Leu Gly Val Lys Leu
1285 1290 1295

Lys Leu

<210> SEQ ID NO 10
<211> LENGTH: 587
<212> TYPE: PRT
<213> ORGANISM: Artificial Sequence
<220> FEATURE:
<223> OTHER INFORMATION: Protein M with peptide tags (aka: armY) protein

<400> SEQUENCE: 10

Met Tyr Arg Met Gln Leu Leu Ser Cys Ile Ala Leu Ser Leu Ala Leu
1 5 10 15

Val Thr Asn Ser Met Ala Gly Gly Leu Asn Asp Ile Phe Glu Ala Gln
20 25 30

Lys Ile Glu Trp His Glu Gly Gly Glu Gln Lys Leu Ile Ser Glu Glu
35 40 45

Asp Leu Leu Arg Lys Arg Ala Ala Asn Gly Gly Gly Gly Ser Gly Gly
50 55 60

Gly Gly Ser Thr Asn Leu Val Asn Gln Ser Gly Tyr Ala Leu Val Ala
65 70 75 80

Ser Gly Arg Ser Gly Asn Leu Gly Phe Lys Leu Phe Ser Thr Gln Ser
85 90 95

-continued

```
Pro Ser Ala Glu Val Lys Leu Lys Ser Leu Ser Leu Asn Asp Gly Ser
            100                 105                 110

Tyr Gln Ser Glu Ile Asp Leu Ser Gly Gly Ala Asn Phe Arg Glu Lys
        115                 120                 125

Phe Arg Asn Phe Ala Asn Glu Leu Ser Glu Ala Ile Thr Asn Ser Pro
    130                 135                 140

Lys Gly Leu Asp Arg Pro Val Pro Lys Thr Glu Ile Ser Gly Leu Ile
145                 150                 155                 160

Lys Thr Gly Asp Asn Phe Ile Thr Pro Ser Phe Lys Ala Gly Tyr Tyr
                165                 170                 175

Asp His Val Ala Ser Asp Gly Ser Leu Leu Ser Tyr Tyr Gln Ser Thr
            180                 185                 190

Glu Tyr Phe Asn Asn Arg Val Leu Met Pro Ile Leu Gln Thr Thr Asn
        195                 200                 205

Gly Thr Leu Met Ala Asn Asn Arg Gly Tyr Asp Asp Val Phe Arg Gln
    210                 215                 220

Val Pro Ser Phe Ser Gly Trp Ser Asn Thr Lys Ala Thr Thr Val Ser
225                 230                 235                 240

Thr Ser Asn Asn Leu Thr Tyr Asp Lys Trp Thr Tyr Phe Ala Ala Lys
                245                 250                 255

Gly Ser Pro Leu Tyr Asp Ser Tyr Pro Asn His Phe Phe Glu Asp Val
            260                 265                 270

Lys Thr Leu Ala Ile Asp Ala Lys Asp Ile Ser Ala Leu Lys Thr Thr
        275                 280                 285

Ile Asp Ser Glu Lys Pro Thr Tyr Leu Ile Ile Arg Gly Leu Ser Gly
    290                 295                 300

Asn Gly Ser Gln Leu Asn Glu Leu Gln Leu Pro Glu Ser Val Lys Lys
305                 310                 315                 320

Val Ser Leu Tyr Gly Asp Tyr Thr Gly Val Asn Val Ala Lys Gln Ile
                325                 330                 335

Phe Ala Asn Val Val Glu Leu Glu Phe Tyr Ser Thr Ser Lys Ala Asn
            340                 345                 350

Ser Phe Gly Phe Asn Pro Leu Val Leu Gly Ser Lys Thr Asn Val Ile
        355                 360                 365

Tyr Asp Leu Phe Ala Ser Lys Pro Phe Thr His Ile Asp Leu Thr Gln
    370                 375                 380

Val Thr Leu Gln Asn Ser Asp Asn Ser Ala Ile Asp Ala Asn Lys Leu
385                 390                 395                 400

Lys Gln Ala Val Gly Asp Ile Tyr Asn Tyr Arg Arg Phe Glu Arg Gln
                405                 410                 415

Phe Gln Gly Tyr Phe Ala Gly Gly Tyr Ile Asp Lys Tyr Leu Val Lys
            420                 425                 430

Asn Val Asn Thr Asn Lys Asp Ser Asp Asp Asp Leu Val Tyr Arg Ser
        435                 440                 445

Leu Lys Glu Leu Asn Leu His Leu Glu Glu Ala Tyr Arg Glu Gly Asp
    450                 455                 460

Asn Thr Tyr Tyr Arg Val Asn Glu Asn Tyr Tyr Pro Gly Ala Ser Ile
465                 470                 475                 480

Tyr Glu Asn Glu Arg Ala Ser Arg Asp Ser Glu Phe Gln Asn Glu Ile
                485                 490                 495

Leu Lys Arg Ala Glu Gln Asn Gly Val Thr Phe Asp Glu Asn Ile Lys
            500                 505                 510

Arg Ile Thr Ala Ser Gly Lys Tyr Ser Val Gln Phe Gln Lys Leu Glu
```

```
        515                 520                 525

Asn Asp Thr Asp Ser Ser Leu Glu Arg Met Thr Lys Ala Val Glu Gly
    530                 535                 540

Leu Val Thr Val Ile Gly Glu Glu Lys Phe Glu Thr Val Asp Ile Thr
545                 550                 555                 560

Gly Val Ser Ser Asp Thr Asn Glu Val Lys Ser Leu Ala Lys Glu Leu
                565                 570                 575

Lys Thr Asn Ala Leu Gly Val Lys Leu Lys Leu
            580                 585


<210> SEQ ID NO 11
<211> LENGTH: 876
<212> TYPE: PRT
<213> ORGANISM: Artificial Sequence
<220> FEATURE:
<223> OTHER INFORMATION: Protein M-horseradish peroxidase (HRP) fusion
      protein

<400> SEQUENCE: 11

Met Tyr Arg Met Gln Leu Leu Ser Cys Ile Ala Leu Ser Leu Ala Leu
1               5                   10                  15

Val Thr Asn Ser Glu Gln Lys Leu Ile Ser Glu Glu Asp Leu Ala Ala
            20                  25                  30

Asn Gln Leu Thr Pro Thr Phe Tyr Asp Asn Ser Cys Pro Asn Val Ser
        35                  40                  45

Asn Ile Val Arg Asp Thr Ile Val Asn Glu Leu Arg Ser Asp Pro Arg
    50                  55                  60

Ile Ala Ala Ser Ile Leu Arg Leu His Phe His Asp Cys Phe Val Asn
65                  70                  75                  80

Gly Cys Asp Ala Ser Ile Leu Leu Asp Asn Thr Thr Ser Phe Arg Thr
                85                  90                  95

Glu Lys Asp Ala Phe Gly Asn Ala Asn Ser Ala Arg Gly Phe Pro Val
            100                 105                 110

Ile Asp Arg Met Lys Ala Ala Val Glu Ser Ala Cys Pro Arg Thr Val
        115                 120                 125

Ser Cys Ala Asp Leu Leu Thr Ile Ala Ala Gln Gln Ser Val Thr Leu
    130                 135                 140

Ala Gly Gly Pro Ser Trp Arg Val Pro Leu Gly Arg Arg Asp Ser Leu
145                 150                 155                 160

Gln Ala Phe Leu Asp Leu Ala Asn Ala Asn Leu Pro Ala Pro Phe Phe
                165                 170                 175

Thr Leu Pro Gln Leu Lys Asp Ser Phe Arg Asn Val Gly Leu Asn Arg
            180                 185                 190

Ser Ser Asp Leu Val Ala Leu Ser Gly Gly His Thr Phe Gly Lys Asn
        195                 200                 205

Gln Cys Arg Phe Ile Met Asp Arg Leu Tyr Asn Phe Ser Asn Thr Gly
    210                 215                 220

Leu Pro Asp Pro Thr Leu Asn Thr Thr Tyr Leu Gln Thr Leu Arg Gly
225                 230                 235                 240

Leu Cys Pro Leu Asn Gly Asn Leu Ser Ala Leu Val Asp Phe Asp Leu
                245                 250                 255

Arg Thr Pro Thr Ile Phe Asp Asn Lys Tyr Tyr Val Asn Leu Glu Glu
            260                 265                 270

Gln Lys Gly Leu Ile Gln Ser Asp Gln Glu Leu Phe Ser Ser Pro Asn
        275                 280                 285
```

```
Ala Thr Asp Thr Ile Pro Leu Val Arg Ser Phe Ala Asn Ser Thr Gln
    290                 295                 300

Thr Phe Phe Asn Ala Phe Val Glu Ala Met Asp Arg Met Gly Asn Ile
305                 310                 315                 320

Thr Pro Leu Thr Gly Thr Gln Gly Gln Ile Arg Leu Asn Cys Arg Val
                325                 330                 335

Val Asn Ser Asn Ser Gly Gly Gly Gly Ser Gly Gly Gly Gly Ser Gly
            340                 345                 350

Gly Gly Gly Ser Thr Asn Leu Val Asn Gln Ser Gly Tyr Ala Leu Val
        355                 360                 365

Ala Ser Gly Arg Ser Gly Asn Leu Gly Phe Lys Leu Phe Ser Thr Gln
    370                 375                 380

Ser Pro Ser Ala Glu Val Lys Leu Lys Ser Leu Ser Leu Asn Asp Gly
385                 390                 395                 400

Ser Tyr Gln Ser Glu Ile Asp Leu Ser Gly Gly Ala Asn Phe Arg Glu
                405                 410                 415

Lys Phe Arg Asn Phe Ala Asn Glu Leu Ser Glu Ala Ile Thr Asn Ser
            420                 425                 430

Pro Lys Gly Leu Asp Arg Pro Val Pro Lys Thr Glu Ile Ser Gly Leu
        435                 440                 445

Ile Lys Thr Gly Asp Asn Phe Ile Thr Pro Ser Phe Lys Ala Gly Tyr
    450                 455                 460

Tyr Asp His Val Ala Ser Asp Gly Ser Leu Leu Ser Tyr Tyr Gln Ser
465                 470                 475                 480

Thr Glu Tyr Phe Asn Asn Arg Val Leu Met Pro Ile Leu Gln Thr Thr
                485                 490                 495

Asn Gly Thr Leu Met Ala Asn Asn Arg Gly Tyr Asp Asp Val Phe Arg
            500                 505                 510

Gln Val Pro Ser Phe Ser Gly Trp Ser Asn Thr Lys Ala Thr Thr Val
        515                 520                 525

Ser Thr Ser Asn Asn Leu Thr Tyr Asp Lys Trp Thr Tyr Phe Ala Ala
    530                 535                 540

Lys Gly Ser Pro Leu Tyr Asp Ser Tyr Pro Asn His Phe Phe Glu Asp
545                 550                 555                 560

Val Lys Thr Leu Ala Ile Asp Ala Lys Asp Ile Ser Ala Leu Lys Thr
                565                 570                 575

Thr Ile Asp Ser Glu Lys Pro Thr Tyr Leu Ile Ile Arg Gly Leu Ser
            580                 585                 590

Gly Asn Gly Ser Gln Leu Asn Glu Leu Gln Leu Pro Glu Ser Val Lys
        595                 600                 605

Lys Val Ser Leu Tyr Gly Asp Tyr Thr Gly Val Asn Val Ala Lys Gln
    610                 615                 620

Ile Phe Ala Asn Val Val Glu Leu Glu Phe Tyr Ser Thr Ser Lys Ala
625                 630                 635                 640

Asn Ser Phe Gly Phe Asn Pro Leu Val Leu Gly Ser Lys Thr Asn Val
                645                 650                 655

Ile Tyr Asp Leu Phe Ala Ser Lys Pro Phe Thr His Ile Asp Leu Thr
            660                 665                 670

Gln Val Thr Leu Gln Asn Ser Asp Asn Ser Ala Ile Asp Ala Asn Lys
        675                 680                 685

Leu Lys Gln Ala Val Gly Asp Ile Tyr Asn Tyr Arg Arg Phe Glu Arg
    690                 695                 700

Gln Phe Gln Gly Tyr Phe Ala Gly Gly Tyr Ile Asp Lys Tyr Leu Val
```

705 710 715 720

Lys Asn Val Asn Thr Asn Lys Asp Ser Asp Asp Asp Leu Val Tyr Arg
725 730 735

Ser Leu Lys Glu Leu Asn Leu His Leu Glu Glu Ala Tyr Arg Glu Gly
740 745 750

Asp Asn Thr Tyr Tyr Arg Val Asn Glu Asn Tyr Tyr Pro Gly Ala Ser
755 760 765

Ile Tyr Glu Asn Glu Arg Ala Ser Arg Asp Ser Glu Phe Gln Asn Glu
770 775 780

Ile Leu Lys Arg Ala Glu Gln Asn Gly Val Thr Phe Asp Glu Asn Ile
785 790 795 800

Lys Arg Ile Thr Ala Ser Gly Lys Tyr Ser Val Gln Phe Gln Lys Leu
805 810 815

Glu Asn Asp Thr Asp Ser Ser Leu Glu Arg Met Thr Lys Ala Val Glu
820 825 830

Gly Leu Val Thr Val Ile Gly Glu Glu Lys Phe Glu Thr Val Asp Ile
835 840 845

Thr Gly Val Ser Ser Asp Thr Asn Glu Val Lys Ser Leu Ala Lys Glu
850 855 860

Leu Lys Thr Asn Ala Leu Gly Val Lys Leu Lys Leu
865 870 875

<210> SEQ ID NO 12
<211> LENGTH: 15
<212> TYPE: PRT
<213> ORGANISM: Artificial Sequence
<220> FEATURE:
<223> OTHER INFORMATION: Set of three Glycine (G4)-Serine (S1) linker

<400> SEQUENCE: 12

Gly Gly Gly Gly Ser Gly Gly Gly Gly Ser Gly Gly Gly Gly Ser
1 5 10 15

<210> SEQ ID NO 13
<211> LENGTH: 10
<212> TYPE: PRT
<213> ORGANISM: Artificial Sequence
<220> FEATURE:
<223> OTHER INFORMATION: Set of two Glycine (G4)-Serine (S1) linker

<400> SEQUENCE: 13

Gly Gly Gly Gly Ser Gly Gly Gly Gly Ser
1 5 10

<210> SEQ ID NO 14
<211> LENGTH: 5
<212> TYPE: PRT
<213> ORGANISM: Artificial Sequence
<220> FEATURE:
<223> OTHER INFORMATION: Set of one Glycine (G4)-Serine (S1) linker

<400> SEQUENCE: 14

Gly Gly Gly Gly Ser
1 5

<210> SEQ ID NO 15
<211> LENGTH: 723
<212> TYPE: PRT
<213> ORGANISM: Artificial Sequence
<220> FEATURE:
<223> OTHER INFORMATION: Angiotensin-converting enzyme 2 (ACE2)
extracellular domain protein sequence

<400> SEQUENCE: 15

Gln Ser Thr Ile Glu Glu Gln Ala Lys Thr Phe Leu Asp Lys Phe Asn
1 5 10 15

His Glu Ala Glu Asp Leu Phe Tyr Gln Ser Ser Leu Ala Ser Trp Asn
20 25 30

Tyr Asn Thr Asn Ile Thr Glu Glu Asn Val Gln Asn Met Asn Asn Ala
35 40 45

Gly Asp Lys Trp Ser Ala Phe Leu Lys Glu Gln Ser Thr Leu Ala Gln
50 55 60

Met Tyr Pro Leu Gln Glu Ile Gln Asn Leu Thr Val Lys Leu Gln Leu
65 70 75 80

Gln Ala Leu Gln Gln Asn Gly Ser Ser Val Leu Ser Glu Asp Lys Ser
85 90 95

Lys Arg Leu Asn Thr Ile Leu Asn Thr Met Ser Thr Ile Tyr Ser Thr
100 105 110

Gly Lys Val Cys Asn Pro Asp Asn Pro Gln Glu Cys Leu Leu Leu Glu
115 120 125

Pro Gly Leu Asn Glu Ile Met Ala Asn Ser Leu Asp Tyr Asn Glu Arg
130 135 140

Leu Trp Ala Trp Glu Ser Trp Arg Ser Glu Val Gly Lys Gln Leu Arg
145 150 155 160

Pro Leu Tyr Glu Glu Tyr Val Val Leu Lys Asn Glu Met Ala Arg Ala
165 170 175

Asn His Tyr Glu Asp Tyr Gly Asp Tyr Trp Arg Gly Asp Tyr Glu Val
180 185 190

Asn Gly Val Asp Gly Tyr Asp Tyr Ser Arg Gly Gln Leu Ile Glu Asp
195 200 205

Val Glu His Thr Phe Glu Glu Ile Lys Pro Leu Tyr Glu His Leu His
210 215 220

Ala Tyr Val Arg Ala Lys Leu Met Asn Ala Tyr Pro Ser Tyr Ile Ser
225 230 235 240

Pro Ile Gly Cys Leu Pro Ala His Leu Leu Gly Asp Met Trp Gly Arg
245 250 255

Phe Trp Thr Asn Leu Tyr Ser Leu Thr Val Pro Phe Gly Gln Lys Pro
260 265 270

Asn Ile Asp Val Thr Asp Ala Met Val Asp Gln Ala Trp Asp Ala Gln
275 280 285

Arg Ile Phe Lys Glu Ala Glu Lys Phe Phe Val Ser Val Gly Leu Pro
290 295 300

Asn Met Thr Gln Gly Phe Trp Glu Asn Ser Met Leu Thr Asp Pro Gly
305 310 315 320

Asn Val Gln Lys Ala Val Cys His Pro Thr Ala Trp Asp Leu Gly Lys
325 330 335

Gly Asp Phe Arg Ile Leu Met Cys Thr Lys Val Thr Met Asp Asp Phe
340 345 350

Leu Thr Ala His His Glu Met Gly His Ile Gln Tyr Asp Met Ala Tyr
355 360 365

Ala Ala Gln Pro Phe Leu Leu Arg Asn Gly Ala Asn Glu Gly Phe His
370 375 380

Glu Ala Val Gly Glu Ile Met Ser Leu Ser Ala Ala Thr Pro Lys His
385 390 395 400

Leu Lys Ser Ile Gly Leu Leu Ser Pro Asp Phe Gln Glu Asp Asn Glu

```
                405                 410                 415

Thr Glu Ile Asn Phe Leu Leu Lys Gln Ala Leu Thr Ile Val Gly Thr
            420                 425                 430

Leu Pro Phe Thr Tyr Met Leu Glu Lys Trp Arg Trp Met Val Phe Lys
        435                 440                 445

Gly Glu Ile Pro Lys Asp Gln Trp Met Lys Lys Trp Trp Glu Met Lys
    450                 455                 460

Arg Glu Ile Val Gly Val Val Glu Pro Val Pro His Asp Glu Thr Tyr
465                 470                 475                 480

Cys Asp Pro Ala Ser Leu Phe His Val Ser Asn Asp Tyr Ser Phe Ile
                485                 490                 495

Arg Tyr Tyr Thr Arg Thr Leu Tyr Gln Phe Gln Phe Gln Glu Ala Leu
            500                 505                 510

Cys Gln Ala Ala Lys His Glu Gly Pro Leu His Lys Cys Asp Ile Ser
        515                 520                 525

Asn Ser Thr Glu Ala Gly Gln Lys Leu Phe Asn Met Leu Arg Leu Gly
    530                 535                 540

Lys Ser Glu Pro Trp Thr Leu Ala Leu Glu Asn Val Val Gly Ala Lys
545                 550                 555                 560

Asn Met Asn Val Arg Pro Leu Leu Asn Tyr Phe Glu Pro Leu Phe Thr
                565                 570                 575

Trp Leu Lys Asp Gln Asn Lys Asn Ser Phe Val Gly Trp Ser Thr Asp
            580                 585                 590

Trp Ser Pro Tyr Ala Asp Gln Ser Ile Lys Val Arg Ile Ser Leu Lys
        595                 600                 605

Ser Ala Leu Gly Asp Lys Ala Tyr Glu Trp Asn Asp Asn Glu Met Tyr
    610                 615                 620

Leu Phe Arg Ser Ser Val Ala Tyr Ala Met Arg Gln Tyr Phe Leu Lys
625                 630                 635                 640

Val Lys Asn Gln Met Ile Leu Phe Gly Glu Glu Asp Val Arg Val Ala
                645                 650                 655

Asn Leu Lys Pro Arg Ile Ser Phe Asn Phe Phe Val Thr Ala Pro Lys
            660                 665                 670

Asn Val Ser Asp Ile Ile Pro Arg Thr Glu Val Glu Lys Ala Ile Arg
        675                 680                 685

Met Ser Arg Ser Arg Ile Asn Asp Ala Phe Arg Leu Asn Asp Asn Ser
    690                 695                 700

Leu Glu Phe Leu Gly Ile Gln Pro Thr Leu Gly Pro Pro Asn Gln Pro
705                 710                 715                 720

Pro Val Ser


<210> SEQ ID NO 16
<211> LENGTH: 346
<212> TYPE: PRT
<213> ORGANISM: Homo sapiens
<220> FEATURE:
<223> OTHER INFORMATION: CD209 (DC-SIGN) extracellular domain protein

<400> SEQUENCE: 16

Gln Val Ser Lys Val Pro Ser Ser Ile Ser Gln Glu Gln Ser Arg Gln
1               5                   10                  15

Asp Ala Ile Tyr Gln Asn Leu Thr Gln Leu Lys Ala Ala Val Gly Glu
            20                  25                  30

Leu Ser Glu Lys Ser Lys Leu Gln Glu Ile Tyr Gln Glu Leu Thr Gln
        35                  40                  45
```

```
Leu Lys Ala Ala Val Gly Glu Leu Pro Glu Lys Ser Lys Leu Gln Glu
    50                  55                  60

Ile Tyr Gln Glu Leu Thr Arg Leu Lys Ala Ala Val Gly Glu Leu Pro
65                  70                  75                  80

Glu Lys Ser Lys Leu Gln Glu Ile Tyr Gln Glu Leu Thr Trp Leu Lys
                85                  90                  95

Ala Ala Val Gly Glu Leu Pro Glu Lys Ser Lys Met Gln Glu Ile Tyr
            100                 105                 110

Gln Glu Leu Thr Arg Leu Lys Ala Ala Val Gly Glu Leu Pro Glu Lys
        115                 120                 125

Ser Lys Gln Gln Glu Ile Tyr Gln Glu Leu Thr Arg Leu Lys Ala Ala
    130                 135                 140

Val Gly Glu Leu Pro Glu Lys Ser Lys Gln Gln Glu Ile Tyr Gln Glu
145                 150                 155                 160

Leu Thr Arg Leu Lys Ala Ala Val Gly Glu Leu Pro Glu Lys Ser Lys
                165                 170                 175

Gln Gln Glu Ile Tyr Gln Glu Leu Thr Gln Leu Lys Ala Ala Val Glu
            180                 185                 190

Arg Leu Cys His Pro Cys Pro Trp Glu Trp Thr Phe Phe Gln Gly Asn
        195                 200                 205

Cys Tyr Phe Met Ser Asn Ser Gln Arg Asn Trp His Asp Ser Ile Thr
    210                 215                 220

Ala Cys Lys Glu Val Gly Ala Gln Leu Val Val Ile Lys Ser Ala Glu
225                 230                 235                 240

Glu Gln Asn Phe Leu Gln Leu Gln Ser Ser Arg Ser Asn Arg Phe Thr
                245                 250                 255

Trp Met Gly Leu Ser Asp Leu Asn Gln Glu Gly Thr Trp Gln Trp Val
            260                 265                 270

Asp Gly Ser Pro Leu Leu Pro Ser Phe Lys Gln Tyr Trp Asn Arg Gly
        275                 280                 285

Glu Pro Asn Asn Val Gly Glu Glu Asp Cys Ala Glu Phe Ser Gly Asn
    290                 295                 300

Gly Trp Asn Asp Asp Lys Cys Asn Leu Ala Lys Phe Trp Ile Cys Lys
305                 310                 315                 320

Lys Ser Ala Ala Ser Cys Ser Arg Asp Glu Glu Gln Phe Leu Ser Pro
                325                 330                 335

Ala Pro Ala Thr Pro Asn Pro Pro Pro Ala
            340                 345


<210> SEQ ID NO 17
<211> LENGTH: 329
<212> TYPE: PRT
<213> ORGANISM: Homo sapiens
<220> FEATURE:
<223> OTHER INFORMATION: C-type lectin domain family 4 member M
      extracellular domain protein

<400> SEQUENCE: 17

Gln Val Ser Lys Val Pro Ser Ser Leu Ser Gln Glu Gln Ser Glu Gln
1               5                   10                  15

Asp Ala Ile Tyr Gln Asn Leu Thr Gln Leu Lys Ala Ala Val Gly Glu
            20                  25                  30

Leu Ser Glu Lys Ser Lys Leu Gln Glu Ile Tyr Gln Glu Leu Thr Gln
        35                  40                  45

Leu Lys Ala Ala Val Gly Glu Leu Pro Glu Lys Ser Lys Leu Gln Glu
```

```
    50                  55                  60

Ile Tyr Gln Glu Leu Thr Arg Leu Lys Ala Ala Val Gly Glu Leu Pro
65                  70                  75                  80

Glu Lys Ser Lys Leu Gln Glu Ile Tyr Gln Glu Leu Thr Arg Leu Lys
                85                  90                  95

Ala Ala Val Gly Glu Leu Pro Glu Lys Ser Lys Leu Gln Glu Ile Tyr
            100                 105                 110

Gln Glu Leu Thr Arg Leu Lys Ala Ala Val Gly Glu Leu Pro Glu Lys
        115                 120                 125

Ser Lys Leu Gln Glu Ile Tyr Gln Glu Leu Thr Glu Leu Lys Ala Ala
    130                 135                 140

Val Gly Glu Leu Pro Glu Lys Ser Lys Leu Gln Glu Ile Tyr Gln Glu
145                 150                 155                 160

Leu Thr Gln Leu Lys Ala Ala Val Gly Glu Leu Pro Asp Gln Ser Lys
                165                 170                 175

Gln Gln Gln Ile Tyr Gln Glu Leu Thr Asp Leu Lys Thr Ala Phe Glu
            180                 185                 190

Arg Leu Cys Arg His Cys Pro Lys Asp Trp Thr Phe Phe Gln Gly Asn
        195                 200                 205

Cys Tyr Phe Met Ser Asn Ser Gln Arg Asn Trp His Asp Ser Val Thr
    210                 215                 220

Ala Cys Gln Glu Val Arg Ala Gln Leu Val Val Ile Lys Thr Ala Glu
225                 230                 235                 240

Glu Gln Asn Phe Leu Gln Leu Gln Thr Ser Arg Ser Asn Arg Phe Ser
                245                 250                 255

Trp Met Gly Leu Ser Asp Leu Asn Gln Glu Gly Thr Trp Gln Trp Val
            260                 265                 270

Asp Gly Ser Pro Leu Ser Pro Ser Phe Gln Arg Tyr Trp Asn Ser Gly
        275                 280                 285

Glu Pro Asn Asn Ser Gly Asn Glu Asp Cys Ala Glu Phe Ser Gly Ser
    290                 295                 300

Gly Trp Asn Asp Asn Arg Cys Asp Val Asp Asn Tyr Trp Ile Cys Lys
305                 310                 315                 320

Lys Pro Ala Ala Cys Phe Arg Asp Glu
                325


<210> SEQ ID NO 18
<211> LENGTH: 371
<212> TYPE: PRT
<213> ORGANISM: Homo sapiens
<220> FEATURE:
<223> OTHER INFORMATION: CD4 extracellular domain protein

<400> SEQUENCE: 18

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
```

```
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Val Tyr Lys Lys Glu Gly Glu
            180                 185                 190

Gln Val Glu Phe Ser Phe Pro Leu Ala Phe Thr Val Glu Lys Leu Thr
        195                 200                 205

Gly Ser Gly Glu Leu Trp Trp Gln Ala Glu Arg Ala Ser Ser Ser Lys
    210                 215                 220

Ser Trp Ile Thr Phe Asp Leu Lys Asn Lys Glu Val Ser Val Lys Arg
225                 230                 235                 240

Val Thr Gln Asp Pro Lys Leu Gln Met Gly Lys Lys Leu Pro Leu His
                245                 250                 255

Leu Thr Leu Pro Gln Ala Leu Pro Gln Tyr Ala Gly Ser Gly Asn Leu
            260                 265                 270

Thr Leu Ala Leu Glu Ala Lys Thr Gly Lys Leu His Gln Glu Val Asn
        275                 280                 285

Leu Val Val Met Arg Ala Thr Gln Leu Gln Lys Asn Leu Thr Cys Glu
    290                 295                 300

Val Trp Gly Pro Thr Ser Pro Lys Leu Met Leu Ser Leu Lys Leu Glu
305                 310                 315                 320

Asn Lys Glu Ala Lys Val Ser Lys Arg Glu Lys Ala Val Trp Val Leu
                325                 330                 335

Asn Pro Glu Ala Gly Met Trp Gln Cys Leu Leu Ser Asp Ser Gly Gln
            340                 345                 350

Val Leu Leu Glu Ser Asn Ile Lys Val Leu Pro Thr Trp Ser Thr Pro
        355                 360                 365

Val Gln Pro
    370


<210> SEQ ID NO 19
<211> LENGTH: 130
<212> TYPE: PRT
<213> ORGANISM: Homo sapiens
<220> FEATURE:
<223> OTHER INFORMATION: Synaptic vesicle glycoprotein 2A extracellular
      domain protein

<400> SEQUENCE: 19

Pro Asp Met Ile Arg His Leu Gln Ala Val Asp Tyr Ala Ser Arg Thr
1               5                   10                  15

Lys Val Phe Pro Gly Glu Arg Val Glu His Val Thr Phe Asn Phe Thr
            20                  25                  30

Leu Glu Asn Gln Ile His Arg Gly Gly Gln Tyr Phe Asn Asp Lys Phe
        35                  40                  45

Ile Gly Leu Arg Leu Lys Ser Val Ser Phe Glu Asp Ser Leu Phe Glu
    50                  55                  60
```

```
Glu Cys Tyr Phe Glu Asp Val Thr Ser Ser Asn Thr Phe Phe Arg Asn
65                  70                  75                  80

Cys Thr Phe Ile Asn Thr Val Phe Tyr Asn Thr Asp Leu Phe Glu Tyr
                85                  90                  95

Lys Phe Val Asn Ser Arg Leu Ile Asn Ser Thr Phe Leu His Asn Lys
            100                 105                 110

Glu Gly Cys Pro Leu Asp Val Thr Gly Thr Gly Glu Gly Ala Tyr Met
        115                 120                 125

Val Tyr
    130


<210> SEQ ID NO 20
<211> LENGTH: 124
<212> TYPE: PRT
<213> ORGANISM: Homo sapiens
<220> FEATURE:
<223> OTHER INFORMATION: Synaptic vesicle glycoprotein 2B extracellular
      domain protein

<400> SEQUENCE: 20

Pro Asp Met Ile Arg Tyr Phe Gln Asp Glu Glu Tyr Lys Ser Lys Met
1               5                   10                  15

Lys Val Phe Phe Gly Glu His Val Tyr Gly Ala Thr Ile Asn Phe Thr
            20                  25                  30

Met Glu Asn Gln Ile His Gln His Gly Lys Leu Val Asn Asp Lys Phe
        35                  40                  45

Thr Arg Met Tyr Phe Lys His Val Leu Phe Glu Asp Thr Phe Phe Asp
    50                  55                  60

Glu Cys Tyr Phe Glu Asp Val Thr Ser Thr Asp Thr Tyr Phe Lys Asn
65                  70                  75                  80

Cys Thr Ile Glu Ser Thr Ile Phe Tyr Asn Thr Asp Leu Tyr Glu His
                85                  90                  95

Lys Phe Ile Asn Cys Arg Phe Ile Asn Ser Thr Phe Leu Glu Gln Lys
            100                 105                 110

Glu Gly Cys His Met Asp Leu Glu Gln Asp Asn Asp
        115                 120


<210> SEQ ID NO 21
<211> LENGTH: 120
<212> TYPE: PRT
<213> ORGANISM: Homo sapiens
<220> FEATURE:
<223> OTHER INFORMATION: Synaptic vesicle glycoprotein 2C extracellular
      domain protein sequence (459-578 amino acid)

<400> SEQUENCE: 21

Lys Pro Leu Gln Ser Asp Glu Tyr Ala Leu Leu Thr Arg Asn Val Glu
1               5                   10                  15

Arg Asp Lys Tyr Ala Asn Phe Thr Ile Asn Phe Thr Met Glu Asn Gln
            20                  25                  30

Ile His Thr Gly Met Glu Tyr Asp Asn Gly Arg Phe Ile Gly Val Lys
        35                  40                  45

Phe Lys Ser Val Thr Phe Lys Asp Ser Val Phe Lys Ser Cys Thr Phe
    50                  55                  60

Glu Asp Val Thr Ser Val Asn Thr Tyr Phe Lys Asn Cys Thr Phe Ile
65                  70                  75                  80

Asp Thr Val Phe Asp Asn Thr Asp Phe Glu Pro Tyr Lys Phe Ile Asp
                85                  90                  95
```

```
Ser Glu Phe Lys Asn Cys Ser Phe Phe His Asn Lys Thr Gly Cys Gln
            100                 105                 110

Ile Thr Phe Asp Asp Asp Tyr Ser
        115                 120
```

<210> SEQ ID NO 22
<211> LENGTH: 57
<212> TYPE: PRT
<213> ORGANISM: Homo sapiens
<220> FEATURE:
<223> OTHER INFORMATION: Synaptotagmin I extracellular domain protein sequence (1-57 amino acid)

<400> SEQUENCE: 22

```
Met Val Ser Glu Ser His His Glu Ala Leu Ala Ala Pro Pro Val Thr
1               5                   10                  15

Thr Val Ala Thr Val Leu Pro Ser Asn Ala Thr Glu Pro Ala Ser Pro
            20                  25                  30

Gly Glu Gly Lys Glu Asp Ala Phe Ser Lys Leu Lys Glu Lys Phe Met
        35                  40                  45

Asn Glu Leu His Lys Ile Pro Leu Pro
    50                  55
```

<210> SEQ ID NO 23
<211> LENGTH: 62
<212> TYPE: PRT
<213> ORGANISM: Homo sapiens
<220> FEATURE:
<223> OTHER INFORMATION: Synaptotagmin II extracellular domain protein sequence (1-62 amino acid)

<400> SEQUENCE: 23

```
Met Arg Asn Ile Phe Lys Arg Asn Gln Glu Pro Ile Val Ala Pro Ala
1               5                   10                  15

Thr Thr Thr Ala Thr Met Pro Ile Gly Pro Val Asp Asn Ser Thr Glu
            20                  25                  30

Ser Gly Gly Ala Gly Glu Ser Gln Glu Asp Met Phe Ala Lys Leu Lys
        35                  40                  45

Glu Lys Leu Phe Asn Glu Ile Asn Lys Ile Pro Leu Pro Pro
    50                  55                  60
```

<210> SEQ ID NO 24
<211> LENGTH: 198
<212> TYPE: PRT
<213> ORGANISM: Homo sapiens
<220> FEATURE:
<223> OTHER INFORMATION: HLA class II histocompatibility antigen, DRB1 beta chain extracellular domain protein sequence (30-227 amino acids)

<400> SEQUENCE: 24

```
Gly Asp Thr Arg Pro Arg Phe Leu Trp Gln Pro Lys Arg Glu Cys His
1               5                   10                  15

Phe Phe Asn Gly Thr Glu Arg Val Arg Phe Leu Asp Arg Tyr Phe Tyr
            20                  25                  30

Asn Gln Glu Glu Ser Val Arg Phe Asp Ser Asp Val Gly Glu Phe Arg
        35                  40                  45

Ala Val Thr Glu Leu Gly Arg Pro Asp Ala Glu Tyr Trp Asn Ser Gln
    50                  55                  60

Lys Asp Ile Leu Glu Gln Ala Arg Ala Ala Val Asp Thr Tyr Cys Arg
65                  70                  75                  80
```

-continued

His Asn Tyr Gly Val Val Glu Ser Phe Thr Val Gln Arg Arg Val Gln
85 90 95

Pro Lys Val Thr Val Tyr Pro Ser Lys Thr Gln Pro Leu Gln His His
100 105 110

Asn Leu Leu Val Cys Ser Val Ser Gly Phe Tyr Pro Gly Ser Ile Glu
115 120 125

Val Arg Trp Phe Leu Asn Gly Gln Glu Glu Lys Ala Gly Met Val Ser
130 135 140

Thr Gly Leu Ile Gln Asn Gly Asp Trp Thr Phe Gln Thr Leu Val Met
145 150 155 160

Leu Glu Thr Val Pro Arg Ser Gly Glu Val Tyr Thr Cys Gln Val Glu
165 170 175

His Pro Ser Val Thr Ser Pro Leu Thr Val Glu Trp Arg Ala Arg Ser
180 185 190

Glu Ser Ala Gln Ser Lys
195

<210> SEQ ID NO 25
<211> LENGTH: 191
<212> TYPE: PRT
<213> ORGANISM: Homo sapiens
<220> FEATURE:
<223> OTHER INFORMATION: HLA class II histocompatibility antigen, DR alpha chain extracellular domain protein sequence (26-216 amino acids)

<400> SEQUENCE: 25

Ile Lys Glu Glu His Val Ile Ile Gln Ala Glu Phe Tyr Leu Asn Pro
1 5 10 15

Asp Gln Ser Gly Glu Phe Met Phe Asp Phe Asp Gly Asp Glu Ile Phe
20 25 30

His Val Asp Met Ala Lys Lys Glu Thr Val Trp Arg Leu Glu Glu Phe
35 40 45

Gly Arg Phe Ala Ser Phe Glu Ala Gln Gly Ala Leu Ala Asn Ile Ala
50 55 60

Val Asp Lys Ala Asn Leu Glu Ile Met Thr Lys Arg Ser Asn Tyr Thr
65 70 75 80

Pro Ile Thr Asn Val Pro Pro Glu Val Thr Val Leu Thr Asn Ser Pro
85 90 95

Val Glu Leu Arg Glu Pro Asn Val Leu Ile Cys Phe Ile Asp Lys Phe
100 105 110

Thr Pro Pro Val Val Asn Val Thr Trp Leu Arg Asn Gly Lys Pro Val
115 120 125

Thr Thr Gly Val Ser Glu Thr Val Phe Leu Pro Arg Glu Asp His Leu
130 135 140

Phe Arg Lys Phe His Tyr Leu Pro Phe Leu Pro Ser Thr Glu Asp Val
145 150 155 160

Tyr Asp Cys Arg Val Glu His Trp Gly Leu Asp Glu Pro Leu Leu Lys
165 170 175

His Trp Glu Phe Asp Ala Pro Ser Pro Leu Pro Glu Thr Thr Glu
180 185 190

<210> SEQ ID NO 26
<211> LENGTH: 94
<212> TYPE: PRT
<213> ORGANISM: Homo sapiens
<220> FEATURE:
<223> OTHER INFORMATION: T cell receptor beta variable 7-9 mature protein sequence (22-115 amino acids)

<400> SEQUENCE: 26

Gly Val Ser Gln Asn Pro Arg His Lys Ile Thr Lys Arg Gly Gln Asn
1 5 10 15

Val Thr Phe Arg Cys Asp Pro Ile Ser Glu His Asn Arg Leu Tyr Trp
20 25 30

Tyr Arg Gln Thr Leu Gly Gln Gly Pro Glu Phe Leu Thr Tyr Phe Gln
35 40 45

Asn Glu Ala Gln Leu Glu Lys Ser Arg Leu Leu Ser Asp Arg Phe Ser
50 55 60

Ala Glu Arg Pro Lys Gly Ser Phe Ser Thr Leu Glu Ile Gln Arg Thr
65 70 75 80

Glu Gln Gly Asp Ser Ala Met Tyr Leu Cys Ala Ser Ser Leu
85 90

<210> SEQ ID NO 27
<211> LENGTH: 93
<212> TYPE: PRT
<213> ORGANISM: Homo sapiens
<220> FEATURE:
<223> OTHER INFORMATION: T cell receptor beta variable 19 mature protein sequence (22-114 amino acids)

<400> SEQUENCE: 27

Gly Ile Thr Gln Ser Pro Lys Tyr Leu Phe Arg Lys Glu Gly Gln Asn
1 5 10 15

Val Thr Leu Ser Cys Glu Gln Asn Leu Asn His Asp Ala Met Tyr Trp
20 25 30

Tyr Arg Gln Asp Pro Gly Gln Gly Leu Arg Leu Ile Tyr Tyr Ser Gln
35 40 45

Ile Val Asn Asp Phe Gln Lys Gly Asp Ile Ala Glu Gly Tyr Ser Val
50 55 60

Ser Arg Glu Lys Lys Glu Ser Phe Pro Leu Thr Val Thr Ser Ala Gln
65 70 75 80

Lys Asn Pro Thr Ala Phe Tyr Leu Cys Ala Ser Ser Ile
85 90

<210> SEQ ID NO 28
<211> LENGTH: 344
<212> TYPE: PRT
<213> ORGANISM: Homo sapiens
<220> FEATURE:
<223> OTHER INFORMATION: Hepatitis A virus cellular receptor 1 extracellular domain protein sequence (21-364 amino acid)

<400> SEQUENCE: 28

Ser Val Lys Val Gly Gly Glu Ala Gly Pro Ser Val Thr Leu Pro Cys
1 5 10 15

His Tyr Ser Gly Ala Val Thr Ser Met Cys Trp Asn Arg Gly Ser Cys
20 25 30

Ser Leu Phe Thr Cys Gln Asn Gly Ile Val Trp Thr Asn Gly Thr His
35 40 45

Val Thr Tyr Arg Lys Asp Thr Arg Tyr Lys Leu Leu Gly Asp Leu Ser
50 55 60

Arg Arg Asp Val Ser Leu Thr Ile Glu Asn Thr Ala Val Ser Asp Ser
65 70 75 80

Gly Val Tyr Cys Cys Arg Val Glu His Arg Gly Trp Phe Asn Asp Met
85 90 95

```
Lys Ile Thr Val Ser Leu Glu Ile Val Pro Pro Lys Val Thr Thr Thr
            100                 105                 110

Pro Ile Val Thr Thr Val Pro Thr Val Thr Thr Val Arg Thr Ser Thr
        115                 120                 125

Thr Val Pro Thr Thr Thr Thr Val Pro Met Thr Thr Val Pro Thr Thr
    130                 135                 140

Thr Val Pro Thr Thr Met Ser Ile Pro Thr Thr Thr Thr Val Leu Thr
145                 150                 155                 160

Thr Met Thr Val Ser Thr Thr Thr Ser Val Pro Thr Thr Thr Ser Ile
                165                 170                 175

Pro Thr Thr Thr Ser Val Pro Val Thr Thr Thr Val Ser Thr Phe Val
            180                 185                 190

Pro Pro Met Pro Leu Pro Arg Gln Asn His Glu Pro Val Ala Thr Ser
        195                 200                 205

Pro Ser Ser Pro Gln Pro Ala Glu Thr His Pro Thr Thr Leu Gln Gly
    210                 215                 220

Ala Ile Arg Arg Glu Pro Thr Ser Ser Pro Leu Tyr Ser Tyr Thr Thr
225                 230                 235                 240

Asp Gly Asn Asp Thr Val Thr Glu Ser Ser Asp Gly Leu Trp Asn Asn
                245                 250                 255

Asn Gln Thr Gln Leu Phe Leu Glu His Ser Leu Leu Thr Ala Asn Thr
            260                 265                 270

Thr Lys Gly Ile Tyr Ala Gly Val Cys Ile Ser Val Leu Val Leu Leu
        275                 280                 285

Ala Leu Leu Gly Val Ile Ile Ala Lys Lys Tyr Phe Phe Lys Lys Glu
    290                 295                 300

Val Gln Gln Leu Ser Val Ser Phe Ser Ser Leu Gln Ile Lys Ala Leu
305                 310                 315                 320

Gln Asn Ala Val Glu Lys Glu Val Gln Ala Glu Asp Asn Ile Tyr Ile
                325                 330                 335

Glu Asn Ser Leu Tyr Ala Thr Asp
            340
```

<210> SEQ ID NO 29
<211> LENGTH: 153
<212> TYPE: PRT
<213> ORGANISM: Homo sapiens
<220> FEATURE:
<223> OTHER INFORMATION: Myelin and lymphocyte protein protein sequence (1-153 amino acid)

<400> SEQUENCE: 29

```
Met Ala Pro Ala Ala Ala Thr Gly Gly Ser Thr Leu Pro Ser Gly Phe
1               5                   10                  15

Ser Val Phe Thr Thr Leu Pro Asp Leu Leu Phe Ile Phe Glu Phe Ile
            20                  25                  30

Phe Gly Gly Leu Val Trp Ile Leu Val Ala Ser Ser Leu Val Pro Trp
        35                  40                  45

Pro Leu Val Gln Gly Trp Val Met Phe Val Ser Val Phe Cys Phe Val
    50                  55                  60

Ala Thr Thr Thr Leu Ile Ile Leu Tyr Ile Ile Gly Ala His Gly Gly
65                  70                  75                  80

Glu Thr Ser Trp Val Thr Leu Asp Ala Ala Tyr His Cys Thr Ala Ala
                85                  90                  95

Leu Phe Tyr Leu Ser Ala Ser Val Leu Glu Ala Leu Ala Thr Ile Thr
```

```
            100                 105                 110

Met Gln Asp Gly Phe Thr Tyr Arg His Tyr His Glu Asn Ile Ala Ala
        115                 120                 125

Val Val Phe Ser Tyr Ile Ala Thr Leu Leu Tyr Val Val His Ala Val
    130                 135                 140

Phe Ser Leu Ile Arg Trp Lys Ser Ser
145                 150


<210> SEQ ID NO 30
<211> LENGTH: 1213
<212> TYPE: PRT
<213> ORGANISM: Homo sapiens
<220> FEATURE:
<223> OTHER INFORMATION: Complement factor H mature protein sequence
      (19-1231 amino acid)

<400> SEQUENCE: 30

Glu Asp Cys Asn Glu Leu Pro Pro Arg Arg Asn Thr Glu Ile Leu Thr
1               5                   10                  15

Gly Ser Trp Ser Asp Gln Thr Tyr Pro Glu Gly Thr Gln Ala Ile Tyr
            20                  25                  30

Lys Cys Arg Pro Gly Tyr Arg Ser Leu Gly Asn Val Ile Met Val Cys
        35                  40                  45

Arg Lys Gly Glu Trp Val Ala Leu Asn Pro Leu Arg Lys Cys Gln Lys
    50                  55                  60

Arg Pro Cys Gly His Pro Gly Asp Thr Pro Phe Gly Thr Phe Thr Leu
65                  70                  75                  80

Thr Gly Gly Asn Val Phe Glu Tyr Gly Val Lys Ala Val Tyr Thr Cys
                85                  90                  95

Asn Glu Gly Tyr Gln Leu Leu Gly Glu Ile Asn Tyr Arg Glu Cys Asp
            100                 105                 110

Thr Asp Gly Trp Thr Asn Asp Ile Pro Ile Cys Glu Val Val Lys Cys
        115                 120                 125

Leu Pro Val Thr Ala Pro Glu Asn Gly Lys Ile Val Ser Ser Ala Met
    130                 135                 140

Glu Pro Asp Arg Glu Tyr His Phe Gly Gln Ala Val Arg Phe Val Cys
145                 150                 155                 160

Asn Ser Gly Tyr Lys Ile Glu Gly Asp Glu Glu Met His Cys Ser Asp
                165                 170                 175

Asp Gly Phe Trp Ser Lys Glu Lys Pro Lys Cys Val Glu Ile Ser Cys
            180                 185                 190

Lys Ser Pro Asp Val Ile Asn Gly Ser Pro Ile Ser Gln Lys Ile Ile
        195                 200                 205

Tyr Lys Glu Asn Glu Arg Phe Gln Tyr Lys Cys Asn Met Gly Tyr Glu
    210                 215                 220

Tyr Ser Glu Arg Gly Asp Ala Val Cys Thr Glu Ser Gly Trp Arg Pro
225                 230                 235                 240

Leu Pro Ser Cys Glu Glu Lys Ser Cys Asp Asn Pro Tyr Ile Pro Asn
                245                 250                 255

Gly Asp Tyr Ser Pro Leu Arg Ile Lys His Arg Thr Gly Asp Glu Ile
            260                 265                 270

Thr Tyr Gln Cys Arg Asn Gly Phe Tyr Pro Ala Thr Arg Gly Asn Thr
        275                 280                 285

Ala Lys Cys Thr Ser Thr Gly Trp Ile Pro Ala Pro Arg Cys Thr Leu
    290                 295                 300
```

```
Lys Pro Cys Asp Tyr Pro Asp Ile Lys His Gly Gly Leu Tyr His Glu
305                 310                 315                 320

Asn Met Arg Arg Pro Tyr Phe Pro Val Ala Val Gly Lys Tyr Tyr Ser
                325                 330                 335

Tyr Tyr Cys Asp Glu His Phe Glu Thr Pro Ser Gly Ser Tyr Trp Asp
            340                 345                 350

His Ile His Cys Thr Gln Asp Gly Trp Ser Pro Ala Val Pro Cys Leu
        355                 360                 365

Arg Lys Cys Tyr Phe Pro Tyr Leu Glu Asn Gly Tyr Asn Gln Asn Tyr
    370                 375                 380

Gly Arg Lys Phe Val Gln Gly Lys Ser Ile Asp Val Ala Cys His Pro
385                 390                 395                 400

Gly Tyr Ala Leu Pro Lys Ala Gln Thr Thr Val Thr Cys Met Glu Asn
                405                 410                 415

Gly Trp Ser Pro Thr Pro Arg Cys Ile Arg Val Lys Thr Cys Ser Lys
            420                 425                 430

Ser Ser Ile Asp Ile Glu Asn Gly Phe Ile Ser Glu Ser Gln Tyr Thr
        435                 440                 445

Tyr Ala Leu Lys Glu Lys Ala Lys Tyr Gln Cys Lys Leu Gly Tyr Val
    450                 455                 460

Thr Ala Asp Gly Glu Thr Ser Gly Ser Ile Thr Cys Gly Lys Asp Gly
465                 470                 475                 480

Trp Ser Ala Gln Pro Thr Cys Ile Lys Ser Cys Asp Ile Pro Val Phe
                485                 490                 495

Met Asn Ala Arg Thr Lys Asn Asp Phe Thr Trp Phe Lys Leu Asn Asp
            500                 505                 510

Thr Leu Asp Tyr Glu Cys His Asp Gly Tyr Glu Ser Asn Thr Gly Ser
        515                 520                 525

Thr Thr Gly Ser Ile Val Cys Gly Tyr Asn Gly Trp Ser Asp Leu Pro
    530                 535                 540

Ile Cys Tyr Glu Arg Glu Cys Glu Leu Pro Lys Ile Asp Val His Leu
545                 550                 555                 560

Val Pro Asp Arg Lys Lys Asp Gln Tyr Lys Val Gly Glu Val Leu Lys
                565                 570                 575

Phe Ser Cys Lys Pro Gly Phe Thr Ile Val Gly Pro Asn Ser Val Gln
            580                 585                 590

Cys Tyr His Phe Gly Leu Ser Pro Asp Leu Pro Ile Cys Lys Glu Gln
        595                 600                 605

Val Gln Ser Cys Gly Pro Pro Pro Glu Leu Leu Asn Gly Asn Val Lys
    610                 615                 620

Glu Lys Thr Lys Glu Glu Tyr Gly His Ser Glu Val Val Glu Tyr Tyr
625                 630                 635                 640

Cys Asn Pro Arg Phe Leu Met Lys Gly Pro Asn Lys Ile Gln Cys Val
                645                 650                 655

Asp Gly Glu Trp Thr Thr Leu Pro Val Cys Ile Val Glu Glu Ser Thr
            660                 665                 670

Cys Gly Asp Ile Pro Glu Leu Glu His Gly Trp Ala Gln Leu Ser Ser
        675                 680                 685

Pro Pro Tyr Tyr Tyr Gly Asp Ser Val Glu Phe Asn Cys Ser Glu Ser
    690                 695                 700

Phe Thr Met Ile Gly His Arg Ser Ile Thr Cys Ile His Gly Val Trp
705                 710                 715                 720

Thr Gln Leu Pro Gln Cys Val Ala Ile Asp Lys Leu Lys Lys Cys Lys
```

-continued

```
                725                 730                 735

Ser Ser Asn Leu Ile Ile Leu Glu Glu His Leu Lys Asn Lys Lys Glu
            740                 745                 750

Phe Asp His Asn Ser Asn Ile Arg Tyr Arg Cys Arg Gly Lys Glu Gly
        755                 760                 765

Trp Ile His Thr Val Cys Ile Asn Gly Arg Trp Asp Pro Glu Val Asn
    770                 775                 780

Cys Ser Met Ala Gln Ile Gln Leu Cys Pro Pro Pro Pro Gln Ile Pro
785                 790                 795                 800

Asn Ser His Asn Met Thr Thr Thr Leu Asn Tyr Arg Asp Gly Glu Lys
                805                 810                 815

Val Ser Val Leu Cys Gln Glu Asn Tyr Leu Ile Gln Glu Gly Glu Glu
            820                 825                 830

Ile Thr Cys Lys Asp Gly Arg Trp Gln Ser Ile Pro Leu Cys Val Glu
        835                 840                 845

Lys Ile Pro Cys Ser Gln Pro Pro Gln Ile Glu His Gly Thr Ile Asn
    850                 855                 860

Ser Ser Arg Ser Ser Gln Glu Ser Tyr Ala His Gly Thr Lys Leu Ser
865                 870                 875                 880

Tyr Thr Cys Glu Gly Gly Phe Arg Ile Ser Glu Glu Asn Glu Thr Thr
                885                 890                 895

Cys Tyr Met Gly Lys Trp Ser Ser Pro Pro Gln Cys Glu Gly Leu Pro
            900                 905                 910

Cys Lys Ser Pro Pro Glu Ile Ser His Gly Val Val Ala His Met Ser
        915                 920                 925

Asp Ser Tyr Gln Tyr Gly Glu Glu Val Thr Tyr Lys Cys Phe Glu Gly
    930                 935                 940

Phe Gly Ile Asp Gly Pro Ala Ile Ala Lys Cys Leu Gly Glu Lys Trp
945                 950                 955                 960

Ser His Pro Pro Ser Cys Ile Lys Thr Asp Cys Leu Ser Leu Pro Ser
                965                 970                 975

Phe Glu Asn Ala Ile Pro Met Gly Glu Lys Lys Asp Val Tyr Lys Ala
            980                 985                 990

Gly Glu Gln Val Thr Tyr Thr Cys Ala Thr Tyr Tyr Lys Met Asp Gly
        995                 1000                1005

Ala Ser Asn Val Thr Cys Ile Asn Ser Arg Trp Thr Gly Arg Pro Thr
    1010                1015                1020

Cys Arg Asp Thr Ser Cys Val Asn Pro Pro Thr Val Gln Asn Ala Tyr
1025                1030                1035                1040

Ile Val Ser Arg Gln Met Ser Lys Tyr Pro Ser Gly Glu Arg Val Arg
                1045                1050                1055

Tyr Gln Cys Arg Ser Pro Tyr Glu Met Phe Gly Asp Glu Glu Val Met
            1060                1065                1070

Cys Leu Asn Gly Asn Trp Thr Glu Pro Pro Gln Cys Lys Asp Ser Thr
        1075                1080                1085

Gly Lys Cys Gly Pro Pro Pro Pro Ile Asp Asn Gly Asp Ile Thr Ser
    1090                1095                1100

Phe Pro Leu Ser Val Tyr Ala Pro Ala Ser Ser Val Glu Tyr Gln Cys
1105                1110                1115                1120

Gln Asn Leu Tyr Gln Leu Glu Gly Asn Lys Arg Ile Thr Cys Arg Asn
                1125                1130                1135

Gly Gln Trp Ser Glu Pro Pro Lys Cys Leu His Pro Cys Val Ile Ser
            1140                1145                1150
```

Arg Glu Ile Met Glu Asn Tyr Asn Ile Ala Leu Arg Trp Thr Ala Lys
1155 1160 1165

Gln Lys Leu Tyr Ser Arg Thr Gly Glu Ser Val Glu Phe Val Cys Lys
1170 1175 1180

Arg Gly Tyr Arg Leu Ser Ser Arg Ser His Thr Leu Arg Thr Thr Cys
1185 1190 1195 1200

Trp Asp Gly Lys Leu Glu Tyr Pro Thr Cys Ala Lys Arg
1205 1210

<210> SEQ ID NO 31
<211> LENGTH: 908
<212> TYPE: PRT
<213> ORGANISM: Homo sapiens
<220> FEATURE:
<223> OTHER INFORMATION: Hepatocyte growth factor receptor extracellular domain protein sequence (25-932 amino acid)

<400> SEQUENCE: 31

Glu Cys Lys Glu Ala Leu Ala Lys Ser Glu Met Asn Val Asn Met Lys
1 5 10 15

Tyr Gln Leu Pro Asn Phe Thr Ala Glu Thr Pro Ile Gln Asn Val Ile
20 25 30

Leu His Glu His His Ile Phe Leu Gly Ala Thr Asn Tyr Ile Tyr Val
35 40 45

Leu Asn Glu Glu Asp Leu Gln Lys Val Ala Glu Tyr Lys Thr Gly Pro
50 55 60

Val Leu Glu His Pro Asp Cys Phe Pro Cys Gln Asp Cys Ser Ser Lys
65 70 75 80

Ala Asn Leu Ser Gly Gly Val Trp Lys Asp Asn Ile Asn Met Ala Leu
85 90 95

Val Val Asp Thr Tyr Tyr Asp Asp Gln Leu Ile Ser Cys Gly Ser Val
100 105 110

Asn Arg Gly Thr Cys Gln Arg His Val Phe Pro His Asn His Thr Ala
115 120 125

Asp Ile Gln Ser Glu Val His Cys Ile Phe Ser Pro Gln Ile Glu Glu
130 135 140

Pro Ser Gln Cys Pro Asp Cys Val Val Ser Ala Leu Gly Ala Lys Val
145 150 155 160

Leu Ser Ser Val Lys Asp Arg Phe Ile Asn Phe Phe Val Gly Asn Thr
165 170 175

Ile Asn Ser Ser Tyr Phe Pro Asp His Pro Leu His Ser Ile Ser Val
180 185 190

Arg Arg Leu Lys Glu Thr Lys Asp Gly Phe Met Phe Leu Thr Asp Gln
195 200 205

Ser Tyr Ile Asp Val Leu Pro Glu Phe Arg Asp Ser Tyr Pro Ile Lys
210 215 220

Tyr Val His Ala Phe Glu Ser Asn Asn Phe Ile Tyr Phe Leu Thr Val
225 230 235 240

Gln Arg Glu Thr Leu Asp Ala Gln Thr Phe His Thr Arg Ile Ile Arg
245 250 255

Phe Cys Ser Ile Asn Ser Gly Leu His Ser Tyr Met Glu Met Pro Leu
260 265 270

Glu Cys Ile Leu Thr Glu Lys Arg Lys Lys Arg Ser Thr Lys Lys Glu
275 280 285

Val Phe Asn Ile Leu Gln Ala Ala Tyr Val Ser Lys Pro Gly Ala Gln

```
    290                 295                 300

Leu Ala Arg Gln Ile Gly Ala Ser Leu Asn Asp Asp Ile Leu Phe Gly
305                 310                 315                 320

Val Phe Ala Gln Ser Lys Pro Asp Ser Ala Glu Pro Met Asp Arg Ser
                325                 330                 335

Ala Met Cys Ala Phe Pro Ile Lys Tyr Val Asn Asp Phe Phe Asn Lys
            340                 345                 350

Ile Val Asn Lys Asn Asn Val Arg Cys Leu Gln His Phe Tyr Gly Pro
        355                 360                 365

Asn His Glu His Cys Phe Asn Arg Thr Leu Leu Arg Asn Ser Ser Gly
    370                 375                 380

Cys Glu Ala Arg Arg Asp Glu Tyr Arg Thr Glu Phe Thr Thr Ala Leu
385                 390                 395                 400

Gln Arg Val Asp Leu Phe Met Gly Gln Phe Ser Glu Val Leu Leu Thr
                405                 410                 415

Ser Ile Ser Thr Phe Ile Lys Gly Asp Leu Thr Ile Ala Asn Leu Gly
            420                 425                 430

Thr Ser Glu Gly Arg Phe Met Gln Val Val Val Ser Arg Ser Gly Pro
        435                 440                 445

Ser Thr Pro His Val Asn Phe Leu Leu Asp Ser His Pro Val Ser Pro
    450                 455                 460

Glu Val Ile Val Glu His Thr Leu Asn Gln Asn Gly Tyr Thr Leu Val
465                 470                 475                 480

Ile Thr Gly Lys Lys Ile Thr Lys Ile Pro Leu Asn Gly Leu Gly Cys
                485                 490                 495

Arg His Phe Gln Ser Cys Ser Gln Cys Leu Ser Ala Pro Pro Phe Val
            500                 505                 510

Gln Cys Gly Trp Cys His Asp Lys Cys Val Arg Ser Glu Glu Cys Leu
        515                 520                 525

Ser Gly Thr Trp Thr Gln Gln Ile Cys Leu Pro Ala Ile Tyr Lys Val
    530                 535                 540

Phe Pro Asn Ser Ala Pro Leu Glu Gly Gly Thr Arg Leu Thr Ile Cys
545                 550                 555                 560

Gly Trp Asp Phe Gly Phe Arg Arg Asn Asn Lys Phe Asp Leu Lys Lys
                565                 570                 575

Thr Arg Val Leu Leu Gly Asn Glu Ser Cys Thr Leu Thr Leu Ser Glu
            580                 585                 590

Ser Thr Met Asn Thr Leu Lys Cys Thr Val Gly Pro Ala Met Asn Lys
        595                 600                 605

His Phe Asn Met Ser Ile Ile Ile Ser Asn Gly His Gly Thr Thr Gln
    610                 615                 620

Tyr Ser Thr Phe Ser Tyr Val Asp Pro Val Ile Thr Ser Ile Ser Pro
625                 630                 635                 640

Lys Tyr Gly Pro Met Ala Gly Gly Thr Leu Leu Thr Leu Thr Gly Asn
                645                 650                 655

Tyr Leu Asn Ser Gly Asn Ser Arg His Ile Ser Ile Gly Gly Lys Thr
            660                 665                 670

Cys Thr Leu Lys Ser Val Ser Asn Ser Ile Leu Glu Cys Tyr Thr Pro
        675                 680                 685

Ala Gln Thr Ile Ser Thr Glu Phe Ala Val Lys Leu Lys Ile Asp Leu
    690                 695                 700

Ala Asn Arg Glu Thr Ser Ile Phe Ser Tyr Arg Glu Asp Pro Ile Val
705                 710                 715                 720
```

```
Tyr Glu Ile His Pro Thr Lys Ser Phe Ile Ser Gly Gly Ser Thr Ile
                725                 730                 735

Thr Gly Val Gly Lys Asn Leu Asn Ser Val Ser Val Pro Arg Met Val
            740                 745                 750

Ile Asn Val His Glu Ala Gly Arg Asn Phe Thr Val Ala Cys Gln His
        755                 760                 765

Arg Ser Asn Ser Glu Ile Ile Cys Cys Thr Thr Pro Ser Leu Gln Gln
    770                 775                 780

Leu Asn Leu Gln Leu Pro Leu Lys Thr Lys Ala Phe Phe Met Leu Asp
785                 790                 795                 800

Gly Ile Leu Ser Lys Tyr Phe Asp Leu Ile Tyr Val His Asn Pro Val
                805                 810                 815

Phe Lys Pro Phe Glu Lys Pro Val Met Ile Ser Met Gly Asn Glu Asn
            820                 825                 830

Val Leu Glu Ile Lys Gly Asn Asp Ile Asp Pro Glu Ala Val Lys Gly
        835                 840                 845

Glu Val Leu Lys Val Gly Asn Lys Ser Cys Glu Asn Ile His Leu His
    850                 855                 860

Ser Glu Ala Val Leu Cys Thr Val Pro Asn Asp Leu Leu Lys Leu Asn
865                 870                 875                 880

Ser Glu Leu Asn Ile Glu Trp Lys Gln Ala Ile Ser Ser Thr Val Leu
                885                 890                 895

Gly Lys Val Ile Val Gln Pro Asp Gln Asn Phe Thr
            900                 905


<210> SEQ ID NO 32
<211> LENGTH: 309
<212> TYPE: PRT
<213> ORGANISM: Homo sapiens
<220> FEATURE:
<223> OTHER INFORMATION: Membrane cofactor protein (CD46) extracellular
      domain protein sequence (35-343 amino acid)

<400> SEQUENCE: 32

Cys Glu Glu Pro Pro Thr Phe Glu Ala Met Glu Leu Ile Gly Lys Pro
1               5                   10                  15

Lys Pro Tyr Tyr Glu Ile Gly Glu Arg Val Asp Tyr Lys Cys Lys Lys
            20                  25                  30

Gly Tyr Phe Tyr Ile Pro Pro Leu Ala Thr His Thr Ile Cys Asp Arg
        35                  40                  45

Asn His Thr Trp Leu Pro Val Ser Asp Asp Ala Cys Tyr Arg Glu Thr
    50                  55                  60

Cys Pro Tyr Ile Arg Asp Pro Leu Asn Gly Gln Ala Val Pro Ala Asn
65                  70                  75                  80

Gly Thr Tyr Glu Phe Gly Tyr Gln Met His Phe Ile Cys Asn Glu Gly
                85                  90                  95

Tyr Tyr Leu Ile Gly Glu Glu Ile Leu Tyr Cys Glu Leu Lys Gly Ser
            100                 105                 110

Val Ala Ile Trp Ser Gly Lys Pro Pro Ile Cys Glu Lys Val Leu Cys
        115                 120                 125

Thr Pro Pro Pro Lys Ile Lys Asn Gly Lys His Thr Phe Ser Glu Val
    130                 135                 140

Glu Val Phe Glu Tyr Leu Asp Ala Val Thr Tyr Ser Cys Asp Pro Ala
145                 150                 155                 160

Pro Gly Pro Asp Pro Phe Ser Leu Ile Gly Glu Ser Thr Ile Tyr Cys
```

```
                165                 170                 175

Gly Asp Asn Ser Val Trp Ser Arg Ala Ala Pro Glu Cys Lys Val Val
            180                 185                 190

Lys Cys Arg Phe Pro Val Val Glu Asn Gly Lys Gln Ile Ser Gly Phe
        195                 200                 205

Gly Lys Lys Phe Tyr Tyr Lys Ala Thr Val Met Phe Glu Cys Asp Lys
    210                 215                 220

Gly Phe Tyr Leu Asp Gly Ser Asp Thr Ile Val Cys Asp Ser Asn Ser
225                 230                 235                 240

Thr Trp Asp Pro Pro Val Pro Lys Cys Leu Lys Val Leu Pro Pro Ser
                245                 250                 255

Ser Thr Lys Pro Pro Ala Leu Ser His Ser Val Ser Thr Ser Ser Thr
            260                 265                 270

Thr Lys Ser Pro Ala Ser Ser Ala Ser Gly Pro Arg Pro Thr Tyr Lys
        275                 280                 285

Pro Pro Val Ser Asn Tyr Pro Gly Tyr Pro Lys Pro Glu Glu Gly Ile
    290                 295                 300

Leu Asp Ser Leu Asp
305


<210> SEQ ID NO 33
<211> LENGTH: 72
<212> TYPE: PRT
<213> ORGANISM: Homo sapiens
<220> FEATURE:
<223> OTHER INFORMATION: Glycophorin-A extracellular domain protein
      sequence (20-91 amino acid)

<400> SEQUENCE: 33

Ser Ser Thr Thr Gly Val Ala Met His Thr Ser Thr Ser Ser Ser Val
1               5                   10                  15

Thr Lys Ser Tyr Ile Ser Ser Gln Thr Asn Asp Thr His Lys Arg Asp
            20                  25                  30

Thr Tyr Ala Ala Thr Pro Arg Ala His Glu Val Ser Glu Ile Ser Val
        35                  40                  45

Arg Thr Val Tyr Pro Pro Glu Glu Glu Thr Gly Glu Arg Val Gln Leu
    50                  55                  60

Ala His His Phe Ser Glu Pro Glu
65                  70


<210> SEQ ID NO 34
<211> LENGTH: 264
<212> TYPE: PRT
<213> ORGANISM: Homo sapiens
<220> FEATURE:
<223> OTHER INFORMATION: C-type lectin domain family 4 member K
      (Langerin, CD207) extracellular domain protein sequence (65-328
      amino acid)

<400> SEQUENCE: 34

Pro Arg Phe Met Gly Thr Ile Ser Asp Val Lys Thr Asn Val Gln Leu
1               5                   10                  15

Leu Lys Gly Arg Val Asp Asn Ile Ser Thr Leu Asp Ser Glu Ile Lys
            20                  25                  30

Lys Asn Ser Asp Gly Met Glu Ala Ala Gly Val Gln Ile Gln Met Val
        35                  40                  45

Asn Glu Ser Leu Gly Tyr Val Arg Ser Gln Phe Leu Lys Leu Lys Thr
    50                  55                  60
```

```
Ser Val Glu Lys Ala Asn Ala Gln Ile Gln Ile Leu Thr Arg Ser Trp
65                  70                  75                  80

Glu Glu Val Ser Thr Leu Asn Ala Gln Ile Pro Glu Leu Lys Ser Asp
                85                  90                  95

Leu Glu Lys Ala Ser Ala Leu Asn Thr Lys Ile Arg Ala Leu Gln Gly
            100                 105                 110

Ser Leu Glu Asn Met Ser Lys Leu Leu Lys Arg Gln Asn Asp Ile Leu
        115                 120                 125

Gln Val Val Ser Gln Gly Trp Lys Tyr Phe Lys Gly Asn Phe Tyr Tyr
    130                 135                 140

Phe Ser Leu Ile Pro Lys Thr Trp Tyr Ser Ala Glu Gln Phe Cys Val
145                 150                 155                 160

Ser Arg Asn Ser His Leu Thr Ser Val Thr Ser Glu Ser Glu Gln Glu
                165                 170                 175

Phe Leu Tyr Lys Thr Ala Gly Gly Leu Ile Tyr Trp Ile Gly Leu Thr
            180                 185                 190

Lys Ala Gly Met Glu Gly Asp Trp Ser Trp Val Asp Asp Thr Pro Phe
        195                 200                 205

Asn Lys Val Gln Ser Val Arg Phe Trp Ile Pro Gly Glu Pro Asn Asn
    210                 215                 220

Ala Gly Asn Asn Glu His Cys Gly Asn Ile Lys Ala Pro Ser Leu Gln
225                 230                 235                 240

Ala Trp Asn Asp Ala Pro Cys Asp Lys Thr Phe Leu Phe Ile Cys Lys
                245                 250                 255

Arg Pro Tyr Val Pro Ser Glu Pro
            260
```

<210> SEQ ID NO 35
<211> LENGTH: 532
<212> TYPE: PRT
<213> ORGANISM: Homo sapiens
<220> FEATURE:
<223> OTHER INFORMATION: Anthrax toxin receptor 1 mature protein sequence (33-564 amino acid)

<400> SEQUENCE: 35

```
Glu Asp Gly Gly Pro Ala Cys Tyr Gly Gly Phe Asp Leu Tyr Phe Ile
1               5                   10                  15

Leu Asp Lys Ser Gly Ser Val Leu His His Trp Asn Glu Ile Tyr Tyr
            20                  25                  30

Phe Val Glu Gln Leu Ala His Lys Phe Ile Ser Pro Gln Leu Arg Met
        35                  40                  45

Ser Phe Ile Val Phe Ser Thr Arg Gly Thr Thr Leu Met Lys Leu Thr
    50                  55                  60

Glu Asp Arg Glu Gln Ile Arg Gln Gly Leu Glu Glu Leu Gln Lys Val
65                  70                  75                  80

Leu Pro Gly Gly Asp Thr Tyr Met His Glu Gly Phe Glu Arg Ala Ser
                85                  90                  95

Glu Gln Ile Tyr Tyr Glu Asn Arg Gln Gly Tyr Arg Thr Ala Ser Val
            100                 105                 110

Ile Ile Ala Leu Thr Asp Gly Glu Leu His Glu Asp Leu Phe Phe Tyr
        115                 120                 125

Ser Glu Arg Glu Ala Asn Arg Ser Arg Asp Leu Gly Ala Ile Val Tyr
    130                 135                 140

Cys Val Gly Val Lys Asp Phe Asn Glu Thr Gln Leu Ala Arg Ile Ala
145                 150                 155                 160
```

```
Asp Ser Lys Asp His Val Phe Pro Val Asn Asp Gly Phe Gln Ala Leu
                165                 170                 175

Gln Gly Ile Ile His Ser Ile Leu Lys Lys Ser Cys Ile Glu Ile Leu
            180                 185                 190

Ala Ala Glu Pro Ser Thr Ile Cys Ala Gly Glu Ser Phe Gln Val Val
        195                 200                 205

Val Arg Gly Asn Gly Phe Arg His Ala Arg Asn Val Asp Arg Val Leu
    210                 215                 220

Cys Ser Phe Lys Ile Asn Asp Ser Val Thr Leu Asn Glu Lys Pro Phe
225                 230                 235                 240

Ser Val Glu Asp Thr Tyr Leu Leu Cys Pro Ala Pro Ile Leu Lys Glu
                245                 250                 255

Val Gly Met Lys Ala Ala Leu Gln Val Ser Met Asn Asp Gly Leu Ser
            260                 265                 270

Phe Ile Ser Ser Ser Val Ile Ile Thr Thr Thr His Cys Ser Asp Gly
        275                 280                 285

Ser Ile Leu Ala Ile Ala Leu Leu Ile Leu Phe Leu Leu Leu Ala Leu
    290                 295                 300

Ala Leu Leu Trp Trp Phe Trp Pro Leu Cys Cys Thr Val Ile Ile Lys
305                 310                 315                 320

Glu Val Pro Pro Pro Pro Ala Glu Glu Ser Glu Glu Glu Asp Asp Asp
                325                 330                 335

Gly Leu Pro Lys Lys Lys Trp Pro Thr Val Asp Ala Ser Tyr Tyr Gly
            340                 345                 350

Gly Arg Gly Val Gly Gly Ile Lys Arg Met Glu Val Arg Trp Gly Glu
        355                 360                 365

Lys Gly Ser Thr Glu Glu Gly Ala Lys Leu Glu Lys Ala Lys Asn Ala
    370                 375                 380

Arg Val Lys Met Pro Glu Gln Glu Tyr Glu Phe Pro Glu Pro Arg Asn
385                 390                 395                 400

Leu Asn Asn Asn Met Arg Arg Pro Ser Ser Pro Arg Lys Trp Tyr Ser
                405                 410                 415

Pro Ile Lys Gly Lys Leu Asp Ala Leu Trp Val Leu Leu Arg Lys Gly
            420                 425                 430

Tyr Asp Arg Val Ser Val Met Arg Pro Gln Pro Gly Asp Thr Gly Arg
        435                 440                 445

Cys Ile Asn Phe Thr Arg Val Lys Asn Asn Gln Pro Ala Lys Tyr Pro
    450                 455                 460

Leu Asn Asn Ala Tyr His Thr Ser Ser Pro Pro Pro Ala Pro Ile Tyr
465                 470                 475                 480

Thr Pro Pro Pro Pro Ala Pro His Cys Pro Pro Pro Pro Pro Ser Ala
                485                 490                 495

Pro Thr Pro Pro Ile Pro Ser Pro Pro Ser Thr Leu Pro Pro Pro Pro
            500                 505                 510

Gln Ala Pro Pro Pro Asn Arg Ala Pro Pro Pro Ser Arg Pro Pro Pro
        515                 520                 525

Arg Pro Ser Val
    530
```

<210> SEQ ID NO 36
<211> LENGTH: 285
<212> TYPE: PRT
<213> ORGANISM: Homo sapiens
<220> FEATURE:

<223> OTHER INFORMATION: Anthrax toxin receptor 2 extracellular domain protein sequence (34-318 amino acid)

<400> SEQUENCE: 36

```
Gln Glu Gln Pro Ser Cys Arg Arg Ala Phe Asp Leu Tyr Phe Val Leu
1               5                   10                  15

Asp Lys Ser Gly Ser Val Ala Asn Asn Trp Ile Glu Ile Tyr Asn Phe
            20                  25                  30

Val Gln Gln Leu Ala Glu Arg Phe Val Ser Pro Glu Met Arg Leu Ser
        35                  40                  45

Phe Ile Val Phe Ser Ser Gln Ala Thr Ile Ile Leu Pro Leu Thr Gly
    50                  55                  60

Asp Arg Gly Lys Ile Ser Lys Gly Leu Glu Asp Leu Lys Arg Val Ser
65                  70                  75                  80

Pro Val Gly Glu Thr Tyr Ile His Glu Gly Leu Lys Leu Ala Asn Glu
                85                  90                  95

Gln Ile Gln Lys Ala Gly Gly Leu Lys Thr Ser Ser Ile Ile Ile Ala
            100                 105                 110

Leu Thr Asp Gly Lys Leu Asp Gly Leu Val Pro Ser Tyr Ala Glu Lys
        115                 120                 125

Glu Ala Lys Ile Ser Arg Ser Leu Gly Ala Ser Val Tyr Cys Val Gly
    130                 135                 140

Val Leu Asp Phe Glu Gln Ala Gln Leu Glu Arg Ile Ala Asp Ser Lys
145                 150                 155                 160

Glu Gln Val Phe Pro Val Lys Gly Gly Phe Gln Ala Leu Lys Gly Ile
                165                 170                 175

Ile Asn Ser Ile Leu Ala Gln Ser Cys Thr Glu Ile Leu Glu Leu Gln
            180                 185                 190

Pro Ser Ser Val Cys Val Gly Glu Glu Phe Gln Ile Val Leu Ser Gly
        195                 200                 205

Arg Gly Phe Met Leu Gly Ser Arg Asn Gly Ser Val Leu Cys Thr Tyr
    210                 215                 220

Thr Val Asn Glu Thr Tyr Thr Thr Ser Val Lys Pro Val Ser Val Gln
225                 230                 235                 240

Leu Asn Ser Met Leu Cys Pro Ala Pro Ile Leu Asn Lys Ala Gly Glu
                245                 250                 255

Thr Leu Asp Val Ser Val Ser Phe Asn Gly Gly Lys Ser Val Ile Ser
            260                 265                 270

Gly Ser Leu Ile Val Thr Ala Thr Glu Cys Ser Asn Gly
        275                 280                 285
```

<210> SEQ ID NO 37
<211> LENGTH: 3897
<212> TYPE: DNA
<213> ORGANISM: Artificial Sequence
<220> FEATURE:
<223> OTHER INFORMATION: armY-ACE2 fusion

<400> SEQUENCE: 37

```
atgtacagga tgcaactcct gtcttgcatt gcactaagtc ttgcacttgt cacaaacagt      60

gagcaaaagc ttatctctga agaggactta ctaagaaagc ggggcagccc aggcggagcg     120

cagagcacaa tcgaggaaca ggccaagacc ttcctggaca agttcaacca cgaagctgaa     180

gacctgttct accaatctag cctggctagt tggaactaca acaccaacat tacagaagag     240

aacgtgcaga acatgaacaa cgcaggcgac aagtggtccg ccttccttaa agagcagtct     300
```

-continued

```
acactggccc agatgtaccc tctgcaagag attcagaatc tgaccgtgaa gctgcagctg    360
caggctctcc agcagaatgg gtccagcgtg ctgtctgagg ataagagcaa gcggctgaac    420
accatcctga atacaatgag caccatctac agcaccggca aagtgtgtaa ccctgacaac    480
ccccaggagt gtctgctgct ggaacctggc ctgaacgaaa tcatggccaa ctccctggac    540
tacaacgaga gactgtgggc ctgggagagc tggcgtagcg aggtgggaaa acagctgcgc    600
cccctgtatg aggagtacgt ggtgctgaag aatgagatgg ccagagccaa ccactacgag    660
gactacggcg actattggag aggcgattat gaagtcaacg gcgttgacgg ctacgactac    720
agccggggac agctgatcga agacgtggaa catacgtttg aggagatcaa gcctctgtac    780
gagcacctgc acgcctacgt aagagccaaa ctgatgaatg cctaccccag ctacatctcc    840
cctatcggct gcctgcccgc ccatctgctc ggcgacatgt ggggcagatt ctggaccaac    900
ctgtattctc tgacagtgcc tttcggccag aaacctaaca tcgacgtgac agatgccatg    960
gtggaccagg cctgggatgc ccaaagaatc ttcaaggaag ccgagaaatt cttcgtgtcc   1020
gtggggctgc ctaatatgac ccagggcttc tgggaaaaca gcatgctcac cgatcctggc   1080
aacgtgcaga aggcagtgtg ccaccccacc gcctgggacc ttggaaaggg cgacttccgg   1140
attctgatgt gcaccaaggt gaccatggac gacttcctga ccgctcacca cgagatgggc   1200
cacatccagt acgacatggc ctacgccgct cagcctttcc tcctgagaaa cggcgctaat   1260
gaaggcttcc acgaggccgt gggcgaaatc atgagcctga gcgccgccac ccctaagcac   1320
ctgaagtcta tcggactgct gagccccgac tttcaggagg acaacgaaac tgagatcaac   1380
ttcttgctga aacaggccct gacaatcgtt ggcaccctgc cctttaccta catgctggaa   1440
aagtggagat ggatggtctt taagggcgaa atccccaagg accaatggat gaagaagtgg   1500
tgggagatga agcgggaaat cgtgggcgtg gtggaacctg tgccccacga cgagacatac   1560
tgcgatcctg ctagcctctt tcacgtgagc aatgattact cattcatccg gtactacacc   1620
agaactctgt accagttcca gttccaggag gccctgtgcc aggccgccaa gcacgagggc   1680
cctctgcaca agtgcgacat ctctaacagc accgaggccg gccagaagct gttcaacatg   1740
ctgagactgg gcaagagcga accttggaca ctggccctgg agaacgtggt cggagccaag   1800
aacatgaacg tgagaccact gctgaactac ttcgagcccc tgttcacctg gctgaaggat   1860
caaaacaaga acagcttcgt gggctggtcc acagactgga gcccatacgc tgatcagagc   1920
atcaaagtga ggatctctct gaagagcgcc ctgggagata aggcctacga gtggaacgat   1980
aatgagatgt acctgttcag aagcagcgtg gcctacgcca tgcggcagta cttcctgaaa   2040
gtgaagaacc agatgatcct gtttggcgag gaggatgtga gagtggccaa tctgaaacca   2100
agaatcagct ttaacttttt cgttaccgct cctaagaacg tgtctgatat catccctaga   2160
accgaggtgg aaaaggccat cagaatgagc cggtccagaa tcaacgatgc cttccgactg   2220
aatgacaact ccctggagtt cctgggaatc cagcccaccc tgggccctcc taaccagcct   2280
ccagtcagcg gcggaggagg atctggcggt ggaggctctg gcggcggcgg ttcaacaaat   2340
ctggtgaacc agagcggcta cgccctggtg gccagcggca gatccggcaa tctgggcttc   2400
aagctgttca gcacccagtc tccatctgcc gaggtgaagc tgaagagcct gagccttaac   2460
gacggcagct accagtccga gatcgacctg tcaggcggcg ccaacttccg agaaaagttc   2520
agaaacttcg ccaatgagct gagcgaggcc atcacaaaca gccctaaagg cctggacaga   2580
cctgtgccca agacggaaat cagcggcctg atcaagacag gcgacaactt tatcacccct   2640
agcttcaagg ccggatatta tgaccacgtg gcctctgatg gctccctact gagctactac   2700
```

```
cagtccaccg agtacttcaa caacagagtt ctgatgccta tcctgcagac aacaaacggc   2760

actctgatgg ccaacaaccg gggctacgac gacgttttca gacaagtgcc ctctttcagc   2820

ggctggagca acacaaaggc caccactgtg tccacaagca acaatctgac atacgataag   2880

tggacctatt tcgccgccaa aggcagcccc ctgtacgaca gctaccccaa ccacttcttc   2940

gaggacgtga agacactggc cattgacgct aaggacatca gcgccctgaa aaccaccatc   3000

gacagcgaga agcctaccta cctgattatc cggggactga gcggaaacgg cagccagctg   3060

aacgagctgc aactgcctga gtccgtgaaa aaggtgagcc tgtacggcga ctacaccggc   3120

gtgaacgtgg ctaagcagat cttcgccaac gttgtggaac tggaattcta cagcaccagc   3180

aaggctaact cttttggctt taacccccctg gtcctgggat ctaaaacgaa cgtgatctac   3240

gacctgttcg caagcaagcc cttcacccac atcgacctga cacaggtgac cctgcaaaac   3300

agcgataatt ccgccatcga tgccaacaag ctgaagcaag ctgtgggcga tatctacaac   3360

tacaggcggt tcgagagaca gtttcagggc tacttcgccg gaggctacat cgacaagtac   3420

ctggtgaaga acgtcaatac caacaaggat agcgatgacg atctggtcta ccggagcctg   3480

aaagagctga acctccacct ggaggaagcc tacagagaag gcgataacac ctactacaga   3540

gtgaatgaga actattaccc tggagctagc atctacgaga acgagagagc cagcagagac   3600

agcgagttcc agaacgagat cctgaagcga gccgagcaga acggcgtgac atttgacgag   3660

aacatcaaaa gaatcacagc cagcggcaag tatagcgtgc agttccaaaa gctagaaaat   3720

gataccgatt ccagcctgga aagaatgacc aaggccgtgg aaggccttgt gaccgtgatc   3780

ggcgaggaaa agttcgagac agtggatatc accggcgtgt ctagcgatac caatgaagtg   3840

aaaagcctgg ccaaggaact gaagaccaac gccctgggcg tcaagctgaa actctaa      3897
```

<210> SEQ ID NO 38
<211> LENGTH: 1764
<212> TYPE: DNA
<213> ORGANISM: Artificial Sequence
<220> FEATURE:
<223> OTHER INFORMATION: Protein M with N-terminal peptide Avi- and Myc-tags (aka: armY) codon-optimized (for human)

<400> SEQUENCE: 38

```
atgtacagga tgcaactcct gtcttgcatt gcactaagtc ttgcacttgt cacaaacagt     60

atggctggtg gcctgaatga catctttgag gcccagaaga tcgagtggca tgagggagga    120

gagcagaagc tgatctccga ggaagatctg ctgagaaagc gggccgccaa cggcggagga    180

ggatctggcg gtggaggctc taccaatctg gtgaaccaga gcggatacgc cctggtggcc    240

tctgggagaa gcggaaatct gggatttaag ctgttcagta cccagtctcc aagcgctgaa    300

gtgaagctga aaagcctctc cctgaacgac ggctcttatc agagcgagat cgacctgagc    360

ggcggcgcta acttccggga gaagttccgc aacttcgcta atgagctgtc tgaagccatc    420

acaaacagcc ctaagggcct ggatagacct gtgcccaaga cagaaatcag cggcctgatc    480

aagactggag ataactttat caccccctagc tttaaggccg gctactacga ccatgtggct    540

agcgacggtt cactgctgtc ctactaccag tctacagagt actttaacaa ccgggtgctg    600

atgcctatac tgcagaccac caacggcacc ctgatggcca ataacagagg ctacgatgac    660

gtgttccggc aggtgcccag cttcagcggc tggagcaaca caaaggccac aaccgtgagc    720

acctccaaca acctgaccta cgacaagtgg acctacttcg ccgccaaggg ctctccactg    780

tatgacagct atcctaacca cttcttcgag gacgtgaaga cactggccat cgacgccaag    840
```

```
gacatctctg ccctgaagac caccatcgac agtgagaaac ctacatacct gattatcaga    900

ggactgtccg gcaacggcag ccagctgaac gagcttcagc tgcctgagag cgtgaaaaag    960

gtgagcctgt acggcgacta cacaggcgtc aatgtagcta agcaaatctt cgccaacgtg   1020

gtggaactcg aattctacag cacatccaag gccaacagct tcggcttcaa ccccctggtg   1080

ctgggcagca agaccaacgt gatctacgac ctgttcgcca gcaagccttt cacccacatc   1140

gacctgacac aagtgaccct gcagaacagc gataacagcg ccattgatgc caacaagctc   1200

aaacaggccg tgggcgatat ctacaactac agaagattcg agaggcagtt tcagggctac   1260

ttcgccggag gctatatcga taagtacctg gtcaagaacg tgaacaccaa caaggactcc   1320

gacgacgacc tggtgtaccg gagcctgaag gaactgaacc tgcacctgga agaggcctac   1380

agagagggcg ataataccta ctacagagtg aacgagaact actaccccgg agctagcatc   1440

tacgagaacg agagagcctc tagagatagc gagttccaga acgagatcct gaagcgggcc   1500

gagcagaatg gcgtgacatt cgacgagaac atcaagcgga tcaccgccag cggcaagtac   1560

tccgtgcagt tccaaaaact ggaaaatgac accgacagca gcctggaaag aatgaccaag   1620

gctgtggaag gcctggttac agttatcggc gaggagaagt ttgaaaccgt ggacatcacc   1680

ggcgtgagct ccgataccaa tgaggtgaaa tctctggcca aagaactgaa gacaaatgcc   1740

ctgggcgtca aattaaaact gtaa                                          1764
```

<210> SEQ ID NO 39
<211> LENGTH: 2631
<212> TYPE: DNA
<213> ORGANISM: Artificial Sequence
<220> FEATURE:
<223> OTHER INFORMATION: Protein M horseradish peroxidase (HRP) fusion
      protein with N-terminal Myc-tag codon-optimized (for human)

<400> SEQUENCE: 39

```
atgtacagga tgcaactcct gtcttgcatt gcactaagtc ttgcacttgt cacaaacagt     60

gagcagaaac tcatctcaga agaggatctg gcagcaaatc agctgacccc aaccttctac    120

gacaattctt gtccaaacgt ctccaacatc gtgcgggaca ccattgtgaa cgagctgaga    180

agcgacccta gaatcgccgc ttctatcctg agactgcatt tccacgactg cttcgtgaat    240

ggctgcgacg cctccatcct gctggacaac accaccagct tccggacaga gaaagacgcc    300

ttcggaaatg ccaacagcgc tagaggcttc cccgttatcg acagaatgaa ggctgccgtg    360

gaatctgcct gccctcggac cgtgagctgt gccgacctgc tgaccatcgc cgcccagcag    420

agcgtgaccc tggccggcgg tcctagctgg cgggtgcctc tgggccggag agatagtctg    480

caggccttcc tggatctggc taatgctaac ctccccgctc ctttctttac cctgcctcag    540

ctgaaggaca gctttcggaa cgtcggccta aacagaagca gcgacctggt ggccctgtcc    600

ggaggccaca ccttcggcaa gaaccagtgc agattcatca tggaccggct gtacaacttc    660

agcaataccg gcctgccaga tcctacactg aacacaacct acctgcagac actgagaggc    720

ctgtgccccc tcaacgggaa tctgagcgcc ttggtggact tcgacctgag aacccctacc    780

atcttcgaca acaagtacta cgtgaacctg gaagaacaga agggcctgat ccaaagcgat    840

caggagctgt tctcttcccc taatgccaca gacaccatcc ccctggtgcg gtcattcgcc    900

aacagtaccc agaccttttt taacgctttt gtggaagcca tggatagaat gggcaacatc    960

acccctctga ccggaacaca gggacagatc agactgaatt gcagagtggt gaacagcaac   1020

tctggcggag gaggatctgg cggtggaggc tctggcggcg gcggttcaac aaatctggtg   1080
```

aaccagagcg gctacgccct ggtggccagc ggcagatccg gcaatctggg cttcaagctg 1140
ttcagcaccc agtctccatc tgccgaggtg aagctgaaga gcctgagcct taacgacggc 1200
agctaccagt ccgagatcga cctgtcaggc ggcgccaact tccgagaaaa gttcagaaac 1260
ttcgccaatg agctgagcga ggccatcaca aacagcccta aaggcctgga cagacctgtg 1320
cccaagacgg aaatcagcgg cctgatcaag acaggcgaca actttatcac ccctagcttc 1380
aaggccggat attatgacca cgtggcctct gatggctccc tactgagcta ctaccagtcc 1440
accgagtact tcaacaacag agttctgatg cctatcctgc agacaacaaa cggcactctg 1500
atggccaaca accggggcta cgacgacgtt ttcagacaag tgccctcttt cagcggctgg 1560
agcaacacaa aggccaccac tgtgtccaca agcaacaatc tgacatacga taagtggacc 1620
tatttcgccg ccaaaggcag ccccctgtac gacagctacc ccaaccactt cttcgaggac 1680
gtgaagacac tggccattga cgctaaggac atcagcgccc tgaaaaccac catcgacagc 1740
gagaagccta cctacctgat tatccgggga ctgagcggaa acggcagcca gctgaacgag 1800
ctgcaactgc ctgagtccgt gaaaaaggtg agcctgtacg gcgactacac cggcgtgaac 1860
gtggctaagc agatcttcgc caacgttgtg gaactggaat tctacagcac cagcaaggct 1920
aactcttttg gctttaaccc cctggtcctg ggatctaaaa cgaacgtgat ctacgacctg 1980
ttcgcaagca agcccttcac ccacatcgac ctgacacagg tgaccctgca aaacagcgat 2040
aattccgcca tcgatgccaa caagctgaag caagctgtgg gcgatatcta caactacagg 2100
cggttcgaga gacagtttca gggctacttc gccggaggct acatcgacaa gtacctggtg 2160
aagaacgtca ataccaacaa ggatagcgat gacgatctgg tctaccggag cctgaaagag 2220
ctgaacctcc acctggagga agcctacaga gaaggcgata acacctacta cagagtgaat 2280
gagaactatt accctggagc tagcatctac gagaacgaga gagccagcag agacagcgag 2340
ttccagaacg agatcctgaa gcgagccgag cagaacggcg tgacatttga cgagaacatc 2400
aaaagaatca cagccagcgg caagtatagc gtgcagttcc aaaagctaga aaatgatacc 2460
gattccagcc tggaaagaat gaccaaggcc gtggaaggcc ttgtgaccgt gatcggcgag 2520
gaaaagttcg agacagtgga tatcaccggc gtgtctagcg ataccaatga agtgaaaagc 2580
ctggccaagg aactgaagac caacgccctg ggcgtcaagc tgaaactcta a 2631

<210> SEQ ID NO 40
<211> LENGTH: 3837
<212> TYPE: DNA
<213> ORGANISM: Artificial Sequence
<220> FEATURE:
<223> OTHER INFORMATION: armY-Angiotensin-converting enzyme 2 (ACE2) fusion protein codon-optimized (for human)

<400> SEQUENCE: 40
atgtacagga tgcaactcct gtcttgcatt gcactaagtc ttgcacttgt cacaaacagt 60
cagagcacaa tcgaggaaca ggccaagacc ttcctggaca agttcaacca cgaagctgaa 120
gacctgttct accaatctag cctggctagt tggaactaca acaccaacat tacagaagag 180
aacgtgcaga acatgaacaa cgcaggcgac aagtggtccg ccttccttaa agagcagtct 240
acactggccc agatgtaccc tctgcaagag attcagaatc tgaccgtgaa gctgcagctg 300
caggctctcc agcagaatgg gtccagcgtg ctgtctgagg ataagagcaa gcggctgaac 360
accatcctga atacaatgag caccatctac agcaccggca aagtgtgtaa ccctgacaac 420
ccccaggagt gtctgctgct ggaacctggc ctgaacgaaa tcatggccaa ctccctggac 480

```
tacaacgaga gactgtgggc ctgggagagc tggcgtagcg aggtgggaaa acagctgcgc    540
cccctgtatg aggagtacgt ggtgctgaag aatgagatgg ccagagccaa ccactacgag    600
gactacggcg actattggag aggcgattat gaagtcaacg gcgttgacgg ctacgactac    660
agccggggac agctgatcga agacgtggaa catacgtttg aggagatcaa gcctctgtac    720
gagcacctgc acgcctacgt aagagccaaa ctgatgaatg cctaccccag ctacatctcc    780
cctatcggct gcctgcccgc ccatctgctc ggcgacatgt ggggcagatt ctggaccaac    840
ctgtattctc tgacagtgcc tttcggccag aaacctaaca tcgacgtgac agatgccatg    900
gtggaccagg cctgggatgc ccaaagaatc ttcaaggaag ccgagaaatt cttcgtgtcc    960
gtggggctgc ctaatatgac ccagggcttc tgggaaaaca gcatgctcac cgatcctggc   1020
aacgtgcaga aggcagtgtg ccaccccacc gcctgggacc ttggaaaggg cgacttccgg   1080
attctgatgt gcaccaaggt gaccatggac gacttcctga ccgctcacca cgagatgggc   1140
cacatccagt acgacatggc ctacgccgct cagcctttcc tcctgagaaa cggcgctaat   1200
gaaggcttcc acgaggccgt gggcgaaatc atgagcctga gcgccgccac ccctaagcac   1260
ctgaagtcta tcggactgct gagccccgac tttcaggagg acaacgaaac tgagatcaac   1320
ttcttgctga aacaggccct gacaatcgtt ggcaccctgc cctttaccta catgctggaa   1380
aagtggagat ggatggtctt taagggcgaa atccccaagg accaatggat gaagaagtgg   1440
tgggagatga agcgggaaat cgtgggcgtg gtggaacctg tgccccacga cgagacatac   1500
tgcgatcctg ctagcctctt tcacgtgagc aatgattact cattcatccg gtactacacc   1560
agaactctgt accagttcca gttccaggag gccctgtgcc aggccgccaa gcacgagggc   1620
cctctgcaca agtgcgacat ctctaacagc accgaggccg gccagaagct gttcaacatg   1680
ctgagactgg gcaagagcga accttggaca ctggccctgg agaacgtggt cggagccaag   1740
aacatgaacg tgagaccact gctgaactac ttcgagcccc tgttcacctg gctgaaggat   1800
caaaacaaga acagcttcgt gggctggtcc acagactgga gcccatacgc tgatcagagc   1860
atcaaagtga ggatctctct gaagagcgcc ctgggagata aggcctacga gtggaacgat   1920
aatgagatgt acctgttcag aagcagcgtg gcctacgcca tgcggcagta cttcctgaaa   1980
gtgaagaacc agatgatcct gtttggcgag gaggatgtga gagtggccaa tctgaaacca   2040
agaatcagct ttaacttttt cgttaccgct cctaagaacg tgtctgatat catccctaga   2100
accgaggtgg aaaaggccat cagaatgagc cggtccagaa tcaacgatgc cttccgactg   2160
aatgacaact ccctggagtt cctgggaatc cagcccaccc tgggccctcc taaccagcct   2220
ccagtcagcg gcggaggagg atctggcggt ggaggctctg gcggcggcgg ttcaacaaat   2280
ctggtgaacc agagcggcta cgccctggtg gccagcggca gatccggcaa tctgggcttc   2340
aagctgttca gcacccagtc tccatctgcc gaggtgaagc tgaagagcct gagccttaac   2400
gacggcagct accagtccga gatcgacctg tcaggcggcg ccaacttccg agaaaagttc   2460
agaaacttcg ccaatgagct gagcgaggcc atcacaaaca gccctaaagg cctggacaga   2520
cctgtgccca agacggaaat cagcggcctg atcaagacag gcgacaactt tatcacccct   2580
agcttcaagg ccggatatta tgaccacgtg gcctctgatg gctccctact gagctactac   2640
cagtccaccg agtacttcaa caacagagtt ctgatgccta tcctgcagac aacaaacggc   2700
actctgatgg ccaacaaccg gggctacgac gacgttttca gacaagtgcc ctctttcagc   2760
ggctggagca acacaaaggc caccactgtg tccacaagca acaatctgac atacgataag   2820
```

-continued

```
tggacctatt tcgccgccaa aggcagcccc ctgtacgaca gctaccccaa ccacttcttc   2880

gaggacgtga agacactggc cattgacgct aaggacatca gcgccctgaa aaccaccatc   2940

gacagcgaga agcctaccta cctgattatc cggggactga gcggaaacgg cagccagctg   3000

aacgagctgc aactgcctga gtccgtgaaa aaggtgagcc tgtacggcga ctacaccggc   3060

gtgaacgtgg ctaagcagat cttcgccaac gttgtggaac tggaattcta cagcaccagc   3120

aaggctaact cttttggctt taaccccctg gtcctgggat ctaaaacgaa cgtgatctac   3180

gacctgttcg caagcaagcc cttcacccac atcgacctga cacaggtgac cctgcaaaac   3240

agcgataatt ccgccatcga tgccaacaag ctgaagcaag ctgtgggcga tatctacaac   3300

tacaggcggt tcgagagaca gtttcagggc tacttcgccg gaggctacat cgacaagtac   3360

ctggtgaaga acgtcaatac caacaaggat agcgatgacg atctggtcta ccggagcctg   3420

aaagagctga acctccacct ggaggaagcc tacagagaag gcgataacac ctactacaga   3480

gtgaatgaga actattaccc tggagctagc atctacgaga acgagagagc cagcagagac   3540

agcgagttcc agaacgagat cctgaagcga gccgagcaga acggcgtgac atttgacgag   3600

aacatcaaaa gaatcacagc cagcggcaag tatagcgtgc agttccaaaa gctagaaaat   3660

gataccgatt ccagcctgga aagaatgacc aaggccgtgg aaggccttgt gaccgtgatc   3720

ggcgaggaaa agttcgagac agtggatatc accggcgtgt ctagcgatac caatgaagtg   3780

aaaagcctgg ccaaggaact gaagaccaac gccctgggcg tcaagctgaa actctaa      3837
```

<210> SEQ ID NO 41
<211> LENGTH: 2706
<212> TYPE: DNA
<213> ORGANISM: Artificial Sequence
<220> FEATURE:
<223> OTHER INFORMATION: armY-CD209 (DC-SIGN) fusion protein codon-
      optimized (for human)

<400> SEQUENCE: 41

```
atgtaccgaa tgcagctgct gtcttgtatt gccctgtccc tggccctggt taccaattct     60

caagtgagca aggtgcccag cagcatctct caggagcaga gcagacagga cgccatctac    120

cagaacctga ctcaactgaa ggcggctgtg ggcgaactga gcgagaagtc taagctgcag    180

gagatctatc aggaactgac acaactgaag gctgccgtgg gggaattacc cgagaagagc    240

aagctgcagg aaatctacca ggagctgacc agactcaaag ccgccgtggg cgagctgcca    300

gagaagtcta aactgcagga aatctaccag gaattgacat ggctgaaggc agctgttggc    360

gagctgcctg agaaaagcaa gatgcaggag atttaccagg agctcacacg gctgaaggcc    420

gccgtcggcg aactccccga gaaaagcaag cagcaggaga tctaccagga gcttacaaga    480

cttaaggccg ctgtgggaga gctgcctgag aagtccaaac aacaggaaat ctaccaagaa    540

ctgaccagac tgaaagccgc cgtgggagaa ctgccagaaa aaagcaagca gcaggagatc    600

taccaagaac tgacacagct taaagcagct gttgagcggc tgtgtcaccc atgcccttgg    660

gagtggacat tcttccaggg caactgctac ttcatgagca atagccaaag gaactggcac    720

gacagcatca cagcctgcaa ggaagtgggg gcccagctgg tggtgatcaa gtccgccgaa    780

gaacaaaatt tcctgcagct gcagtcctcc agaagcaaca gattcacatg gatgggcctg    840

tcagacctga accaagaagg cacctggcag tgggtcgatg gcagccccct gctgccctct    900

ttcaagcagt actggaaccg cggcgagcct aacaatgtgg gcgaggaaga ttgcgccgag    960

tttagcggca acggctggaa tgacgacaag tgcaacctcg ccaagttctg gatctgtaaa   1020
```

-continued

```
aagtccgccg cctcctgcag ccgcgacgag gagcagtttc tgtcccctgc ccccgccacc   1080
cctaatcctc ctcccgccgg cggtggcgga agcggcggcg gcggcagcgg aggaggcggc   1140
agcaccaacc tggtgaatca gagcggctac gccctggtgg cctctggtag atctggcaac   1200
ctgggattca agctgttcag cacacagtct cctagtgccg aagtgaagct gaagtcactg   1260
agcctgaacg acggcagcta ccagagcgaa atcgacctgt ctggcggtgc taacttcaga   1320
gagaagttcc ggaacttcgc caacgagctg tccgaggcca ttaccaacag tcccaagggc   1380
ctggaccggc ctgtgcctaa gaccgagatc agcggcctga tcaagaccgg cgacaacttc   1440
atcaccccta gctttaaggc tggctactac gaccacgtgg cctccgatgg ctctctgctg   1500
tcctattatc agagcacaga gtacttcaac aatagagtgc tgatgcctat cctgcaaaca   1560
accaacggca ccctgatggc caataatagg ggatacgacg acgtctttcg gcaggtgcct   1620
agcttctccg gctggagcaa caccaaggcc acaaccgtgt ctacaagcaa caacctgaca   1680
tacgacaagt ggacctactt tgccgccaag gggagccctc tgtacgactc ttatcctaat   1740
catttcttcg aggacgtgaa gaccctggcc atcgatgcca aggatatcag cgccctgaag   1800
accaccatcg acagcgaaaa acccacctac ctgatcatcc ggggcctgag cggcaatggc   1860
agccagctga acgaactgca gctgccagaa agcgtgaaga aggtgtctct gtacggcgac   1920
tacaccggcg tgaacgtggc taagcagatc ttcgccaatg ttgttgagct tgagttctac   1980
agcacgagca aggccaactc attcggcttc aaccccctgg tgctgggaag taagacaaac   2040
gtgatctatg acctgtttgc cagcaaacct ttcacccaca tcgacctgac ccaggtgacc   2100
ctgcagaaca gcgacaacag cgccattgat gctaacaagc tgaaacaggc cgtgggagac   2160
atctacaact accggagatt cgagagacag ttccaaggct acttcgccgg cggctatatc   2220
gataagtacc tggtgaaaaa cgtgaacacc aacaaggata gcgatgacga cctggtgtac   2280
agaagcctga aggaactgaa cctgcacctg gaggaagcct acagagaagg cgataacaca   2340
tactacagag tgaacgagaa ctactaccct ggagccagca tctacgagaa cgagagagcc   2400
tctcgggact ccgagttcca gaacgaaatc ctgaaacggg ccgagcagaa cggcgtgaca   2460
tttgatgaaa acatcaagag aatcaccgct agcggcaagt acagcgtgca gtttcagaag   2520
ctggagaacg acactgattc tagcctggaa agaatgacca aggcggtcga gggcctggtg   2580
accgtgatcg gcgaggagaa gttcgaaacc gtggacatca ccggcgtgtc cagcgacacc   2640
aatgaggtga aatctctggc caaagagctg aagaccaacg ccctcggagt gaagctgaag   2700
ctgtaa                                                              2706
```

<210> SEQ ID NO 42
<211> LENGTH: 2655
<212> TYPE: DNA
<213> ORGANISM: Artificial Sequence
<220> FEATURE:
<223> OTHER INFORMATION: armY-C-type lectin domain family 4 member M fusion protein codon-optimized (for human)

<400> SEQUENCE: 42

```
atgtaccgga tgcagctgct gtcttgtatc gccctgagcc tggccctggt caccaattct     60
caggtgtcta aggtgccttc tagcctgagc caggagcagt ctgagcagga cgctatctac    120
cagaacctga cacagcttaa ggccgctgtg ggcgaactgt cagaaaagtc taagctccaa    180
gagatctacc aggagcttac acagctgaaa gccgccgtgg gcgagctgcc tgagaagtcc    240
aagttgcaag agatctacca ggagctgacc cggctgaaag ccgccgtggg agagctgccc    300
```

-continued

```
gagaagagca aactgcagga aatctatcag gagctgacca gactgaaggc cgccgtggga    360
gagctgcccg agaaatccaa gctacaggag atctaccagg agctgacaag actgaaggcc    420
gcagtgggcg agctgccaga aaagagcaag ctgcaggaga tctaccagga actgacagag    480
ctgaaggccg ccgttggaga actgcctgaa aagtccaaac tgcaggaaat ctatcaggag    540
ctgacacagc tgaaggctgc cgtgggcgaa ctccctgacc agtccaagca gcagcagatt    600
taccaggaac tgaccgacct gaaaacagcc ttcgagagac tgtgtagaca ctgccctaag    660
gactggacat tcttccaggg caactgctac ttcatgagca acagccagcg gaactggcac    720
gacagcgtga ccgcctgtca ggaggtgcgg gcccagctgg tggtcatcaa gaccgccgaa    780
gagcaaaact tcctgcagct gcaaacaagc agaagcaaca gattcagctg gatgggcctg    840
agcgatctga accaggaggg cacctggcag tgggtggatg gaagccctct gtctccaagc    900
ttccaaagat actggaacag cggagagcct aacaactctg gaaatgagga ctgcgccgag    960
ttcagcggtt ctggctggaa tgacaacaga tgcgacgtgg acaactactg gatctgcaag   1020
aaacccgccg cctgcttccg agatgagggc ggtggcggaa gcggcggcgg aggcagcgga   1080
ggcggcggga gtaccaacct ggtgaatcag agcggctacg ccctggtcgc ctcgggcaga   1140
tccggcaatc tgggcttcaa gctgttcagc acacaaagcc cttctgctga agtgaaactg   1200
aagagcctga gcctgaatga tggctcttac cagagcgaga tcgacttatc cgggggagcc   1260
aactttcggg aaaaattcag aaacttcgct aacgagctga gcgaggccat caccaactcc   1320
cccaagggcc tggatagacc tgtgcccaag acagagatca gcggcctgat caagaccggc   1380
gataacttca tcacccctag ctttaaggcc ggatactacg accacgtggc ttccgatggc   1440
agcctgctga gctactacca gagcaccgag tacttcaaca acagagtact gatgcctatc   1500
ctgcagacaa caaatggcac cctgatggcc aacaataggg gctacgatga cgtgttcaga   1560
caggttcctt cattcagcgg ctggagcaat acgaaggcta caaccgtgtc gaccagcaac   1620
aacctgacct atgacaagtg gacctacttc gccgctaagg gcagccctct gtacgacagc   1680
taccccaacc acttcttcga ggatgtgaaa accctggcca ttgacgccaa ggacatcagc   1740
gccctgaaaa ccaccatcga cagcgagaag cctacatacc tgatcatcag aggcctgtca   1800
ggcaacggct cccagctgaa cgaactgcaa ctgccagaga gtgttaagaa ggtgagcctg   1860
tacggcgact atacaggagt gaacgtggct aagcagatct tcgctaatgt ggtggaactg   1920
gaattctaca gcaccagcaa agccaacagc ttcggcttta acccccctggt gctgggcagc   1980
aagaccaacg tgatctacga ccttttcgcc agcaagccct tcacccacat cgacctgacc   2040
caggtgaccc tgcagaatag cgacaattct gccattgacg ccaacaagct gaaacaggcc   2100
gtgggcgata tctacaacta caggcggttc gaaagacagt tccaaggcta ttttgccggc   2160
ggctacatcg acaagtacct ggtcaagaac gtgaacacca acaaggattc cgacgacgat   2220
ctagtgtacc ggagcttgaa ggaactcaac ctgcatctgg aagaggccta cagagaaggc   2280
gacaacacat actaccgcgt gaacgagaac tactaccctg gcgccagcat ctacgagaac   2340
gaacgggctt ctagagatag cgagtttcag aatgaaatcc tgaagagagc cgaacagaac   2400
ggcgtgacct tcgacgagaa cattaagcgg atcacagcct ctggcaagta cagcgtgcag   2460
tttcagaagc tggaaaacga caccgacagc tctctcgaga gaatgaccaa ggccgttgag   2520
ggcctggtga cagtgatcgg cgaggaaaag ttcgaaaccg tggacatcac cggcgtgtcc   2580
tctgatacca acgaggtgaa gagcctggca aaggaactga agaccaacgc cctgggcgtg   2640
aagctgaagc tgtaa                                                    2655
```

<210> SEQ ID NO 43
<211> LENGTH: 2781
<212> TYPE: DNA
<213> ORGANISM: Artificial Sequence
<220> FEATURE:
<223> OTHER INFORMATION: armY-CD4 fusion protein codon-optimized (for human)

<400> SEQUENCE: 43
atgtacagaa tgcagctgct gagctgcatc gccctgtccc tggccctggt tacaaacagc 60
aagaaggtgg tgctgggaaa aaagggcgac accgtggaac tgacctgcac cgctagccag 120
aagaagagca tccaatttca ctggaagaac agcaaccaga tcaaaatcct ggggaaccag 180
ggctctttcc tgacaaaggg cccctctaag ctgaatgata gagccgacag ccggagatcg 240
ctgtgggacc agggcaactt ccccctgatc atcaagaacc tgaagatcga ggatagtgac 300
acatacatct gcgaggtgga agatcagaag gaagaggtgc aactgctggt gttcggactg 360
accgccaaca gcgacactca cctgctgcag ggccagtctc tcacactaac cctggaaagc 420
cctcctggaa gctctccaag cgtccagtgt agatctccta gaggcaagaa catccagggc 480
ggcaagaccc tttctgtgtc tcagctggag ctgcaggact caggcacctg gacatgtacc 540
gtactgcaaa atcagaaaaa ggtggaattc aagatcgaca tcgttgtgct ggccttccag 600
aaggccagca gcatcgtgta caagaaggaa ggagagcagg tggagttttc tttccctctc 660
gcctttaccg tggaaaaact gaccggttca ggcgagctgt ggtggcaggc cgagcgcgca 720
agctccagca agagctggat cacattcgac cttaagaaca aagaggtgag cgtgaagaga 780
gtgacccagg accccaagct gcagatgggc aagaagctgc ccctgcacct gaccctcccg 840
caagccctgc ctcagtacgc cggatccggc aacctgacac tggccctcga agccaaaacc 900
ggaaagctgc accaggaggt gaacctggtg gtgatgagag ccacccagct gcagaaaaat 960
ctgacctgcg aagtgtgggg ccctacaagc cctaagctca tgctgagtct taaactggag 1020
aacaaggagg ctaaagtgag caagcgggaa aaggccgtgt gggtgctgaa tcctgaggcc 1080
ggcatgtggc agtgcctgct gtctgacagc gggcaagtgc tgctggaatc taacatcaag 1140
gtcctgccca cctggtccac ccctgtgcag ccaggcggcg gaggatctgg cggcggcggc 1200
agcggaggcg gcggctccac caacctggtg aatcagagcg gctacgccct ggtggctagc 1260
ggtagatccg gcaatctggg attcaagctt ttctccacac agagccctag cgccgaagtg 1320
aagttgaaat ctctgagcct gaacgacggc tcctaccagt ccgagatcga cctgagcggc 1380
ggcgctaatt tcagagagaa gtttcggaac ttcgccaatg agctgtctga agctatcacc 1440
aacagcccta aggacttgga tcgcccagtg cccaagaccg agattagcgg cctgatcaag 1500
acaggcgata actttatcac ccctagtttc aaggctggct attatgacca cgtggccagc 1560
gacggaagcc tgctgagcta ctaccagagc acagagtact tcaacaaccg ggtgctgatg 1620
cctatcctgc agaccaccaa cggcacgctg atggccaaca acagaggcta cgacgacgtg 1680
ttccggcagg tgcctagctt tagcggatgg agcaacacca aggctacaac tgtgagcacc 1740
agcaacaacc tgacctacga taagtggacc tacttcgccg ccaaaggcag ccctctgtac 1800
gatagctacc ctaaccactt cttcgaggac gtgaagacac tggctatcga cgccaaggac 1860
attagcgccc tgaaaaccac aattgactct gaaaagccca cctacctgat catcagagga 1920
ctgagcggca acggcagcca gctgaacgag ctgcagctgc ctgaatctgt gaaaaaagtc 1980
agcctttacg gcgactacac cggcgtgaac gtggccaagc agatcttcgc caatgtggtg 2040

```
gaactggagt tctacagcac ctctaaagcc aacagtttcg gcttcaaccc cctggtgctg   2100

ggctctaaaa ccaatgtaat ttatgacctc ttcgctagca agcctttcac acacatcgat   2160

ctgacccagg tgacactgca gaactctgac aacagcgcca tcgatgccaa taagctgaag   2220

caggccgtgg gcgacatcta caactaccgg agattcgaga gacagtttca gggctacttt   2280

gccggcggct acatcgataa gtacctggtt aagaacgtga ataccaacaa ggactctgat   2340

gacgacctgg tgtacagaag cctgaaggaa ctgaacctgc atctggaaga ggcctacaga   2400

gaaggcgaca acacctacta tcgggtgaat gagaactact atcccggcgc ttctatctac   2460

gagaatgagc gggccagcag agatagtgag ttccaaaatg agatcctgaa gcgggcagag   2520

caaaacggcg tgaccttcga cgagaacatc aagagaatca ccgcctccgg caaatacagc   2580

gtgcagttcc agaaactgga aaacgacact gatagcagcc tggaacggat gaccaaggcc   2640

gtagagggcc tggtcaccgt gatcggcgag gagaagtttg agacagtgga catcacaggc   2700

gtgagctccg ataccaacga ggtgaagagc ctggccaagg aactgaagac caacgccctg   2760

ggagtgaagc tgaagctata a                                              2781
```

<210> SEQ ID NO 44
<211> LENGTH: 2058
<212> TYPE: DNA
<213> ORGANISM: Artificial Sequence
<220> FEATURE:
<223> OTHER INFORMATION: armY-Synaptic vesicle glycoprotein 2A fusion
      protein codon-optimized (for human)

<400> SEQUENCE: 44

```
atgtacagaa tgcagctgct gtcatgcatc gccctctccc tcgccctggt gaccaacagc     60

cccgacatga tcagacacct gcaggccgtc gactacgcca gcagaaccaa agtgttcccc    120

ggagaacggg tggaacacgt gacatttaac ttcaccctgg aaaaccagat ccacagaggc    180

ggccagtact tcaacgacaa gttcatcggc ctgagactga agtccgtgtc cttcgaggat    240

agcctgtttg aggaatgcta ctttgaggac gtgacatcta gcaatacctt tttccggaac    300

tgcacattca tcaacaccgt gttctacaac accgatctgt ttgaatacaa gttcgtgaac    360

agcagactga tcaacagcac ctttctgcac aacaaggagg gctgtccttt agatgtgacc    420

ggaacgggcg agggcgccta catggtgtac ggcggcggag gctccggcgg cggtggcagc    480

ggtggaggag gcagcaccaa tctggtcaac caatctggct atgccctggt cgccagtggc    540

agaagcggga acctgggctt caagctgttc agcacacaga gccctagcgc tgaagtgaaa    600

ctgaagagcc tgtctctgaa cgacggctct tatcagagcg agatcgacct gtccggaggc    660

gccaatttca gagagaagtt caggaacttc gccaacgagc tgagcgaggc catcaccaat    720

tcccctaagg gactggatag acctgtgcca aaaaccgaga ttagcggcct gattaagacc    780

ggagataatt tcatcacacc cagctttaag gccggatatt acgaccacgt ggcctctgac    840

ggcagcctgc tgagctacta ccagagcacc gagtacttca acaaccgggt gctgatgcct    900

atcctgcaaa caacaaatgg cacactgatg gccaacaacc ggggatatga cgacgtgttc    960

cgccaggtgc ccagcttcag cggctggagc aacacaaagg ctacaaccgt gtctaccagc   1020

aacaacctga cctacgataa gtggacctac ttcgccgcta aaggcagccc tctgtacgac   1080

agctacccca accacttctt cgaggacgtc aagaccctgg cgatagacgc caaagacatc   1140

agcgctctga agaccaccat cgacagcgaa aagccaacat acctgatcat cagaggcctg   1200

agcggcaacg gctcacagct gaacgagctg cagctgcctg agagcgtgaa aaaggtgtca   1260
```

ctgtacggcg attacaccgg cgtgaacgtg gccaagcaga tcttcgcaaa cgttgtggaa 1320
ctggaattct actctacaag caaggccaac agcttcggct ttaatcctct ggtgctgggg 1380
tctaagacaa acgtgatcta cgacctgttc gccagtaagc ctttcaccca catcgacctg 1440
acccaggtta cactgcagaa ctccgacaac agcgccatcg acgccaacaa gctgaaacag 1500
gccgtgggcg acatctacaa ctacaggaga ttcgaaagac agttccaggg ctattttgcc 1560
ggcggctaca tcgacaagta cctggtgaag aacgtgaata ccaacaagga ctctgatgac 1620
gatctcgtgt accggagcct gaaggaactg aatctgcatc tggaagaagc ttaccgggaa 1680
ggcgacaata cctactacag agtgaacgag aactactacc ctggcgctag catctacgag 1740
aacgaacggg ccagcagaga ttctgagttc caaaacgaga tcctgaagcg ggccgagcag 1800
aatggcgtca ccttcgacga gaacatcaag agaatcaccg cctctggcaa atacagcgtg 1860
cagttccaaa aactggaaaa cgatactgat agctcccttg agagaatgac caaggccgtg 1920
gaaggactgg tgaccgtgat cggcgaagag aagttcgaga cagtggacat cacaggcgtg 1980
tccagcgata ccaatgaggt gaagagcctg gccaaggagc tgaaaaccaa cgccctcggc 2040
gtgaagctga agctgtaa 2058

<210> SEQ ID NO 45
<211> LENGTH: 2040
<212> TYPE: DNA
<213> ORGANISM: Artificial Sequence
<220> FEATURE:
<223> OTHER INFORMATION: armY-Synaptic vesicle glycoprotein 2B fusion
protein codon-optimized (for human)

<400> SEQUENCE: 45
atgtacagaa tgcagttgct gtcttgtatc gccctcagcc tggctctggt gacgaatagc 60
ccagacatga tccgctactt ccaggacgag gaatacaaga gcaagatgaa ggtgttcttt 120
ggcgagcatg tgtacggcgc caccatcaac ttcaccatgg aaaaccagat ccaccagcac 180
ggcaagctgg ttaatgacaa gtttacaaga atgtacttta agcacgtgct gttcgaggat 240 acctttttttg atgagtgcta cttcgaggac gtgacaagca ccgacacata cttcaagaac 300
tgcaccatcg agagcaccat cttctacaac accgacctgt atgagcacaa gttcatcaac 360
tgcagattta tcaacagcac cttcctggaa cagaaagagg gctgccacat ggacctggaa 420
caagacaatg atggaggcgg aggaagcggc ggcggaggca gcggcggcgg gggaagcacc 480
aatctggtga atcaaagcgg ctacgccctg gtggctagcg gcagaagcgg caacctgggc 540
ttcaagctgt ttagcacaca gagccctagc gctgaagtga agctgaagtc tctctctctg 600
aatgacggct cctaccagtc tgagatcgac ctcagcggag gcgccaactt cagggaaaag 660
ttccggaact tcgccaacga gctgagcgag gccattacaa acagccctaa gggcctggac 720
agacctgtgc ccaagaccga gatcagcggc ctgatcaaga ctggagataa ttttattacc 780
cctagcttca aggcaggcta ctacgaccac gtggcctccg atggctctct gctgtcctat 840
tatcagagca cagagtactt taacaacaga gtgctgatgc ctatcctgca gaccacaaac 900
ggcaccctga tggccaacaa tagaggctat gatgatgtgt tcagacaggt gccttctttc 960
agcggatggt ccaacacaaa ggccacaaca gtttctacaa gcaacaacct gacctacgat 1020
aagtggacat acttcgccgc caagggctct ccactgtacg acagctaccc taaccacttc 1080
ttcgaagatg tgaagaccct ggccatcgac gccaaggaca tcagcgccct taaaacaacc 1140
attgacagcg agaagcctac ctacctgatc atcagaggac tgagcggaaa cggctcccag 1200
ctgaacgaac tgcaactgcc tgagtctgtg aaaaaggtga gcctgtacgg cgattacacc 1260
ggcgttaacg tggctaaaca gatcttcgcc aacgtggtgg aactggagtt ctacagcacc 1320
agcaaggcca atagcttcgg gttcaacccc ctggtccttg gctccaaaac caacgtcatc 1380
tacgacctgt tcgcttctaa gcccttcaca cacatcgacc tgacccaggt taccctgcag 1440
aactcagaca acagtgctat cgacgccaac aaactgaagc aggccgtggg cgatatctat 1500
aactaccgga gattcgagcg gcagttccaa ggctacttcg ccggcggata tatcgacaag 1560
tacctggtca agaacgtgaa caccaacaag gacagcgatg acgacctggt gtaccggagc 1620
ctgaaggaac tgaacctgca cctggaagaa gcctaccggg aaggcgacaa cacctactac 1680
cgggtgaacg agaattacta ccccggcgct agcatctacg agaacgagag agcctccaga 1740
gattcagagt tccagaacga gatcctgaaa agagccgagc agaatggcgt gaccttcgac 1800
gagaacatca agcggatcac agcctctggc aaatacagcg tgcagttcca gaagctggaa 1860
aatgataccg atagcagcct ggaaagaatg accaaggcgg tggaaggctt ggtcaccgtg 1920
atcggcgagg agaagttcga gacagtggac atcaccggcg tgtccagcga caccaacgag 1980
gtgaaaagcc tggccaagga actgaagacc aacgccctgg gcgtgaagct gaagctgtaa 2040

<210> SEQ ID NO 46
<211> LENGTH: 2028
<212> TYPE: DNA
<213> ORGANISM: Artificial Sequence
<220> FEATURE:
<223> OTHER INFORMATION: armY-Synaptic vesicle glycoprotein 2C fusion
protein codon-optimized (for human)

<400> SEQUENCE: 46
atgtaccgca tgcagctgct gagctgcatc gccctgagcc tggctctggt gacaaacagc 60
aaacctctgc agagcgacga gtacgccctg ctgacaagaa acgtcgagcg ggacaagtac 120
gccaatttta ccatcaactt taccatggaa aaccagatcc acaccggaat ggaatacgat 180
aatggcagat tcattggcgt taagttcaaa agcgtgacat tcaaagatag cgtgttcaag 240
agctgtacat tcgaagatgt gaccagcgta aatacctact tcaaaaactg caccttcatc 300
gacaccgtgt tcgacaacac cgatttcgag ccttacaagt tcatcgacag cgagttcaag 360
aactgcagct ttttccacaa caaaaccgga tgtcagatca ccttcgacga cgactacagc 420
ggcggcggcg gctcgggcgg aggaggctct ggtggcggcg gcagcacaaa cctggtcaac 480
cagagcgggt atgccctggt ggccagcggc agaagcggca atctgggctt caagctgttc 540
agcacacagt ccccaagcgc tgaggtgaag ctcaaatctc tgtcccttaa cgacggcagt 600
taccaaagcg agatcgacct gagcggcgga gccaacttcc gggaaaagtt cagaaatttc 660
gctaatgaac tgagcgaggc catcacgaat agccctaagg gcctggatag acccgtgccc 720
aagactgaga tcagcggcct gattaagaca ggagataact tcatcacacc tagcttcaag 780
gccggctatt acgaccacgt ggcctcagac ggctccctgc tgagctacta ccagagcaca 840
gagtacttca acaaccgggt gctgatgcct atcctgcaga ccaccaacgg aacactgatg 900
gccaacaaca gaggctatga cgatgtgttt agacaggtcc cctcttttag cggatggtcc 960
aacaccaagg ctacaacagt gtccaccagc aacaacctga cctacgacaa gtggacatat 1020
ttcgccgcca agggaagccc tctgtacgac agctacccaa accacttctt cgaggacgtg 1080
aagaccctgg ccattgacgc caaagacatc agcgccctga agaccacaat cgattctgag 1140
aaacctacct atctgatcat cagaggactc tctggcaacg gcagccagct gaacgagctg 1200

-continued

```
cagctgcctg agagcgtgaa aaaggtgtcc ctgtacggcg attacaccgg cgtgaacgtg   1260

gccaagcaga tcttcgccaa cgtggtggaa cttgagttct acagcaccag caaggccaat   1320

tctttcggct tcaaccccct ggtcctgggc agcaagacaa atgtgatcta cgacctgttc   1380

gcctctaagc ctttcaccca catcgacctg acccaggtga cactgcaaaa ttccgataac   1440

agcgccatcg acgctaacaa gctgaagcag gccgtgggcg acatctacaa ctaccggcgg   1500

tttgagcggc agtttcaggg ctactttgct ggcggataca tcgacaagta cctggtgaag   1560

aacgtgaaca caaacaagga ctctgatgac gacctggttt accggtctct gaaggaactg   1620

aacctccatc tggaagaagc ctacagagaa ggcgacaaca cctactacag ggtgaacgag   1680

aactactacc ccggcgctag catctacgag aacgaaagag cctctagaga tagcgaattt   1740

cagaacgaga tcctgaagag agctgaacag aatggcgtga cctttgatga gaacatcaag   1800

cggatcaccg cctccggcaa gtacagcgtg cagttccaaa agctggagaa tgataccgac   1860

tccagcctgg aaagaatgac caaggcagtg gagggcctgg tgaccgtgat cggcgaggaa   1920

aagttcgaga cagtggacat caccggcgtt agcagcgaca ccaacgaggt gaagtctctg   1980

gccaaggaac tgaagaccaa cgccctggga gtgaaactga agctgtaa                 2028
```

<210> SEQ ID NO 47
<211> LENGTH: 1839
<212> TYPE: DNA
<213> ORGANISM: Artificial Sequence
<220> FEATURE:
<223> OTHER INFORMATION: armY-Synaptotagmin I fusion protein codon-optimized (for human)

<400> SEQUENCE: 47

```
atgtacagaa tgcagctgct gagctgcatc gccctgagcc tggccctggt tacaaacagc     60

atggtgtccg agagccacca cgaggcctta gcagctcctc ctgtgaccac cgtggctaca    120

gtgctgccca gcaatgccac cgagcctgcc agccctggag agggaaaaga ggacgccttt    180

agcaagctga aggagaagtt catgaacgag ctgcataaga tccctctgcc tggaggtggc    240

ggcagcggag gaggtggctc cggcggcggc ggctccacca acctggtgaa ccagagcggc    300

tacgccctgg tggccagcgg aagaagcggc aacctgggct tcaagctgtt ttctacgcag    360

agccccagcg ccgaagtgaa gctgaagagc ctgtcactga acgacggcag ctatcagtct    420

gagatcgacc tgtctggcgg ggccaatttc agagagaaat ttagaaactt cgctaatgag    480

ctgagcgagg ccatcaccaa ctcgcccaag ggcctggaca gacctgtgcc caagaccgaa    540

atcagcggcc tgattaaaac aggcgataac ttcatcaccc cttcttttaa ggctggctac    600

tacgaccacg tggccagcga tggcagcctg ctgtcttact accagagcac agagtacttt    660

aacaacagag tgctgatgcc tatcctgcag accaccaacg gaacactgat ggccaacaac    720

cggggctacg acgacgtctt cagacaggtg cctagcttct ctggctggtc caacaccaag    780

gcgacaaccg tgtccaccag caacaatctg acatacgata agtggaccta cttcgctgcc    840

aagggctccc cactgtacga ctcttatcca aaccacttct tcgaggatgt gaaaactctg    900

gctatcgacg ccaaggacat cagcgctctg aagaccacaa tcgacagcga aaagcccacc    960

tacctgatca tcagaggact gagcggaaat ggctcacagc tgaacgaact gcagctgcct   1020

gagtctgtga agaaggtgtc cctctacggc gactacaccg gcgtcaacgt ggccaagcaa   1080

atcttcgcca atgtggtgga actggaattc tacagcacca gcaaggccaa cagcttcggc   1140

ttcaaccccc tggtgctggg gagcaaaaca aacgtgatct atgacctgtt cgccagcaag   1200
```

cctttcaccc acatcgatct gacccaagtg accctgcaga acagcgataa tagcgccatc 1260
gacgccaaca agctcaagca ggccgtgggc gatatctaca actacaggcg gttcgagaga 1320
cagtttcagg gctacttcgc cggcggctac atcgacaaat acctggtcaa gaacgtgaac 1380
accaacaaag actctgatga cgacctggtc taccggagcc tgaaagagct taatctgcac 1440
ctggaagagg cctaccggga aggcgacaac acatactaca gagtgaacga gaactactac 1500
ccaggcgcca gtatttacga gaacgaacgc gcctctagag atagcgagtt ccaaaatgag 1560
attttaaaaa gagccgagca gaacggcgtg acattcgacg agaacatcaa gcggatcacc 1620
gcctccggca agtacagcgt gcagttccag aagctggaaa atgataccga cagcagcctg 1680
gaacggatga ccaaggccgt ggaaggcctg gtgaccgtga tcggcgagga aaagttcgaa 1740
accgtcgaca tcacaggcgt gtctagcgac accaatgagg tgaagagcct tgctaaggaa 1800
ctgaagacaa acgccctggg cgtgaaactg aagctgtaa 1839

<210> SEQ ID NO 48
<211> LENGTH: 1854
<212> TYPE: DNA
<213> ORGANISM: Artificial Sequence
<220> FEATURE:
<223> OTHER INFORMATION: armY-Synaptotagmin II fusion protein codon-
      optimized (for human)

<400> SEQUENCE: 48
atgtaccgga tgcagctgct gagctgcatc gccctgtccc tggccctggt gacaaacagc 60
atgagaaaca ttttcaagag aaaccaggag cctatcgtgg cccctgctac aaccacagcc 120
acaatgccta tcggccctgt ggataattcg actgaaagcg gcggagccgg cgagtcccaa 180
gaagatatgt tcgccaagct gaaagagaaa ctgttcaacg agatcaacaa gatccccctg 240
cctccaggcg gcggcggcag cggaggaggc ggcagcggtg gcggcggcag cacaaatctg 300
gtaaaccaga gcggctacgc cctggttgcc tccggaagaa gcggaaacct gggatttaag 360
ctgttcagca cccagtcccc atctgctgaa gtgaaactga agagcctgag cctgaatgac 420
ggctcttacc agagcgagat cgacctgagt ggaggcgcca atttcagaga gaaattccgc 480
aacttcgcca atgagctgag cgaggccatc accaacagcc ctaagggcct ggacagacct 540
gtgcccaaga ccgaaatcag cggactgatc aagaccggcg acaacttcat cacccccttct 600 tttaaggctg gatattacga ccacgtggcc tctgacggat ctctgctgag ctactaccag 660
tctaccgagt acttcaacaa ccgggtgctg atgccaattc ttcagacaac caacggcacc 720
ctgatggcca acaatagagg ctacgacgat gtgttccggc aagtgcctag cttttctggc 780
tggagcaaca ccaaggccac caccgtgtcc accagcaaca acctcaccta tgataagtgg 840
acctactttg ctgctaaagg cagccccctg tacgactctt atcctaacca cttcttcgaa 900
gatgtgaaga ccctggctat cgatgccaag gacatcagcg ccctgaaaac caccatcgac 960
agcgagaagc ccacctacct gatcatcaga ggcctatctg gcaacggcag ccagctgaac 1020
gagctgcagc tccctgagag cgtgaagaag gtgtctctgt acggcgatta caccggcgtt 1080
aatgtggcta aacagatctt cgccaacgtg gtggaactgg aattctacag cacatctaaa 1140
gcaaacagtt ttggcttcaa tcctctggtg ctgggcagca agaccaacgt gatctacgac 1200
ctgtttgcta gcaagccctt cacacacatc gatctgaccc aggtgaccct gcaaaactcc 1260
gataatagcg ccattgacgc caacaaactc aagcaggccg tgggcgatat ctacaactac 1320
aggcggttcg agagacagtt ccagggctac ttcgccggcg gatatatcga caagtacctg 1380

-continued

```
gtcaagaacg tcaacacaaa caaggacagc gatgacgacc tggtctaccg gagcctgaag   1440

gaactgaacc tgcatctgga ggaagcctac agagaaggcg acaacaccta ctacagagtg   1500

aacgagaact actaccccgg cgccagcatc tacgagaatg aaagagcctc aagagattcc   1560

gagttccaga acgagatcct gaagcgggcc gagcagaacg gcgtgacatt cgacgagaac   1620

atcaagcgga tcaccgccag cggcaagtac agcgtgcagt ttcagaagct ggaaaacgac   1680

accgactcaa gcctggaaag aatgacaaag gccgtggaag gcctggtgac tgtgatcggc   1740

gaagagaagt tcgagacagt ggacatcaca ggcgtgtcta gcgacaccaa cgaggtgaaa   1800

agcctggcca aggaactgaa gacaaacgcc ctgggcgtga agctgaagct ataa         1854
```

<210> SEQ ID NO 49
<211> LENGTH: 2262
<212> TYPE: DNA
<213> ORGANISM: Artificial Sequence
<220> FEATURE:
<223> OTHER INFORMATION: armY-HLA class II histocompatibility antigen,
      DRB1 beta chain fusion protein codon-optimized (for human)

<400> SEQUENCE: 49

```
atgtaccgga tgcagctgct gagctgcatc gccctgtctc ttgccctggt gaccaactct     60

ggagacacca gacctagatt cctgtggcag cccaagaggg aatgtcactt tttcaacggt    120

acagagcggg tgagattcct ggaccggtac ttctacaacc aggaggaaag cgtgcggttt    180

gatagcgacg tgggcgagtt ccgggctgtg actgaactgg gccggcccga tgccgagtac    240

tggaacagcc agaaggatat cctggagcag gccagagccg cagtggacac ctactgcaga    300

cacaactacg gcgttgtgga aagcttcacc gtgcaaagaa gagtgcagcc taaagtgacc    360

gtgtacccat ctaaaacaca gcctctgcag caccacaatc tgctggtatg cagcgtgtcc    420

ggcttctacc ctggcagcat cgaggtgcgg tggttcctga acggccagga ggaaaaagcc    480

ggcatggtgt ctaccggcct gatccagaat ggcgactgga ccttccagac cctggtgatg    540

ctggaaacag tgcctagatc cggcgaggtg tacacctgcc aggtggagca ccccagcgtc    600

accagcccac tgaccgtgga atggcgggcc agatctgaga gcgctcagag caagggcggc    660

ggcggaagcg gcggcggagg aagcggcggc ggcggcagca caaatctggt caaccagagc    720

ggctacgccc tggtggccag tggcagaagc gggaacctgg gctttaagct gtttagcacc    780

cagagcccca gcgccgaagt gaagctgaaa agcctgtccc tgaacgacgg cagctaccag    840

agcgagatcg acctgtccgg cggagccaac ttcagagaga agttcagaaa ctttgccaac    900

gagctgagcg aggccattac aaatagccct aagggcctgg atagaccagt gcctaagacc    960

gagattagcg gcctgatcaa gaccggcgat aacttcatca caccttcctt taaggccggt   1020

tactatgacc acgtggccag cgacggctcc ctcctgagct actatcagtc taccgagtac   1080

ttcaacaacc gggtgctgat gcctatcctg caaacaacaa acggcaccct gatggccaac   1140

aacagaggct acgacgatgt gttcagacaa gtgccctctt tcagcggatg gagcaacacc   1200

aaggctacaa ccgtctccac tagcaacaac ctcacctacg acaagtggac ctattttgcc   1260

gccaagggca gccctctgta cgacagctac cctaaccact tcttcgagga cgtgaagacc   1320

ctggccatcg acgctaagga catcagcgcc cttaagacca caatcgattc tgagaagcct   1380

acctacctga tcatccgggg cttatctggc aacggctctc agctgaatga gctgcagctg   1440

ccggaaagcg tgaagaaggt gtccctctac ggcgactaca caggcgtgaa tgttgccaag   1500

cagatcttcg ccaacgtggt ggaactagaa ttctactcca ccagcaaggc taacagcttt   1560
```

ggcttcaatc ctctggtgct gggcagcaaa accaatgtga tctatgatct gttcgcttct 1620
aagcccttca cccacatcga tctgacacag gtgaccctgc agaacagcga caatagcgcc 1680
atcgacgcta acaagctgaa acaggctgtg ggcgacatct acaactaccg gagattcgag 1740
agacaattcc agggctactt cgccggagga tatatcgaca agtacctggt gaaaaacgtg 1800
aacaccaaca aggattctga tgacgacctg gtttacagga gcctgaagga actgaacctt 1860
catctggaag aagcctacag agagggcgac aatacatact acagagtgaa cgagaattac 1920
taccccggcg ccagcatcta cgagaacgaa agagcctcta gagacagcga gttccaaaac 1980
gaaatcctca agcgcgctga gcagaacgga gtgacattcg acgagaacat taagcggatc 2040
accgccagcg gcaagtacag cgtccagttc cagaaactgg aaaacgacac cgattctagc 2100
ctggaaagga tgaccaaggc cgtggaaggc ctggtaacag tgatcggaga ggagaaattc 2160
gagacagttg acatcaccgg ggtgagcagc gatacaaatg aggtgaagtc tctggccaag 2220
gaactgaaaa ccaacgccct gggagtcaag ctgaagctgt aa 2262

<210> SEQ ID NO 50
<211> LENGTH: 2241
<212> TYPE: DNA
<213> ORGANISM: Artificial Sequence
<220> FEATURE:
<223> OTHER INFORMATION: armY-HLA class II histocompatibility antigen, DR alpha chain fusion protein codon-optimized (for human)

<400> SEQUENCE: 50
atgtaccgga tgcagctgct gtcatgcatc gccctgagcc tcgctctggt taccaatagc 60
atcaaggaag agcacgtgat catccaggcc gagttctacc tgaatcctga tcagagcgga 120
gagttcatgt tcgacttcga cggcgatgag atctttcatg tggacatggc caaaaaggaa 180
accgtgtggc ggctggaaga gtttggccgg ttcgcctcct tcgaggccca gggagctttg 240
gccaatatcg ccgtggacaa ggccaatctg gagatcatga ccaagcggag caactacacc 300
cctatcacca acgtgccacc tgaggtgaca gtgctgacca atagccccgt ggagctgcgg 360
gaacctaacg ttctgatctg cttcatcgac aagtttacac cccccgtggt gaatgttaca 420
tggctgagaa acgggaagcc tgtgaccaca ggagtgtccg agacagtgtt cctgcctaga 480
gaagaccacc tgttccggaa gttccactac ctgcccttcc tgccttccac cgaggacgtg 540
tacgattgta gagtggaaca ctggggcctg gacgagcctc tcctgaagca ctgggagttt 600
gacgcaccat cccctctgcc tgagacaacc gaaggcggag gcggctccgg cggcggaggt 660
agcggaggcg gcggcagcac caacctggtc aaccagtccg gatacgccct ggtggccagc 720
ggcagatctg gcaatctcgg cttcaagctt ttcagcacgc agtcccctag cgccgaagtg 780
aaactgaaat ctctgtctct gaacgacggc agctaccaga gcgagatcga cctgagcggc 840
ggcgccaatt tcagagagaa gtttcggaac ttcgccaacg agctgtccga ggctattacc 900
aacagtccaa agggactgga tagacctgtg cccaagaccg agatcagcgg cctgatcaag 960
acaggcgaca acttcatcac ccctagcttc aaggccggct actacgacca cgtggcttct 1020
gatggctctc tactgagcta ctaccagagc acagaatact ttaacaatag agtgctgatg 1080
cctatcctgc agaccactaa cggcaccctg atggccaaca acagaggcta cgacgacgtg 1140
ttcagacaag tgccttcttt tagcggatgg tccaacacga aggccaccac agtgtctaca 1200
tctaacaacc tgacatatga caagtggacc tacttcgccg ccaagggcag ccctctgtac 1260
gacagctatc ctaatcactt cttcgaggat gtgaaaacac tggctatcga cgcgaaagac 1320

```
attagcgccc tgaagaccac catcgatagc gaaaagccca cctacctgat catcagaggc   1380

ctctctggca acggctctca gctgaacgag ctgcaacttc cggagagcgt gaagaaagtg   1440

tccctgtacg gcgactacac cggcgtgaac gtcgctaaac agatctttgc caacgtcgtg   1500

gaactggaat tctatagcac cagcaaggcc aacagcttcg gcttcaaccc cctggtgctg   1560

ggaagcaaga ccaacgtgat ctatgacctc tttgcttcta aacctttcac ccacatcgac   1620

ctgacccagg tcacactgca gaacagcgac aacagcgcca tcgacgccaa caagctgaag   1680

caggctgtgg gcgatatcta caactaccgt agattcgagc gccagttcca gggctatttc   1740

gccggcggct acatcgacaa gtacctggtg aagaacgtga acacaaacaa ggacagcgac   1800

gatgatctgg tctacagaag cctgaaggag ctgaacctgc acctggaaga agcctacaga   1860

gagggcgata acacctacta cagggttaat gagaattact accccggcgc tagcatctac   1920

gagaacgagc gcgccagcag agattctgaa ttccaaaacg agatcctgaa aagagccgaa   1980

cagaacggcg tgacattcga tgagaacatc aagcggatca cagccagcgg caagtacagt   2040

gtgcagtttc agaaactgga aaacgacacc gacagcagcc tggagagaat gaccaaggcc   2100

gtggaaggcc tggtgaccgt gatcggcgag gaaaagttcg aaaccgttga cattaccggc   2160

gtgtctagcg ataccaacga ggtgaagagc ctggccaagg agctgaagac aaacgccctg   2220

ggggtgaagc tgaagttata a                                              2241
```

<210> SEQ ID NO 51
<211> LENGTH: 1950
<212> TYPE: DNA
<213> ORGANISM: Artificial Sequence
<220> FEATURE:
<223> OTHER INFORMATION: armY-T cell receptor beta variable 7-9 fusion
      protein codon-optimized (for human)

<400> SEQUENCE: 51

```
atgtaccgca tgcagctgct gagctgcatc gccctgagcc tcgccctggt gaccaacagc     60

ggcgttagcc agaacccccg gcacaagatt accaagcggg gccagaacgt gaccttcaga    120

tgtgacccca tcagcgaaca caaccggctg tactggtaca gacagacact gggccaagga    180

cctgagttcc tgacctactt ccagaacgaa gcccagctgg agaaatctag actgctttcc    240

gatagattca gcgccgagag gcctaagggc tcttttagca cactggagat ccagagaaca    300

gagcagggcg atagcgcaat gtacctgtgc gccagcagcc tgggcggcgg cggcagcggc    360

ggaggcggct ccggcggcgg cggatctacc aacctggtga accagtctgg ctacgccctg    420

gtggcctctg gtagaagcgg caacctgggc tttaagctgt ttagcacaca gagtccctct    480

gccgaggtga agctgaagag cctgtccctg aacgacggca gctatcagtc cgagatcgat    540

ctgagtggcg gagctaactt ccgggaaaag ttcagaaact tcgccaatga gctgtctgaa    600

gccatcacca atagccctaa gggcctggac agacctgtgc ctaagaccga gatttctggc    660

ctgatcaaga caggtgataa tttcatcacc cctagcttta aggctggcta ctacgaccac    720

gtggccagcg atggaagcct gctgagctac taccagtcca ccgagtactt caacaacaga    780

gtgctcatgc ctatcctgca aaccacaaac ggaacactga tggccaacaa cagaggatat    840

gatgacgtgt tcagacaggt gccatctttt tccggctgga gcaacaccaa ggccaccacc    900

gtgtctacaa gcaacaacct gacatatgac aagtggacct acttcgccgc caagggctcc    960

ccactgtacg acagctaccc taaccacttc ttcgaggacg taaagacact ggctatcgat   1020

gccaaagaca tcagcgcctt aaagaccacc atcgacagcg agaagcccac ctacctgatc   1080
```

atcagaggac tgagtggcaa cggcagccag ctgaatgaac tgcagctgcc tgaatctgtg 1140
aagaaggtgt ccctgtacgg cgactacacc ggagtgaacg tggccaagca gatcttcgct 1200
aatgtggtcg agctggaatt ctacagcacc agcaaggcca atagcttcgg cttcaaccct 1260
ctggtcctcg gctctaagac caacgtcatc tacgacctat tcgctagcaa gcctttcacc 1320
cacatcgacc tgacccaggt gaccctgcag aacagtgaca atagcgccat cgacgccaac 1380
aagctgaagc aagccgtggg ggacatctac aactaccgga gatttgagcg gcagttccag 1440
ggctatttcg ctggcggata catcgacaag tacctggtga aaaacgtgaa tacaaacaag 1500
gacagcgacg acgatctggt gtaccgctct ctgaaggaac tgaacctgca tctggaagag 1560
gcctacagag agggcgataa tacctactac cgggtgaacg agaactacta ccccggcgcc 1620
tccatctacg agaacgaacg ggccagccgg gacagcgaat tccaaaacga gatcctgaaa 1680
agagctgaac agaatggcgt gaccttcgac gagaacatca agagaatcac cgcctccggc 1740
aagtacagcg tgcagttcca gaagctggaa aatgacactg attctagctt ggaaagaatg 1800
acaaaagccg tggaaggcct ggtcacagtg atcggcgagg aaaagttcga gacagtggac 1860
atcacaggcg tgagcagcga taccaacgag gtgaaaagcc tggctaaaga gctgaagacc 1920
aacgccctgg gcgttaaact gaaactgtaa 1950

<210> SEQ ID NO 52
<211> LENGTH: 1947
<212> TYPE: DNA
<213> ORGANISM: Artificial Sequence
<220> FEATURE:
<223> OTHER INFORMATION: armY-T cell receptor beta variable 19 fusion protein codon-optimized (for human)

<400> SEQUENCE: 52
atgtatagaa tgcagctgct gtcctgcata gccctgtctc tggctctggt gaccaactct 60
gggatcaccc agtccccaaa gtacttgttt agaaaggagg gccagaacgt caccctgtct 120
tgtgaacaga acctcaacca cgacgccatg tactggtacc ggcaggaccc tggacagggc 180
ctgagactga tctactacag ccaaatcgtt aatgatttcc aaaagggaga tattgctgag 240
ggctacagcg tgtccagaga aaagaaagaa agcttccctc tgaccgtgac cagcgcccag 300
aagaacccta ccgccttcta cctgtgcgcc tccagcattg gcggcggcgg cagcggaggc 360
ggaggcagcg gaggcggcgg ctcaacaaac ctggttaacc agtccggcta cgccctggtc 420
gcctccggaa gaagcggcaa cctcggcttc aagctgttca gcacccagag cccttccgcc 480
gaggtgaagc tgaagagcct gagcctgaac gacggcagct accagagcga gatcgacctg 540
tctggcggag ctaatttccg cgagaagttc agaaacttcg ccaacgagct gagcgaggcc 600
atcacaaaca gccctaaggg cctggacaga cctgtgccta agacagagat cagcggcctg 660
atcaagaccg gcgataattt catcacacca tcttttaagg ccggatatta cgaccacgtg 720
gccagcgatg gcagcctgct gagctactac cagtctaccg agtactttaa caacagggtc 780
cttatgccaa tcctgcaaac aacaaacggc acactgatgg ccaacaatcg gggctatgat 840
gatgtgttca gacaggtgcc ctctttcagc ggatggtcca acaccaaggc caccacagtg 900
tctaccagca acaacctgac ctacgataag tggacttact tcgccgccaa gggctcaccc 960
ctgtacgaca gctaccctaa ccatttcttc gaagatgtga agacgctggc catcgacgca 1020
aaggacatca gcgccctgaa gaccaccatc gacagcgaaa aacccaccta cctgatcatc 1080
cggggcctaa gcgggaatgg tagccagctg aacgagctgc agctgcctga gagcgtgaaa 1140

```
aaggtgagcc tgtacggcga ctacacaggc gtgaacgtgg ccaaacagat cttcgctaat   1200

gtggtggaac tggaattcta ttctacatcc aaggccaaca gcttcggctt caaccccctg   1260

gtgctgggct ctaaaacaaa cgtgatctac gacctgttcg ctagcaagcc tttcacccac   1320

atcgacctga cccaagtgac cctgcagaat agcgataaca gcgctatcga cgccaacaag   1380

ctgaagcagg ccgtgggaga catctacaat tacagaagat ttgaaagaca gttccagggc   1440

tacttcgccg gcggctacat cgacaaatac ctggtgaaga acgtgaatac caacaaggat   1500

tctgacgacg acctggtcta ccggtctctg aaagagctga acctgcacct ggaagaggcc   1560

taccgggagg gagataacac ctattaccgg gtgaacgaga attactaccc cggcgcctcc   1620

atctatgaga acgagagagc cagcagagac agcgagttcc agaacgagat cctgaaaaga   1680

gccgagcaga acggcgtgac cttcgacgag aacatcaagc ggatcaccgc cagtggcaag   1740

tacagcgtgc agtttcaaaa gctagaaaac gacacagata gcagcctgga aagaatgacc   1800

aaggctgtgg aaggcctggt gaccgtgatc ggcgaggaaa agtttgagac agtggacatc   1860

accggcgtga gctctgacac caatgaggtc aaaagcctgg ctaaggaact gaagaccaac   1920

gccctgggcg tgaagctgaa actctaa                                       1947
```

<210> SEQ ID NO 53
<211> LENGTH: 2700
<212> TYPE: DNA
<213> ORGANISM: Artificial Sequence
<220> FEATURE:
<223> OTHER INFORMATION: armY-Hepatitis A virus cellular receptor 1 fusion protein codon-optimized (for human)

<400> SEQUENCE: 53

```
atgtaccgca tgcagcttct gtcttgtatc gccctgagcc tggcgctggt caccaacagc     60

agcgtgaaag ttggcggaga ggccggtcct agcgtcaccc tgccttgcca ctactctggc    120

gctgtgacca gcatgtgctg gaaccggggc agctgtagcc tgttcacctg ccagaatggc    180

atcgtgtgga caaacggtac acacgtgaca tacagaaagg acacaagata caagctgctg    240

ggcgacctgt caagacggga tgtgtctctg accatcgaga acaccgctgt ttccgacagc    300

ggcgtgtact gctgcagagt ggagcacaga ggctggttca atgacatgaa gatcaccgtg    360

agcctggaga tcgtgcctcc aaaggtgacc accacgccta tcgtgacaac cgtacctaca    420

gtgaccaccg tgcggaccag cacaaccgtg cctaccacca ccaccgtgcc catgaccacg    480

gtgcccacca caaccgtgcc aaccaccatg agcatcccca ccacgacaac agtgctgaca    540

accatgaccg tttctacaac aacatcagtg cctaccacaa caagcattcc cacaaccaca    600

agcgtgcctg tcacaacaac cgtgtccaca ttcgtgcctc ctatgcccct gcctagacag    660

aatcacgagc ctgtggctac ctctcctagc tcccctcagc ctgccgagac acaccctact    720

accctgcagg gcgccatccg gagagaaccc accagcagcc ctctgtatag ttacaccacc    780

gacggcaatg ataccgtgac cgaaagcagc gatggactgt ggaacaacaa ccaaacacag    840

ctgttcctgg aacattccct gctgacagcc aatacaacca agggcatcta cgccggagtg    900

tgcatctccg tgctggtcct gctggcactg ctgggagtta tcatcgccaa gaagtacttt    960

ttcaagaagg aagtgcagca gctgagcgtg agcttctcca gcctgcagat caaagctttg   1020

cagaacgccg tggaaaagga agtgcaagcc gaagataaca tctacatcga gaactccctg   1080

tacgccaccg atggcggcgg aggctccggc ggcggaggaa gcggcggcgg cggctccaca   1140

aatctggtga accagagcgg gtacgccctg gtggccagcg gcagaagcgg aaatctgggc   1200
```

-continued

```
ttcaagctgt ttagcaccca gagcccttct gccgaggtga aactgaaaag cctgtccctc   1260

aacgacggca gctaccagag cgagattgac ctgagcggcg gagccaattt cagagagaag   1320

ttccgcaact tcgctaacga gctgtctgaa gcaatcacaa actcccctaa gggactggat   1380

agacccgtgc ctaaaaccga gatcagcggc ctgatcaaga ctggagacaa tttcatcacc   1440

cctagcttta aggccggcta ctatgaccac gttgcctccg acggcagcct gctgagctac   1500

taccagtcta cagagtactt taacaacaga gtgctgatgc ctattctgca gacaactaac   1560

ggcacactga tggccaacaa tcggggctac gatgacgtgt tcagacaagt gcccagcttt   1620

agcggctgga gcaacaccaa ggctactacc gtgtctacca gcaacaacct gacctacgac   1680

aagtggacct acttcgccgc taagggctcc ccactgtatg acagttaccc caaccacttc   1740

ttcgaggacg taaagaccct ggccattgac gccaaggata tcagcgccct gaaaaccacc   1800

atcgacagtg agaagcccac ctacctgatc atccggggcc tgagcggcaa cggctctcag   1860

cttaacgagc tgcagctgcc tgagagcgtg aaaaaggtga gtctatacgg cgactacacc   1920

ggcgtgaacg tggccaaaca gatcttcgcc aacgtggtgg agctggaatt ctacagcacc   1980

agcaaggcca actctttcgg cttcaacccc ctcgtgctgg gctccaagac aaacgtgatc   2040

tacgacctgt ttgcttctaa acctttcacc cacatcgacc tcacccaggt gaccctgcaa   2100

aatagcgata acagcgccat cgacgccaac aagctgaagc aggctgttgg agatatctat   2160

aactaccgga gattcgaaag acagttccaa ggctatttcg ccggcggcta catcgacaaa   2220

tacctggtga aaaacgtgaa taccaacaag gacagcgacg atgacctggt gtacagatct   2280

ctgaaggagc tgaacctgca cctggaagag gcctacagag aaggcgacaa cacatactac   2340

agagtgaacg agaactacta cccaggagct tctatctacg agaatgaaag agccagcaga   2400

gactctgagt tccagaacga gatcctgaag cgggccgagc agaacggcgt gaccttcgac   2460

gagaatatca agagaatcac cgcctccggc aagtacagcg tgcagtttca gaagctggaa   2520

aacgatacag actccagcct ggaacggatg acaaaggccg tggagggcct ggtgaccgtg   2580

atcggcgagg aaaaattcga aaccgtggac atcaccggcg tctccagcga taccaacgag   2640

gtgaagagcc tggccaagga actgaagacc aacgccctgg gagtgaagct gaagctataa   2700
```

<210> SEQ ID NO 54
<211> LENGTH: 2127
<212> TYPE: DNA
<213> ORGANISM: Artificial Sequence
<220> FEATURE:
<223> OTHER INFORMATION: armY-Myelin and lymphocyte protein fusion
      protein codon-optimized (for human)

<400> SEQUENCE: 54

```
atgtacagaa tgcagctgct gagctgcatc gccctgtccc tggccctggt gaccaatagc     60

atggcccctg ccgccgctac cggcggtagc acactgccta gcggcttcag cgtgtttaca    120

acactgcctg acctgctctt tatcttcgag ttcatcttcg gcggcctggt gtggatcctg    180

gtggcctcta gcctggtccc ttggcccctg gtgcagggct gggtcatgtt cgtgtccgtg    240

ttctgcttcg tggcaacaac cacactgatc atcctgtaca ttatcggcgc ccacggtggc    300

gagacaagct gggtgacact ggacgccgct tatcattgta ccgccgctct gttttacctg    360

tcagcaagcg tgctggaagc ccttgccacc atcaccatgc aggatggctt tacctacagg    420

cactaccacg agaacatcgc cgccgtggtg ttctcctaca tcgccacact gctgtatgtc    480

gtgcacgccg tgttcagcct gattagatgg aagtccagcg gcggcggcgg atctggcgga    540
```

```
ggcggaagcg gcggcggagg ctctaccaac ctggtgaacc agagcggata cgccctggtg    600

gcctctggca gaagcggaaa cctgggcttc aaactgttca gcacccagtc cccaagcgcc    660

gaggtgaaac tgaagagcct gagcctgaat gacggcagct accagagcga gattgacctc    720

tctggtggag ccaatttcag agagaagttc cggaacttcg ccaacgaact gtctgaagcc    780

atcaccaaca gcccaaaagg cctcgataga ccagtgccca agaccgaaat cagcggactg    840

atcaagaccg gcgataattt cattacccct agctttaagg ctggctatta cgaccacgtg    900

gcttctgacg gcagcctgct gagctactac cagagcaccg agtactttaa caatagagtg    960

ctgatgccta tcctgcagac caccaacggc accctgatgg ccaacaacag aggttacgac   1020

gacgtgttca gacaggtgcc tagcttcagc ggctggtcca acaccaaggc gactaccgtc   1080

tccacaagca acaacctgac ctacgataag tggacctact tcgccgcaaa gggctctcct   1140

ctgtacgaca gctaccccaa ccacttcttc gaagatgtga agaccctggc tatcgatgct   1200

aaagatatca gtgccctgaa gacaacaatc gacagcgaga aacctaccta cctgatcatc   1260

agaggcctga gcggaaatgg ctcgcagctg aacgagctgc agctgcctga gtccgtgaaa   1320

aaggtgtccc tctacggcga ctataccggc gtgaacgttg ccaagcagat ctttgctaat   1380

gtggttgagc tggagttcta cagcacctct aaggccaatt cttttggctt caacccccctg   1440

gtgctgggca gcaagaccaa cgtgatctac gacctgttcg ccagcaagcc cttcacccac   1500

atcgatctca cccaagtgac actgcaaaac tccgacaaca gcgccatcga cgccaacaag   1560

ctgaagcagg ccgtgggcga tatctacaac tacagacggt tcgagagaca gttccaggga   1620

tatttcgccg gcggctacat cgacaagtac ctggtcaaga acgtgaacac gaacaaggat   1680

agcgatgacg acctggtgta ccggagcctg aaggaactga acctgcacct ggaagaggct   1740

taccgggaag gcgacaacac ctactaccgc gtgaatgaaa actactaccc tggcgccagc   1800

atctacgaga acgagcgggc ctcccgggac agcgaattcc agaatgaaat cctgaaaaga   1860

gccgagcaga acggggtgac cttcgacgag aacatcaagc ggatcaccgc cagcggcaag   1920

tactccgtgc agttccaaaa gctggaaaac gataccgaca gcagcctgga aagaatgact   1980

aaggccgtcg agggcctggt tacagtgatc ggcgaggaaa aatttgagac agtggacatc   2040

acaggcgtca gcagcgacac aaacgaggtg aagtctctgg ccaaggagct gaagaccaac   2100

gcccttggag ttaagctgaa gttataa                                       2127
```

<210> SEQ ID NO 55
<211> LENGTH: 5307
<212> TYPE: DNA
<213> ORGANISM: Artificial Sequence
<220> FEATURE:
<223> OTHER INFORMATION: armY-Complement factor H fusion protein codon-
optimized (for human)

<400> SEQUENCE: 55

```
atgtacagaa tgcagctgct gtcctgcatc gccctgtctc tggccctggt taccaattca     60

gaagattgca acgagctgcc tcctcggcgg aacaccgaaa tcctgaccgg atcctggagc    120

gaccagacat accccgaggg cacccaggcc atttacaagt gtcggcctgg ctacaggtca    180

ctggggaacg ttatcatggt gtgccggaaa ggcgagtggg tggccctgaa ccctctgcgg    240

aagtgccaga aacggccatg tggccaccct ggcgacaccc ctttcggaac cttcaccctc    300

acaggtggca acgtctttga gtacggcgtg aaagccgttt acacatgcaa tgagggatac    360

cagctgctcg gagagatcaa ctacagagag tgtgataccg acggatggac caacgacatc    420
```

-continued

```
cccatctgtg aagtggtgaa gtgcctccct gtcacagccc ctgaaaacgg caagatcgtg    480
tcttctgcta tggagcctga tagagaatat cactttggcc aggccgtgag attcgtgtgc    540
aactctgggt acaaaatcga gggagatgag gaaatgcact gctctgatga cggcttctgg    600
agcaaggaaa agcctaagtg cgtggagatc agctgcaaga gtcctgacgt gatcaacggc    660
tcccctatct cacagaagat catttacaag gagaacgaaa gattccagta caaatgtaac    720
atgggatacg agtactctga aagaggtgat gccgtttgta ctgaatccgg ctggcggcct    780
ctgcctagct gcgaggagaa gagctgtgac aatccttaca tccccaatgg agattacagc    840
cctctcagaa tcaagcaccg caccggcgac gagatcacct accagtgtcg caacggattt    900
taccccgcta cccggggcaa caccgccaag tgtacctcca caggctggat ccctgccccc    960
agatgcaccc tgaaaccctg cgactaccct gatatcaagc acggcggcct gtatcacgag   1020
aacatgagaa gaccttactt ccctgtggcc gtgggcaagt actactctta ttactgcgat   1080
gaacactttg aaacccctag cggcagctac tgggatcaca tccactgtac ccaggatggc   1140
tggtctccag ctgtgccatg tctgcgcaag tgctacttcc cctacctgga aaacggctac   1200
aaccagaact acggtagaaa gttcgtgcag ggcaagtcta tcgacgtggc atgccacccc   1260
ggctacgccc tacctaaggc tcagaccaca gtgacctgta tggaaaacgg ttggtctccc   1320
accccacgct gcatccgggt gaagacctgc tccaagtctt ctatcgatat tgaaaacggc   1380
ttcatctctg aatcccaata cacctatgct ctgaaggaaa aggccaagta ccagtgtaag   1440
ctgggatacg tgaccgccga cggcgagaca tctggctcca tcacctgtgg caaggacggc   1500
tggagcgcac agcccacatg cattaagtct tgcgacatcc cggtgttcat gaacgccaga   1560
accaagaacg atttcacctg gttcaagctg aacgacacac tggattacga gtgtcacgac   1620
ggatatgaaa gcaataccgg cagcaccacc ggcagcatag tgtgcggcta caacggctgg   1680
agcgatctgc ccatctgcta cgaaagagaa tgcgagctgc ctaagatcga tgtgcacctg   1740
gtgcccgatc ggaagaagga ccagtacaag gtgggcgaag tgctgaagtt tagctgcaag   1800
cccggattca caatcgtggg accaaattct gtgcagtgct accacttcgg cctgagcccc   1860
gacctgccca tctgcaagga acaagtgcag agctgtggac ctcctcctga gctgctgaac   1920
ggaaacgtga aagagaagac aaaggaggag tacggccatt ctgaggtggt cgagtactac   1980
tgtaacccta gattcctgat gaagggccct aacaagatcc aatgcgtgga cggagagtgg   2040
accaccctgc ccgtttgcat agtggaggaa agcacctgtg gcgacatccc ggaactggaa   2100
cacggctggg cccagctgag cagccctccc tactactacg gcgattctgt cgaatttaac   2160
tgtagcgagt cattcaccat gatcggccat agaagcatta cttgcatcca cggagtgtgg   2220
actcagttac ctcagtgcgt tgccatcgac aagctgaaga agtgtaaatc tagcaacctg   2280
atcattctgg aagaacacct gaagaacaag aaagaattcg accacaattc aaacatcaga   2340
tacagatgcc ggggcaaaga gggctggatc cacaccgtgt gcatcaacgg cagatgggac   2400
cccgaggtga actgcagcat ggcccagatc cagctgtgtc ctcctccccc ccagatccca   2460
aacagccaca acatgaccac cacgctgaac taccgagacg gcgagaaggt gagcgtgctg   2520
tgccaggaga actacctgat ccaggagggc gaagagatca catgtaagga cggtcgttgg   2580
cagagcatcc ccctgtgcgt tgaaaagatc ccctgcagcc agcctcctca aatcgagcac   2640
ggcaccatca acagctccag atcctcccag gagtcctacg cccacggcac aaaactgagc   2700
tacacatgcg aaggcggatt ccggatttct gaagagaacg agaccacctg ctacatgggc   2760
```

```
aagtggagct ctccccctca atgtgagggc ctgccttgca agagccctcc tgagatcagc   2820
cacggcgtgg ttgcccacat gtctgatagc taccaatacg gcgaggaagt gacttataag   2880
tgcttcgagg ggtttgggat cgatggtccc gccattgcca agtgcctggg agaaaaatgg   2940
tctcatccac catcatgtat caagaccgac tgcctgagtt tgcctagctt tgagaatgct   3000
atccctatgg gcgagaagaa ggacgtatac aaagccggcg agcaggtgac atacacatgt   3060
gccacctact acaaaatgga cggcgccagc aatgtaacgt gtataaatag cagatggaca   3120
ggcagaccta cctgcagaga tacaagctgc gtgaatcctc ccacagtcca aaatgcttat   3180
atcgtgagtc ggcagatgag caagtaccct agcggcgaga gagtgagata ccagtgcagg   3240
tcccccctacg agatgttcgg cgacgaggag gtgatgtgcc taaacggcaa ctggacggaa   3300
cctcctcagt gcaaagacag caccggaaaa tgcggccctc ctcctcctat tgacaacggc   3360
gatatcacca gctttccact gagcgtgtac gctcctgctt catctgtcga gtaccaatgc   3420
cagaatctgt accagctgga aggtaataag agaatcacct gcagaaacgg acagtggagc   3480
gaacctccta agtgcctgca cccttgcgtg atctccagag agatcatgga aaactacaac   3540
atcgccctga gatggaccgc caaacagaag ctgtacagcc ggaccggcga gagcgtcgag   3600
ttcgtgtgta agagaggtta ccgactgtcc tctagaagcc ataccctgcg gaccacctgc   3660
tgggacggca aactagagta ccctacgtgc gccaagcggg gcggaggtgg ctcaggaggc   3720
ggcggctctg gcggcggcgg ctctacaaac ctggtgaacc agagcggtta tgccctggtg   3780
gccagcggca ggtctggaaa tctgggcttt aagctgtttt caacgcagag cccttccgcc   3840
gaagttaagc tgaaatcact gagcctgaat gacggctcct accagagcga gatcgacctg   3900
tctggaggag ctaactttag agagaagttc aggaacttcg ctaacgagct gagcgaagcc   3960
atcaccaata gccctaaagg cttggacaga cctgtgccca agactgagat cagcggcttg   4020
atcaagaccg gcgacaactt catcacccca tcttttaagg ccggctacta cgaccacgtg   4080
gcctctgacg gaagcctgct atcctactat cagtctactg agtacttcaa caacagagtg   4140
ctgatgccta tcttgcagac caccaatggc accctgatgg ccaacaaccg gggatatgac   4200
gatgtgttca gacaggtgcc tagcttcagc ggatggagca acaccaaggc gacaaccgtg   4260
agcacatcca acaacctgac atacgacaag tggacatatt ttgcggccaa gggctctcca   4320
ctgtatgata gctaccccaa tcacttcttc gaggacgtga agaccctggc catcgacgcc   4380
aaagacatca gcgcccttaa gacaacgatc gattccgaga agcctaccta cctgatcatt   4440
agaggcctga gcggcaacgg cagccagctg aacgagctgc agctgccaga gtccgtgaag   4500
aaagtgtccc tgtatggcga ctacacaggc gtcaacgtgg ccaagcaaat cttcgctaat   4560
gtggtggaac ttgagttcta cagcacatcg aaggctaact ctttcggctt caaccccctg   4620
gtgctgggca gcaagaccaa tgtgatttac gacctgttcg ccagcaagcc cttcacacac   4680
atcgacctga cccaagtgac actgcaaaac agcgataaca gcgccatcga cgccaacaag   4740
ctgaagcagg ctgtgggcga catctacaac taccggagat tcgagagaca gttccagggc   4800
tacttcgccg gcggctacat cgataagtac ctggtgaaga acgtgaatac caacaaagac   4860
tctgatgacg acctggtgta cagaagcctg aaagagctga acctgcatct ggaagaagcc   4920
taccgggagg gcgataacac ctactaccgg gtgaacgaaa actactatcc tggcgctagc   4980
atctacgaga acgaacgagc cagcagggat tctgaattcc agaacgagat cctgaagcgg   5040
gccgagcaga acggagtgac atttgatgag aacatcaaac ggatcaccgc cagcggcaaa   5100
tactccgttc agttccaaaa actggaaaat gatacagaca gcagcctgga gagaatgacc   5160
```

aaggccgtgg aaggcctggt gacggtgatc ggcgaagaga aattcgagac cgtggacatc 5220
accggcgtaa gctctgacac caacgaagtg aagagcctgg ctaaggaact gaagaccaac 5280
gccctggggg tcaagctgaa gctgtaa 5307

<210> SEQ ID NO 56
<211> LENGTH: 4392
<212> TYPE: DNA
<213> ORGANISM: Artificial Sequence
<220> FEATURE:
<223> OTHER INFORMATION: armY-Hepatocyte growth factor receptor fusion
protein codon-optimized (for human)

<400> SEQUENCE: 56
atgtaccgga tgcaactgct gagctgcata gccttatctc tggcactggt gaccaacagc 60
gagtgcaagg aagccctcgc caagagtgaa atgaacgtga atatgaaata ccagctgcct 120
aacttcaccg ccgaaacccc tatccagaac gtcatcctgc atgagcacca catcttcctg 180
ggcgctacaa attacatcta cgtgctgaat gaggaggact tgcagaaagt cgccgaatac 240
aagaccggac ccgtgctgga gcacccggac tgcttcccat gtcaggattg cagttctaag 300
gccaacctga gtggtggcgt ttggaaggac aacatcaaca tggccctggt ggtcgacaca 360
tattacgacg atcagctgat tagctgtggc agcgtgaacc ggggcacctg ccagagacac 420
gtgttccctc acaaccacac tgccgacatc cagagcgaag tgcactgcat cttcagcccc 480
cagatcgagg agcctagcca gtgtcctgac tgcgtggtgt cagccctggg tgctaaggta 540
ctgtccagcg ttaaggacag attcatcaac tttttcgtgg gtaacacaat caacagcagc 600
tacttccccg atcaccctct gcacagcata tccgtgcgga gactcaagga aacaaaggac 660
ggcttcatgt tcctgacaga ccagagctat atcgatgtgc tgcctgagtt cagagattct 720
taccccatca agtacgtgca cgccttcgag agcaacaatt ttatctattt cctgacagtc 780
caaagggaga cactcgatgc ccagaccttc cacaccagaa tcatccggtt ctgcagcatt 840
aacagtggac tgcactctta tatggaaatg cccctggaat gtatcctcac agagaaaagg 900
aagaaaagaa gcactaagaa ggaggtgttc aacattctgc aggctgctta cgtgtccaag 960
cctggcgctc agctggccag acagatcggc gccagcctga acgatgacat cctgttcggc 1020
gtcttcgccc aatctaagcc tgacagcgcc gagcccatgg acagatctgc tatgtgcgct 1080
ttccccatca agtacgtgaa tgacttcttc aacaagatcg tgaacaagaa caacgtgcgg 1140
tgcctgcaac acttctacgg ccctaaccac gagcactgtt ttaatagaac cctactgcgg 1200
aactcctctg gttgtgaagc tagaagagac gaataccgga ccgagttcac caccgccctg 1260
cagagggtgg acctgttcat gggccaattc agcgaggtcc tgctgacatc tataagcacc 1320
ttcatcaagg gagatctgac aatcgccaac ctgggcacca gtgagggcag attcatgcag 1380
gtggtggtga gtagatccgg ccctagtaca ccccatgtta acttcctgct ggactcacac 1440
cccgtgtccc ctgaggtgat cgtggaacat acactgaacc agaatggcta tacactggtg 1500
atcaccggaa agaagattac caagattcct ctgaacggcc tgggctgcag acacttccag 1560
agctgtagcc agtgcctgag cgcccctcct tttgtgcagt gcggctggtg ccacgacaag 1620
tgcgtgcgca gcgaggagtg cctgagcggc acctggacac agcagatctg tctgcctgcc 1680
atctacaagg tctttccaaa cagcgcccca ttggaaggcg gaactcggct gacaatctgc 1740
ggctgggact tcggctttcg gcggaacaac aagtttgacc tgaagaagac ccgggtgctg 1800
ctgggcaacg agagctgtac cctgaccctg agcgaaagca ccatgaacac gctgaaatgc 1860

```
accgtgggcc cagccatgaa caaacacttc aacatgtcta tcatcatcag caatggccac   1920
ggcacaaccc agtacagcac gttcagctac gtggaccctg tgatcaccag catctcaccg   1980
aagtacggcc ctatggccgg cggcacattg ctgaccctga ccggaaatta tctgaactcg   2040
ggcaacagcc gtcacatctc cataggcgga aagacatgca cgctgaagtc ggtgtctaac   2100
agcatcctgg agtgctacac accagcccag accatctcga cagaattcgc tgtaaagctg   2160
aagatcgatc tcgctaatcg agagacaagc atcttttctt acagagagga tcctatcgtg   2220
tacgagatcc accctacaaa gtctttcatc agcggcggca gcaccatcac aggcgtggga   2280
aaaaacctga actctgtgtc tgtgccgaga atggtgatca acgtgcacga ggctggcaga   2340
aacttcacag tggcctgcca gcatagaagc aacagcgaaa tcatctgctg caccaccccc   2400
tcgctgcagc agcttaatct gcagctgccc ctgaaaacga aggccttctt catgctggat   2460
gggatcctgt ctaagtactt cgatctcatc tacgtgcaca atcctgtgtt taagccattc   2520
gagaagcccg tcatgatctc tatgggcaac gagaacgtgc tcgagatcaa gggcaatgat   2580
atcgaccctg aggccgtgaa aggcgaggtg ctgaaagtgg gcaacaaaag ctgcgaaaac   2640
atccacctgc acagcgaagc cgtgctgtgc accgtgccta acgacttgct gaagctgaac   2700
tccgagctga atatcgagtg gaagcaggcc atcagctcta ccgtcctggg caaggtgatt   2760
gtgcaacctg accagaactt caccggcggt ggcggtagtg gaggcggcgg gagcggaggc   2820
ggaggaagca ccaacctggt gaaccagagc gggtacgccc tggtagctag cggcagaagc   2880
ggcaacctgg gctttaagct gttttctacc cagagcccta gcgccgaagt gaagctgaag   2940
agcctgagcc tgaacgacgg cagttaccaa tccgagatcg acctgtctgg cggcgccaac   3000
ttcagagaga agttcagaaa cttcgctaat gagctgtctg aggccatcac caacagccct   3060
aagggcctgg atagacctgt gccaaagacc gagatctccg gcctgatcaa aaccggcgat   3120
aactttatca cacctagctt taaggccggc tactacgacc acgtggcctc cgacggctcc   3180
ctgctgtcct actaccagag cacagaatac ttcaacaaca gagtgctgat gcctatcctg   3240
caaaccacaa acggcaccct gatggccaac aacagaggct acgacgatgt gttccggcag   3300
gtgcctagct tctccggctg gagcaacacc aaggccacta ccgtttctac cagtaacaac   3360
ctgacctacg ataagtggac ctactttgcc gccaagggca gccccctgta cgactcatac   3420
cccaatcact tctttgaaga tgtgaagacc ctggccatcg atgccaaaga tatcagcgct   3480
ctgaaaacaa ccatcgactc cgagaagccc acctacctta ttatcagagg cctgtccggc   3540
aacggctctc agctgaatga gctgcagctc ccagaaagcg tgaagaaggt gtcgctgtac   3600
ggcgactaca ccggcgtcaa tgtggccaaa cagatatttg ccaacgtagt agaattggaa   3660
ttctactcta caagcaaagc caactctttt ggatttaacc ccttagtgct aggatctaag   3720
acaaacgtga tctacgacct gttcgccagc aaacctttca cccacatcga cctgacccaa   3780
gtgaccctgc agaacagcga caacagcgct atcgacgcca acaagctgaa gcaggccgtc   3840
ggcgatatat acaattaccg gcggttcgag agacagttcc agggctactt cgccggagga   3900
tacatcgaca agtacctggt gaagaacgtg aacactaata aggacagcga cgacgacctc   3960
gtgtacagaa gcctgaaaga actgaatctg cacctggaag aagcctaccg ggaaggagac   4020
aacacctact acagagtgaa cgaaaactac taccctggcg ccagcatcta tgagaacgag   4080
agagccagca gagattctga attccagaac gagattctga aacgggccga gcagaatggc   4140
gtgaccttcg acgagaatat taagcgcatc accgccagcg gcaaatattc cgtccagttt   4200
```

cagaagctcg agaacgacac cgacagcagc ctggaaagaa tgaccaaggc cgtggaaggc 4260
ctggtgaccg tgatcggcga ggaaaaattc gagaccgtgg atatcaccgg cgtgagcagc 4320
gacacaaacg aagtgaagag cctggccaag gaactgaaga ccaacgccct gggagtgaag 4380
ctcaagctgt aa 4392

<210> SEQ ID NO 57
<211> LENGTH: 2595
<212> TYPE: DNA
<213> ORGANISM: Artificial Sequence
<220> FEATURE:
<223> OTHER INFORMATION: armY-Membrane cofactor protein (CD46) fusion protein codon-optimized (for human)

<400> SEQUENCE: 57
atgtaccgca tgcagctgct gagctgcatc gccctgtctc tggctctggt gaccaacagc 60
tgcgaggaac ctccaacctt cgaggccatg gaactgatcg gcaagccaaa gccctactat 120
gagattggcg aaagagtgga ttacaaatgc aagaaaggct acttttacat ccccccccctg 180 gccacccaca ccatctgtga tagaaaccac acatggctgc ctgtctccga cgacgcctgt 240
taccgggaga catgccctta catccgagac cctctcaatg gacaggccgt gcctgctaat 300
ggcacatatg agttcggata ccaaatgcac ttcatctgca acgagggcta ctacctgatc 360
ggcgaagaaa tcctgtactg cgagctgaaa ggctcggtgg ctatttggtc cggcaaacct 420
cctatctgtg aaaaggtgct gtgcacccct cctcctaaga tcaaaaacgg caagcacacc 480
tttagcgagg tggaagtgtt cgagtacctg gatgccgtga catatagctg tgaccccgcc 540
cctggccctg atcccttcag cctgattggc gagagcacca tctattgcgg cgataactct 600
gtgtggagcc gggccgcccc tgaatgcaag gtggtgaagt gcagattccc tgtggtggaa 660
aacggaaagc agatctccgg ctttggcaaa aagttctact ataaggctac cgtgatgttc 720
gagtgcgaca agggattcta cctggacggc tctgatacaa tcgtgtgcga cagcaactct 780
acgtgggacc ctccagtgcc taagtgtctg aaagttctgc ctcctagctc tacaaagccc 840
cccgccctga gccacagcgt gtccaccagc agcacaacca agtccccagc cagcagcgcc 900
agcggaccta gacccaccta caagcctcct gtgtccaact accctggcta ccccaagcct 960
gaggaaggca tcctggatag cctggatggc ggcggcggct ccggcggtgg aggatctggc 1020
ggcggaggaa gcacaaatct ggtgaatcag agcggctacg ccctggttgc cagcggcaga 1080
agcggcaacc tgggcttcaa gctgtttagc acacagagcc ccagcgccga ggtgaagctg 1140
aagagcttgt cgctaaatga tggctcctac cagtctgaga tcgatctgag cgggggcgcc 1200
aattttagag agaagttccg gaacttcgca aacgagctgt ctgaagccat caccaacagc 1260
cctaaggggc tggacagacc tgtgccaaag accgagatta gcggcctcat caagacaggc 1320
gacaatttca tcacacctag cttcaaggcc ggatactatg accacgtggc ctccgacggc 1380
agcctgctga gctactacca gagcacagag tacttcaaca acagagtgct gatgcctatc 1440
ctgcagacca ccaacggcac cctcatggcc aacaatcggg gctatgacga cgtgttcagg 1500
caggtgccta gcttcagcgg ctggagcaac accaaggcca ccactgtgtc tacctccaac 1560
aacctgacct acgacaagtg gacctacttc gcagctaaag gctctccact gtacgatagc 1620
tacccaaacc acttcttcga ggacgtgaag accctggcta ttgacgccaa ggacatctct 1680
gccctgaaga ccacaatcga cagcgagaag cctacctacc tgatcatccg ggcctgagc 1740 ggaaacggca gccagctgaa cgagctgcag ctgcccgagt ccgtgaaaaa agtgtccctg 1800

```
tacggcgact acaccggcgt gaacgtggcc aagcagatct tcgctaatgt ggtggaactt   1860

gagttctact ctaccagtaa ggccaactcc tttggattta accccctggt gctgggcagc   1920

aagaccaacg tgatctacga cctgttcgcc tctaaacctt tcacccatat cgacctgacc   1980

caggttacac tgcaaaacag cgataactct gccatcgatg ccaacaagct gaagcaagcc   2040

gtgggcgaca tctacaacta ccgcagattt gaacggcagt tccagggcta cttcgccggc   2100

ggctacatcg acaagtactt ggtcaagaac gtgaatacca acaaggatag cgacgatgac   2160

ctggtctacc ggagcctgaa ggaactgaac ctgcacctgg aagaagccta cagagaaggt   2220

gacaatacct actatagagt gaacgagaac tactacccgg gagccagtat ctacgagaac   2280

gaaagagcct ctagagatag cgagttccaa aacgagatcc tgaaaagagc tgaacagaac   2340

ggcgtgacct tcgacgagaa catcaagaga atcaccgcca gcggcaagta cagcgtgcag   2400

tttcagaagc tggaaaacga caccgacagc tccctggaac ggatgaccaa ggctgttgag   2460

ggcctggtca cagtgatcgg agaggaaaag ttcgaaacag tggatatcac gggcgttagc   2520

agcgacacca acgaggtcaa gagcctggcc aaagagctga agacaaacgc cctgggcgtg   2580

aagctgaagc tgtaa                                                    2595
```

<210> SEQ ID NO 58
<211> LENGTH: 1884
<212> TYPE: DNA
<213> ORGANISM: Artificial Sequence
<220> FEATURE:
<223> OTHER INFORMATION: armY-Glycophorin-A fusion protein codon-
      optimized (for human)

<400> SEQUENCE: 58

```
atgtaccgta tgcagctgct gtcttgcatc gccctcagcc tggctctggt gaccaacagc     60

tctagcacaa caggcgttgc catgcacacc agcaccagct ctagcgtgac caagagttac    120

atctcttctc agaccaacga tacccacaag agagacacgt acgccgccac cccaagagcc    180

catgaggtgt ctgaaatcag cgtgcggacc gtgtaccccc ccgaggaaga aaccggcgag    240

cgggtgcagc tggcccacca cttttctgag cctgagggag gtggaggcag cggcggcggc    300

ggcagcggcg gaggcggcag caccaacctg gttaaccagt ccggctatgc cctggtggct    360

agcggcagat ccggcaacct gggctttaag ctgttcagca cccagagccc cagcgccgag    420

gtgaaactga agagtctgag cctgaatgac ggctcttatc agagcgagat cgacctgagc    480

ggcggcgcca atttcagaga gaagtttcgg aacttcgcca atgaactgtc cgaagccatc    540

accaacagcc caaagggcct ggacagaccc gtgcctaaaa cagaaatcag cggactgatc    600

aagaccggcg ataatttcat cacacctagc ttcaaggccg gctactacga ccacgtggcc    660

agcgacggct ccctcctgag ctactaccaa agcacagagt acttcaacaa ccgggtgctg    720

atgcctatcc tgcagaccac aaatggcacc ctcatggcca ataacagagg ctatgatgac    780

gtgttccggc aggtgcccag ctttagcgga tggagcaaca ccaaggccac aaccgtgtcc    840

acatccaaca acctgaccta cgacaagtgg acctacttcg ctgctaaggg cagccctctg    900

tacgactctt accctaacca cttcttcgag gatgtgaaga cgctggctat cgacgccaag    960

gacatctcgg ccctgaagac cacaatcgac agcgagaagc ctacatacct gatcatcaga   1020

ggactgagcg gcaacggcag ccaactgaat gagctgcagc tgcctgagag cgtgaaaaag   1080

gtgagcctgt acggcgacta taccggcgtg aatgtggcta agcagatctt cgccaacgtc   1140

gtggaactgg aattctacag caccagcaag gctaactcct tcggctttaa cccccctggtg  1200
```

```
ctgggctcca aaacaaacgt gatctacgac ctgttcgcct ccaaaccttt cacccacatc   1260

gacctgacac aagtgacact gcaaaatagc gataacagcg ccatcgacgc caacaagctt   1320

aagcaggccg tgggcgacat ctacaactac agaagattcg agagacagtt tcagggctat   1380

ttcgccggag gctatattga taaatacctg gtgaagaacg tgaacaccaa caaagatagc   1440

gacgacgatc tggtgtacag atctctgaaa gagctgaacc tgcacctgga agaggcctac   1500

cgggaaggag ataacaccta ctacagggtc aacgagaact actaccctgg agccagcatc   1560

tacgagaacg agagagcttc tagagatagc gagttccaga atgaaatcct gaagcgggcc   1620

gaacagaacg gagtgacatt cgacgagaac attaagcgga tcaccgcctc tgggaagtac   1680

agcgtgcagt tccagaagct ggagaacgac accgattctt ctctggaaag aatgaccaag   1740

gcagtcgagg gcctggtgac cgtgatcgga gaggaaaagt tcgagacagt cgacatcact   1800

ggcgtgagct cggacaccaa cgaggtaaag agcctggcca aggaactgaa gaccaacgcc   1860

ctgggcgtga agctcaaact gtaa                                          1884
```

<210> SEQ ID NO 59
<211> LENGTH: 2460
<212> TYPE: DNA
<213> ORGANISM: Artificial Sequence
<220> FEATURE:
<223> OTHER INFORMATION: armY-C-type lectin domain family 4 member K (Langerin, CD207) fusion protein codon-optimized (for human)

<400> SEQUENCE: 59

```
atgtatcgga tgcagctgct gagctgcatc gccttatccc tggctctggt gacaaactcc     60

cctagattca tgggcaccat cagcgacgtg aaaacgaacg tgcagctgct gaagggaaga    120

gtggacaaca tctctaccct ggattctgag atcaaaaaga actccgatgg catggaagct    180

gctggcgtgc aaatccagat ggtgaatgag agcctgggct acgtgcggtc ccagttcctg    240

aagctgaaga ccagcgtgga aaaggccaac gcccagattc agatcctgac aagaagctgg    300

gaggaagtgt ctacactgaa tgctcagatc cccgagctga aaagcgatct cgagaaggct    360

agcgccctga acaccaagat ccgggccttg caaggctctc tggaaaacat gagcaagctg    420

ctgaagagac agaacgatat cctgcaggtc gtgtctcagg gctggaagta cttcaagggc    480

aacttctact actttttctct gatccctaag acctggtact ctgccgagca gttctgcgtg    540

tccagaaaca gccacctgac cagcgttacc agtgagagcg agcaggagtt cctgtataag    600

acagccggag gcctgatcta ttggatcggc ctgaccaagg ccggcatgga gggcgattgg    660

agctgggtcg acgacacccc tttcaacaaa gtgcagagcg tgcggttttg gatccccggc    720

gagcctaaca acgccggcaa caacgagcac tgcggcaata tcaaagcccc tagcctgcag    780

gcctggaacg atgccccgtg cgacaagaca tttctgttca tctgtaaaag gccttacgtg    840

cccagcgaac ccggcggcgg cggcagcgga ggcggcggct ctggcggagg aggaagcacc    900

aacctggtga accagagcgg ctacgccctg gtcgccagcg gcagaagcgg aaatctgggc    960

ttcaagctgt ttagcacaca gagcccatct gcagaggtga aactgaagag cctgagcctg   1020

aacgacggca gctaccagtc tgagatcgac ctgtctggcg gggccaattt ccgggaaaag   1080

ttccggaact tcgctaacga gctgtctgaa gccatcacca atagtccaaa gggcctggac   1140

cggcctgtgc ctaagactga gatttctggc cttatcaaga caggcgacaa cttcatcacc   1200

cctagcttta aggccggcta ctacgaccac gtggccagcg atgggtctct gctgagctac   1260

taccagagca cagagtactt caacaataga gtgctgatgc caatcctgca aacaacaaat   1320
```

```
ggcacactga tggccaacaa ccggggctac gacgatgtgt tcagacaggt tcctagcttc   1380

agcggctggt ccaacaccaa ggccaccacc gtgagcacaa gcaacaacct gacatatgat   1440

aagtggacct acttcgccgc taagggcagc cctctgtacg acagctaccc taaccatttc   1500

ttcgaggacg tgaagacgct ggccattgac gccaaagaca tctcggccct gaagaccacc   1560

atcgacagcg aaaaacctac ctacctgatc atcagaggcc tgagcggcaa cggatctcag   1620

ctgaacgagc tgcagctgcc cgagagcgtg aagaaggtga gcctctacgg cgactacacc   1680

ggcgtgaacg tggccaagca gattttcgca aacgtggtgg aactggaatt ttacagcacc   1740

tccaaggcta acagcttcgg ctttaacccc ctggtgctgg gatctaagac caatgtgatc   1800

tacgacctct tcgcttccaa gccctttacc cacatcgacc tgacccaggt gaccctgcaa   1860

aattcagata atagcgccat cgacgccaac aagctgaaac aagccgtggg cgacatctac   1920

aactacagaa gattcgagcg ccagttccag ggctattttg ctggcggtta catcgacaag   1980

tacctggtga aaaacgtgaa caccaacaag gacagcgacg atgacctggt gtacagatcc   2040

ctgaaagagc tgaacctgca cctggaagag gcctacagag agggcgataa tacctactat   2100

agagtgaatg agaactacta ccctggcgcc agtatctacg agaacgaaag agctagcaga   2160

gacagcgagt tccagaacga gatcctgaag cgggccgagc agaatggcgt gaccttcgac   2220

gagaacatca agcggatcac agccagcggc aagtacagcg tgcagttcca gaaactggaa   2280

aacgacacag atagcagcct cgagagaatg accaaggccg tggaaggact ggtgaccgtc   2340

atcggcgaag aaaagttcga aacggtggac atcaccggag tgtcctccga caccaatgag   2400

gtgaagtccc tggccaagga actgaagacc aatgccctcg gagtgaagct gaagctataa   2460
```

```
<210> SEQ ID NO 60
<211> LENGTH: 3264
<212> TYPE: DNA
<213> ORGANISM: Artificial Sequence
<220> FEATURE:
<223> OTHER INFORMATION: armY-Anthrax toxin receptor 1 fusion protein
      codon-optimized (for human)

<400> SEQUENCE: 60

atgtacagaa tgcagctgtt gagctgtatc gccctgagcc tggccctggt gaccaacagc     60

gaggacggtg gccctgcctg ctacggcggg tttgacctgt acttcatcct ggataagtcc    120

ggttctgtgc tgcaccactg gaacgaaatc tactacttcg tggaacagct ggcccacaag    180

tttatctccc ctcagctgcg gatgagcttc atcgtgttct ccacaagagg caccaccctg    240

atgaagctga ccgaggatcg cgagcagatc agacagggac tggaagagct gcagaaagtg    300

ctgcctggcg gcgatacata catgcacgag ggatttgaga gagcctccga gcagatctat    360

tacgagaaca gacagggcta ccgcaccgcc agcgtgatca ttgccctgac agacggcgag    420

ctgcatgaag atctgttctt ctacagcgag cgcgaggcca acagaagccg ggacctgggc    480

gccatcgtgt actgtgtggg cgtgaaggac ttcaacgaaa cccagctggc cagaatcgcc    540

gatagcaagg atcacgtgtt ccctgtgaac gacggattcc aggccctgca gggcatcatc    600

cacagcattc taaagaagtc ctgcatcgag atcctggctg ctgaacccag caccatctgc    660

gccggcgaga gcttccaggt ggtggtgcgg ggcaacggct tccggcacgc cagaaacgtg    720

gacagagttc tgtgcagctt taagatcaat gatagcgtga cacttaacga gaagcccttc    780

agcgtggaag atacctacct gctgtgtcct gctccaatct taaaagaggt gggaatgaaa    840

gccgccctgc aagtgtccat gaacgatggc ctctctttta tcagttccag cgtgatcatc    900
```

```
accacaaccc actgttctga tggtagcatc ctggccatcg ccctgctcat cctgtttctg    960
ctgctggcct tggccctgct gtggtggttc tggcctctgt gctgcaccgt gatcatcaaa   1020
gaagtgcctc ctcctcccgc tgaagagagc gaagaggagg acgacgacgg cctgcctaag   1080
aaaaagtggc ccacagtcga tgcttcttac tacggcggca gaggcgttgg cgggatcaag   1140
cggatggaag tgcggtgggg agaaaagggc agtaccgagg aaggagctaa gctggaaaag   1200
gccaagaatg ccagagtgaa gatgcctgag caggagtacg agttccccga gcctcggaac   1260
ctgaacaaca acatgagacg gccctcctct ccaagaaagt ggtacagccc tatcaagggc   1320
aagctggacg ccctctgggt cctgctgaga aagggctacg acagagtgag cgtgatgcgg   1380
ccccagcctg gcgacactgg cagatgcatc aactttacca gggtgaagaa caaccagcct   1440
gccaagtacc ccctgaacaa cgcctaccac acaagctctc ctcctcccgc tcccatctac   1500
actccgcccc ccccagcccc acactgccct cccccaccac cctctgcccc tacccctccc   1560
atccccagcc ccccttcaac cctgcctccc cctccgcaag cccctccacc aaacagagca   1620
cctccaccta gcagaccccc tcctagacct tctgtgggcg gcggcggcag cggcggaggc   1680
ggcagcggcg gaggcgggag caccaacctg gtgaaccaga gcggctacgc cctggtggcc   1740
tccggcagaa gcggcaacct gggcttcaag ctgttctcga cccagagccc ttctgccgag   1800
gtgaagctga aaagcctgtc actgaatgac ggctcttacc agagcgagat cgacctgagc   1860
ggcggagcta acttcagaga aaagttccgg aacttcgcca acgagctgtc tgaggccatc   1920
accaacagcc ctaagggcct ggacagaccc gtacccaaga ccgagatcag cggactgatt   1980
aagacgggcg acaacttcat cacaccttcc ttcaaggctg gatactacga tcatgtggcc   2040
agcgacggca gcctgctgag ctactaccag tccacagagt acttcaacaa cagagtcctg   2100
atgcctatcc tccagaccac caatggcacc ctgatggcca acaatagagg ctacgacgac   2160
gtgttcaggc aggttccttc tttctccggc tggagcaaca caaaggccac cacagtgagc   2220
acaagcaata acctcaccta cgacaaatgg acctacttcg ctgccaaggg cagccccctc   2280
tacgactctt atcctaacca ctttttcgag gatgtgaaaa cactggctat cgatgccaag   2340
gacatcagcg cccttaaaac aacaatcgac tccgagaaac ctacctacct gatcatcaga   2400
ggcctgtccg gcaatggcag ccagctgaac gagctgcaac tgcctgaaag cgtgaaaaaa   2460
gtgagcctgt atggggacta caccggcgtg aacgtggcca agcagatctt cgccaatgtg   2520
gtggaactgg agttctacag cactagcaag gccaattctt tcggctttaa ccccctggtg   2580
ctgggcagca agacaaacgt gatctacgat ctgttcgcca gcaagccttt cacccacatc   2640
gacctgacac aggtgacgct gcagaacagc gacaacagcg ccatcgacgc caacaagctg   2700
aagcaggccg tgggcgacat ttacaactac cggagattcg agagacaatt tcagggctat   2760
ttcgccggcg gatacatcga caagtatctg gtcaaaaatg tgaataccaa caaggatagc   2820
gacgacgacc tggtataccg gtccctgaaa gaactgaacc tgcacttgga ggaagcctac   2880
agagagggcg acaataccta ctatagagtc aacgagaact actaccctgg cgcctccatc   2940
tacgaaaatg aacgggcctc tagagactct gagttccaaa acgagatcct gaaaagagca   3000
gagcagaatg gcgtcacctt cgacgagaac atcaagcgca ttaccgccag cggaaagtac   3060
tccgtgcagt tccagaagct ggagaacgat accgacagct ctctggaacg gatgaccaag   3120
gccgtggagg gactggtcac cgtgatcggc gaagagaagt tcgaaaccgt ggacatcacc   3180
ggcgtgtctt ctgacacaaa cgaagtgaaa agcctggcta aagagctgaa gacaaacgcc   3240
ctgggagtga agctgaagct gtaa                                          3264
```

<210> SEQ ID NO 61
<211> LENGTH: 2523
<212> TYPE: DNA
<213> ORGANISM: Artificial Sequence
<220> FEATURE:
<223> OTHER INFORMATION: armY-Anthrax toxin receptor 2 fusion protein
codon-optimized (for human)

<400> SEQUENCE: 61
atgtacagaa tgcagctgct ctcttgcatt gccctgagcc tggccctggt gaccaatagc 60
caggagcaac ctagctgcag aagagccttc gacctctact tcgtgctgga taagtccggc 120
agcgtcgcca acaattggat cgagatctac aacttcgtac agcagctggc cgaacgcttc 180
gtgagccccg agatgagact gagcttcatc gtgttctctt cccaggccac catcatcctg 240
cctctgaccg gcgacagagg caaaatctca aagggcctgg aagatctgaa aagagtgtcc 300
cccgtcggcg agacatacat ccacgagggc ctgaagctgg ccaatgaaca gatccagaag 360
gccggcggac tgaagaccag cagcatcatc attgccctga ccgacggcaa actggacggc 420
ctggtcccta gctacgccga gaaggaagcc aagatcagcc ggagcctggg cgcttctgtg 480
tactgcgtgg gagtgctgga cttcgagcag gctcaactgg agaggatcgc tgatagcaag 540
gagcaggttt tcccagtgaa aggcggcttt caagccctga aaggcatcat caacagcatc 600
ctggcccaga gctgtacaga gatcctggaa ctccagccta gcagcgtgtg cgtcggcgaa 660
gagttccaga tcgtgttaag cggcagaggc ttcatgctgg gcagcagaaa cggcagcgtg 720
ctgtgcacat acaccgtcaa tgagacctac acaacaagcg tgaagcccgt gtccgtgcag 780
ctgaatagca tgctgtgtcc tgcccctatc ctcaacaagg ccggcgaaac cctggacgtg 840
tccgtgtctt tcaatggcgg caagagcgta atctccggct ctctgatcgt gacagccacc 900
gagtgcagca acggaggcgg aggcggatct ggtggcggag gatcgggcgg tggcggtagc 960
accaacctgg tgaaccagtc aggctacgcc cttgtggcca gcggaagatc cggcaacctg 1020
ggctttaagc tgttttctac acagagccca tctgctgaag tgaagctgaa gtctctcagc 1080
ctgaacgacg gctcttatca gtccgagatc gatctgagcg gaggagccaa tttccgggag 1140
aagttcagaa actttgctaa tgagctgagc gaagccatca caaacagccc taagggcctg 1200
gatagacctg tgcccaagac cgagatcagc ggactgatca agacaggcga caacttcatc 1260
accccaagct tcaaggctgg ctactatgac cacgtggcct ctgatggatc cctgctgtct 1320
tattaccaga gcacagaata cttcaacaac agagtgctga tgcctatcct gcaaaccacc 1380
aatggaacgc tgatggccaa caaccggggc tacgatgacg tgttcagaca ggtgcctagc 1440
ttcagcggat ggagcaacac caaggccaca acagtcagca cctctaacaa cctgacctac 1500
gacaagtgga cctactttgc cgctaagggc tctccactgt acgatagcta ccccaaccac 1560
ttctttgagg acgtgaagac actggccatc gatgccaaag acatatctgc gctgaagacc 1620
accatcgaca gcgagaagcc tacatatctg atcatcagag gcttgagcgg caacgggtct 1680
cagctgaacg agcttcagct gcctgagagc gtgaaaaagg tgagcctgta cggcgactac 1740
accggcgtga acgtggccaa gcagatcttc gctaacgtgg tggaattaga gttctacagc 1800
accagcaagg ccaacagctt cggcttcaac cccctggtgc tgggctctaa gacaaacgtg 1860
atctacgatc tgttcgccag caaacccttc acccacatcg atctgaccca ggtgaccctg 1920
cagaactccg acaacagcgc catcgacgcc aacaagctga aacaggccgt gggcgacatc 1980
tacaattacc ggagattcga gcggcaattc cagggctact ttgcgggcgg ctacatcgac 2040

```
aagtacctgg tgaagaacgt gaacacgaac aaggacagcg acgacgacct ggtgtaccgg   2100

agccttaagg agctgaacct gcatctggaa gaagcctacc gggagggcga taacacatat   2160

taccgggtga atgagaacta ctaccctggc gccagcatct acgagaacga gagagccagc   2220

agagatagcg aattccaaaa cgaaatcctg aagcgggccg agcagaacgg cgtgactttc   2280

gacgagaata ttaagagaat caccgcctcc ggaaagtaca gcgtgcagtt tcagaaactg   2340

gaaaacgata cagactcaag cttggagcgc atgaccaagg ccgtggaagg cctggtgacc   2400

gtaatcggcg aggaaaaatt cgaaaccgtg gacattaccg gcgtgtcttc tgacaccaac   2460

gaggtgaaga gcctggctaa agagctgaag accaacgccc tgggcgtcaa gctgaagctg   2520

taa                                                                 2523


<210> SEQ ID NO 62
<211> LENGTH: 555
<212> TYPE: PRT
<213> ORGANISM: Artificial Sequence
<220> FEATURE:
<223> OTHER INFORMATION: Protein M with radiolabel peptide tag (KGRPLVY)

<400> SEQUENCE: 62

Met Tyr Arg Met Gln Leu Leu Ser Cys Ile Ala Leu Ser Leu Ala Leu
1               5                   10                  15

Val Thr Asn Ser Lys Gly Arg Pro Leu Val Tyr Gly Gly Ser Gly Gly
            20                  25                  30

Gly Gly Ser Thr Asn Leu Val Asn Gln Ser Gly Tyr Ala Leu Val Ala
        35                  40                  45

Ser Gly Arg Ser Gly Asn Leu Gly Phe Lys Leu Phe Ser Thr Gln Ser
    50                  55                  60

Pro Ser Ala Glu Val Lys Leu Lys Ser Leu Ser Leu Asn Asp Gly Ser
65                  70                  75                  80

Tyr Gln Ser Glu Ile Asp Leu Ser Gly Gly Ala Asn Phe Arg Glu Lys
                85                  90                  95

Phe Arg Asn Phe Ala Asn Glu Leu Ser Glu Ala Ile Thr Asn Ser Pro
            100                 105                 110

Lys Gly Leu Asp Arg Pro Val Pro Lys Thr Glu Ile Ser Gly Leu Ile
        115                 120                 125

Lys Thr Gly Asp Asn Phe Ile Thr Pro Ser Phe Lys Ala Gly Tyr Tyr
    130                 135                 140

Asp His Val Ala Ser Asp Gly Ser Leu Leu Ser Tyr Tyr Gln Ser Thr
145                 150                 155                 160

Glu Tyr Phe Asn Asn Arg Val Leu Met Pro Ile Leu Gln Thr Thr Asn
                165                 170                 175

Gly Thr Leu Met Ala Asn Asn Arg Gly Tyr Asp Asp Val Phe Arg Gln
            180                 185                 190

Val Pro Ser Phe Ser Gly Trp Ser Asn Thr Lys Ala Thr Thr Val Ser
        195                 200                 205

Thr Ser Asn Asn Leu Thr Tyr Asp Lys Trp Thr Tyr Phe Ala Ala Lys
    210                 215                 220

Gly Ser Pro Leu Tyr Asp Ser Tyr Pro Asn His Phe Phe Glu Asp Val
225                 230                 235                 240

Lys Thr Leu Ala Ile Asp Ala Lys Asp Ile Ser Ala Leu Lys Thr Thr
                245                 250                 255

Ile Asp Ser Glu Lys Pro Thr Tyr Leu Ile Ile Arg Gly Leu Ser Gly
            260                 265                 270
```

```
Asn Gly Ser Gln Leu Asn Glu Leu Gln Leu Pro Glu Ser Val Lys Lys
        275                 280                 285

Val Ser Leu Tyr Gly Asp Tyr Thr Gly Val Asn Val Ala Lys Gln Ile
    290                 295                 300

Phe Ala Asn Val Val Glu Leu Glu Phe Tyr Ser Thr Ser Lys Ala Asn
305                 310                 315                 320

Ser Phe Gly Phe Asn Pro Leu Val Leu Gly Ser Lys Thr Asn Val Ile
                325                 330                 335

Tyr Asp Leu Phe Ala Ser Lys Pro Phe Thr His Ile Asp Leu Thr Gln
            340                 345                 350

Val Thr Leu Gln Asn Ser Asp Asn Ser Ala Ile Asp Ala Asn Lys Leu
        355                 360                 365

Lys Gln Ala Val Gly Asp Ile Tyr Asn Tyr Arg Arg Phe Glu Arg Gln
    370                 375                 380

Phe Gln Gly Tyr Phe Ala Gly Gly Tyr Ile Asp Lys Tyr Leu Val Lys
385                 390                 395                 400

Asn Val Asn Thr Asn Lys Asp Ser Asp Asp Asp Leu Val Tyr Arg Ser
                405                 410                 415

Leu Lys Glu Leu Asn Leu His Leu Glu Glu Ala Tyr Arg Glu Gly Asp
            420                 425                 430

Asn Thr Tyr Tyr Arg Val Asn Glu Asn Tyr Tyr Pro Gly Ala Ser Ile
        435                 440                 445

Tyr Glu Asn Glu Arg Ala Ser Arg Asp Ser Glu Phe Gln Asn Glu Ile
    450                 455                 460

Leu Lys Arg Ala Glu Gln Asn Gly Val Thr Phe Asp Glu Asn Ile Lys
465                 470                 475                 480

Arg Ile Thr Ala Ser Gly Lys Tyr Ser Val Gln Phe Gln Lys Leu Glu
                485                 490                 495

Asn Asp Thr Asp Ser Ser Leu Glu Arg Met Thr Lys Ala Val Glu Gly
            500                 505                 510

Leu Val Thr Val Ile Gly Glu Glu Lys Phe Glu Thr Val Asp Ile Thr
        515                 520                 525

Gly Val Ser Ser Asp Thr Asn Glu Val Lys Ser Leu Ala Lys Glu Leu
    530                 535                 540

Lys Thr Asn Ala Leu Gly Val Lys Leu Lys Leu
545                 550                 555
```

<210> SEQ ID NO 63
<211> LENGTH: 520
<212> TYPE: PRT
<213> ORGANISM: Artificial Sequence
<220> FEATURE:
<223> OTHER INFORMATION: mutated Protein M

<400> SEQUENCE: 63

```
Thr Asn Leu Val Asn Gln Ser Gly Tyr Ala Leu Val Ala Ser Gly Arg
1               5                   10                  15

Ser Gly Asn Leu Gly Phe Lys Leu Phe Ser Thr Gln Ser Pro Ser Ala
            20                  25                  30

Glu Val Lys Leu Lys Ser Leu Ser Leu Asn Asp Gly Ser Tyr Gln Ser
        35                  40                  45

Glu Ile Asp Leu Ser Gly Gly Ala Asn Phe Arg Glu Lys Phe Arg Asn
    50                  55                  60

Phe Ala Asn Glu Leu Ser Glu Ala Ile Thr Asn Ser Pro Lys Gly Leu
65                  70                  75                  80
```

-continued

```
Asp Arg Pro Val Pro Lys Thr Glu Ile Ser Gly Leu Ile Lys Thr Gly
                85                  90                  95

Asp Asn Phe Ile Thr Pro Ser Phe Lys Ala Gly Tyr Tyr Asp His Val
            100                 105                 110

Ala Ser Asp Gly Ser Leu Leu Ser Tyr Tyr Gln Ser Thr Glu Tyr Phe
        115                 120                 125

Asn Asn Arg Val Leu Met Pro Ile Leu Gln Thr Thr Asn Gly Thr Leu
    130                 135                 140

Met Ala Asn Asn Arg Gly Tyr Asp Asp Val Phe Arg Gln Val Pro Ser
145                 150                 155                 160

Phe Ser Gly Trp Ser Asn Thr Lys Ala Thr Thr Val Ser Thr Ser Asn
                165                 170                 175

Asn Leu Thr Tyr Asp Lys Trp Thr Tyr Phe Ala Ala Lys Gly Ser Pro
            180                 185                 190

Leu Tyr Asp Ser Tyr Pro Asn His Phe Phe Glu Asp Val Lys Thr Leu
        195                 200                 205

Ala Ile Asp Ala Lys Asp Ile Ser Ala Leu Lys Thr Thr Ile Asp Ser
    210                 215                 220

Glu Lys Pro Thr Tyr Leu Ile Ile Arg Gly Leu Ser Gly Asn Gly Ser
225                 230                 235                 240

Gln Leu Asn Glu Leu Gln Leu Pro Glu Ser Val Lys Lys Val Ser Leu
                245                 250                 255

Tyr Gly Asp Tyr Thr Gly Val Asn Val Ala Lys Gln Ile Phe Ala Asn
            260                 265                 270

Val Val Glu Leu Glu Phe Tyr Ser Thr Ser Lys Ala Asn Ser Phe Gly
        275                 280                 285

Phe Asn Pro Leu Val Leu Gly Ser Lys Thr Asn Val Ile Tyr Asp Leu
    290                 295                 300

Phe Ala Ser Lys Pro Phe Thr His Ile Asp Leu Thr Gln Val Thr Leu
305                 310                 315                 320

Gln Asn Ser Asp Asn Ser Ala Ile Asp Ala Asn Lys Leu Lys Gln Ala
                325                 330                 335

Val Gly Asp Ile Tyr Asn Tyr Arg Arg Phe Glu Arg Gln Phe Gln Gly
            340                 345                 350

Tyr Phe Ala Gly Gly Tyr Ile Asp Lys Tyr Leu Val Lys Asn Val Asn
        355                 360                 365

Thr Asn Lys Asp Ser Asp Asp Asp Leu Val Tyr Arg Ser Leu Lys Glu
    370                 375                 380

Leu Asn Leu His Leu Glu Glu Ala Tyr Arg Glu Gly Asp Asn Thr Tyr
385                 390                 395                 400

Tyr Arg Val Asn Glu Asn Tyr Tyr Pro Gly Ala Ser Ile Tyr Glu Asn
                405                 410                 415

Glu Arg Ala Ser Arg Asp Ser Glu Phe Gln Asn Glu Ile Leu Lys Arg
            420                 425                 430

Ala Glu Gln Asn Gly Val Thr Phe Asp Glu Asn Ile Lys Arg Ile Thr
        435                 440                 445

Ala Ser Gly Lys Tyr Ser Val Gln Phe Gln Ala Leu Ala Asn Ala Thr
    450                 455                 460

Ala Ser Ala Leu Ala Ala Met Thr Lys Ala Val Glu Gly Leu Val Thr
465                 470                 475                 480

Val Ile Gly Glu Glu Lys Phe Glu Thr Val Ala Ile Ala Gly Val Ala
                485                 490                 495
```

```
Ser Ala Thr Asn Ala Val Ala Ser Leu Ala Lys Glu Leu Lys Thr Asn
            500                 505                 510

Ala Leu Gly Val Lys Leu Lys Leu
        515                 520


<210> SEQ ID NO 64
<211> LENGTH: 520
<212> TYPE: PRT
<213> ORGANISM: Artificial Sequence
<220> FEATURE:
<223> OTHER INFORMATION: mutated Protein M

<400> SEQUENCE: 64

Thr Asn Leu Val Asn Gln Ser Gly Tyr Ala Leu Val Ala Ser Gly Arg
1               5                   10                  15

Ser Gly Asn Leu Gly Phe Lys Leu Phe Ser Thr Gln Ser Pro Ser Ala
            20                  25                  30

Glu Val Lys Leu Lys Ser Leu Ser Leu Asn Asp Gly Ser Tyr Gln Ser
        35                  40                  45

Glu Ile Asp Leu Ser Gly Gly Ala Asn Phe Arg Glu Lys Phe Arg Asn
    50                  55                  60

Phe Ala Asn Glu Leu Ser Glu Ala Ile Thr Asn Ser Pro Lys Gly Leu
65                  70                  75                  80

Asp Arg Pro Val Pro Lys Thr Glu Ile Ser Gly Leu Ile Lys Thr Gly
                85                  90                  95

Asp Asn Phe Ile Thr Pro Ser Phe Lys Ala Gly Tyr Tyr Asp His Val
            100                 105                 110

Ala Ser Asp Gly Ser Leu Leu Ser Tyr Tyr Gln Ser Thr Glu Tyr Phe
        115                 120                 125

Asn Asn Arg Val Leu Met Pro Ile Leu Gln Thr Thr Asn Gly Thr Leu
    130                 135                 140

Met Ala Asn Asn Arg Gly Tyr Asp Asp Val Phe Arg Gln Val Pro Ser
145                 150                 155                 160

Phe Ser Gly Trp Ser Asn Thr Lys Ala Thr Thr Val Ser Thr Ser Asn
                165                 170                 175

Asn Leu Thr Tyr Asp Lys Trp Thr Tyr Phe Ala Ala Lys Gly Ser Pro
            180                 185                 190

Leu Tyr Asp Ser Tyr Pro Asn His Phe Phe Glu Asp Val Lys Thr Leu
        195                 200                 205

Ala Ile Asp Ala Lys Asp Ile Ser Ala Leu Lys Thr Thr Ile Asp Ser
    210                 215                 220

Glu Lys Pro Thr Tyr Leu Ile Ile Arg Gly Leu Ser Gly Asn Gly Ser
225                 230                 235                 240

Gln Leu Asn Glu Leu Gln Leu Pro Glu Ser Val Lys Lys Val Ser Leu
                245                 250                 255

Tyr Gly Asp Tyr Thr Gly Val Asn Val Ala Lys Gln Ile Phe Ala Asn
            260                 265                 270

Val Val Glu Leu Glu Phe Tyr Ser Thr Ser Lys Ala Asn Ser Phe Gly
        275                 280                 285

Phe Asn Pro Leu Val Leu Gly Ser Lys Thr Asn Val Ile Tyr Asp Leu
    290                 295                 300

Phe Ala Ser Lys Pro Phe Thr His Ile Asp Leu Thr Gln Val Thr Leu
305                 310                 315                 320

Gln Asn Ser Asp Asn Ser Ala Ile Asp Ala Asn Lys Leu Lys Gln Ala
                325                 330                 335
```

```
Val Gly Asp Ile Tyr Asn Tyr Arg Arg Phe Glu Arg Gln Phe Gln Gly
            340                 345                 350

Tyr Phe Ala Gly Gly Tyr Ile Asp Lys Tyr Leu Val Lys Asn Val Asn
        355                 360                 365

Thr Asn Lys Asp Ser Asp Asp Asp Leu Val Tyr Arg Ser Leu Lys Glu
    370                 375                 380

Leu Asn Leu His Leu Glu Glu Ala Tyr Arg Glu Gly Asp Asn Thr Tyr
385                 390                 395                 400

Tyr Arg Val Asn Glu Asn Tyr Tyr Pro Gly Ala Ser Ile Tyr Glu Asn
                405                 410                 415

Glu Arg Ala Ser Arg Asp Ser Glu Phe Gln Asn Glu Ile Leu Lys Arg
            420                 425                 430

Ala Glu Gln Asn Gly Val Thr Phe Asp Glu Asn Ile Lys Arg Ile Thr
        435                 440                 445

Ala Ser Gly Lys Tyr Ser Val Gln Phe Ala Lys Leu Ala Asn Ala Thr
    450                 455                 460

Ala Ser Ala Leu Ala Arg Met Thr Lys Ala Val Glu Gly Leu Val Thr
465                 470                 475                 480

Val Ile Gly Glu Glu Lys Phe Glu Thr Val Ala Ile Ala Gly Val Ala
                485                 490                 495

Ser Ala Thr Asn Ala Val Lys Ser Leu Ala Lys Glu Leu Lys Thr Asn
            500                 505                 510

Ala Leu Gly Val Lys Leu Lys Leu
        515                 520


<210> SEQ ID NO 65
<211> LENGTH: 520
<212> TYPE: PRT
<213> ORGANISM: Artificial Sequence
<220> FEATURE:
<223> OTHER INFORMATION: mutated Protein M

<400> SEQUENCE: 65

Thr Asn Leu Val Asn Gln Ser Gly Tyr Ala Leu Val Ala Ser Gly Arg
1               5                   10                  15

Ser Gly Asn Leu Gly Phe Lys Leu Phe Ser Thr Gln Ser Pro Ser Ala
            20                  25                  30

Glu Val Lys Leu Lys Ser Leu Ser Leu Asn Asp Gly Ser Tyr Gln Ser
        35                  40                  45

Glu Ile Asp Leu Ser Gly Gly Ala Asn Phe Arg Glu Lys Phe Arg Asn
    50                  55                  60

Phe Ala Asn Glu Leu Ser Glu Ala Ile Thr Asn Ser Pro Lys Gly Leu
65                  70                  75                  80

Asp Arg Pro Val Pro Lys Thr Glu Ile Ser Gly Leu Ile Lys Thr Gly
                85                  90                  95

Asp Asn Phe Ile Thr Pro Ser Phe Lys Ala Gly Tyr Tyr Asp His Val
            100                 105                 110

Ala Ser Asp Gly Ser Leu Leu Ser Tyr Tyr Gln Ser Thr Glu Tyr Phe
        115                 120                 125

Asn Asn Arg Val Leu Met Pro Ile Leu Gln Thr Thr Asn Gly Thr Leu
    130                 135                 140

Met Ala Asn Asn Arg Gly Tyr Asp Asp Val Phe Arg Gln Val Pro Ser
145                 150                 155                 160

Phe Ser Gly Trp Ser Asn Thr Lys Ala Thr Thr Val Ser Thr Ser Asn
                165                 170                 175
```

```
Asn Leu Thr Tyr Asp Lys Trp Thr Tyr Phe Ala Ala Lys Gly Ser Pro
            180                 185                 190

Leu Tyr Asp Ser Tyr Pro Asn His Phe Phe Glu Asp Val Lys Thr Leu
        195                 200                 205

Ala Ile Asp Ala Lys Asp Ile Ser Ala Leu Lys Thr Thr Ile Asp Ser
    210                 215                 220

Glu Lys Pro Thr Tyr Leu Ile Ile Arg Gly Leu Ser Gly Asn Gly Ser
225                 230                 235                 240

Gln Leu Asn Glu Leu Gln Leu Pro Glu Ser Val Lys Lys Val Ser Leu
                245                 250                 255

Tyr Gly Asp Tyr Thr Gly Val Asn Val Ala Lys Gln Ile Phe Ala Asn
            260                 265                 270

Val Val Glu Leu Glu Phe Tyr Ser Thr Ser Lys Ala Asn Ser Phe Gly
        275                 280                 285

Phe Asn Pro Leu Val Leu Gly Ser Lys Thr Asn Val Ile Tyr Asp Leu
    290                 295                 300

Phe Ala Ser Lys Pro Phe Thr His Ile Asp Leu Thr Gln Val Thr Leu
305                 310                 315                 320

Gln Asn Ser Asp Asn Ser Ala Ile Asp Ala Asn Lys Leu Lys Gln Ala
                325                 330                 335

Val Gly Asp Ile Tyr Asn Tyr Arg Arg Phe Glu Arg Gln Phe Gln Gly
            340                 345                 350

Tyr Phe Ala Gly Gly Tyr Ile Asp Lys Tyr Leu Val Lys Asn Val Asn
        355                 360                 365

Thr Asn Lys Asp Ser Asp Asp Asp Leu Val Tyr Arg Ser Leu Lys Glu
    370                 375                 380

Leu Asn Leu His Leu Glu Glu Ala Tyr Arg Glu Gly Asp Asn Thr Tyr
385                 390                 395                 400

Tyr Arg Val Asn Glu Asn Tyr Tyr Pro Gly Ala Ser Ile Tyr Glu Asn
                405                 410                 415

Glu Arg Ala Ser Arg Asp Ser Glu Phe Gln Asn Glu Ile Leu Lys Arg
            420                 425                 430

Ala Glu Gln Asn Gly Val Thr Phe Asp Glu Asn Ile Lys Arg Ile Thr
        435                 440                 445

Ala Ser Gly Lys Tyr Ser Val Gln Phe Gln Ala Leu Glu Ala Asp Ala
    450                 455                 460

Asp Ser Ala Leu Glu Ala Met Thr Lys Ala Val Glu Gly Leu Val Thr
465                 470                 475                 480

Val Ile Gly Glu Glu Lys Phe Glu Thr Val Asp Ile Ala Gly Val Ser
                485                 490                 495

Ala Asp Thr Ala Glu Val Ala Ser Leu Ala Lys Glu Leu Lys Thr Asn
            500                 505                 510

Ala Leu Gly Val Lys Leu Lys Leu
        515                 520
```

<210> SEQ ID NO 66
<211> LENGTH: 520
<212> TYPE: PRT
<213> ORGANISM: Artificial Sequence
<220> FEATURE:
<223> OTHER INFORMATION: mutated Protein M

<400> SEQUENCE: 66

```
Thr Asn Leu Val Asn Gln Ser Gly Tyr Ala Leu Val Ala Ser Gly Arg
1               5                   10                  15
```

-continued

```
Ser Gly Asn Leu Gly Phe Lys Leu Phe Ser Thr Gln Ser Pro Ser Ala
            20                  25                  30

Glu Val Lys Leu Lys Ser Leu Ser Leu Asn Asp Gly Ser Tyr Gln Ser
        35                  40                  45

Glu Ile Asp Leu Ser Gly Gly Ala Asn Phe Arg Glu Lys Phe Arg Asn
    50                  55                  60

Phe Ala Asn Glu Leu Ser Glu Ala Ile Thr Asn Ser Pro Lys Gly Leu
65                  70                  75                  80

Asp Arg Pro Val Pro Lys Thr Glu Ile Ser Gly Leu Ile Lys Thr Gly
                85                  90                  95

Asp Asn Phe Ile Thr Pro Ser Phe Lys Ala Gly Tyr Tyr Asp His Val
            100                 105                 110

Ala Ser Asp Gly Ser Leu Leu Ser Tyr Tyr Gln Ser Thr Glu Tyr Phe
        115                 120                 125

Asn Asn Arg Val Leu Met Pro Ile Leu Gln Thr Thr Asn Gly Thr Leu
    130                 135                 140

Met Ala Asn Asn Arg Gly Tyr Asp Asp Val Phe Arg Gln Val Pro Ser
145                 150                 155                 160

Phe Ser Gly Trp Ser Asn Thr Lys Ala Thr Thr Val Ser Thr Ser Asn
                165                 170                 175

Asn Leu Thr Tyr Asp Lys Trp Thr Tyr Phe Ala Ala Lys Gly Ser Pro
            180                 185                 190

Leu Tyr Asp Ser Tyr Pro Asn His Phe Phe Glu Asp Val Lys Thr Leu
        195                 200                 205

Ala Ile Asp Ala Lys Asp Ile Ser Ala Leu Lys Thr Thr Ile Asp Ser
    210                 215                 220

Glu Lys Pro Thr Tyr Leu Ile Ile Arg Gly Leu Ser Gly Asn Gly Ser
225                 230                 235                 240

Gln Leu Asn Glu Leu Gln Leu Pro Glu Ser Val Lys Lys Val Ser Leu
                245                 250                 255

Tyr Gly Asp Tyr Thr Gly Val Asn Val Ala Lys Gln Ile Phe Ala Asn
            260                 265                 270

Val Val Glu Leu Glu Phe Tyr Ser Thr Ser Lys Ala Asn Ser Phe Gly
        275                 280                 285

Phe Asn Pro Leu Val Leu Gly Ser Lys Thr Asn Val Ile Tyr Asp Leu
    290                 295                 300

Phe Ala Ser Lys Pro Phe Thr His Ile Asp Leu Thr Gln Val Thr Leu
305                 310                 315                 320

Gln Asn Ser Asp Asn Ser Ala Ile Asp Ala Asn Lys Leu Lys Gln Ala
                325                 330                 335

Val Gly Asp Ile Tyr Asn Tyr Arg Arg Phe Glu Arg Gln Phe Gln Gly
            340                 345                 350

Tyr Phe Ala Gly Gly Tyr Ile Asp Lys Tyr Leu Val Lys Asn Val Asn
        355                 360                 365

Thr Asn Lys Asp Ser Asp Asp Asp Leu Val Tyr Arg Ser Leu Lys Glu
    370                 375                 380

Leu Asn Leu His Leu Glu Glu Ala Tyr Arg Glu Gly Asp Asn Thr Tyr
385                 390                 395                 400

Tyr Arg Val Asn Glu Asn Tyr Tyr Pro Gly Ala Ser Ile Tyr Glu Asn
                405                 410                 415

Glu Arg Ala Ser Arg Asp Ser Glu Phe Gln Asn Glu Ile Leu Lys Arg
            420                 425                 430

Ala Glu Gln Asn Gly Val Thr Phe Asp Glu Asn Ile Lys Arg Ile Thr
```

-continued

```
        435                 440                 445

Ala Ser Gly Lys Tyr Ser Val Gln Phe Ala Lys Leu Ala Asn Asp Thr
    450                 455                 460

Ala Ser Ser Ala Glu Arg Ala Thr Lys Ala Val Glu Gly Leu Val Thr
465                 470                 475                 480

Val Ile Gly Glu Glu Lys Phe Glu Thr Val Ala Ile Thr Gly Ala Ser
                485                 490                 495

Ser Ala Thr Asn Ala Val Lys Ala Leu Ala Lys Glu Leu Lys Thr Asn
            500                 505                 510

Ala Leu Gly Val Lys Leu Lys Leu
        515                 520


<210> SEQ ID NO 67
<211> LENGTH: 308
<212> TYPE: PRT
<213> ORGANISM: Armoracia rusticana
<220> FEATURE:
<223> OTHER INFORMATION: Horseradish peroxidase mature protein sequence
      (31-338 amino acids)

<400> SEQUENCE: 67

Gln Leu Thr Pro Thr Phe Tyr Asp Asn Ser Cys Pro Asn Val Ser Asn
1               5                   10                  15

Ile Val Arg Asp Thr Ile Val Asn Glu Leu Arg Ser Asp Pro Arg Ile
            20                  25                  30

Ala Ala Ser Ile Leu Arg Leu His Phe His Asp Cys Phe Val Asn Gly
        35                  40                  45

Cys Asp Ala Ser Ile Leu Leu Asp Asn Thr Thr Ser Phe Arg Thr Glu
    50                  55                  60

Lys Asp Ala Phe Gly Asn Ala Asn Ser Ala Arg Gly Phe Pro Val Ile
65                  70                  75                  80

Asp Arg Met Lys Ala Ala Val Glu Ser Ala Cys Pro Arg Thr Val Ser
                85                  90                  95

Cys Ala Asp Leu Leu Thr Ile Ala Ala Gln Gln Ser Val Thr Leu Ala
            100                 105                 110

Gly Gly Pro Ser Trp Arg Val Pro Leu Gly Arg Arg Asp Ser Leu Gln
        115                 120                 125

Ala Phe Leu Asp Leu Ala Asn Ala Asn Leu Pro Ala Pro Phe Phe Thr
    130                 135                 140

Leu Pro Gln Leu Lys Asp Ser Phe Arg Asn Val Gly Leu Asn Arg Ser
145                 150                 155                 160

Ser Asp Leu Val Ala Leu Ser Gly Gly His Thr Phe Gly Lys Asn Gln
                165                 170                 175

Cys Arg Phe Ile Met Asp Arg Leu Tyr Asn Phe Ser Asn Thr Gly Leu
            180                 185                 190

Pro Asp Pro Thr Leu Asn Thr Thr Tyr Leu Gln Thr Leu Arg Gly Leu
        195                 200                 205

Cys Pro Leu Asn Gly Asn Leu Ser Ala Leu Val Asp Phe Asp Leu Arg
    210                 215                 220

Thr Pro Thr Ile Phe Asp Asn Lys Tyr Tyr Val Asn Leu Glu Glu Gln
225                 230                 235                 240

Lys Gly Leu Ile Gln Ser Asp Gln Glu Leu Phe Ser Ser Pro Asn Ala
                245                 250                 255

Thr Asp Thr Ile Pro Leu Val Arg Ser Phe Ala Asn Ser Thr Gln Thr
            260                 265                 270
```

```
Phe Phe Asn Ala Phe Val Glu Ala Met Asp Arg Met Gly Asn Ile Thr
        275                 280                 285

Pro Leu Thr Gly Thr Gln Gly Gln Ile Arg Leu Asn Cys Arg Val Val
    290                 295                 300

Asn Ser Asn Ser
305


<210> SEQ ID NO 68
<211> LENGTH: 450
<212> TYPE: PRT
<213> ORGANISM: Escherichia coli
<220> FEATURE:
<223> OTHER INFORMATION: Alkaline phosphatase mature protein sequence
      (22-471 amino acids)

<400> SEQUENCE: 68

Arg Thr Pro Glu Met Pro Val Leu Glu Asn Arg Ala Ala Gln Gly Asp
1               5                   10                  15

Ile Thr Ala Pro Gly Gly Ala Arg Arg Leu Thr Gly Asp Gln Thr Ala
            20                  25                  30

Ala Leu Arg Asp Ser Leu Ser Asp Lys Pro Ala Lys Asn Ile Ile Leu
        35                  40                  45

Leu Ile Gly Asp Gly Met Gly Asp Ser Glu Ile Thr Ala Ala Arg Asn
    50                  55                  60

Tyr Ala Glu Gly Ala Gly Gly Phe Phe Lys Gly Ile Asp Ala Leu Pro
65                  70                  75                  80

Leu Thr Gly Gln Tyr Thr His Tyr Ala Leu Asn Lys Lys Thr Gly Lys
                85                  90                  95

Pro Asp Tyr Val Thr Asp Ser Ala Ala Ser Ala Thr Ala Trp Ser Thr
            100                 105                 110

Gly Val Lys Thr Tyr Asn Gly Ala Leu Gly Val Asp Ile His Glu Lys
        115                 120                 125

Asp His Pro Thr Ile Leu Glu Met Ala Lys Ala Ala Gly Leu Ala Thr
    130                 135                 140

Gly Asn Val Ser Thr Ala Glu Leu Gln Asp Ala Thr Pro Ala Ala Leu
145                 150                 155                 160

Val Ala His Val Thr Ser Arg Lys Cys Tyr Gly Pro Ser Ala Thr Ser
                165                 170                 175

Glu Lys Cys Pro Gly Asn Ala Leu Glu Lys Gly Gly Lys Gly Ser Ile
            180                 185                 190

Thr Glu Gln Leu Leu Asn Ala Arg Ala Asp Val Thr Leu Gly Gly Gly
        195                 200                 205

Ala Lys Thr Phe Ala Glu Thr Ala Thr Ala Gly Glu Trp Gln Gly Lys
    210                 215                 220

Thr Leu Arg Glu Gln Ala Gln Ala Arg Gly Tyr Gln Leu Val Ser Asp
225                 230                 235                 240

Ala Ala Ser Leu Asn Ser Val Thr Glu Ala Asn Gln Gln Lys Pro Leu
                245                 250                 255

Leu Gly Leu Phe Ala Asp Gly Asn Met Pro Val Arg Trp Leu Gly Pro
            260                 265                 270

Lys Ala Thr Tyr His Gly Asn Ile Asp Lys Pro Ala Val Thr Cys Thr
        275                 280                 285

Pro Asn Pro Gln Arg Asn Asp Ser Val Pro Thr Leu Ala Gln Met Thr
    290                 295                 300

Asp Lys Ala Ile Glu Leu Leu Ser Lys Asn Glu Lys Gly Phe Phe Leu
305                 310                 315                 320
```

```
Gln Val Glu Gly Ala Ser Ile Asp Lys Gln Asp His Ala Ala Asn Pro
                325                 330                 335

Cys Gly Gln Ile Gly Glu Thr Val Asp Leu Asp Glu Ala Val Gln Arg
            340                 345                 350

Ala Leu Glu Phe Ala Lys Lys Glu Gly Asn Thr Leu Val Ile Val Thr
        355                 360                 365

Ala Asp His Ala His Ala Ser Gln Ile Val Ala Pro Asp Thr Lys Ala
    370                 375                 380

Pro Gly Leu Thr Gln Ala Leu Asn Thr Lys Asp Gly Ala Val Met Val
385                 390                 395                 400

Met Ser Tyr Gly Asn Ser Glu Glu Asp Ser Gln Glu His Thr Gly Ser
                405                 410                 415

Gln Leu Arg Ile Ala Ala Tyr Gly Pro His Ala Ala Asn Val Val Gly
            420                 425                 430

Leu Thr Asp Gln Thr Asp Leu Phe Tyr Thr Met Lys Ala Ala Leu Gly
        435                 440                 445

Leu Lys
    450


<210> SEQ ID NO 69
<211> LENGTH: 550
<212> TYPE: PRT
<213> ORGANISM: Photinus pyralis
<220> FEATURE:
<223> OTHER INFORMATION: Luciferase protein sequence (1-550 amino acid)

<400> SEQUENCE: 69

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220
```

-continued

```
Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ser Lys Leu
545                 550
```

<210> SEQ ID NO 70
<211> LENGTH: 8
<212> TYPE: PRT
<213> ORGANISM: Artificial Sequence
<220> FEATURE:
<223> OTHER INFORMATION: Xpress tag, a peptide recognized by an antibody

<400> SEQUENCE: 70

```
Asp Leu Tyr Asp Asp Asp Asp Lys
1               5
```

<210> SEQ ID NO 71

<211> LENGTH: 13
<212> TYPE: PRT
<213> ORGANISM: Artificial Sequence
<220> FEATURE:
<223> OTHER INFORMATION: E-tag, a peptide recognized by an antibody

<400> SEQUENCE: 71

Gly Ala Pro Val Pro Tyr Pro Asp Pro Leu Glu Pro Arg
1 5 10

<210> SEQ ID NO 72
<211> LENGTH: 8
<212> TYPE: PRT
<213> ORGANISM: Artificial Sequence
<220> FEATURE:
<223> OTHER INFORMATION: FLAG-tag

<400> SEQUENCE: 72

Asp Tyr Lys Asp Asp Asp Asp Lys
1 5

<210> SEQ ID NO 73
<211> LENGTH: 9
<212> TYPE: PRT
<213> ORGANISM: Artificial Sequence
<220> FEATURE:
<223> OTHER INFORMATION: HA-tag

<400> SEQUENCE: 73

Tyr Pro Tyr Asp Val Pro Asp Tyr Ala
1 5

<210> SEQ ID NO 74
<211> LENGTH: 9
<212> TYPE: PRT
<213> ORGANISM: Artificial Sequence
<220> FEATURE:
<223> OTHER INFORMATION: HA-tag, a peptide recognized by an antibody

<400> SEQUENCE: 74

Tyr Pro Tyr Asp Val Pro Asp Tyr Ala
1 5

<210> SEQ ID NO 75
<211> LENGTH: 6
<212> TYPE: PRT
<213> ORGANISM: Artificial Sequence
<220> FEATURE:
<223> OTHER INFORMATION: His6-tag

<400> SEQUENCE: 75

His His His His His His
1 5

<210> SEQ ID NO 76
<211> LENGTH: 14
<212> TYPE: PRT
<213> ORGANISM: Artificial Sequence
<220> FEATURE:
<223> OTHER INFORMATION: Myc-tag

<400> SEQUENCE: 76

Glu Gln Lys Leu Ile Ser Glu Glu Asp Leu Leu Arg Lys Arg
1 5 10

<210> SEQ ID NO 77
<211> LENGTH: 15

<212> TYPE: PRT
<213> ORGANISM: Artificial Sequence
<220> FEATURE:
<223> OTHER INFORMATION: S-tag

<400> SEQUENCE: 77

Lys Glu Thr Ala Ala Ala Lys Phe Glu Arg Gln His Met Asp Ser
1 5 10 15

<210> SEQ ID NO 78
<211> LENGTH: 13
<212> TYPE: PRT
<213> ORGANISM: Artificial Sequence
<220> FEATURE:
<223> OTHER INFORMATION: Softag 1

<400> SEQUENCE: 78

Ser Leu Ala Glu Leu Leu Asn Ala Gly Leu Gly Gly Ser
1 5 10

<210> SEQ ID NO 79
<211> LENGTH: 11
<212> TYPE: PRT
<213> ORGANISM: Artificial Sequence
<220> FEATURE:
<223> OTHER INFORMATION: VSV-tag

<400> SEQUENCE: 79

Tyr Thr Asp Ile Glu Met Asn Arg Leu Gly Lys
1 5 10

<210> SEQ ID NO 80
<211> LENGTH: 8
<212> TYPE: PRT
<213> ORGANISM: Artificial Sequence
<220> FEATURE:
<223> OTHER INFORMATION: Softag 3, for prokaryotic expression

<400> SEQUENCE: 80

Thr Gln Asp Pro Ser Arg Val Gly
1 5

<210> SEQ ID NO 81
<211> LENGTH: 14
<212> TYPE: PRT
<213> ORGANISM: Artificial Sequence
<220> FEATURE:
<223> OTHER INFORMATION: V5 tag

<400> SEQUENCE: 81

Gly Lys Pro Ile Pro Asn Pro Leu Leu Gly Leu Asp Ser Thr
1 5 10

<210> SEQ ID NO 82
<211> LENGTH: 20
<212> TYPE: PRT
<213> ORGANISM: Artificial Sequence
<220> FEATURE:
<223> OTHER INFORMATION: Avi-Tag, a peptide allowing biotinylation by the enzyme BirA and so the protein can be isolated by streptavidin and/or avidin

<400> SEQUENCE: 82

Met Ala Gly Gly Leu Asn Asp Ile Phe Glu Ala Gln Lys Ile Glu Trp
1 5 10 15

His Glu Gly Gly
20

```
<210> SEQ ID NO 83
<211> LENGTH: 38
<212> TYPE: PRT
<213> ORGANISM: Artificial Sequence
<220> FEATURE:
<223> OTHER INFORMATION: SBP-tag, a peptide which binds to streptavidin

<400> SEQUENCE: 83

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35


<210> SEQ ID NO 84
<211> LENGTH: 8
<212> TYPE: PRT
<213> ORGANISM: Artificial Sequence
<220> FEATURE:
<223> OTHER INFORMATION: Strep-tag (Strep-tag II), a peptide which binds
      to streptavidin or the modified streptavidin called streptactin

<400> SEQUENCE: 84

Trp Ser His Pro Gln Phe Glu Lys
1               5


<210> SEQ ID NO 85
<211> LENGTH: 84
<212> TYPE: PRT
<213> ORGANISM: Escherichia coli
<220> FEATURE:
<223> OTHER INFORMATION: BCCP (Biotin Carboxyl Carrier Protein), a
      protein domain biotinylated by BirA enabling recognition by
      streptavidin (73-156 amino acids)

<400> SEQUENCE: 85

Pro Ala Ala Ala Glu Ile Ser Gly His Ile Val Arg Ser Pro Met Val
1               5                   10                  15

Gly Thr Phe Tyr Arg Thr Pro Ser Pro Asp Ala Lys Ala Phe Ile Glu
            20                  25                  30

Val Gly Gln Lys Val Asn Val Gly Asp Thr Leu Cys Ile Val Glu Ala
        35                  40                  45

Met Lys Met Met Asn Gln Ile Glu Ala Asp Lys Ser Gly Thr Val Lys
    50                  55                  60

Ala Ile Leu Val Glu Ser Gly Gln Pro Val Glu Phe Asp Glu Pro Leu
65                  70                  75                  80

Val Val Ile Glu


<210> SEQ ID NO 86
<211> LENGTH: 6
<212> TYPE: PRT
<213> ORGANISM: Artificial Sequence
<220> FEATURE:
<223> OTHER INFORMATION: TC tag, a tetracysteine tag that is recognized
      by FlAsH and ReAsH biarsenical compounds

<400> SEQUENCE: 86

Cys Cys Pro Gly Cys Cys
1               5


<210> SEQ ID NO 87
```

-continued

```
<211> LENGTH: 26
<212> TYPE: PRT
<213> ORGANISM: Artificial Sequence
<220> FEATURE:
<223> OTHER INFORMATION: Calmodulin-tag, a peptide bound by the protein
      calmodulin

<400> SEQUENCE: 87

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25


<210> SEQ ID NO 88
<211> LENGTH: 6
<212> TYPE: PRT
<213> ORGANISM: Artificial Sequence
<220> FEATURE:
<223> OTHER INFORMATION: Polyglutamate tag, a peptide binding
      efficiently to anion-exchange resin such as Mono-Q

<400> SEQUENCE: 88

Glu Glu Glu Glu Glu Glu
1               5


<210> SEQ ID NO 89
<211> LENGTH: 297
<212> TYPE: PRT
<213> ORGANISM: Artificial Sequence
<220> FEATURE:
<223> OTHER INFORMATION: Halo-tag, a mutated hydrolase that covalently
      attaches to the HaloLin Resin

<400> SEQUENCE: 89

Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205
```

-continued

```
Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu Glu Ile Ser Gly
    290                 295


<210> SEQ ID NO 90
<211> LENGTH: 370
<212> TYPE: PRT
<213> ORGANISM: Escherichia coli
<220> FEATURE:
<223> OTHER INFORMATION: Maltose binding protein-tag, a protein which
      binds to amylose agarose (27-396 amino acid)

<400> SEQUENCE: 90

Lys Ile Glu Glu Gly Lys Leu Val Ile Trp Ile Asn Gly Asp Lys Gly
1               5                   10                  15

Tyr Asn Gly Leu Ala Glu Val Gly Lys Lys Phe Glu Lys Asp Thr Gly
            20                  25                  30

Ile Lys Val Thr Val Glu His Pro Asp Lys Leu Glu Glu Lys Phe Pro
        35                  40                  45

Gln Val Ala Ala Thr Gly Asp Gly Pro Asp Ile Ile Phe Trp Ala His
    50                  55                  60

Asp Arg Phe Gly Gly Tyr Ala Gln Ser Gly Leu Leu Ala Glu Ile Thr
65                  70                  75                  80

Pro Asp Lys Ala Phe Gln Asp Lys Leu Tyr Pro Phe Thr Trp Asp Ala
                85                  90                  95

Val Arg Tyr Asn Gly Lys Leu Ile Ala Tyr Pro Ile Ala Val Glu Ala
            100                 105                 110

Leu Ser Leu Ile Tyr Asn Lys Asp Leu Leu Pro Asn Pro Pro Lys Thr
        115                 120                 125

Trp Glu Glu Ile Pro Ala Leu Asp Lys Glu Leu Lys Ala Lys Gly Lys
    130                 135                 140

Ser Ala Leu Met Phe Asn Leu Gln Glu Pro Tyr Phe Thr Trp Pro Leu
145                 150                 155                 160

Ile Ala Ala Asp Gly Gly Tyr Ala Phe Lys Tyr Glu Asn Gly Lys Tyr
                165                 170                 175

Asp Ile Lys Asp Val Gly Val Asp Asn Ala Gly Ala Lys Ala Gly Leu
            180                 185                 190

Thr Phe Leu Val Asp Leu Ile Lys Asn Lys His Met Asn Ala Asp Thr
        195                 200                 205

Asp Tyr Ser Ile Ala Glu Ala Ala Phe Asn Lys Gly Glu Thr Ala Met
    210                 215                 220

Thr Ile Asn Gly Pro Trp Ala Trp Ser Asn Ile Asp Thr Ser Lys Val
225                 230                 235                 240

Asn Tyr Gly Val Thr Val Leu Pro Thr Phe Lys Gly Gln Pro Ser Lys
                245                 250                 255

Pro Phe Val Gly Val Leu Ser Ala Gly Ile Asn Ala Ala Ser Pro Asn
            260                 265                 270
```

```
Lys Glu Leu Ala Lys Glu Phe Leu Glu Asn Tyr Leu Leu Thr Asp Glu
        275                 280                 285

Gly Leu Glu Ala Val Asn Lys Asp Lys Pro Leu Gly Ala Val Ala Leu
    290                 295                 300

Lys Ser Tyr Glu Glu Glu Leu Ala Lys Asp Pro Arg Ile Ala Ala Thr
305                 310                 315                 320

Met Glu Asn Ala Gln Lys Gly Glu Ile Met Pro Asn Ile Pro Gln Met
                325                 330                 335

Ser Ala Phe Trp Tyr Ala Val Arg Thr Ala Val Ile Asn Ala Ala Ser
            340                 345                 350

Gly Arg Gln Thr Val Asp Glu Ala Leu Lys Asp Ala Gln Thr Arg Ile
        355                 360                 365

Thr Lys
    370


<210> SEQ ID NO 91
<211> LENGTH: 495
<212> TYPE: PRT
<213> ORGANISM: Escherichia coli
<220> FEATURE:
<223> OTHER INFORMATION: Nus-tag, recognized by an antibody (1-495)

<400> SEQUENCE: 91

Met Asn Lys Glu Ile Leu Ala Val Val Glu Ala Val Ser Asn Glu Lys
1               5                   10                  15

Ala Leu Pro Arg Glu Lys Ile Phe Glu Ala Leu Glu Ser Ala Leu Ala
            20                  25                  30

Thr Ala Thr Lys Lys Lys Tyr Glu Gln Glu Ile Asp Val Arg Val Gln
        35                  40                  45

Ile Asp Arg Lys Ser Gly Asp Phe Asp Thr Phe Arg Arg Trp Leu Val
    50                  55                  60

Val Asp Glu Val Thr Gln Pro Thr Lys Glu Ile Thr Leu Glu Ala Ala
65                  70                  75                  80

Arg Tyr Glu Asp Glu Ser Leu Asn Leu Gly Asp Tyr Val Glu Asp Gln
                85                  90                  95

Ile Glu Ser Val Thr Phe Asp Arg Ile Thr Thr Gln Thr Ala Lys Gln
            100                 105                 110

Val Ile Val Gln Lys Val Arg Glu Ala Glu Arg Ala Met Val Val Asp
        115                 120                 125

Gln Phe Arg Glu His Glu Gly Glu Ile Ile Thr Gly Val Val Lys Lys
    130                 135                 140

Val Asn Arg Asp Asn Ile Ser Leu Asp Leu Gly Asn Asn Ala Glu Ala
145                 150                 155                 160

Val Ile Leu Arg Glu Asp Met Leu Pro Arg Glu Asn Phe Arg Pro Gly
                165                 170                 175

Asp Arg Val Arg Gly Val Leu Tyr Ser Val Arg Pro Glu Ala Arg Gly
            180                 185                 190

Ala Gln Leu Phe Val Thr Arg Ser Lys Pro Glu Met Leu Ile Glu Leu
        195                 200                 205

Phe Arg Ile Glu Val Pro Glu Ile Gly Glu Glu Val Ile Glu Ile Lys
    210                 215                 220

Ala Ala Ala Arg Asp Pro Gly Ser Arg Ala Lys Ile Ala Val Lys Thr
225                 230                 235                 240

Asn Asp Lys Arg Ile Asp Pro Val Gly Ala Cys Val Gly Met Arg Gly
                245                 250                 255
```

```
Ala Arg Val Gln Ala Val Ser Thr Glu Leu Gly Gly Glu Arg Ile Asp
            260                 265                 270

Ile Val Leu Trp Asp Asp Asn Pro Ala Gln Phe Val Ile Asn Ala Met
        275                 280                 285

Ala Pro Ala Asp Val Ala Ser Ile Val Val Asp Glu Asp Lys His Thr
    290                 295                 300

Met Asp Ile Ala Val Glu Ala Gly Asn Leu Ala Gln Ala Ile Gly Arg
305                 310                 315                 320

Asn Gly Gln Asn Val Arg Leu Ala Ser Gln Leu Ser Gly Trp Glu Leu
                325                 330                 335

Asn Val Met Thr Val Asp Asp Leu Gln Ala Lys His Gln Ala Glu Ala
            340                 345                 350

His Ala Ala Ile Asp Thr Phe Thr Lys Tyr Leu Asp Ile Asp Glu Asp
        355                 360                 365

Phe Ala Thr Val Leu Val Glu Glu Gly Phe Ser Thr Leu Glu Glu Leu
    370                 375                 380

Ala Tyr Val Pro Met Lys Glu Leu Leu Glu Ile Glu Gly Leu Asp Glu
385                 390                 395                 400

Pro Thr Val Glu Ala Leu Arg Glu Arg Ala Lys Asn Ala Leu Ala Thr
                405                 410                 415

Ile Ala Gln Ala Gln Glu Glu Ser Leu Gly Asp Asn Lys Pro Ala Asp
            420                 425                 430

Asp Leu Leu Asn Leu Glu Gly Val Asp Arg Asp Leu Ala Phe Lys Leu
        435                 440                 445

Ala Ala Arg Gly Val Cys Thr Leu Glu Asp Leu Ala Glu Gln Gly Ile
    450                 455                 460

Asp Asp Leu Ala Asp Ile Glu Gly Leu Thr Asp Glu Lys Ala Gly Ala
465                 470                 475                 480

Leu Ile Met Ala Ala Arg Asn Ile Cys Trp Phe Gly Asp Glu Ala
                485                 490                 495


<210> SEQ ID NO 92
<211> LENGTH: 108
<212> TYPE: PRT
<213> ORGANISM: Escherichia coli
<220> FEATURE:
<223> OTHER INFORMATION: Thioredoxin-tag is commonly used in expression
      and purification of recombinant proteins. It improves the
      solubility of that protein of interest. Recognized by an antibody
      (2-109 amino acid)

<400> SEQUENCE: 92

Ser Asp Lys Ile Ile His Leu Thr Asp Asp Ser Phe Asp Thr Asp Val
1               5                   10                  15

Leu Lys Ala Asp Gly Ala Ile Leu Val Asp Phe Trp Ala Glu Trp Cys
            20                  25                  30

Gly Pro Cys Lys Met Ile Ala Pro Ile Leu Asp Glu Ile Ala Asp Glu
        35                  40                  45

Tyr Gln Gly Lys Leu Thr Val Ala Lys Leu Asn Ile Asp Gln Asn Pro
    50                  55                  60

Gly Thr Ala Pro Lys Tyr Gly Ile Arg Gly Ile Pro Thr Leu Leu Leu
65                  70                  75                  80

Phe Lys Asn Gly Glu Val Ala Ala Thr Lys Val Gly Ala Leu Ser Lys
                85                  90                  95

Gly Gln Leu Lys Glu Phe Leu Asp Ala Asn Leu Ala
            100                 105
```

<210> SEQ ID NO 93
<211> LENGTH: 16
<212> TYPE: PRT
<213> ORGANISM: Artificial Sequence
<220> FEATURE:
<223> OTHER INFORMATION: Isopeptag, a peptide which binds covalently to pilin-C protein

<400> SEQUENCE: 93

```
Thr Asp Lys Asp Met Thr Ile Thr Phe Thr Asn Lys Lys Asp Ala Glu
1               5                   10                  15
```

<210> SEQ ID NO 94
<211> LENGTH: 13
<212> TYPE: PRT
<213> ORGANISM: Artificial Sequence
<220> FEATURE:
<223> OTHER INFORMATION: SpyTag, a peptide which binds covalently to SpyCatcher protein

<400> SEQUENCE: 94

```
Ala His Ile Val Met Val Asp Ala Tyr Lys Pro Thr Lys
1               5                   10
```

<210> SEQ ID NO 95
<211> LENGTH: 238
<212> TYPE: PRT
<213> ORGANISM: Aequorea victoria
<220> FEATURE:
<223> OTHER INFORMATION: Green fluorescent protein tag

<400> SEQUENCE: 95

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
```

```
    210                 215                 220

Thr Ala Ala Gly Ile Thr His Gly Met Asp Glu Leu Tyr Lys
225                 230                 235


<210> SEQ ID NO 96
<211> LENGTH: 7
<212> TYPE: PRT
<213> ORGANISM: Artificial Sequence
<220> FEATURE:
<223> OTHER INFORMATION: Allows for cleavage by TEV protease between the
      Gln and Ser residues

<400> SEQUENCE: 96

Glu Asn Leu Tyr Phe Gln Ser
1               5


<210> SEQ ID NO 97
<211> LENGTH: 6
<212> TYPE: PRT
<213> ORGANISM: Artificial Sequence
<220> FEATURE:
<223> OTHER INFORMATION: Allows for cleavage by Thrombin protease
      between Arg and Gly residues

<400> SEQUENCE: 97

Leu Val Pro Arg Gly Ser
1               5


<210> SEQ ID NO 98
<211> LENGTH: 8
<212> TYPE: PRT
<213> ORGANISM: Artificial Sequence
<220> FEATURE:
<223> OTHER INFORMATION: Allows for cleavage by PreScission protease
      between the Gln and Gly residues

<400> SEQUENCE: 98

Leu Glu Val Leu Phe Gln Gly Pro
1               5


<210> SEQ ID NO 99
<211> LENGTH: 223
<212> TYPE: PRT
<213> ORGANISM: Homo sapiens
<220> FEATURE:
<223> OTHER INFORMATION: C1q A-chain mature amino acid sequence
      (23-245 amino acid)

<400> SEQUENCE: 99

Glu Asp Leu Cys Arg Ala Pro Asp Gly Lys Lys Gly Glu Ala Gly Arg
1               5                   10                  15

Pro Gly Arg Arg Gly Arg Pro Gly Leu Lys Gly Glu Gln Gly Glu Pro
            20                  25                  30

Gly Ala Pro Gly Ile Arg Thr Gly Ile Gln Gly Leu Lys Gly Asp Gln
        35                  40                  45

Gly Glu Pro Gly Pro Ser Gly Asn Pro Gly Lys Val Gly Tyr Pro Gly
    50                  55                  60

Pro Ser Gly Pro Leu Gly Ala Arg Gly Ile Pro Gly Ile Lys Gly Thr
65                  70                  75                  80

Lys Gly Ser Pro Gly Asn Ile Lys Asp Gln Pro Arg Pro Ala Phe Ser
                85                  90                  95

Ala Ile Arg Arg Asn Pro Pro Met Gly Gly Asn Val Val Ile Phe Asp
            100                 105                 110
```

-continued

```
Thr Val Ile Thr Asn Gln Glu Glu Pro Tyr Gln Asn His Ser Gly Arg
        115                 120                 125

Phe Val Cys Thr Val Pro Gly Tyr Tyr Tyr Phe Thr Phe Gln Val Leu
    130                 135                 140

Ser Gln Trp Glu Ile Cys Leu Ser Ile Val Ser Ser Ser Arg Gly Gln
145                 150                 155                 160

Val Arg Arg Ser Leu Gly Phe Cys Asp Thr Thr Asn Lys Gly Leu Phe
                165                 170                 175

Gln Val Val Ser Gly Gly Met Val Leu Gln Leu Gln Gln Gly Asp Gln
            180                 185                 190

Val Trp Val Glu Lys Asp Pro Lys Lys Gly His Ile Tyr Gln Gly Ser
        195                 200                 205

Glu Ala Asp Ser Val Phe Ser Gly Phe Leu Ile Phe Pro Ser Ala
    210                 215                 220


<210> SEQ ID NO 100
<211> LENGTH: 226
<212> TYPE: PRT
<213> ORGANISM: Homo sapiens
<220> FEATURE:
<223> OTHER INFORMATION: C1q B-chain mature amino acid sequence (28-253
      amino acid)

<400> SEQUENCE: 100

Gln Leu Ser Cys Thr Gly Pro Pro Ala Ile Pro Gly Ile Pro Gly Ile
1               5                   10                  15

Pro Gly Thr Pro Gly Pro Asp Gly Gln Pro Gly Thr Pro Gly Ile Lys
            20                  25                  30

Gly Glu Lys Gly Leu Pro Gly Leu Ala Gly Asp His Gly Glu Phe Gly
        35                  40                  45

Glu Lys Gly Asp Pro Gly Ile Pro Gly Asn Pro Gly Lys Val Gly Pro
    50                  55                  60

Lys Gly Pro Met Gly Pro Lys Gly Gly Pro Gly Ala Pro Gly Ala Pro
65                  70                  75                  80

Gly Pro Lys Gly Glu Ser Gly Asp Tyr Lys Ala Thr Gln Lys Ile Ala
                85                  90                  95

Phe Ser Ala Thr Arg Thr Ile Asn Val Pro Leu Arg Arg Asp Gln Thr
            100                 105                 110

Ile Arg Phe Asp His Val Ile Thr Asn Met Asn Asn Asn Tyr Glu Pro
        115                 120                 125

Arg Ser Gly Lys Phe Thr Cys Lys Val Pro Gly Leu Tyr Tyr Phe Thr
    130                 135                 140

Tyr His Ala Ser Ser Arg Gly Asn Leu Cys Val Asn Leu Met Arg Gly
145                 150                 155                 160

Arg Glu Arg Ala Gln Lys Val Val Thr Phe Cys Asp Tyr Ala Tyr Asn
                165                 170                 175

Thr Phe Gln Val Thr Thr Gly Gly Met Val Leu Lys Leu Glu Gln Gly
            180                 185                 190

Glu Asn Val Phe Leu Gln Ala Thr Asp Lys Asn Ser Leu Leu Gly Met
        195                 200                 205

Glu Gly Ala Asn Ser Ile Phe Ser Gly Phe Leu Leu Phe Pro Asp Met
    210                 215                 220

Glu Ala
225


<210> SEQ ID NO 101
```

-continued

```
<211> LENGTH: 217
<212> TYPE: PRT
<213> ORGANISM: Homo sapiens
<220> FEATURE:
<223> OTHER INFORMATION: C1q C-chain mature amino acid sequence (29-245
      amino acid)

<400> SEQUENCE: 101

Asn Thr Gly Cys Tyr Gly Ile Pro Gly Met Pro Gly Leu Pro Gly Ala
1               5                   10                  15

Pro Gly Lys Asp Gly Tyr Asp Gly Leu Pro Gly Pro Lys Gly Glu Pro
            20                  25                  30

Gly Ile Pro Ala Ile Pro Gly Ile Arg Gly Pro Lys Gly Gln Lys Gly
        35                  40                  45

Glu Pro Gly Leu Pro Gly His Pro Gly Lys Asn Gly Pro Met Gly Pro
    50                  55                  60

Pro Gly Met Pro Gly Val Pro Gly Pro Met Gly Ile Pro Gly Glu Pro
65                  70                  75                  80

Gly Glu Glu Gly Arg Tyr Lys Gln Lys Phe Gln Ser Val Phe Thr Val
                85                  90                  95

Thr Arg Gln Thr His Gln Pro Pro Ala Pro Asn Ser Leu Ile Arg Phe
            100                 105                 110

Asn Ala Val Leu Thr Asn Pro Gln Gly Asp Tyr Asp Thr Ser Thr Gly
        115                 120                 125

Lys Phe Thr Cys Lys Val Pro Gly Leu Tyr Tyr Phe Val Tyr His Ala
    130                 135                 140

Ser His Thr Ala Asn Leu Cys Val Leu Leu Tyr Arg Ser Gly Val Lys
145                 150                 155                 160

Val Val Thr Phe Cys Gly His Thr Ser Lys Thr Asn Gln Val Asn Ser
                165                 170                 175

Gly Gly Val Leu Leu Arg Leu Gln Val Gly Glu Glu Val Trp Leu Ala
            180                 185                 190

Val Asn Asp Tyr Tyr Asp Met Val Gly Ile Gln Gly Ser Asp Ser Val
        195                 200                 205

Phe Ser Gly Phe Leu Leu Phe Pro Asp
    210                 215
```

PROTEIN M FUSION PROTEINS AND USES

CROSS-REFERENCE TO RELATED APPLICATIONS

This application claims priority to U.S. provisional application 63/079,815 filed Sep. 17, 2020, the content of which is incorporated herein.

STATEMENT REGARDING FEDERALLY SPONSORED RESEARCH OR DEVELOPMENT

Not Applicable.

SEQUENCE LISTING ON ASCII TEXT

This patent application file contains a Sequence Listing submitted in computer readable ASCII text format (file name: DELA-02-US-Sequence-Listing.txt, date recorded: Aug. 30, 2021, size: 267,396 bytes). The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The content of the Sequence Listing file is incorporated herein by reference in its entirety.

TECHNICAL FIELD

The present teachings relate to methods and compositions that utilize Protein M fusion proteins. Some of the disclosed methods and compositions relate to methods of neutralizing or eradicating various human pathogens and toxins.

INTRODUCTION

Many emerging and known pathogens continue to present a serious threat to human health and safety. In the past few decades, many infectious diseases, such as those caused by the SARS-CoV-2 virus, the human immunodeficiency virus (HIV) and others have effectively migrated from animal to human hosts and devastated entire populations and economies. Despite some successes in treatment of these pathogens, the options remain limited or not available, like in the case of the SARS-CoV-2 virus. Thus, there remains a need in the art for an efficient general method for neutralizing pathogens or clearing out pathogens from human body.

SUMMARY

The present teachings include a method for neutralizing a pathogen, wherein the pathogen has a specific binding affinity for a receptor fragment, the method comprising: providing conditions for interaction between the pathogen and a fusion protein that comprises a polypeptide having at least 90% identity over its entire length with either the sequence SEQ ID NO: 1 or the sequence SEQ ID NO: 2 conjugated to the receptor fragment, whereby the fusion protein binds to and neutralizes the pathogen.

In accordance with a further aspect, the receptor fragment is a protein fragment of a cellular receptor.

In accordance with a further aspect, the pathogen is SARS-CoV-2 virus and the receptor fragment has the sequence SEQ ID NO:15.

In accordance with a further aspect, conjugation of the polypeptide and the receptor fragment is made through a spacer.

In accordance with a further aspect, the spacer is a peptide having one of the following sequences: SEQ ID NO: 12-14.

In accordance with a further aspect, the receptor fragment comprises one of the following sequences: SEQ ID NO: 16-36.

In accordance with a further aspect, the receptor fragment has one of the following sequences: SEQ ID NO: 16-36.

In accordance with a further aspect, the fusion protein neutralizes the pathogen via recruitment of C1q protein.

The present teachings also include a method for eradicating a bloodborne pathogen in a subject, wherein the pathogen has a specific binding affinity for a receptor fragment inside the subject's body, the method comprising:

receiving a sample of blood, serum or plasma from the subject or from a donor compatible with the subject, wherein the sample comprises immunoglobulins;

adding a fusion protein that comprises a polypeptide having at least 90% identity over its entire length with either the sequence SEQ ID NO:1 or the sequence SEQ ID NO:2 conjugated to the receptor fragment to the sample, wherein the fusion protein binds to the immunoglobulins present in the sample;

administrating the sample having the fusion protein bound to the immunoglobulins into the subject's body, in an amount sufficient to eradicate the pathogen in the subject.

In accordance with a further aspect, the receptor fragment comprises one of the following sequences: SEQ ID NO: 16-36.

In accordance with a further aspect, the fusion protein bound to the immunoglobulins eradicates the pathogen via recruitment of C1q protein.

The present teachings also include a fusion protein having a specific binding affinity for an immunoglobulin molecule, comprising a polypeptide having at least 90% identity over its entire length with either the sequence SEQ ID NO:1 or the sequence SEQ ID NO:2 conjugated to a fusion partner, wherein the fusion partner has a sequence that is at least 90% identical to one of the following sequences: SEQ ID NO: 15-36.

In accordance with a further aspect, conjugation of the polypeptide and the fusion partner is made through a spacer.

In accordance with a further aspect, the spacer is a cleavable peptide having one of the following sequences: SEQ ID NO: 96-98.

The present teachings also include a method for neutralizing a toxin in a subject, wherein the toxin has a specific binding affinity for a receptor fragment, the method comprising:

receiving a sample of blood, serum or plasma from the subject or from a donor compatible with the subject, wherein the sample comprises immunoglobulins;

adding a conjugated protein that comprises a polypeptide having at least 90% identity over its entire length with either the sequence SEQ ID NO:1 or the sequence SEQ ID NO:2 conjugated to the receptor fragment to the sample, wherein the conjugated protein binds to the immunoglobulins present in the sample;

administrating the sample having the conjugated protein bound to the immunoglobulins into the subject's body, in an amount sufficient to eradicate the toxin in the subject.

In accordance with a further aspect, the receptor fragment comprises one of the following sequences: SEQ ID NO: 16-36.

The present teachings also include a method for detecting immunoglobulins that are present in a solution or on a solid support matrix, but not bound to their cognate antigen, the method comprising: contacting immunoglobulins with conjugated proteins in the solution, wherein each conjugated protein comprises a polypeptide having at least 90% identity over its entire length with either the sequence SEQ ID NO:1 or the sequence SEQ ID NO:2 conjugated to a detectable probe, whereby the conjugated proteins bind to immunoglobulins that are not bound to their cognate antigen; separating conjugated proteins that are bound to immunoglobulins from conjugated proteins that are not bound to immunoglobulins; detecting the conjugated proteins that are bound to immunoglobulins by utilizing the detectable probe, thereby detecting immunoglobulins that are not bound to their cognate antigen. Examples of solid support matrix include: blots, beads, microplate well, resin.

In accordance with a further aspect, conjugation of the polypeptide and the detectable probe is made through a spacer.

In accordance with a further aspect, the spacer is a cleavable peptide having one of the following sequences: SEQ ID NO: 96-98.

In accordance with a further aspect, the detectable probe is an enzyme that has a fluorogenic, luminescent or chromogenic substrate.

In accordance with a further aspect, the detectable probe is a protein having a sequence chosen from SEQ ID NO:67-69.

In accordance with a further aspect, the detectable probe is a fluorescent or a luminescent or a radioactive molecule.

In accordance with a further aspect, the detectable probe is an epitope tag having a sequence chosen from SEQ ID NO: 70-81.

In accordance with a further aspect, the detectable probe is a polypeptide having a sequence chosen from SEQ ID NO:82-85 and configured to bind streptavidin and/or avidin.

In accordance with a further aspect, the detectable probe is a polypeptide having a sequence chosen from SEQ ID NO:86-92 or from SEQ ID NO:93-94, and configured to attach to its cognate binding partner, either covalently or non-covalently.

In accordance with a further aspect, the detectable probe is a fluorescent protein having the sequence SEQ ID NO:95.

The present teachings also include a codon-optimized polynucleotide that encodes the fusion protein according to claim 14.

In accordance with a further aspect, the codon-optimized polynucleotide according to claim 29 has a sequence that is at least 95% identical to one of the following nucleic acid sequences: SEQ ID NO: 40-61.

In accordance with a further aspect, the codon-optimized polynucleotide according to claim 29 is inserted in a vector configured for replication and protein expression in mammalian cells.

These and other features, aspects and advantages of the present teachings will become better understood with reference to the following description, examples and appended claims.

BRIEF DESCRIPTION OF THE DRAWINGS

Those of skill in the art will understand that the drawings, described below, are for illustrative purposes only. The drawings are not intended to limit the scope of the present teachings in any way.

FIG. 5D. Protein M-HRP indirect detection of mouse IgG1 antibody in solution. Protein M-HRP incubated with increasing concentration of mouse IgG1 antibody resulted in the loss of Protein M binding to the human IgG antibody coated on the wells. In the absence of mouse IgG1 antibody in solution, binding of Protein M-HRP to the human IgG antibody coated on the wells is not hindered.

FIG. 7A. Biotinylated irrelevant (non-specific) antibody binds to SARS-CoV-2 spike protein coated on the wells only when the antibody is in a complex with armY-ACE2. ACE2 domain mediates binding between the spike protein and armY-bound antibody since antibody with Protein M lacking the ACE2 domain is unable to bind the spike protein coated on the well. As expected, antibody alone does not bind the SARS-CoV-2 spike protein, which requires a physical association with armY-ACE2 that binds the spike protein coated on the well. Moreover, armY-ACE2 alone does not produce any signals since the presence of signal requires the interaction between the biotinylated antibody and armY-ACE2 bound to the spike protein coated on the well. FIG. 7 B. Anti-histidine (his) tag was used to detect the his (6× histidine)-tagged SARS-CoV-2 spike protein in a complex with armY-ACE2. Although, not included in this experiment, SARS-CoV-2 spike protein does not bind to human IgG (previous observation), a complex between armY-ACE2 and SARS-CoV-2 spike protein was required for detection by anti-his tag antibody. Myc-specific antibody detected myc-tagged armY-ACE2 binding to human IgG coated wells regardless of whether it was bound or not bound to SARS-CoV-2 spike protein.

FIG. 11A. Only a complex between armY-ACE2 and mouse IgM resulted in binding to immobilized human C1q complement component. FIG. 11B. Binding of [armY-ACE2+mouse IgG1] complexes to immobilized human C1q complement component is inhibited by pre-incubation of the complex with soluble human C1q, which also suggest that army-ACE2 primes mouse IgG1 antibody to bind C1q in solution. A complex between Protein M (lacking ACE2) with mouse IgG1 did not result in binding to C1q, suggesting the requirement of the fusion partner domain, ACE2, to induce a conformation resulting in antibody binding to C1q.

FIG. 12A. armY-ACE2 exhibits ACE2 activity in a dose dependent fashion. FIG. 12B. [armY-ACE2+ antibody] complexes exhibit ACE2 activity comparable to armY-ACE2 alone, suggesting that binding of armY-ACE2 to antibodies does not interfere with the enzymatic function of ACE2.

FIG. 13A. Diagram of armY-ACE2 construct showing a myc-tag at the N-terminus, followed by the human ACE2, a linker and Protein M "armY" at the C-terminus. FIG. 13B. Photograph of the SDS-PAGE gel of purified non-reduced (left lane) and reduced (right lane) of armY-ACE2 showing a ~180 kDa protein band.

FIG. 14A. Non-immune serum antibodies armed with armY-ACE2 gain the ability to bind to SARS-CoV-2 spike protein. Unarmed non-immune serum (pre-vaccine) does not bind to SARS-CoV-2 spike protein (a) but gain the ability to bind after incubation with armY-ACE2 (b). Approximately one month post-vaccination with the Moderna Covid19 vaccine, serum antibodies bind to the SARS-CoV-2 spike protein coated on the well as expected and served as an assay positive control (c). The assay does not detect armY-ACE2 alone when added to the SARS-CoV-2 spike protein coated wells (d), suggesting a requirement for serum antibodies to be in a stable complex with armY-ACE2 to bind the SARS-CoV-2 spike protein for assay detection. The photo to the right, representative of the duplicate wells, shows the corresponding SARS-CoV-2 spike protein coated wells 20 minutes after the addition of the mixtures, followed by addition of detecting antibody and addition of the TMB substrate, which give rise to the appearance of the blue color product indicative of antibody presence bound to the SARS-CoV-2 spike protein. FIG. 14B. Non-immune plasma (anticoagulant: ACD-A) antibodies armed with armY-ACE2 also gain the ability bind to SARS-CoV-2 spike protein, comparable to non-immune serum antibodies armed with armY-ACE2. As expected, unarmed serum or plasma antibodies do not bind to SARS-CoV-2 spike protein. FIG. 14C. Less than 1 ug/ml of free-unengaged army-ACE2 remain detectable after a 60 minutes incubation with either serum- or plasma-antibodies at 37° C., suggesting at least 95% of armY-ACE2 added (20 ug/ml) readily engage and arm antibodies in solution.

FIG. 15A. Monoclonal antibody (mAb) armed with armY-ACE2 gains the ability to bind the SARS-CoV-2 spike protein, while in FIG. 15B mAb is no longer able to bind its natural target antigen.

DETAILED DESCRIPTION

Abbreviations and Definitions

Figure 1:
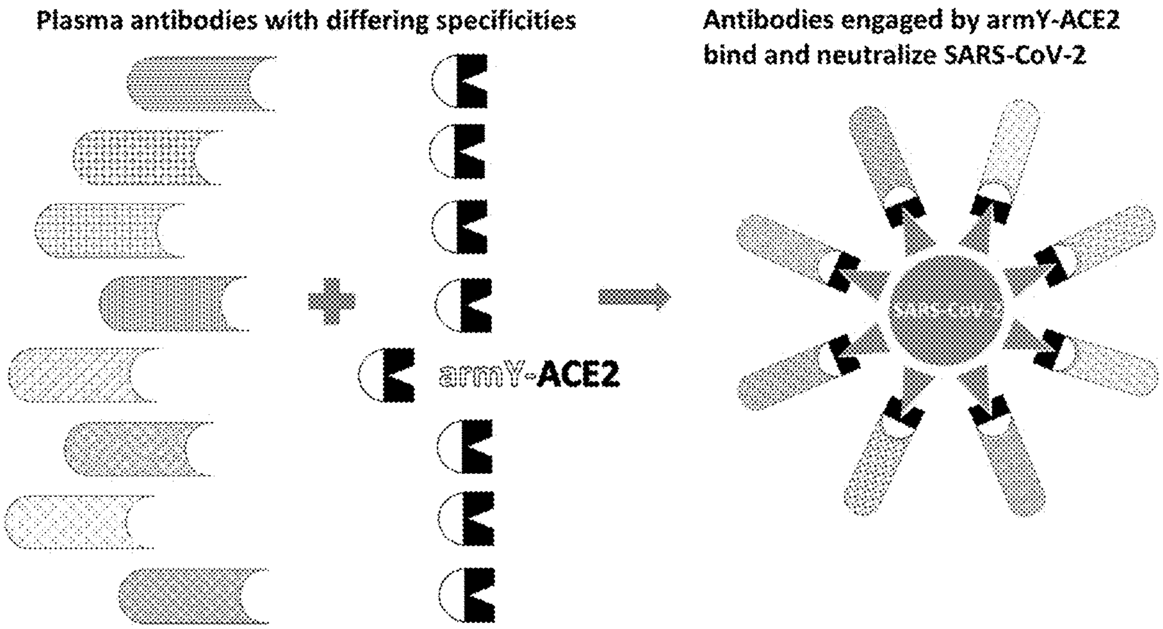
FIG. 1. A schematic representation of plasma antibodies of differing isotypes and differing specificities mixed with armY-ACE2 fusion protein. When armY-ACE2 is added to the plasma, armY-ACE2 binds and blocks the antibody antigen-binding region via the armY component (Protein M). The ACE2 component of the fusion protein endows the antibodies with a new binding specificity to the spike protein of SARS-CoV-2, allowing the antibodies to bind SARS-CoV-2 and mark for eradication.
Figure 2:
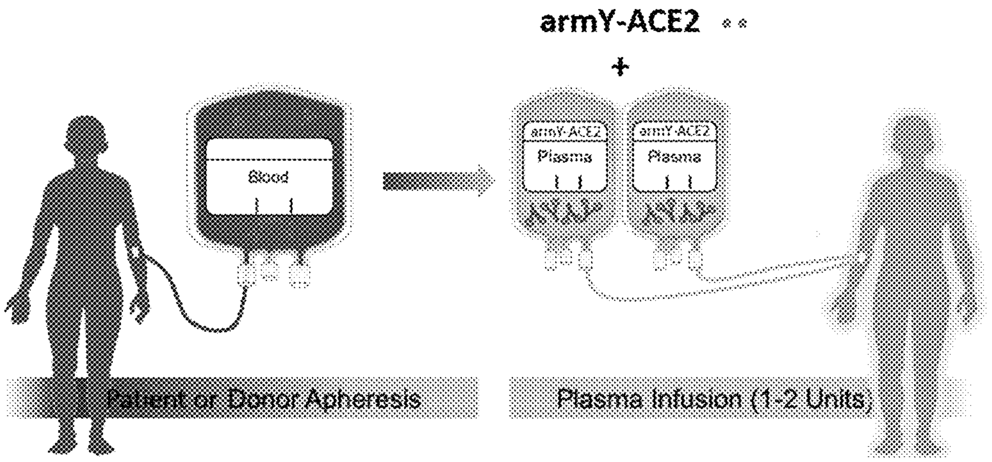
FIG. 2. A schematic representation of one proposed route of administration of armY-ACE2 therapeutic, whereby plasma (containing antibodies) is obtained from the patient or a ABO-compatible donor through apheresis. A measured amount of armY-ACE2 is added to the plasma antibodies, which then acquire SARS-CoV-2 specificity as described in FIG. 1 and as demonstrated in Example 16, FIG. 14 below. A patient with active COVID-19 is treated with armY-ACE2 plasma antibodies and allowed to fully recover.

Unless otherwise noted, technical terms are used according to conventional usage. All publications, patent applications, patents, and other references mentioned herein are incorporated by reference in their entirety for all purposes. To facilitate understanding of the invention, a number of terms and abbreviations as used herein are defined below as follows.

The terms "polypeptide", "protein" and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide", "protein" and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, and the like. Modifications also include intra-molecular crosslinking and covalent attachment of various moieties such as lipids, flavin, biotin, polyethylene glycol or derivatives thereof, and the like. In addition, modifications may also include cyclization, branching and cross-linking. Further, amino acids other than the conventional twenty amino acids encoded by genes may also be included in a polypeptide. The term "polypeptide" or "protein" may also encompass a "purified" polypeptide that is substantially separated from other polypeptides in a cell or organism in which the polypeptide naturally occurs (e.g., 30%, 40%, 50%, 60%, 70%, 80%, 90%, 95%, 96%, 97%, 98%, 99%, 100% free of contaminants).

Conservative changes: As used herein, when referring to mutations in a nucleic acid molecule, “conservative changes” are those in which at least one codon in the protein-coding region of the nucleic acid has been changed such that at least one amino acid of the polypeptide encoded by the nucleic acid sequence is substituted with another amino acid having similar characteristics. Examples of conservative amino acid substitutions are ser for ala, thr, or cys; lys for arg; gin for asn, his, or lys; his for asn; glu for asp or lys; asn for his or gin; asp for glu; pro for gly; leu for ile, phe, met, or val; val for ile or leu; ile for leu, met, or val; arg for lys; met for phe; tyr for phe or trp; thr for ser; trp for tyr; and phe for tyr.

Isolated polypeptide: The term “isolated polypeptide” as used herein means a polypeptide molecule is present in a form other than found in nature in its original environment with respect to its association with other molecules. The term “isolated polypeptide” encompasses a “purified polypeptide”, which is used herein to mean that a specified polypeptide is in a substantially homogenous preparation, substantially free of other cellular components, other polypeptides, viral materials, or culture medium, or when the polypeptide is chemically synthesized, substantially free of chemical precursors or byproducts associated with the chemical synthesis. For a purified polypeptide, preferably the specified polypeptide molecule constitutes at least 15 percent of the total polypeptide in the preparation. A “purified polypeptide” can be obtained from natural or recombinant host cells by standard purification techniques, or by chemical synthesis.

An “isolated” biological component (such as a nucleic acid molecule, protein, or virus) has been substantially separated or purified away from other biological components (e.g., other chromosomal and extra-chromosomal DNA and RNA, proteins and/or organelles). Nucleic acids, proteins, and/or viruses that have been “isolated” include nucleic acids, proteins, and viruses purified by standard purification methods. The term also embraces nucleic acids, proteins, and viruses prepared by recombinant expression in a host cell, as well as chemically synthesized nucleic acids or proteins. The term “isolated” (or purified) does not require absolute purity; rather, it is intended as a relative term. Thus, for example, an isolated or purified nucleic acid, protein, virus, or other active compound is one that is isolated in whole or in part from associated nucleic acids, proteins, and other contaminants.

As used herein, the term “vector” refers to a nucleic acid molecule capable of transporting another nucleic acid to which it has been linked. The term “vector” comprises an “expression vector”, e.g. a vector that is capable of directing the expression of genes to which they are operatively linked. The vector often includes sequences that effect the expression of a desirable molecule, e.g., a promoter, a coding region and a transcriptional termination sequence. An expression vector can be an integrative vector (i.e., a vector that can integrate into the host genome), or a vector that does not integrate but self-replicates, in which case, the vector includes an origin of replication which permits the entire vector to be reproduced once it is within the host cell. Preferred vectors are those capable of autonomous replication and/expression of nucleic acids to which they are linked.

Nucleic acid molecules encoding fusion proteins are also within the scope of the invention. Such nucleic acids can be made by preparing a construct (e g., an expression vector) that expresses a fusion protein when introduced into a suitable host. For example, such a construct can be made by ligating a first polynucleotide encoding a single-domain antibody, or fragment or variant thereof, fused in frame with a second polynucleotide encoding another protein such that expression of the construct in a suitable expression system yields a fusion protein. Polynucleotides that encode fusion proteins can be present in isolation, or can be inserted in a vector for expression in cells. Such vector may be suitable for replication and protein expression in bacterial, mammalian or insect cells. Polynucleotides that encode fusion proteins can be codon-optimized for expression in particular type of cells by standard methods known in the art.

A “codon-optimized” nucleic acid or polynucleotide refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells). Codon optimization does not alter the amino acid sequence of the encoded protein.

The term “neutralizing a pathogen” used herein is synonymous to “inactivating a pathogen” and means that the pathogen will no longer be able to interact with a specific receptor molecule either in vitro or in vivo, or will no longer be able to infect cells of an organism.

The term “neutralizing a toxin” used herein is synonymous to “inactivating a toxin” and means that the toxin will no longer be able to interact with its target, either in vitro, or in a subject’s body.

The term “eradicating a pathogen” used herein refers to neutralizing the pathogen in a subject.

As used herein, the term “Protein M” or “armY” refers to antibody-binding fragment of protein from *Mycoplasma genitalium* that has an amino acid sequence SEQ ID NO:1 (Grover R K, et al., Science, 2014), or to antibody-binding fragment of protein from *Mycoplasma pneumoniae* that has an amino acid sequence SEQ ID NO:2 (Blötz C, et al., Front Microbiol. 2020), or to a polypeptide with immunoglobulin-binding activity having a sequence with at least 90% identity over its entire length to one of the following sequences: SEQ ID NO: 3-8. In some embodiments, the term “Protein M” or “armY” also includes an immunoglobulin-binding fragment of Protein M from *Mycoplasma genitalium* or *Mycoplasma pneumoniae*.

As used herein, the term “ACE2” refers to the human cellular angiotensin-converting enzyme 2 receptor.

As used herein, the term “fusion protein” refers to an artificial, non-natural polypeptide that consists of at least two unrelated covalently linked polypeptides. The linkage between these polypeptides can be of different nature, including a peptide bond, a short flexible amino acid spacer, or a spacer of another type. The spacer joins the polypeptides together, yet preserves some distance between the polypeptides such that both polypeptides can properly fold independently.

The term “immunoglobulin,” “Ig” or “antibody” (used interchangeably herein) refers to a glycoprotein formed in response to administration of bacteria, viruses or other antigens to a mammalian organism, said glycoprotein has the ability to specifically bind cognate antigen and consists of two heavy (H) chains and two light (L) chains connected and stabilized by interchain disulfide bonds. Immunoglobulins or antibodies may be monoclonal or polyclonal and may exist in monomeric or polymeric form, for example. IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', $F(ab')_2$, Fc and/or Fv fragments.

The term "antigen-binding fragment" refers to a polypeptide portion of an immunoglobulin or antibody that binds an antigen or competes with intact antibody (i.e. with the intact antibody from which they were derived) for antigen binding (i.e. specific binding). Binding fragments can be produced by recombinant DNA techniques, or by enzymatic or chemical cleavage of intact immunoglobulins. Binding fragments include Fab, Fab', $F(ab')_2$, Fv, single chains, and single-chain antibodies.

As used herein, the term "toxin" refers to an endogenous entity or exogenous substance that is harmful to a subject (preferably, human subject). Examples of harmful endogenous entities are excessive inflammatory cytokines that may be produced during a cytokine storm in the subject. A harmful endogenous entity can be soluble or membrane bound. Examples of harmful exogenous substances are Botulinum neurotoxin A, Botulinum neurotoxin B, Staphylococcal enterotoxin A and B, Staphylococcal enterotoxin A, Staphylococcal enterotoxin B, *Clostridium perfringens* Epsilon toxin (ETX), Ricin, Anthrax.

As used herein, the term "donor compatible with the subject" refers to a human subject having compatibility for a blood transfusion (compatibility based on ABO blood groups, Rh Type).

As used herein, the term "receptor fragment" refers to a fragment of a protein to which a pathogen (usually, a protein from the pathogen's coat) or a toxin has a specific binding affinity, or can specifically bind. Preferably, receptor fragment is a protein fragment of a cellular receptor that the pathogen or toxin binds to and utilizes to enter the cell. Preferably, receptor fragment is located inside a subject's body.

Unless otherwise defined, technical and scientific terms used in the present teachings described herein shall have the meanings that are commonly understood by those of ordinary skill in the art. Further, unless otherwise required by context, plural terms shall include the singular and singular terms shall include pluralities. Generally, nomenclatures utilized in connection with molecular biology, cell and tissue culture, protein and oligo- or polynucleotide chemistry described herein are well-known and commonly used in the art. Standard techniques are used, for example, for recombinant nucleic acid and protein preparation, purification and analysis, for oligonucleotide synthesis. Purification techniques and enzymatic reactions are performed according to manufacturer's specifications or as described herein or as commonly accomplished in the art. The techniques and procedures described herein are generally performed according to conventional methods well known in the art and as described in various general references that are cited and discussed throughout the instant specification. See, e.g., Sambrook et al., Molecular Cloning: A Laboratory Manual (Third ed., Cold Spring Harbor Laboratory Press, Cold Spring Harbor, N.Y. 2000). The nomenclatures utilized in connection with, and the laboratory procedures and techniques described herein are those well-known and commonly used in the art.

The present invention is directed to methods and compositions for inactivating or eliminating a pathogen, preferably a bloodborne pathogen having a specific binding affinity for a receptor fragment, by utilizing a fusion protein that comprises Protein M and the receptor fragment. Preferably, Protein M is chosen from an extracellular domain of *Mycoplasma genitalium* protein (Grover R K, et al., Science, 2014; SEQ ID NO: 1) or an extracellular domain of *Mycoplasma pneumoniae* protein (Blötz C, et al., Front Microbiol. 2020; SEQ ID NO: 2) that strongly bind to immunoglobulin molecules (antibodies). Typical binding affinities ($K_d$) of Protein M to immunoglobulin molecules are from 1.2 to 5.2 nM (Grover R K, et al., Science, 2014).

Orthologs of Protein M can be found in several related species of *Mycoplasma: M. penetrans, Mycoplasma tullyi, Mycoplasma iowae, Mycoplasma imitans, Mycoplasma alvi* and *M. gallisepticum* (disclosed herein in the Sequence listing). These sequences are also disclosed herein and can be used to create fusions or fusion proteins according to the present invention. Protein M is functionally similar to other bacterial-derived proteins that bind antibodies (e.g., protein A, protein G and protein L) with the exception that Protein M blocks the antibody's binding site and prevent it from binding its cognate antigen. Therefore, harnessing the antibody binding property of Protein M, it can be used to couple any attached compounds (e.g., genetic fusion or chemical conjugation) to an antibody regardless of the antibody's specificity. Consequently, interaction with the Protein M fusion protein will result in the loss of the antibody's specificity and acquire the specificity as that of the attached compound. The properties of Protein M fusion protein with the compound will be a combination of the antibody's stability, antibody's functional properties (such as ability to engage Fc receptors on immune cells, activate the complement system, an increased binding avidity and the compound properties (affinity to a pathogen).

Preferred nucleic acid molecules for use in the invention are polynucleotides that encode fusion proteins shown herein in the appended Sequence Listing. Nucleic acid molecules utilized in the present invention may be in the form of RNA or in the form of DNA (e.g., cDNA, genomic DNA, and synthetic DNA). The nucleic acid molecule may be double-stranded or single-stranded, and if single-stranded may be the coding (sense) strand or non-coding (anti-sense) strand. The coding sequence which encodes a fusion Protein May be identical to one of the nucleotide sequences provided in the appendices, or it may also be a different coding sequence which, as a result of the redundancy or degeneracy of the genetic code, encodes the provided fusion protein.

In some embodiments, variant fusion proteins displaying substantial differences in structure can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histidine, for (or by) an electronegative residue, e.g., glutamic acid or aspartic acid; or (d) a residue having a bulky side chain, e.g., phenylalanine, for (or by) one not having a side chain, e g., glycine.

Sequence Identity: As used herein, the term "sequence identity" means the percentage of identical subunits at corresponding positions in two sequences when the two sequences are aligned to maximize subunit matching, i.e., taking into account gaps and insertions. Sequence identity is present when a subunit position in both of the two sequences is occupied by the same nucleotide or amino acid, e.g., if a given position is occupied by an adenine in each of two DNA molecules, then the molecules are identical at that position. For example, if 7 positions in a sequence of 10 nucleotides in length are identical to the corresponding positions in a second 10-nucleotide sequence, then the two sequences have 70% sequence identity. Sequence identity of a polynucleotide is typically measured using sequence analysis software (e.g., the Sequence Analysis Software Package of the Genetics Computer Group, University of Wisconsin Biotechnology Center, 1710 University Avenue, Madison, Wis. 53705).

In preferred embodiments, variant fusion proteins displaying only non-substantial or negligible differences in structure can be generated by making nucleotide substitutions that cause only conservative amino acid changes in the encoded polypeptide. By doing this, fusion protein variants that comprise a sequence having at least 90% (90%, 91%, 92%, 93%, 94%, 95%, 96%, 97%, 98%, and 99%) sequence identity with the fusion protein sequences provided in the attached appendices, and retain at least one functional activity, e g., immunoglobulin binding activity. The invention also covers non-naturally occurring polynucleotides or variants that encode the fusion protein variants having at least 90% sequence identity over the entire length with the fusion protein sequences provided in the attached appendices, and retain at least one functional activity, e g., immunoglobulin binding activity. Methods of making targeted amino acid substitutions, deletions, truncations, and insertions are generally known in the art. For example, amino acid sequence variants can be prepared by mutations in the DNA. Methods for polynucleotide alterations are well known in the art, for example, Kunkel et al. (1987) Methods in Enzymol. 154: 367-382; U.S. Pat. No. 4,873,192 and the references cited therein.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. By other words, this is an amount of an agent or composition that alone, or together with a pharmaceutically acceptable carrier or one or more additional agents, induces the desired response. Effective amounts of a therapeutic agent can be determined in many different ways, such as assaying for a reduction in symptoms or improvement of physiological condition of a subject. Effective amounts also can be determined through various in vitro, in vivo, or in situ assays.

In some embodiments, variants of fusion proteins having a reduced immunogenicity in humans may be generated by making amino acid substitutions in the fusion proteins that remove or modify human T-cell or B-cell epitopes present in said fusion protein. Fusion proteins that have less potential human T-cell or B-cell epitopes in the sequence are less prone to activate an unwanted immune response in a subject. The unwanted immune response includes development of anti-fusion protein antibodies that may neutralize said fusion protein. Several methods for identifying, modifying and removing potential human T-cell or B-cell epitopes in protein sequences are known and disclosed in, for example, Jawa V, Terry F, Gokemeijer J, et al. T-Cell Dependent Immunogenicity of Protein Therapeutics Pre-clinical Assessment and Mitigation-Updated Consensus and Review 2020. Front Immunol. 2020; 11:1301; Mazor R, Crown D, Addissie S, Jang Y, Kaplan G, Pastan I. Elimination of murine and human T-cell epitopes in recombinant immunotoxin eliminates neutralizing and anti-drug antibodies in vivo. Cell Mol Immunol. 2017; 14(5):432-442; U.S. Ser. No. 10/751,397 B2, US2018161419A1, the contents of which are incorporated herein by reference in its entirety.

Disclosed herein are methods for making and using fusion proteins that comprises amino acid sequences of Protein M or amino acid sequences that are at least 90% identical over the entire length with the sequences of Protein M. An example of such fusion protein is armY-ACE2, which consists of the Protein M sequence fused to the sequence of the ACE2 receptor, or to a fragment of the ACE2 receptor to which the envelope spike S protein of the SARS-CoV-2 virus is bound. Fusion protein armY-ACE2 can bind to immunoglobulin molecules of different classes, blocking their original specificity and instead directing them to interact with the envelope spike S protein of the SARS-CoV-2 virus (FIG. 1). As a result, the SARS-CoV-2 virus will be no longer capable of infecting human cells via its envelope spike S protein, and will be eliminated by macrophages that recognize immunoglobulin-bound targets, and by engaging via a complement factor activated by the bound immunoglobulins, or by other mechanisms. By utilizing knowledge of specific cellular receptors recognized by pathogens (virus or microorganism) and toxins for cellular entry, various armY-fusion proteins may be created and utilized according to the present invention. To make armY-fusion proteins, various fragments of the receptor may be used, including, without restriction, a full extracellular domain of the receptor or a fragment of the receptor which is necessary and sufficient for interaction with the pathogen or toxin.

Non-limiting examples of pathogens and toxins and their cellular attachment receptors suitable to make armY-fusion proteins are listed as follows: (a) armY-ACE2 (Angiotensin-converting enzyme 2) for the SARS-CoV and SARS-CoV-2, as well as human coronavirus NL63/HCoV-NL6; (b) armY-CD209 (DC-SIGN) for HIV-1, HIV-2, Ebolavirus, Cytomegalovirus, HCV, Dengue virus, Measles virus, Herpes simplex virus 1, Influenza virus, SARS-CoV, Japanese encephalitis virus, Lassa virus, Respiratory syncytial virus, Rift valley fever virus, West-nile virus, Marburg virus, Uukuniemi virus, and *Yersinia Pestis*; (c) armY-C-type lectin domain family 4 member M for Ebolavirus, Hepatitis C virus, HIV-1, Human coronavirus 229E, Human cytomegalovirus/HHV-5, Influenza virus, SARS-CoV, West-nile virus, Japanese encephalitis virus, Marburg virus glycoprotein, and *M. bovis*; (d) armY-CD4 for HIV; (e) armY-Synaptic vesicle glycoprotein 2A for the *C. botulinum* neurotoxin type A2 (BoNT/A, botA); (f) armY-Synaptic vesicle glycoprotein 2B for the *C. botulinum* neurotoxin type A2 (BoNT/A, botA). Probably also for the closely related *C. botulinum* neurotoxin type A1; (g) armY-Synaptic vesicle glycoprotein 2C for *C. botulinum* neurotoxin type A (BoNT/A, botA) and *C. botulinum* neurotoxin type A2; (h) armY-Synaptotagmin I for *C. botulinum* neurotoxin type B (BoNT/B, botB); (i) armY-Synaptotagmin II for *C. botulinum* neurotoxin type B (BoNT/B, botB); (j) armY-HLA class II histocompatibility antigen, DRB1 beta chain for Epstein-Barr virus and Staphylococcal enterotoxin A and B; (k) armY-HLA class II histocompatibility antigen, DR alpha chain for Epstein-Barr virus BZLF2/gp42, *Staphylococcus aureus* enterotoxin A/entA, enterotoxin B/entB, enterotoxin C1/entC1, enterotoxin D/entD, and enterotoxin H/entH; (1) armY-T cell receptor beta variable 7-9 for *Staphylococcus aureus* enterotoxin A/entA; (m) armY-T cell receptor beta variable 19 for *Staphylococcus aureus* enterotoxin B/entB; (n) armY-Hepatitis A virus cellular receptor 1 for Hepatitis A virus, Ebola virus, Marburg virus and Dengue virus and *Clostridium perfringens* Epsilon toxin (ETX); (o) armY-Myelin and lymphocyte protein for *Clostridium perfringens* Epsilon toxin (ETX); (p) armY-Complement factor H for *Streptococcus pneumoniae, Neisseria meningitides, Staphylococcus aureus, Borrelia burgdorferi* and West nile virus; (q) armY-Hepatocyte growth factor receptor for *Listeria monocytogenes* internalin InlB; (r) armY-Membrane cofactor protein (CD46) for Adenovirus subgroup B2 and Ad3, Measles virus, Herpesvirus 6/HHV-6, *Neisseria* and *Streptococcus pyogenes*; (s) armY-Glycophorin-A for *Plasmodium falciparum*, Influenza virus, Hepatitis A virus (HAV), *Streptococcus gordonii*; (t) armY-C-type lectin domain family 4 member K (Langerin, CD207) for *Candida* species, *Saccharomyces* species, *Malassezia furfur*, human immunodeficiency virus-1 (HIV-1) and *Yesinia pestis*; (u) armY-Anthrax toxin receptor 1 for Anthrax toxin; and (v) armY-Anthrax toxin receptor 2 for Anthrax toxin.

In some embodiments, codon-optimized polynucleotides are disclosed that contain a nucleic acid sequence at least 95%, at least 96%, at least 97%, at least 98% or at least 99% identical to SEQ ID NO: 40-61. These polynucleotides are codon-optimized for expression in human cells.

Taking as an example armY-ACE2 fusion protein and SARS-CoV-2 as a pathogen, several advantages of the armY-ACE2 approach can be shown over the other known potential virus inactivating strategies, such as (a) monoclonal antibody (mAb) therapy; (b) ACE2 or ACE2-Fc fusion proteins therapy; (c) Convalescent plasma antibody therapy, and (d) anti-viral vaccine.

As to (a), mAb therapy is subject to viral escape due to a mutation in a targeted viral epitope. Most viruses possess a high mutation rate; after a mutation in the mAb-recognizing area the mAb therapy is no longer effective, and mutated viruses will proliferate and eventually will be enriched. Instead, armY-ACE2 will bind the SARS-CoV-2 virus regardless of any mutation, because all SARS-CoV-2 viruses bind ACE2 for entry into human cells. Also, since armY can bind all antibody isotypes, armY-ACE2 can arm all antibody isotypes with the capacity to target SARS-CoV-2 viruses, hence mimicking a generalized antibody-mediated immune response.

As to (b), ACE2 monotherapy suffers from rapid renal clearance due to the small size of ACE2. ACE2-Fc fusion proteins is of a single isotype, usually, an IgG. It is known that other isotypes e.g., IgM, IgA are also efficacious in pathogen clearance. Thus, armY-ACE2 can arm all isotypes or a specific isotype with the capacity to target SARS-CoV-2. In addition, Fc fusion proteins do not activate the complement system. Instead, armY-ACE2 complex with antibody maintains Fc functionality, and is able to prime the antibody to bind the C1q complement factor, a required step for complement activation. Being able to harness the full effector potential of antibodies may be critical in the overall eradication of the targeted pathogen, such as SARS-CoV-2.

As to (c), convalescent plasma therapy requires blood from donors previously exposed to SARS-CoV-2, and no longer with COVID-19 symptoms. It might take as long as 7-10 days to test for lack of blood-borne pathogens, anti-SARS-CoV-2 titer levels and ABO blood type matching requirements. Instead, armY-ACE2 could arm the patient's own plasma antibodies, and can be available to the patient in less than 2-4 hours. Donor plasma can also be used, but these can be from regular donors that have already been screened, so this could be made available to the patient even faster as long as ABO blood type and Rh type match is achieved.

As to (d), SARS-CoV-2 vaccine is prophylactic in its use and the uninfected person will require time to develop a level of protective immunity. Vaccines cannot be a therapeutic for those with on-going COVID-19. Moreover, vaccine efficacy is subject to many variables including state of health of the individual and potential side-effects, e.g., anaphylactic reaction that might hinder completion of immunization protocol. armY-ACE2 is applicable to subjects with on-going COVID-19.

The abovementioned advantages apply to other fusion proteins that are disclosed herein.

Treatment with Protein M fusion proteins changes the specificity of antibodies in plasma to a new target (e.g, a virus, bacterium or a toxin) for immune recognition and elimination; provide more optimal pharmacokinetics and activity of a compound attached to a larger more stable antibody, and improvement of bioavailability of compounds; deliver therapeutic or diagnostic compounds to an antibody-binding target (e.g., antibody binding bacteria, tissue or cell); disrupt interaction between two or more entities required for pathogenicity.

Possible routes of administration for Protein M fusion proteins include parenteral, oral and/or inhalation. In a preferred embodiment, ex-vivo plasma/serum (patient-derived or from a compatible donor) is mixed with Protein M-fusion protein and administered to patient. Preferably, Protein M fusion proteins are administered in the form of a pharmaceutical composition, comprising additional pharmaceutically acceptable excipients.

In some embodiments, Protein M fusion proteins are stored or administered in a suitable formulation that provides stability to the fusion proteins. Such formulation includes one or several pharmaceutically acceptable excipients. By "pharmaceutically acceptable" it is meant the excipient is compatible with the other ingredients of the formulation and not deleterious to the recipient thereof. Excipients for protein formulations may be picked up by methods known in the art, and may include buffers, stabilizers, antioxidants, salts, polysorbates, amino acids, among others.

Other potential uses of Protein M fusion proteins include detecting presence of antibodies and/or antibody-binding factors found in blood, tissue or cells. For example, fusing a reporter enzyme (e.g., Horseradish peroxidase, HRP) or attaching a detectable probe or label (e.g., biotin-avidin, biotin-streptavidin) to Protein M can be used to detect antibodies that are present but not bound to their cognate antigen as observed in immunoassays that exhibit "false-positive" activity and thus serve as a false-positive detection tool.

In some embodiments, Protein M can be conjugated with the following detectable probes: HRP (chromogenic), alkaline phosphatase (chromogenic), biotin (for example, via Avi-Tag peptide), myc epitope antigen, Luciferase (bioluminescence), avidin (attachment of biotin conjugates), streptavidin (attachment of biotin conjugates), streptavidin-binding peptide, phycoerythrin (fluorescence), GFP (fluorescence), a radioactive label. Protein M-radiolabel peptide can be produced by fusing Protein M to the short peptide KGRPLVY (SEQ ID NO:62). As disclosed in Mebrahtu et al. 2013, the KGRPLVY peptide contains a metal chelate attachment [K-lysine for labeling Protein M with Cu-64 and DOTA] and radio-halogen attachment (Y-tyrosine for labeling Protein M with I-125, I-123 or I-131).

In some embodiments, Protein M-detectable probe fusions can be used in ELISA, western blotting, lateral flow assays, multiplex bead array assays, pull down assays, SPR (biacore, octet) assays, flow cytometry assays, for purification or for delivery of a cargo.

Protein M fusion proteins can also be used to: 1) neutralize antibodies by occupying their antigen binding site (Useful in decreasing non-specific signals in immunoassays, useful in in-vitro cell assays as well as in in-vivo settings to determine the role of antibodies or a specific antibody by essentially blocking its binding activity); 2) eliminate antibodies by increasing clearance from circulation or tissue by directing antibodies to immune cells or delivering degrading enzymes or compounds to antibodies; 3) deplete antibodies in solution by promoting clearance of unengaged antibodies, which are not bound to antigen. Protein M can be attached to a resin (e.g., agarose beads), added to a solution to pull down/remove or harvest such antibodies for use in process, for analysis or for elimination.

Protein M fusion proteins can also be used to protect antibodies from degradation by enzymes, microbes and cellular mechanisms; protect antibodies from bacterial escape mechanisms (e.g., protein A of *S. aureus* binds to antibodies and avoid antibody detection and clearance); deliver cargo to an antibody.

In some embodiments, the receptor fragment is a protein fragment of a cellular receptor, which is a target used by a pathogen for cell entry. In some embodiments, the pathogen is a virus, a bacterium or a fungus that can cause illnesses. In one embodiment, an antigen is a cell surface molecule of a pathogen, or antigenic parts or fragments thereof.

A fusion protein can be made by creating a nucleic acid molecule encoding the fusion protein and expressing the fusion protein from such nucleic acid in a recombinant expression system. The nucleic acid molecule encoding the fusion can be generated by linking a nucleic acid sequence encoding Protein M in frame with a nucleic acid sequence encoding a receptor fragment of a pathogen or a ligand of a toxin. Methods for constructing a fusion protein are known in the art (see Sambrook J. et al., Molecular Cloning, Cold Spring Harbor Press, New York (2001)).

In some embodiments, Protein M is fused to the N-terminus of the receptor fragment of a pathogen or the ligand of a toxin. In this orientation, an N-terminal tag can be attached for detection and purification of the fusion protein. In addition, the leader sequence (secretory signal peptide) can be attached for facilitating the secretion of the fusion protein. Alternatively, other appropriate leader sequences, suitable for guiding the fusion protein to the ER and the secretory pathway in the host cell, can be used. In other embodiments, Protein M is fused to the C-terminus of the receptor fragment of a pathogen or the ligand of a toxin.

In still another embodiment, a spacer can be incorporated between the Protein M sequence and the receptor fragment of a pathogen or the ligand of a toxin. In preferred embodiments, spacer is a short peptide sequence that joins both polypeptides, yet preserves some distance between the polypeptides such that both polypeptides can properly fold independently. Generally, the spacer consists of between 2 or 3 amino acids to 50 amino acids, typically between 3 to 25, or 3 to 20, or 3 to 15 amino acids. In a specific embodiment, the space consists of 3-10 amino acids. Although there is no specific restriction on the selection of amino acids for the spacer region, the amino acids can be selected to accommodate the folding, net charge, hydrophobicity or other properties of the fusion protein. Typical amino acids for use in a spacer region include Gly, Ala, Ser, Thr and Asp.

One of skill would recognize that modifications can be made to a fusion protein without diminishing their biological activities. Some modifications may be made to facilitate the cloning, expression, or incorporation of the constituent molecules into a fusion protein. For example, amino acids can be placed on either terminus to create conveniently located restriction sites or termination codons; and a methionine can be added at the amino terminus to provide an initiation site.

Recombinant Expression of the Fusion Proteins.

For recombinant expression of a fusion protein, a nucleic acid molecule encoding the fusion protein is generally placed in an expression vector in an operable linkage to a promoter (such as the T7, trp, or lambda promoters for expression in bacteria, or a CMV promoter for expression in mammalian cells) and a 3' transcription termination sequence, and optionally additional suitable transcriptional and/or translational regulatory elements such as a transcription enhancer sequence and a sequence encoding suitable mRNA ribosomal binding sites. Additional sequences that can be included in the expression vector include an origin of replication, and a selection marker gene to facilitate identification of transformants such as genes conferring resistance to antibiotics (e.g., the amp, kana, gpt, neo, and hyg genes).

Host cells suitable for use in the recombinant expression of the fusion protein include bacterial cells such as *E. coli*, and eukaryotic cells including but not limited to yeast, insect cells (e.g. SF9 cells), and mammalian cells such COS, CHO, HeLa cells and HEK293.

The expression vectors can be introduced into a host cell by well-known methods such as calcium chloride transformation for bacterial cells, and calcium phosphate treatment or electroporation for mammalian cells. Cells transformed by the expression vectors can be selected based on the phenotype provided by the selectable marker gene.

Once expressed, the recombinant fusion proteins can be purified according to standard methods available in the art, such as ammonium sulfate precipitation, affinity columns, chromatography, gel electrophoresis, among others. In one embodiment, the fusion protein is purified based on affinity chromatography using antibodies that bound to Protein M. In another embodiment, a purification tag is inserted at the N-terminus or the C-terminus of the fusion protein and is used for purification. The examples of such tags are: 6 His-tag, myc-tag, strep-tag and others.

In some embodiments, uses for Protein M fusion proteins include the following.

The present teachings include a pharmaceutical composition comprising: a Protein M fusion protein having an antibody-binding domain and an ACE2 cellular receptor (referred to as armY-ACE2), serum or plasma from the subject or from a compatible donor, and a pharmaceutically acceptable carrier or a pharmaceutically acceptable excipient, wherein the fusion protein acts to eradicate SARS-CoV and SARS-COV-2 coronaviruses in patients infected with the virus, wherein the fusion protein arms immunoglobulins to recognize and bind with high affinity to the S1 spike protein expressed by the SARS-CoV and SARS-COV-2 coronaviruses. In some embodiments, the Protein M fusion protein optionally comprises a linker, the antibody-binding domain comprises the Protein M protein from *Mycoplasma* sp., the antibody-binding domain comprises Protein M that binds with high affinity to the antibody Fab domain and blocks the antibody's antigen binding site; the antibody-binding domain comprises Protein M that does not bind to the antibody whose Fab domain binding site is engaged with its cognate antigen; the antigen-binding domain comprises a cellular receptor, ACE2, that binds with high affinity to the S1 spike protein expressed by the SARS-CoV and SARS-COV-2 coronaviruses; the antibody-binding domain comprises Protein M that binds with high affinity to the antibody Fab domain and blocks the antibody's cognate antigen binding site. In some preferred embodiments, immunoglobulins bound with the disclosed fusion proteins retain at least partially Fc-linked functional activities (effector functions), such as Fc-receptor binding and complement activation.

In some embodiments, Protein M fusion proteins comprise a linker between Protein M and receptor fragment. Non-limiting examples of such linkers include

```
                        (SEQ ID NO: 12)
GGGGSGGGGSGGGGS,

                        (SEQ ID NO: 13)
GGGGSGGGGS
or

                        (SEQ ID NO: 14)
GGGGS.
```

The present teachings also include a pharmaceutical composition comprising: a Protein M fusion protein having an antibody-binding domain and a fusion domain comprising a protein, peptide or chemical group able to bind a pathogen, a toxin, any biologic entity or a chemical group, serum or plasma from the subject or from a compatible donor, and a pharmaceutically acceptable carrier or a pharmaceutically acceptable excipient. In some embodiments, the antigen to be bound by the fusion protein comprises an antigen arising from a pathogen, a toxin, a subject, arising from a disease state within the subject, or arising from a disease related organism within the subject and the disease state within the subject is caused by a virus, bacteria, tumor, abnormal cell or by exposure to an external disease-causing agent, wherein the antigen-binding domain comprises one or more protein or peptide or chemical group (collectively referred to as molecules) chosen from the group consisting of: a soluble molecule, a soluble molecule bound to a matrix, an insoluble molecule bound to a matrix, an insoluble aggregate of molecules, a molecule comprising one or more epitopes, a nonviable cell-associated molecule, a nonviable organism-associated molecule, or a molecule conjugated with a liposome.

The present teachings also include a Protein M fusion protein having an antibody-binding domain and a fusion partner domain comprising a protein, peptide or chemical group, wherein the antibody-binding domain comprises Protein M that does not bind to the antibody whose Fab domain binding site is engaged with its cognate antigen. In some embodiments, the fusion partner domain may be an endogenous protein or peptide; the fusion partner domain may be an exogenous protein or peptide; the fusion partner domain may be an enzyme, wherein the enzyme is a reporter enzyme horseradish peroxidase fusion protein (HRP). Protein M-HRP may be used to detect immunoglobulins in solution or in a matrix, wherein the immunoglobulins detected are not engaged with their cognate antigen. Thus, Protein M-HRP may be used to identify or rule out false positive test results in antibody-based detection of antigen. The fusion partner domain may permit for a chemical modification, wherein the chemical modification is, for example, an addition of biotin by an enzymatic conjugation of a single biotin on a unique 15 amino acid peptide tag using the biotin ligase (BirA).

The present teachings also include a Protein M fusion protein having an antibody-binding domain and a fusion partner domain comprising a protein, peptide or chemical group, wherein the antibody-binding domain comprises Protein M that binds with high affinity to the antibody Fab domain and blocks the antibody's antigen binding site, wherein the fusion partner domain may be a cytokine, chemokine, hormone, growth factor, receptor, ligand, neurotransmitters or a synthesized molecule. In some embodiments, the fusion partner domain is made to increase or decrease the bioavailability of bound antibodies, or the fusion partner domain immunogenicity is increased or decreased when bound to antibodies; or the fusion partner domain is made to increase or decrease the immunogenicity of bound antibodies.

In some embodiments, Protein M fusion proteins arm free non-antigen bound immunoglobulin to bind a pathogen or toxin (both referred heretofore as "target") with a high affinity. This is made possible through (a) Protein M component of the fusion protein that engages the immunoglobulin rendering it no longer able to bind its cognate antigen, and (b) the fused receptor or ligand, which is the same attachment receptor or ligand found on cells that the target uses to attach and gain entry. Protein M fusion protein-armed immunoglobulins (referred heretofore as "armY-fusion") binding to their target is the initial step in the mechanism of target eradication. Once bound to target, armY-fusion will block the interaction between the target and the attachment receptor found on host cells, thereby, neutralizing the target and prevent it from infecting the cell. Whereas Protein M fusions serve to associate immunoglobulins with the target and neutralize the target, the immunoglobulin serves to mark the target for destruction and clearance by the innate immune system including cells that bear Fc receptors (e.g., macrophages) and complement factors.

Complement is part of the innate surveillance system involved in the first line of defense against pathogens. One mechanism to direct complement to a specific pathogen is via the classical complement pathway, which is initiated by antibodies that are bound to antigen. C1q recruitment to antibodies is an essential first step in the activation of the complement cascade. Antibody binding to antigen (found on the pathogen or in solution as an immune complex) induces a change in the antibody's three-dimensional structure that exposes a C1q binding site found within the CH2 portion of the antibody Fc region. Upon C1q binding and activation, additional complement factors are recruited resulting in the formation of other effector molecules such as C3b, the main effector of the complement system. These events culminate in the formation of the membrane attack complex (MAC) that forms holes or pores on the surface of pathogens including bacteria, viruses and cancer cells resulting in subsequent clearance. C3b also serves as a potent opsin able to tag pathogens, immune complexes (antigen-antibody), and apoptotic cells for phagocytosis by immune cells that express C3b receptors. Together, MAC and C3b serve to effectively eradicate pathogens targeted by antibodies that recruit C1q. C1q is composed of 18 polypeptide chains: six A-chains, six B-chains, and six C-chains. Each chain contains a collagen-like region located near the N terminus and a C-terminal globular region.

In some embodiments, Protein M fusion protein in complex with an antibody can engage C1q and activate classical complement pathway that would contribute to eradication of the pathogen or a cancer cell, to which the Protein M fusion protein is targeted. Normally, for C1 q to bind the antibody, the antibody must first bind its antigen (immobilized on a cell or pathogen or in solution as an immune complex), and then the antibody undergoes a conformational change that permits C1q binding. However, Protein M fusion protein-IgG complex can specifically recruit C1q as demonstrated, for example, in Example 10, FIG. 11 below. Thus, Protein M-fusions can be considered a tool to specifically induce a conformational change in antibodies (while in solution) resulting in its ability to engage C1q and activate the complement pathway.

EXAMPLES

Aspects of the present teachings may be further understood in light of the following examples, which should not be construed as limiting the scope of the present teachings in any way. Below, exemplary methods to develop and characterize Avi-/myc-tagged Protein M, myc-tagged Protein M-HRP fusion protein and Protein M-ACE2 fusion protein (aka, armY-ACE2) are disclosed. These and similar methods can be applied to generate and use different Protein M fusion proteins.

Example 1. Gene Construction of Protein M

Protein M (also referred to as armY) (SEQ ID NO:10 and 38) was constructed using the mature amino acid sequence of Protein M (37-556 amino acid) containing a myc-tag (EQKLISEEDLLRKR) and linker sequence (AANGGGGSGGGGS) and a mono-biotinylation sequence "Avi-Tag" (MAGGLNDIFEAQKIEWHEGG) at its N-terminal end. The linear amino acid sequence was reverse translated to its corresponding DNA sequence using the free GenSmart™ Codon Optimization Tool by GenScript for expression in human cells (gensmart-free-gene-codon-optimization). This sequence was submitted for gene synthesis and inserted into the plasmid cloning vector pUC57 (GenScript, Inc.). The insert was amplified and cloned into a previously constructed mammalian cell expression vector pcDNA3(−) containing a myc-tag-Protein M sequence by replacing the myc-tag-Protein M sequence with the above myc-tag sequence that included a mono-biotinylation sequence, producing a final Protein M construct (IL-2 leader sequence—biotinylation tag—myc tag—linker—Protein M). The plasmid expression vector construct was verified by restriction enzyme analysis, amplified in *E. coli* and purified using a maxiprep kit (GenScript Inc. and Eton Bioscience, Inc.).

Figure 3:
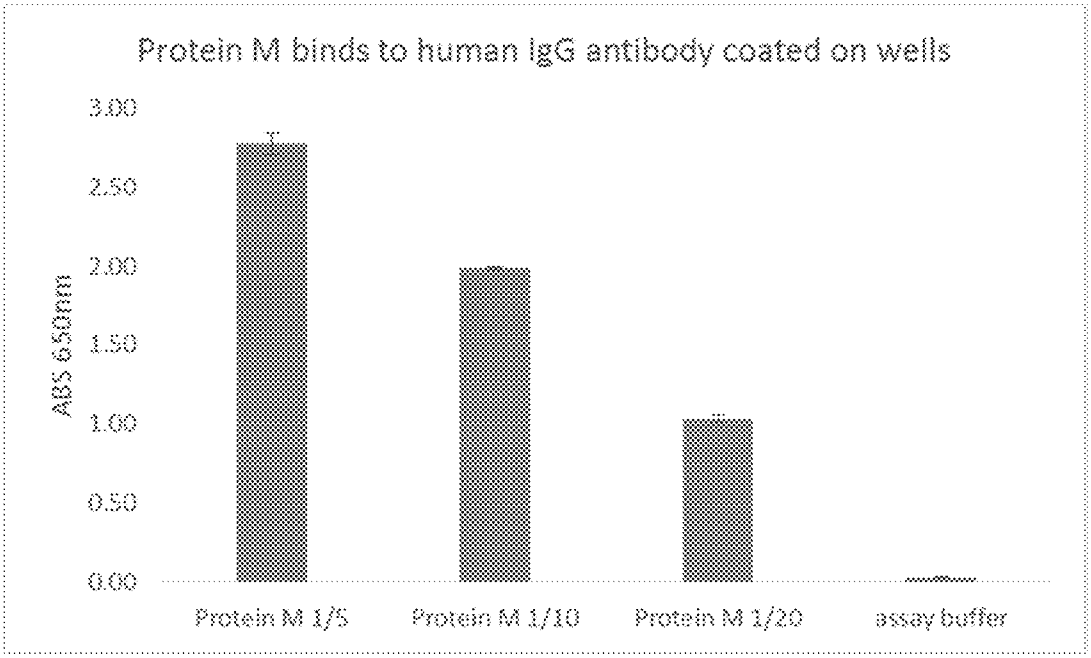
FIG. 3. Myc-tagged Protein M binds to human IgG antibody coated on wells in a dose-dependent fashion. Bound Protein M is detected via its myc-tag using a mouse IgG1 anti-myc antibody followed by an HRP-labeled goat anti-mouse IgG. Neither antibodies bind the human IgG antibody coated on the well (assay buffer, no Protein M).

Example 2A. Characterization of Protein M as an Antibody Neutralizer and Blocking Reagent Tool. Binding of Protein M to Immobilized Antibody (FIG. 3)

Protein M binding to plate bound antibody was demonstrated by measuring the amount of myc-tagged Protein M bound to the antibody coated on a 96-well plate by an ELISA-based method.

Briefly, 5 ug/ml of human IgG (Sigma) was prepared in ELISA coating buffer (Biolegend, Inc.) and added to a flat bottom 96-well plate (Immulon 2HB). The next day, the wells were washed twice with PBS (Gibco) and 100 ul 3% BSA in PBS (Boston Bioproducts, Inc.) was added to block unbound sites on the well. After washing twice with PBS+Tween 20 (wash buffer, Pierce), Protein M in expression medium diluted in assay buffer (0.5% BSA in PBS+Tween 20) or assay buffer was added to antibody-coated wells in duplicate. After approximately 30 minutes at room temperature, the wells were washed and mouse IgG1 anti-myc antibody (clone: 9E10) in assay buffer was added to detect the myc-tagged Protein M. After approximately 30 minutes, the wells were washed 3×s and anti-mouse IgG labeled with HRP was added to the wells. After approximately 30 minutes, the wells were washed 4×s and TMB substrate solution (Biolegend, Inc.) was added to the wells and the absorbance at 650 nm measured using a plate reader (Molecular Devices Thermomax and Softmax Pro software).

Figure 4A:
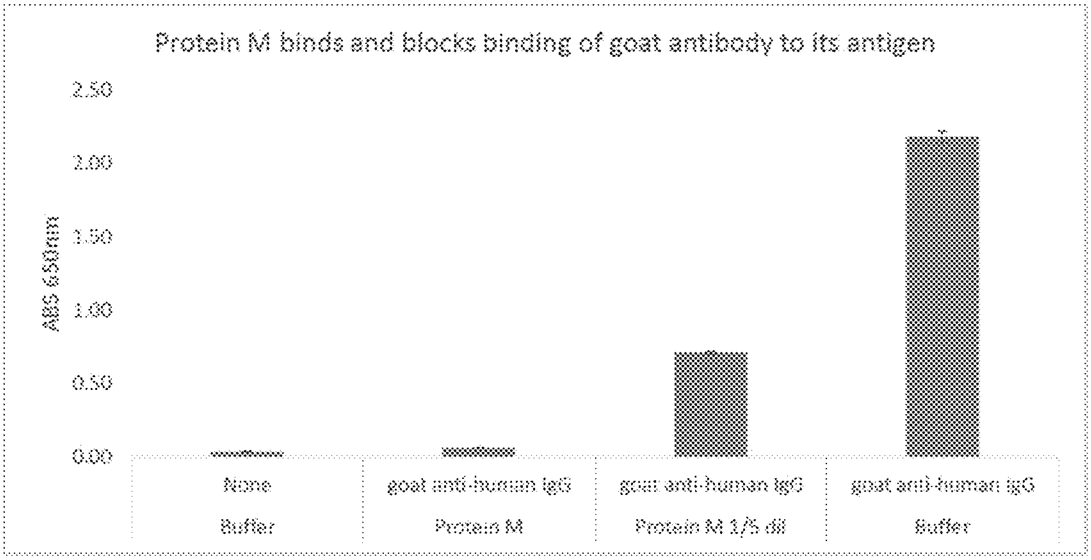
FIG. 4A-B. Goat anti-human IgG (FIG. 4A) or Chicken anti-human IgG (FIG. 4B) is neutralized or blocked by Protein M in a dose-dependent fashion and prevented from binding their antigen human IgG, immobilized on the wells.
Figure 4B:
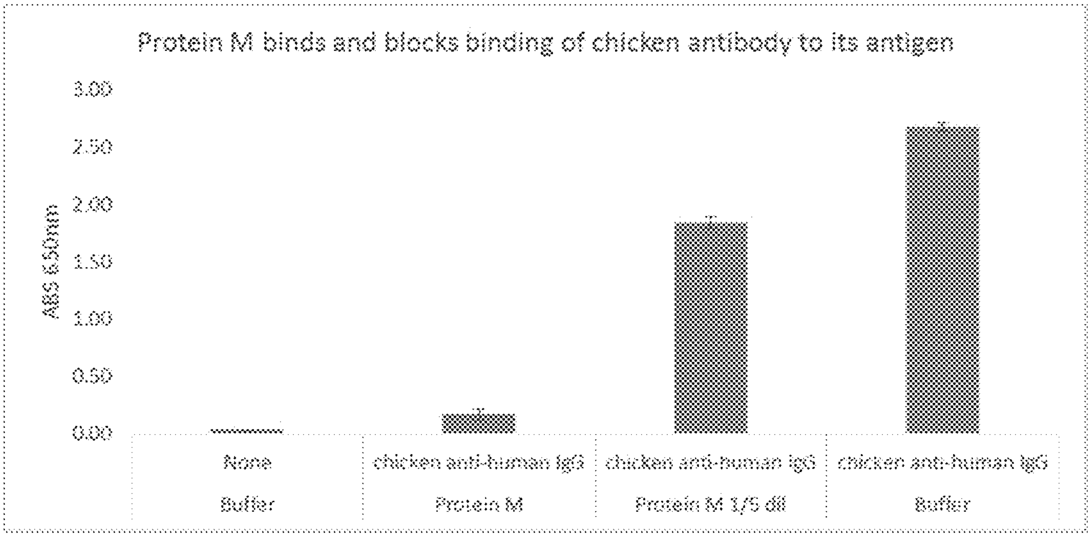
Figure 5A:
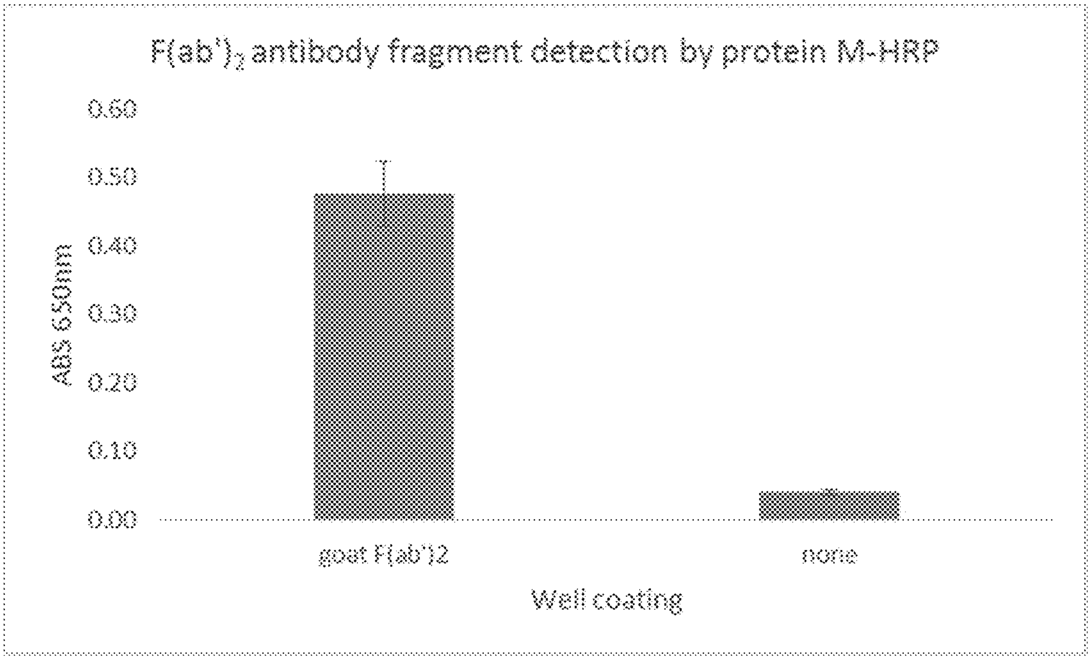
FIG. 5A-D. Protein M-HRP fusion protein detection of antibodies. Detection of goat $F(ab')_2$ antibody fragment (FIG. 5A), dose-dependent detection of human IgG antibody (FIG. 5B) and detection of two mouse monoclonal IgG1 antibodies: anti-myc and anti-CD28 (FIG. 5C) coated on wells.
Figure 5B:
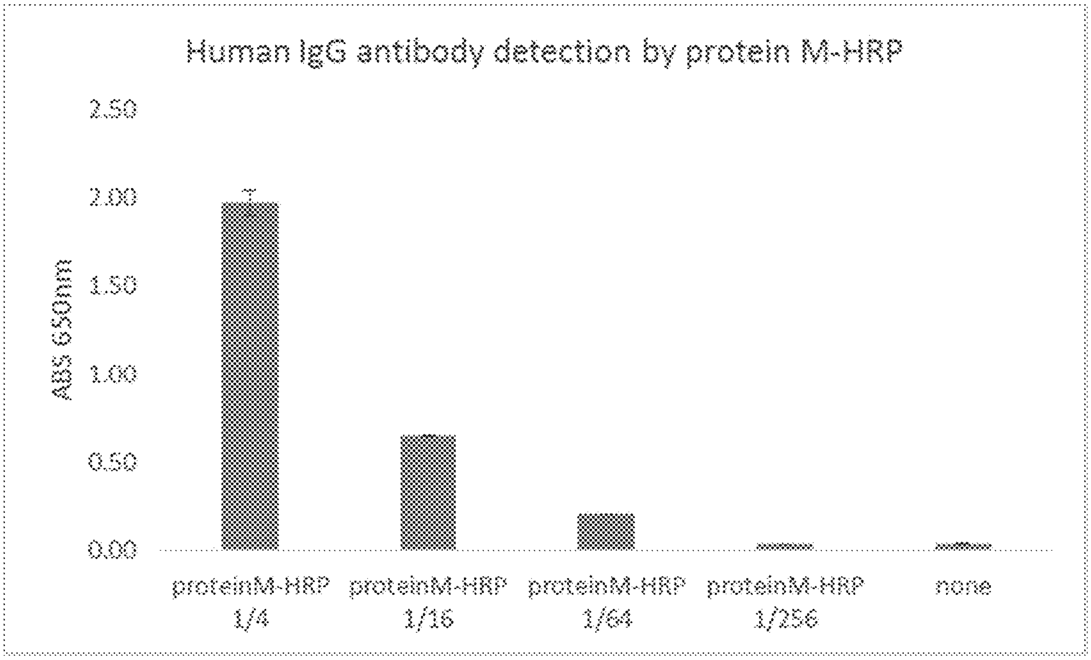
Figure 5C:
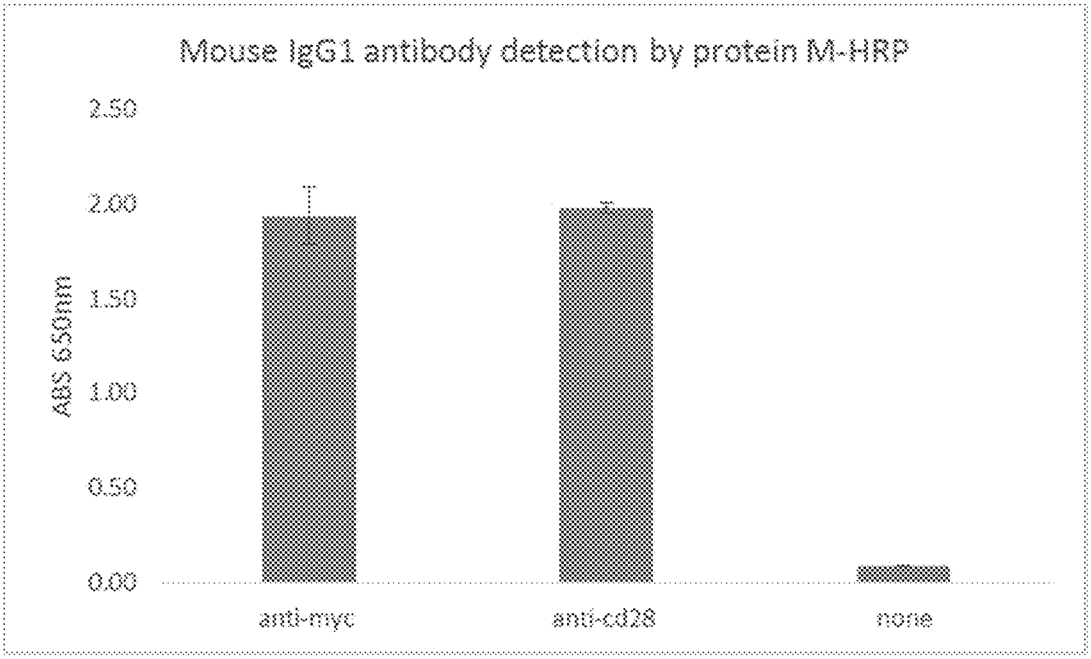
Figure 5D:
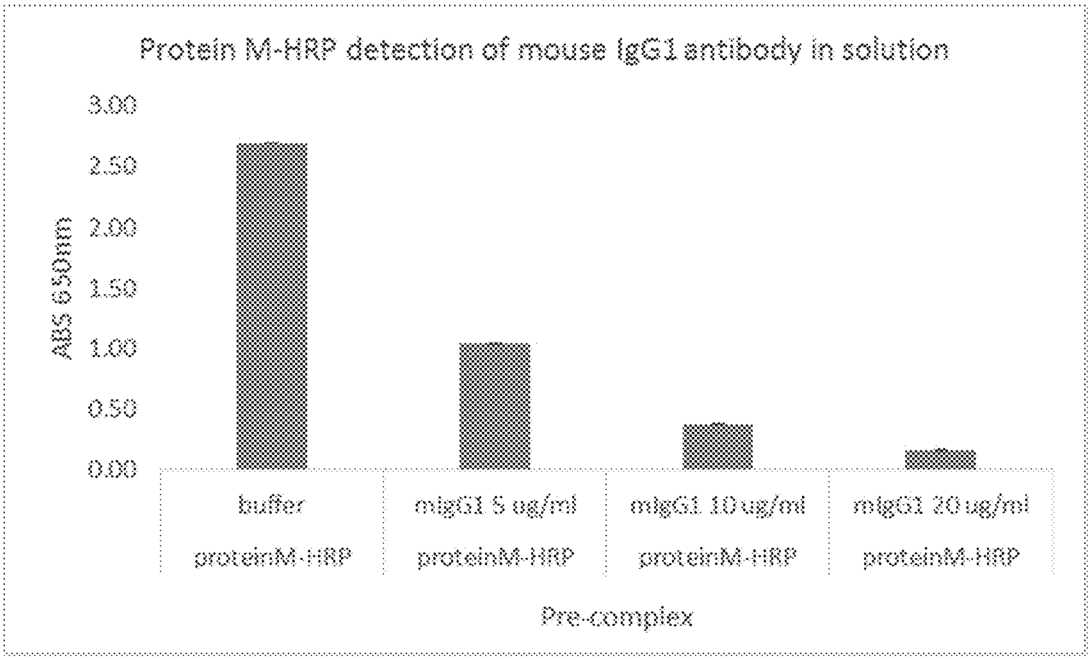

Example 2B. Characterization of Protein M as an Antibody Neutralizer and Blocking Reagent Tool. Protein M Neutralizes/Blocks Antibody Binding to Cognate Antigen (FIG. 4)

The ability of Protein M to block binding to its cognate antigen was demonstrated by measuring the amount of unblocked, free antibody bound to its antigen coated on a 96-well plate by an ELISA-based method.

Briefly, 5 ug/ml of human IgG (Sigma) was prepared in ELISA coating buffer (Biolegend, Inc.) and added to a flat bottom 96-well plate (Immulon 2HB). The next day, the wells were washed twice with PBS (Gibco) and 100 ul 3% BSA in PBS (Boston Bioproducts, Inc.) was added to block unbound sites on the well. RP-labeled goat anti-human IgG antibody (GenScript, Inc.) or a RP-labeled chicken anti-human IgG antibody (Aves Labs, Inc.) was added to Protein M in expression medium or to expression medium alone and allowed to form complexes at room temperature for approximately 2 hours. After washing twice with PBS+Tween 20 (wash buffer, Pierce), samples were added to human IgG coated wells in duplicate. After approximately 45 minutes at room temperature, the wells were washed 3×s and TMB substrate solution (Biolegend, Inc.) was added to the wells and the absorbance at 650 nm measured using a plate reader (Molecular Devices Thermomax and Softmax Pro software).

Example 3. PROTEIN M-HRP Fusion Protein (SEQ ID NO:11 and 39). Gene Construction of Protein M-HRP The mature amino acid sequence of horseradish peroxidase HRP (31-338 amino acid) was generated containing a myc-tag (EQKLISEEDL) and linker (AAN) sequence at its N-terminal end. The amino acid sequence encoding 3 sets of 4 glycine residues and 1 serine residue (e.g., GGGGS)3 linker followed by the mature amino acid sequence of Protein M (37-556 amino acid) was added to its C-terminal end producing a final Protein M-HRP construct containing (IL-2 leader sequence—myc tag—HRP—linker—Protein M). The linear amino acid sequence was reverse translated to its corresponding DNA sequence using the free GenSmart™ Codon Optimization Tool by GenScript for expression in human cells (gensmart-free-gene-codon-optimization). This sequence was submitted for gene synthesis and inserted into the plasmid cloning vector pUC57 (GenScript USA Inc.). The insert was amplified and cloned into a mammalian cell expression vector, pcDNA3(−). The plasmid expression vector construct was verified by restriction enzyme analysis, amplified in *E. coli* and purified using a maxiprep kit (GenScript Inc. and Eton Bioscience, Inc.).

Example 4. Characterization of Protein M-HRP as a Novel Antibody Detection Reagent Tool. Detection of Immobilized $F(Ab')_2$, Antibody or Antibody in Solution by Protein M-HRP Fusion Protein Protein M-HRP direct detection of plate bound $F(ab')_2$, antibody or indirect detection of antibody in solution was demonstrated by measuring the amount of Protein M-HRP bound to antibody coated on a 96-well plate by an ELISA-based method (FIG. 5). Direct detection of antibody by Protein M-HRP fusion protein: Briefly, 2 ug/ml of goat $F(ab')_2$ or 5 ug/ml of human IgG (Sigma) or 2 ug/ml of mouse IgG1 isotype anti-myc or anti-human CD28 antibodies was prepared in ELISA coating buffer (Biolegend, Inc.) and added to a flat bottom 96-well plate (Immulon 2HB). The next day, the wells were washed twice with PBS (Gibco) and 100 ul 3% BSA in PBS (Boston Bioproducts, Inc.) was added to block unbound sites on the well. After washing twice with PBS+Tween 20 (wash buffer, Pierce), Protein M-HRP in expression medium or expression medium diluted in assay buffer (0.5% BSA in PBS+Tween 20) was added to $F(ab')_2$ or antibody-coated wells in duplicate. After approximately 30 minutes at room temperature, the wells were washed 4×s and TMB substrate solution (Biolegend, Inc.) was added to the wells and the absorbance at 650 nm measured using a plate reader (Molecular Devices Thermomax and Softmax Pro software). Indirect detection of antibody in solution by Protein M-HRP fusion protein: Briefly, Protein M-HRP was incubated with varying amounts of mouse IgG1 antibody in assay buffer and allowed to form complexes at room temperature for approximately 30 minutes. Protein M-HRP alone was also included as a positive control. After washing twice with PBS+Tween 20 (wash buffer, Pierce), samples were added to human IgG-coated wells in duplicate. After approximately 30 minutes at room temperature, the wells were washed 4×s and TMB substrate solution (Biolegend, Inc.) was added to the wells and the absorbance at 650 nm measured using a plate reader (Molecular Devices Thermomax and Softmax Pro software).

Figure 6A:
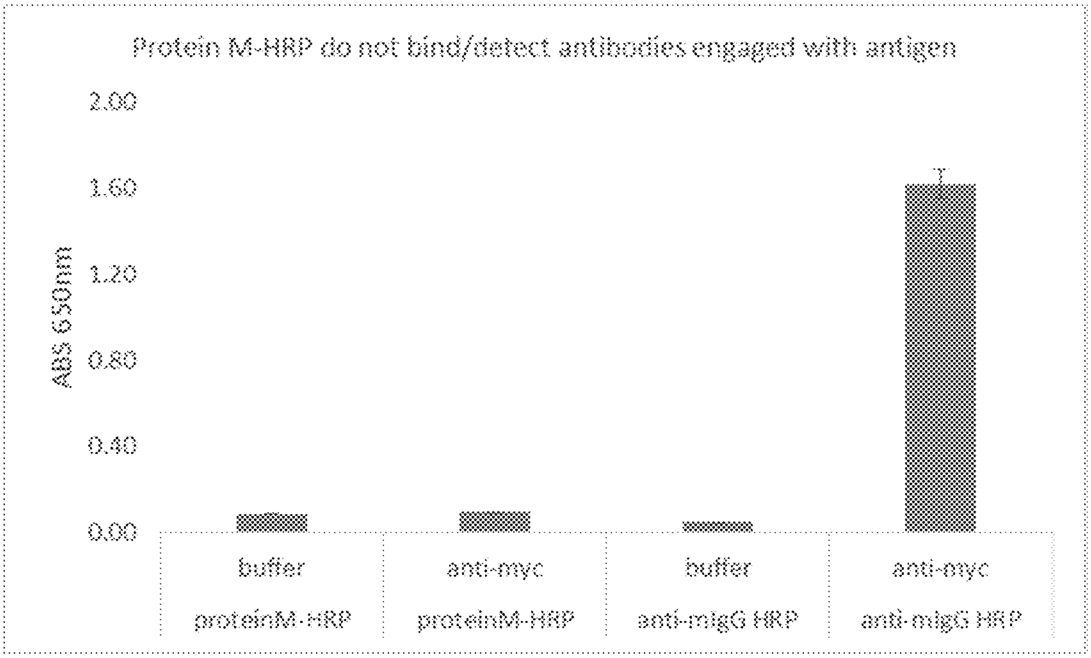
FIG. 6A-B. Antibodies bound to antigen are not detected by Protein M. Myc-specific mouse antibody bound to myc-tagged protein coated on wells in (FIG. 6A) or ASIP-specific rabbit antibody bound to ASIP protein coated on wells in (FIG. 6B) failed to be detected by Protein M-HRP. This is consistent with the described function of Protein M and its inability to bind antibodies already engaged in a complex with their cognate antigen. Presence of antibodies bound to their coated antigen was confirmed using detecting HRP-labeled anti-mouse IgG (A) and anti-rabbit IgG-biotin/streptavidin-HRP (B).
Figure 6B:
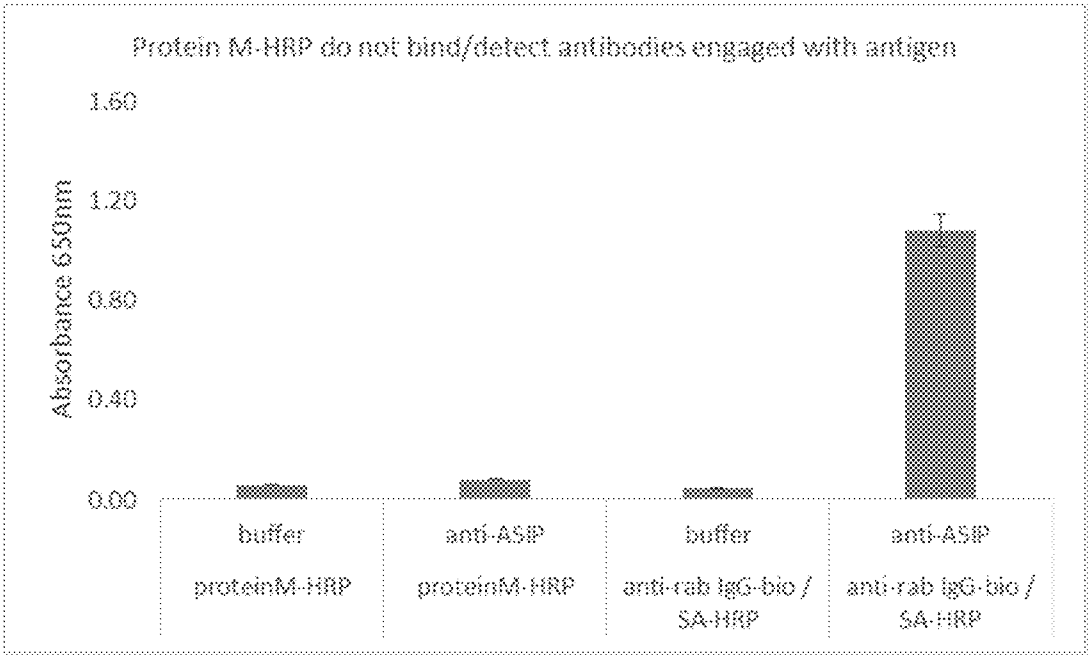

Example 5. Absence of Detection of Antibody Bound to an Immobilized Antigen by Protein M-HRP Fusion Protein Protein M does not bind to antibodies already bound to antigen. The absence of detection of antibody bound to an immobilized antigen by Protein M-HRP fusion protein was demonstrated by measuring the amount of Protein M-HRP bound to the antibody engaged with its antigen on a 96-well plate by an ELISA-based method (FIG. 6).

Briefly, 1 ug/ml of a myc-tagged protein or 2 ug/ml of human ASIP (agouti-signaling protein, RnD Systems) was prepared in ELISA coating buffer (Biolegend, Inc.) and added to a flat bottom 96-well plate (Immulon 2HB). The next day, the wells were washed twice with PBS (Gibco) and 100 ul 3% BSA in PBS (Boston Bioproducts, Inc.) was added to block unbound sites on the well. After washing twice with PBS+Tween 20 (wash buffer, Pierce), mouse IgG1 anti-myc antibody (clone: 9E10) in assay buffer, rabbit anti-ASIP antibody (Thermofisher) or assay buffer alone was added to the myc-tagged protein or ASIP, coated wells, respectively, in duplicates. After approximately 60 minutes, the wells were washed 3×s and Protein M-HRP was added. To show that mouse anti-myc and rabbit anti-ASIP bound to myc-tagged protein or ASIP coated wells, anti-mouse IgG labeled with HRP or biotinylated anti-rabbit IgG+SA-RP was added to another set of coated wells, respectively. After approximately 30 minutes, the wells were washed 4×s and TMB substrate solution (Biolegend, Inc.) was added to the wells and the absorbance at 650 nm measured using a plate reader (Molecular Devices Thermomax and Softmax Pro software).

Example 6. PROTEIN M-ACE2 Fusion Protein (Referred to as armY-ACE2) (SEQ ID NO:9 and 37). Gene Construction of armY-ACE2 (Protein M Fused to Angiotensin I-Converting Enzyme 2 (ACE2))

The mature amino acid sequence of human ACE2 (18-740 amino acid) was generated containing a myc-tag (EQKLISEEDLLRKR) and linker (GSPGGA) sequence at its N-terminal end. The linear amino acid sequence was reverse translated to its corresponding DNA sequence using the free GenSmart™ Codon Optimization Tool by GenScript for expression in human cells (gensmart-free-gene-codon-optimization). This sequence was submitted for gene synthesis and inserted into the plasmid cloning vector pUC57. The insert was amplified and cloned into the mammalian cell expression vector pcDNA3(−) containing the myc-tag-Protein M-HRP sequence (see above) by replacing the myc-tag-HRP sequence with the above myc-tag-ACE2 sequence, upstream of the sequence encoding 3 sets of 4 glycine residues and 1 serine residue (e.g., GGGGS)3 linker followed by the mature amino acid sequence of Protein M (37-556 amino acid), producing a final armY-ACE2 construct containing (IL-2 leader sequence—myc tag—ACE2—linker—Protein M). The plasmid expression vector construct was verified by restriction enzyme analysis, amplified in *E. coli* and purified using a maxiprep kit (GenScript Inc. and Eton Bioscience, Inc.).

Example 7A. Protein M, Protein M-HRP and armY-ACE2 Gene Expression

The human 293T kidney cell line was transfected with the expression vector encoding the Protein M, Protein M-HRP or armY-ACE2 (Protein M-ACE2) fusion protein sequences, by calcium phosphate transfection method. After 7-16 hours, the transfection solution was replaced with protein expression medium and the supernatant harvested after approximately 48 hours. To purify the proteins, the supernatant was harvested and pass through an anti-myc antibody-coupled agarose resin and the captured proteins eluted using 0.1M Glycine pH 2.5 and neutralized by 1M Tris-HCl pH 8.0. The eluted proteins were dialyzed against a phosphate buffered saline solution and stored in 4° C.

Figure 7A:
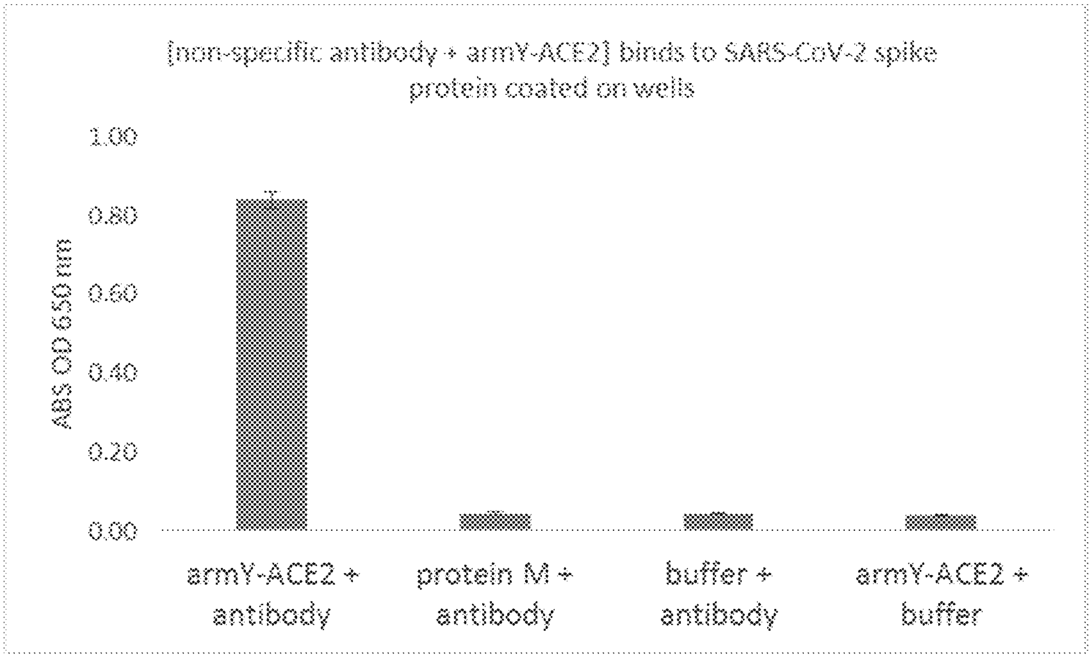
FIG. 7A-B).
Figure 7B:
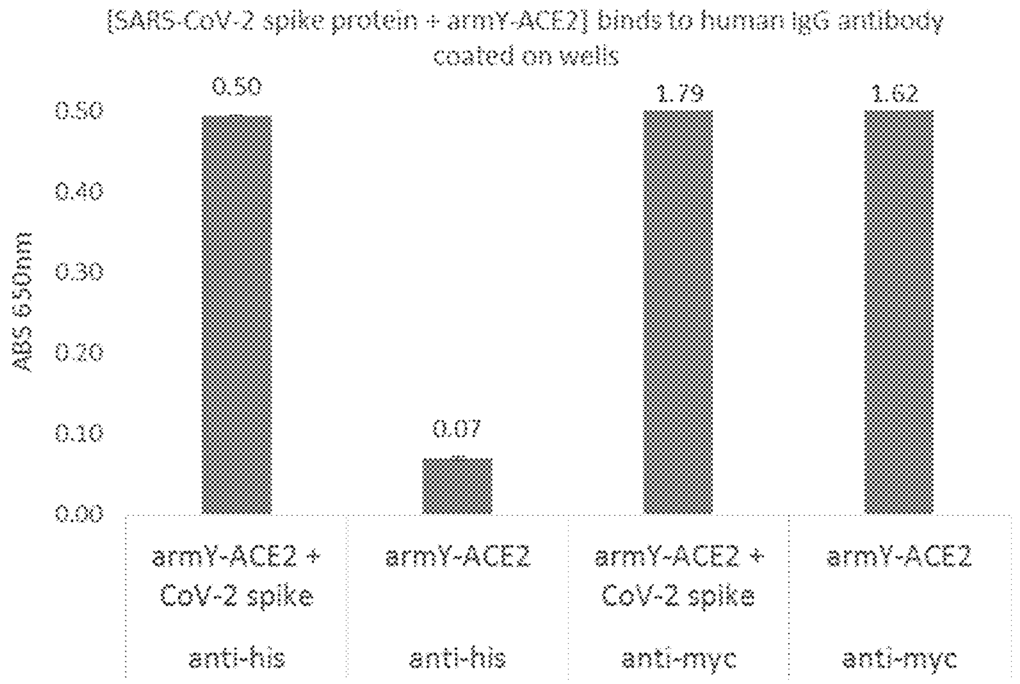

Example 7B. Characterization of armY-ACE2 as a Novel Therapeutic in the Treatment of Coronavirus Infection. Targeting of [armY-ACE2+Antibody] to SARS-CoV-2 Spike Protein and Binding of [armY-ACE2+SARS-CoV-2 Spike Protein] Complex to Antibody Complex [armY-ACE2+antibody] targeting of SARS-CoV-2 spike protein was demonstrated by measuring the amount of [armY-ACE2+antibody] complexes bound to the SARS-CoV-2 spike protein coated on a 96-well plate by an ELISA-based method. Binding of [armY-ACE2+ to SARS-CoV-2 spike protein] complexes to immobilized antibody was demonstrated by measuring the amount of [armY-ACE2+SARS-CoV-2 spike protein] complexes bound to the antibody coated on a 96-well plate by an ELISA-based method (FIG. 7).

Briefly, 50 ul of 1 ug/ml histidine (his)-tagged SARS-CoV-2 spike protein (GenScript, Inc.) or 5 ug/ml of human IgG (Sigma) was prepared in ELISA coating buffer (Biolegend, Inc.) and added to a flat bottom 96-well plate (Immulon 2HB). The next day, the wells were washed twice with PBS (phosphate buffered saline pH 7.4) (Gibco) and 100 ul 3% BSA in PBS (Boston Bioproducts, Inc.) was added to block unbound sites on the well. [armY-ACE2+antibody] complexes were allowed to form at room temperature by adding 0.25 ug/ml biotinylated goat IgG (Jackson ImmunoResearch Inc.) to armY-ACE2 in expression medium for 60 minutes. Biotinylated antibody was also added to Protein M (lacking ACE2 domain) or expression medium as negative controls. armY-ACE2 alone in expression medium was prepared as an additional negative control. The samples were diluted in assay buffer (0.5% BSA in PBS+Tween 20) and added to SARS-CoV-2 spike protein coated wells, washed twice with PBS+Tween 20 (wash buffer, Pierce), in duplicate. After approximately 30 minutes at room temperature, the wells were washed 3×s and streptavidin-horseradish peroxidase (SA-HRP) (Biolegend, Inc.) in assay buffer was added to the wells and allowed to incubate at room temperature for approximately 20 minutes. After four washes, TMB substrate solution (Biolegend, Inc.) was added to the wells and the absorbance at 650 nm measured using a plate reader (Molecular Devices Thermomax and Softmax Pro software). Binding of [armY-ACE2+ to SARS-CoV-2 spike protein] complexes to immobilized human IgG: armY-ACE2+SARS-CoV-2 spike protein complexes were allowed to form at room temperature by adding 2 ug/ml of SARS-CoV-2 spike protein to armY-ACE2 in expression medium. armY-ACE2 alone in expression medium was prepared as a negative control. After approximately 60 minutes at room temperature, the wells were washed and mouse IgG1 anti-histidine tag (GenScript, Inc.) or mouse IgG1 anti-myc antibody (clone: 9E10) in assay buffer was added to detect the histidine-tagged SARS-CoV-2 spike protein or myc-tagged armY-ACE2 bound to human IgG coated on the well, respectively. After approximately 30 minutes, the wells were washed 3×s and anti-mouse IgG labeled with HRP was added to the wells. After approximately 30 minutes, the wells were washed 4×s and TMB substrate solution (Biolegend, Inc.) was added to the wells and the absorbance at 650 nm measured using a plate reader (Molecular Devices Thermomax and Softmax Pro software).

Figure 8:
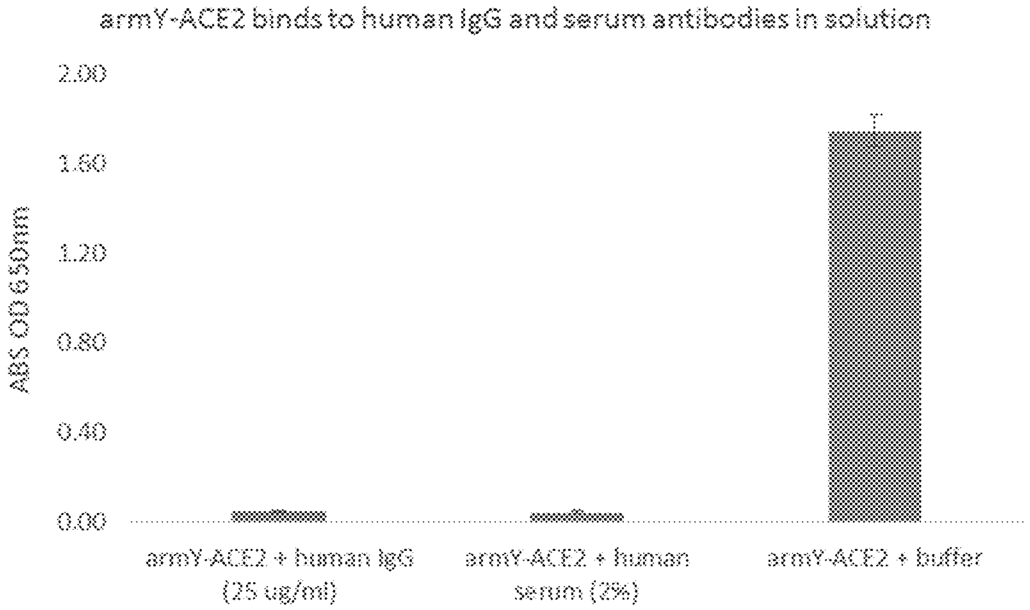
FIG. 8. Purified human IgG or antibodies in human serum formed a complex with armY-ACE2 in solution preventing army-ACE2 binding to antibody coated on the wells. As expected, in the absence of antibody in solution binding of armY-ACE2 to the antibody coated wells was not prevented.

Example 8. ArmY-ACE2 Binding to Immobilized Antibody or Antibody in Solution armY-ACE2 binding to immobilized antibody or antibody in solution was demonstrated by measuring the amount of free or antibody-bound armY-ACE2 in an ELISA based method (FIG. 8).

Briefly, 5 ug/ml of human IgG (Sigma) was prepared in ELISA coating buffer (Biolegend, Inc.) and added to a flat bottom 96-well plate (Immulon 2HB). The next day, the wells were washed twice with PBS (Gibco) and 100 ul 3% BSA in PBS (Boston Bioproducts, Inc.) was added to block unbound sites on the well. Binding of antibody in solution by armY-ACE2: Briefly, armY-ACE2 was incubated with purified human IgG, 2% human serum (containing antibodies) or PBS in assay buffer and allowed to form complexes at room temperature for approximately 2 hours. After washing twice with PBS+Tween 20 (wash buffer, Pierce), samples were added to human IgG-coated wells in duplicate. After approximately 60 minutes at room temperature, the wells were washed and mouse IgG1 anti-myc antibody (clone: 9E10) in assay buffer was added to detect the myc-tagged armY-ACE2 bound to human IgG coated on the well. After approximately 30 minutes, the wells were washed 3×s and anti-mouse IgG labeled with HRP was added to the wells. After approximately 30 minutes, the wells were washed 4×s and TMB substrate solution (Biolegend, Inc.) was added to the wells and the absorbance at 650 nm measured using a plate reader (Molecular Devices Thermomax and Softmax Pro software).

Figure 9:
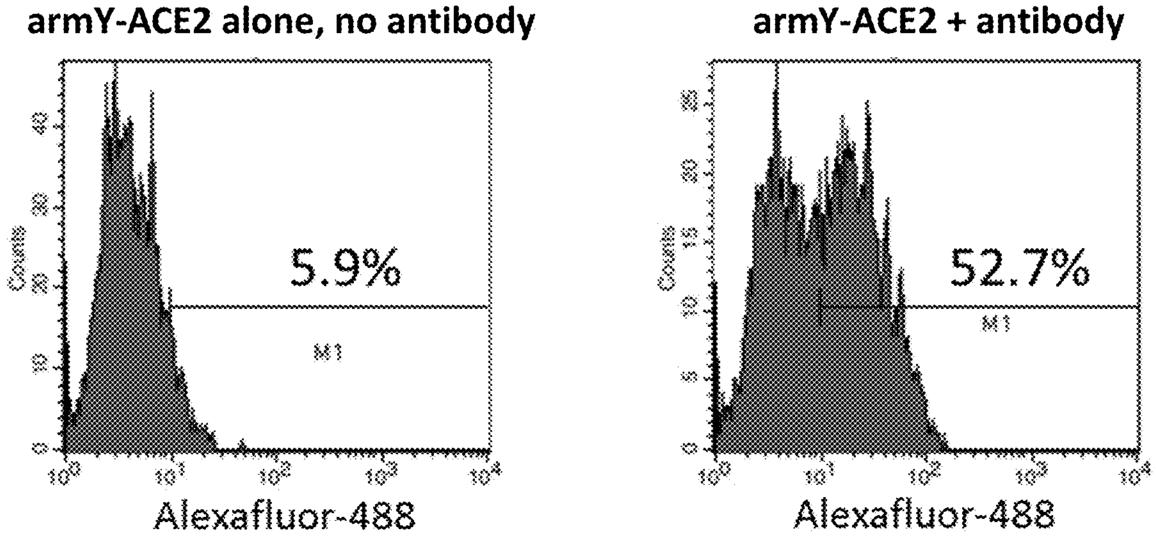
FIG. 9. armY-ACE2 engaged antibody binds to K562 cells expressing FcγRII receptor (right panel, army-ACE2+ antibody). No binding to K562 cells was observed in the absence of antibody (left panel, army-ACE2 alone, no antibody), therefore, the observed binding of armY-ACE2 to K562 cells is dependent upon the association between the antibody and armY-ACE2.

Example 9. [armY-ACE2+Antibody] Complexes Engage Fc Receptors on K562 Erythroleukemic Cell Line Binding of antibodies to Fc-receptor expressed on cells (e.g., innate immune cells, antigen presenting cells) requires interaction with the antibody Fc region. [armY-ACE2+antibody] complex engagement of Fc receptors was demonstrated by measuring the amount of [armY-ACE2+antibody] complexes bound to the human FcγRII (CD32) expressed on K562, a human erythroleukemic cell line, by flow cytometry (FIG. 9).

Briefly, K562 cells were taken from cell culture medium and centrifuged (3000 rpm for 3 minutes) and supernatant removed by vacuum aspiration. After a wash with chilled FACS buffer (0.5% BSA in PBS+0.1% sodium azide), 100,000 cells was transferred to 1.5 ml microcentrifuge tubes in FACS buffer and the supernatant removed after centrifugation and the cells kept on ice. 5 ug/ml of human IgG (Sigma Aldrich) was added to armY-ACE2 in expression medium and kept at room temperature for approximately 30 minutes to form complexes, and tubes transferred to ice to chill. armY-ACE2 alone in expression medium was also prepared as a negative control. 100 ul of [army-ACE2+antibody] complexes or armY-ACE2 alone was added to K562 cells and allowed to incubate on ice for approximately 30 minutes. After two washes in FACS buffer, anti-myc (clone 9E10 mouse antibody) was added to detect the myc-tagged army-ACE2 and allowed to incubate for approximately 20 minutes. After two washes, anti-mouse IgG-Alexafluor-488 (Biolegend, Inc.) was added to detect anti-myc antibody and allowed to incubate for approximately 20 minutes. After two washes, cells were resuspended in FACS buffer and analyzed by flow cytometry (BD FACS Calibur and CellQuest Pro analysis software). At least 5,000 events were acquired per sample. Cells incubated with negative controls as described above served as source of background basal percent value. The percentage of cells staining positive for [army-ACE2+antibody] complexes was determined by the percentage of cells present within a gate established such that <6% of the positive events of cells incubated with negative control samples measured represented background fluorescence.

Figure 10:
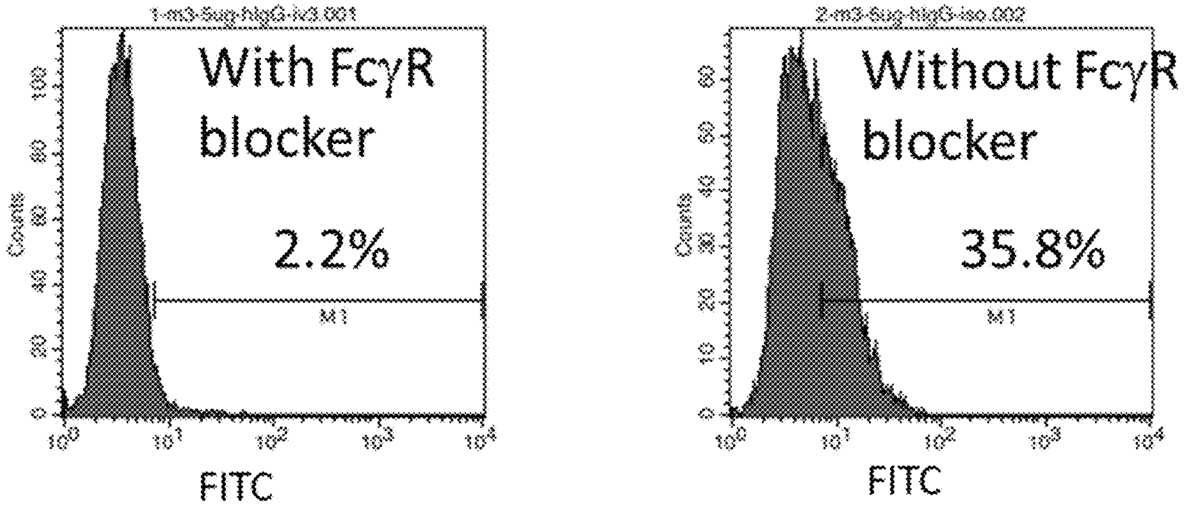
FIG. 10. Binding of [armY-ACE2+antibody] to K562 cells is prevented by blocking FcγRII receptor using anti-CD32 (IV.3) (left panel). Binding is not blocked by the isotype-match antibody (right panel), demonstrating that armY-ACE2 engaged antibody maintains Fc-receptor binding activity.

To demonstrate that binding of [army-ACE2+antibody] complexes to K562 was through a specific interaction with Fc-receptors expressed on the cells, K562 cells were pre-incubated with FcγRII blocking anti-CD32 (clone IV.3, mouse IgG2b, kappa) (FIG. 10).

Briefly, 1 ug of anti-CD32 or an isotype-matched mouse IgG2b, kappa control antibody was added to 100 ul of FACS buffer and added to approximately 100,000 K562 cells and placed on ice for approximately 15 minutes. After 2 washes, 100 ul of [army-ACE2+antibody] complexes prepared as described above was added to the cells and kept on ice for approximately 20 minutes. After two washes, fluorescein (FITC)-labeled anti-myc (Biotium, Inc.) was added to K562 cells and allowed to incubate on ice for approximately 15 minutes. After two washes, cells were resuspended in FACS buffer and analyzed by flow cytometry (BD FACS Calibur and CellQuest Pro analysis software). At least 5,000 events were acquired per sample. Cells incubated with negative control served as source of background basal percent value. The percentage of cells staining positive for [army-ACE2+ antibody] complexes was determined by the percentage of cells present within a gate established such that <2% of the positive events of cells incubated with negative control samples measured represented background fluorescence.

Figure 11A:
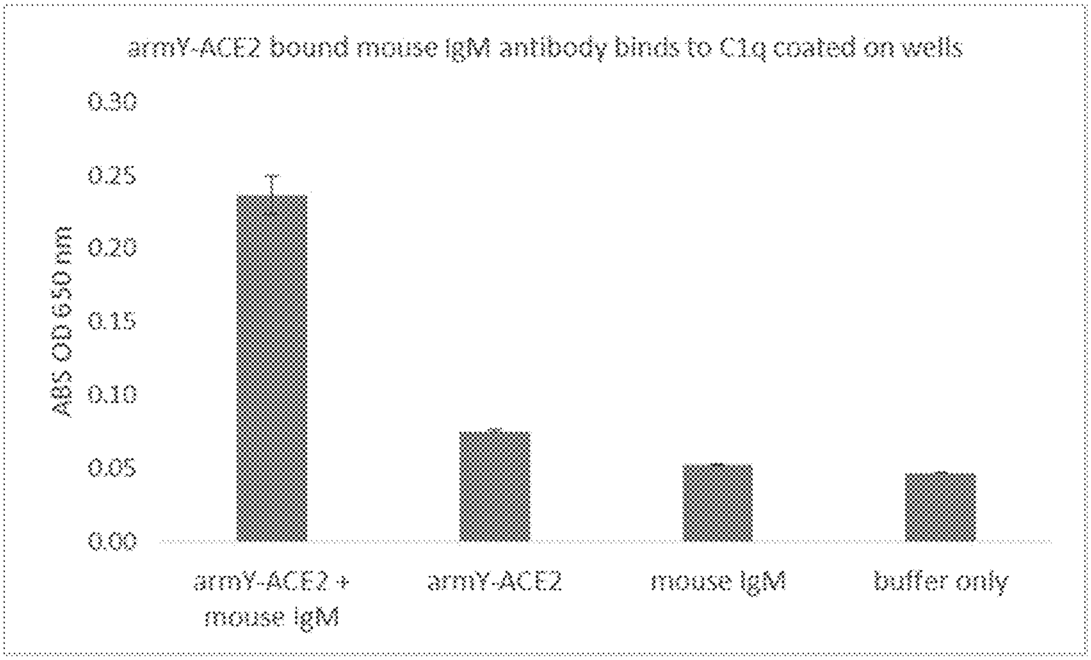
FIG. 11A-B.
Figure 11B:
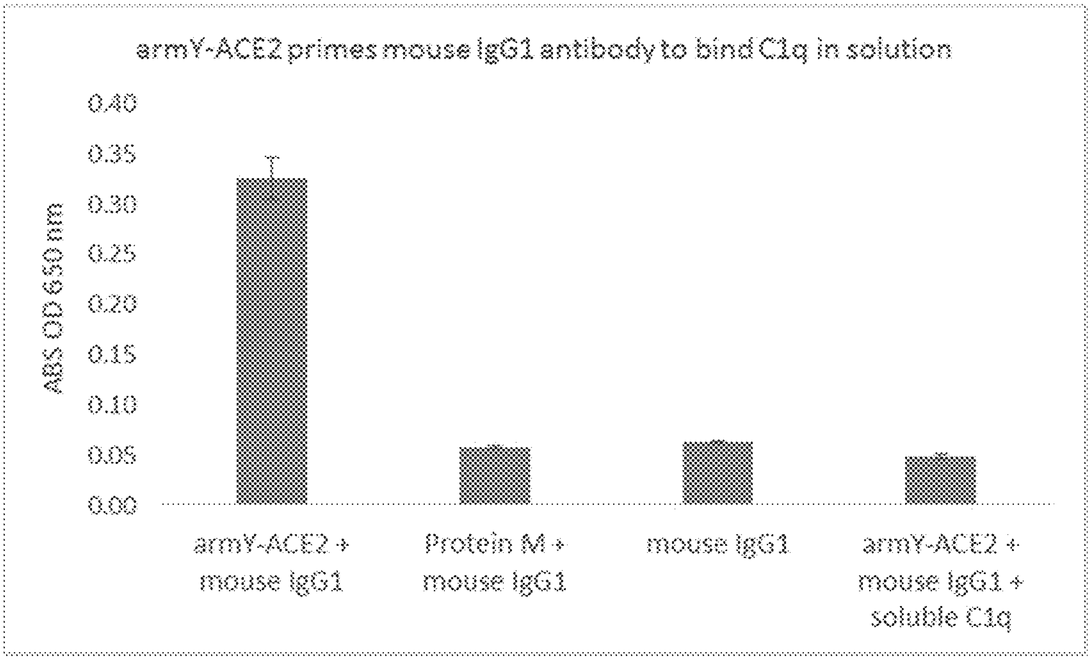

Example 10. [armY-ACE2+Antibody] Complex Binding to Purified Human C1q Complement Component The binding of the C1q complement component to antibody is the initial step towards the activation of the classical complement pathway. The [armY-ACE2+antibody] complex binding to C1q complement component was demonstrated by measuring the amount of [armY-ACE2+antibody] complexes bound to the purified C1q coated on a 96-well plate by an ELISA-based method (FIG. 11).

Briefly, 50 ul of 5 ug/ml purified human C1q (>95% pure by SDS-PAGE analysis, Complement Technology, Inc.) was prepared in ELISA coating buffer (Biolegend, Inc.) and added to a flat bottom 96-well plate (Immulon 2HB). The next day, the wells were washed twice with PBS (Gibco) and 100 ul 3% BSA in PBS (Boston Bioproducts, Inc.) was added to block unbound sites on the well. armY-ACE2+ antibody complexes were allowed to form at room temperature by adding 5 ug/ml FITC-labeled mouse IgM (Biolegend, Inc. Cat #401607) or 10 ug/ml FITC-labeled mouse IgG1 (Biolegend, Inc. Cat #200305) to armY-ACE2 or Protein M (lacking ACE2 domain) in expression medium. FITC-labeled antibody or armY-ACE2 added to expression medium served as negative controls. To block binding of [armY-ACE2+antibody] complex to immobilized C1q coated on the well, 10 ug/ml of soluble C1q was added to the [armY-ACE2+antibody] complexes and allowed to incubate at room temperature for 30 minutes. C1q-coated wells were washed twice with PBS+Tween 20 (wash buffer, Pierce), and the samples were added in duplicate. After approximately 30 minutes at room temperature, the wells were washed 3×s and biotinylated anti-FITC (Biolegend, Inc.) in assay buffer was added to the wells and allowed to incubate at room temperature for approximately 45 minutes. The wells were washed 3×s and SA-HRP (Biolegend, Inc.) in assay buffer was added to the wells and allowed to incubate at room temperature for approximately 25 minutes. After 4 washes, TMB substrate solution (Biolegend, Inc.) was added to the wells and the absorbance at 650 nm measured using a plate reader (Molecular Devices Thermomax and Softmax Pro software).

Figure 12A:
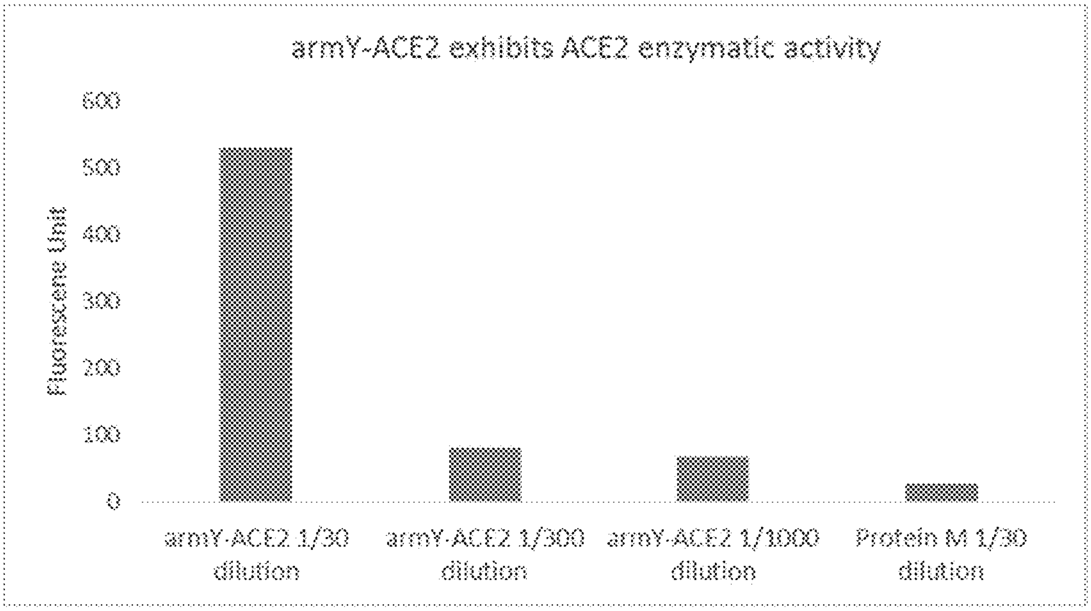
FIG. 12A-B.
Figure 12B:
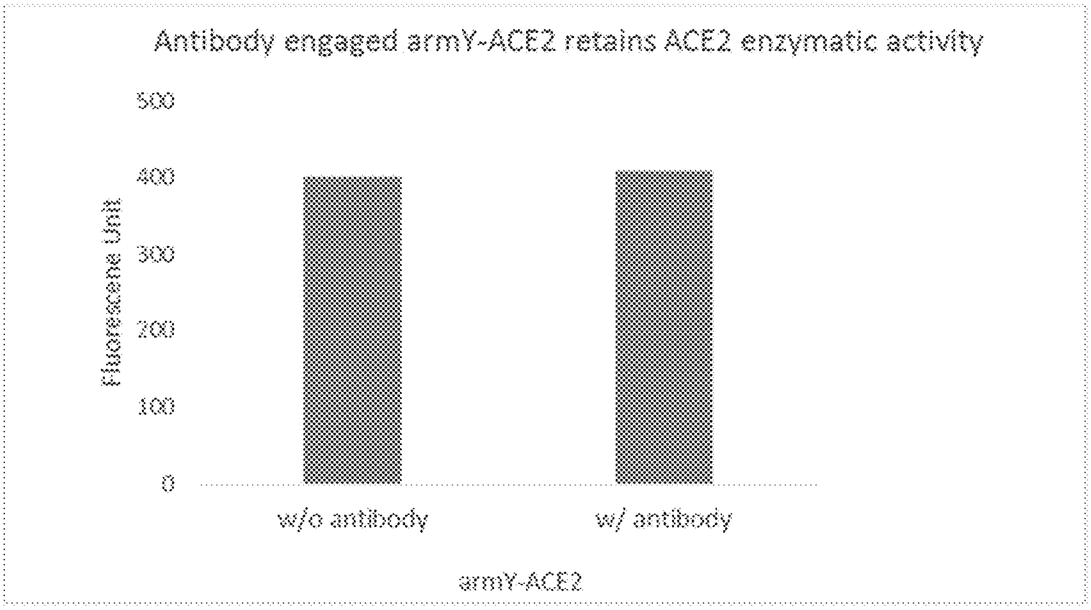

Example 11. armY-ACE2 or [armY-ACE2+Antibody] Complexes Exhibit ACE2 Activity ACE2 activity in armY-ACE2 or [armY-ACE2+antibody] complexes was demonstrated by measuring the fluorescence emitted after cleavage of the ACE2 fluorogenic substrate MCA-APK-(Dnp). ACE2-dependent removal of the quenching Dnp group induces fluorescence, which is measured by a fluorescence plate reader (FIG. 12).

Briefly, armY-ACE2 or [armY-ACE2+antibody] complexes were diluted in ACE2 buffer (1 mol/L NaCl, 75 mmol/L Tris HCl, pH 7.5, and 50 μmol/L ZnCl2) and 30 μl of diluted samples were combined with 170 μl the ACE2 fluorogenic substrate MCA-APK(Dnp) (AnaSpec, Inc. Cat #AS-60757) in ACE2 buffer. The final concentration of ACE2 substrate was 20 μM in a final volume of 200 μl. The samples were kept in the dark for 16 hours at room temperature. 100 μl of samples were transferred to a flat bottom NUNC Black 96 Microwell strip plate and fluorescence measured using a fluorescence plate reader (Cytofluor 4000, Gain 75, Ex 360/40, Em 460/40).

Example 12. SDS-PAGE Analysis of Purified armY-ACE2

Figure 13A:
FIG. 13A-B.
Figure 13B:
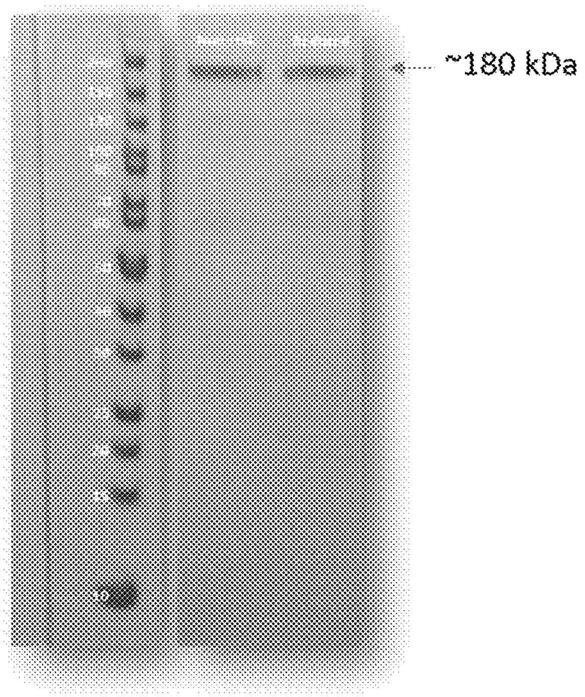

SDS-PAGE analysis of purified armY-ACE2 was performed under non-reducing and reducing conditions and showed the expected band of ~180 kDa (theoretical molecular weight: 150 kDa) (FIG. 13).

Briefly, 8 ul of sample buffer (Invitrogen) was added to 24 ul of eluted fractions and mixed. The sample were heated in 80° C. water bath for 10 minutes. Reducing agent (10×, Invitrogen) was added to some of the tubes containing the samples and mixed. Non-reduced and reduced samples were loaded onto a 4-12% NuPAGE pre-cast SDS-PAGE gel and separated at 175V for 30 minutes in MES-SDS running buffer (Invitrogen). PageRuler unstained protein ladder (10-200 kDa, Invitrogen) was also included. After electrophoresis, the gel was rinsed in distilled water and the protein bands stained using SimplyBlue Safe Stain (Invitrogen) and the gel photographed.

Example 13. Evaluating Neutralization of SARS-CoV-2 by armY-ACE2 In-Vitro

Live SARS-CoV-2 virus has to be handled under biosafety level 3 conditions due to its high pathogenicity and infectivity and the lack of effective vaccines and therapeutics. Recently, a VSV pseudovirus production system, a pseudovirus-based neutralization assay has been developed for evaluating neutralizing antibodies against SARS-CoV-2 in biosafety level 2 facilities (Nie et.al., 2020). Pseudoviruses are useful tools because of their safety and versatility, especially for emerging and re-emerging viruses. This example utilizes a validated Pseudovirus neutralization protocol slightly modified from Nie et.al., to test the efficacy of armY-ACE2 by measuring the ability of armY-ACE2 to inhibit SARS-CoV-2 pseudovirus binding and infection of ACE2 expressing cells.

Briefly, the vesicular stomatitis virus (VSV) pseudovirus system (G*AG-VSV) is used, which packages expression cassettes for firefly luciferase instead of VSV-G in the VSV genome. The SARS-CoV-2 pseudovirus is produced by transfecting human 293T cells with the expression plasmid pcDNA3.1 containing the codon-optimized SARS-CoV-2 spike protein sequence, followed by infection with G*AG-VSV pseudovirus. Post infection, SARS-CoV-2 pseudoviruses is harvested and stored until use.

Huh7 human hepatocellular cell line naturally express the human ACE2 receptor protein and is an ideal cell line for SARS-CoV-2 pseudovirus infection as it demonstrates high luciferase activity upon infection. Viral inocula of approximately 650 TCID50 (the 50% tissue culture infectious dose of SARS-CoV-2 pseudovirus) is used for the assay.

Neutralization of SARS-CoV-2 pseudovirus infection of Huh7 is confirmed by the reduction in luciferase gene expression upon infection. Neutralization condition: SARS-CoV-2 pseudovirus is incubated with serial dilutions of armY-ACE2+human plasma containing immunoglobulins (six, 1:3 dilutions, or half-log dilutions) in duplicate. Human plasma added Protein M or human plasma alone are included as negative controls. Recombinant ACE2-Ig fusion protein (commercially available from GenScript Inc., catalog #Z03484) has been demonstrated to neutralize SARS-CoV-2 pseudovirus infection previously (Lei et.al., 2020) and is used in this assay as a positive control. After incubation for 1 hour at 37° C. in a 96-well plate format, 5×10^4 Huh7 cells is added to each well. After 24 hours of incubation in a 5% CO2 chamber at 37° C., luminescence is measured by adding luciferase substrate and the luminescence measured using a 96-well plate luminescence plate reader. Upon subtraction of background luminescence, relative light units (RLU) versus the concentration of test sample and controls is plotted to generate an inhibitory dose response curve from which the IC50 is calculated. Human plasma added armY-ACE2 is neutralizing SARS-CoV-2 pseudovirus infection of Huh7 in a dose-dependent fashion. Human plasma added Protein M or human plasma alone is not neutralizing SARS-CoV-2 pseudovirus infection in this assay.

Example 14. Evaluating Eradication of SARS-CoV-2 by armY-ACE2 In Vivo

While the Example 13 evaluates the efficacy of armY-ACE2 engaged immunoglobulins to neutralize SARS-CoV-2 in vitro, this Example will demonstrate the efficacy of armY-ACE2 to promote eradication of SARS-CoV-2 in vivo, thereby protecting the animal from a severe clinical disease and succumbing to a lethal infection.

Protein M binds to immunoglobulin of various species including those of man and mice. Commercially available human ACE2 transgenic mice K18-hACE2 (The Jackson Laboratory, Stock #034860) develops severe clinical disease upon infection with SARS-CoV (McCray et.al., 2007) to a similar degree observed in patients with severe Covid-19. According to CDC, "Among patients who developed severe disease, the median time to dyspnea from the onset of illness or symptoms ranged from 5 to 8 days, the median time to acute respiratory distress syndrome (ARDS) from the onset of illness or symptoms ranged from 8 to 12 days, and the median time to ICU admission from the onset of illness or symptoms ranged from 10 to 12 days."

According to JAX laboratory, "These K18-hACE2 mice develop a rapidly lethal infection after intranasal inoculation with a human strain of SARS-CoV. Infection begins in airway epithelia, with subsequent alveolar involvement and extrapulmonary virus spread to the brain. Infection results in macrophage and lymphocyte infiltration in the lungs and upregulation of proinflammatory cytokines and chemokines in both the lung and the brain. By days 3 to 5 postinfection, K18-hACE2 mice begin to lose weight and become lethargic with labored breathing." K18-hACE2 mice become moribund 4 days after inoculation, and all mice are dead 7 days after inoculation.

Recently, it was determined that K18-hACE2 mice "present with more symptomatic disease than other hACE2 mouse models of SARS-CoV-2 infection." (Moreau et.al., 2020) For this reason and because the k18-hACE2 mice are readily commercially available, we employed the k18-hACE2 SARS-CoV model to evaluate the efficacy of army-ACE2 engaged immunoglobulins to eradicate SARS-CoV or SARS-CoV-2 in vivo following the methods as described (McCray et.al., 2007) with slight modifications.

Infection of K18-hACE2 mice with SARS-CoV or SARS-CoV-2. SARS-CoV and SARS-CoV-2 strains is obtained from the Centers for Disease Control, Atlanta, Ga. The virus is propagated and titered on Vero E6 cells in a biosafety level 3 laboratory and the virus titer is determined by a plaque assay.

Mice are lightly anesthetized with isoflurane and infected intranasally with the indicated dosage of SARS-CoV or SARS-CoV-2 in 30 ul of Dulbecco's modified Eagle medium. Infected mice are examined, weighed and evaluated for severe clinical disease on a daily basis monitoring for appearances of lethargy, labored breathing, moribund and death.

Treatment with armY-ACE2. Plasma from mice of the same background (C57BL/6J×SJL/J) as K18-hACE2 mice is harvested and mixed with armY-ACE2 and allowed to incubate at 37° C. for 1-2 hours to permit arming of plasma immunoglobulins. Infected mice (n=6) receive daily injections of 0.2 ml of armY-ACE2 plasma beginning one day after infection for 7 days. Two other cohorts of mice receive Protein M+plasma or plasma alone and serve as negative control treatment groups.

To obtain specimens for virus titers, a few animals are sacrificed before injection and after 1, 2, 3, 4, 5 and 6 days after infection, and organs are aseptically removed into sterile phosphate-buffered saline. In some cases, blood is obtained via catheterization of the inferior vena cava. Tissues are homogenized using a manual homogenizer, and the 50% tissue culture infective dose (TCID) is determined as described previously (Subbarao et.al., 2004) to determine the amount of virus per gram of tissue. Mice treated with army-ACE2 plasma do not succumb to infection, whereas mice in the negative control groups succumb. Surviving mice are permitted to continue in the study over an additional 2 months. These mice developed immunity to the virus and are protected from a subsequent challenge with the virus. Surviving mice are re-infected and examined, weighed daily and evaluated.

At termination, whole-lung lavage is performed and the lavage is evaluated for cellular and biochemical changes using standard techniques. Significantly lower cellular infiltrates and inflammatory markers in armY-ACE2 plasma treated mice are found as compared to mice in the negative control groups. Lungs and other organs are examined by histology and immunohistochemistry to evaluate the degree of disease pathology and detect viral antigen. Significantly lower severe disease pathology and viral presence in the lungs and organs or armY-ACE2 plasma treated mice are found as compared to mice in the negative control groups, indicating effective viral clearance and eradication. Similar findings are observed in armY-ACE2 plasma treated mice that had developed immunity to the virus and re-challenged with the virus.

Extraction of total RNA and quantitative reverse transcription-PCR (RTPCR) are performed to measure levels of viral RNA in various tissue specimen. An aliquot of cDNA is subjected to PCR using a MyiQ single-color real-time PCR detection system with iQ SYBR green Supermix. A set of primers is used for the SARS-CoV or SARS-CoV-2 nucleocapsid (N) gene or a house-keeping gene. Significantly lower viral genes in specimens acquired from armY-ACE2 plasma treated mice are found as compared to mice in the negative control groups, indicating effective viral clearance and eradication. Similar findings are found in armY-ACE2 plasma treated mice that had developed immunity to the virus and re-challenged with the virus.

Example 15. Identification of Two Potential Immunogenic Peptide Regions in Protein M (a.a. 469-556)

The online B-cell epitope prediction tools (IEDB Analysis Resource) were used to determine potential immunogenic peptide regions in Protein M (a.a. 469-556). Using six online prediction tools [Bepipred Linear Epitope Prediction 2.0, Bepipred Linear Epitope Prediction, Chou & Fasman Beta-Turn Prediction, Emini Surface Accessibility Prediction, Karplus & Schulz Flexibility Prediction and Parker Hydrophilicity Prediction] two peptide regions in protein M c-terminal end (469-556 amino acid) were determined to be potentially immunogenic. The following peptide substitutions are proposed for these two regions to mitigate immunogenicity of Protein M C-terminal end (469-556 amino acid), which are listed below in a) an b), and additionally shown in the following Table 1. Complete Protein M amino acid sequences with substitutions are presented as SEQ ID NO: 63-66.

a) 494-507 amino acid of protein M (based on SEQ ID NO: 1)

1. QALANATASALAAM
2. AKLANATASALARM
3. QALEADADSALEAM
4. AKLANDTASSAERA b) 527-540 amino acid of protein M (based on SEQ ID NO: 1)

1. AIAGVASATNAVAS
2. AIAGVASATNAVKS
3. DIAGVSADTAEVAS
4. AITGASSATNAVKA

TABLE 1

Proposed alanine substitutions for Protein M c-terminal end (469-556 amino acid) to mitigate immunogenicity.

| a) | 494 | 495 | 496 | 497 | 498 | 499 | 500 | 501 | 502 | 503 | 504 | 505 | 506 | 507 |
|---|---|---|---|---|---|---|---|---|---|---|---|---|---|---|
| Original | Q | K | L | E | N | D | T | D | S | S | L | E | R | M |
| Subs #1 | Q | A | L | A | N | A | T | A | S | A | L | A | A | M |
| Subs #2 | A | K | L | A | N | A | T | A | S | A | L | A | R | M |
| Subs #3 | Q | A | L | E | A | D | A | D | S | A | L | E | A | M |
| Subs #4 | A | K | L | A | N | D | T | A | S | S | A | E | R | A |
| b) | 527 | 528 | 529 | 530 | 531 | 532 | 533 | 534 | 535 | 536 | 537 | 538 | 539 | 540 |
| Original | D | I | T | G | V | S | S | D | T | N | E | V | K | S |
| Subs #1 | A | I | A | G | V | A | S | A | T | N | A | V | A | S |
| Subs #2 | A | I | A | G | V | A | S | A | T | N | A | V | K | S |
| Subs #3 | D | I | A | G | V | S | A | D | T | A | E | V | A | S |
| Subs #4 | A | I | T | G | A | S | S | A | T | N | A | V | K | A |

Figure 14A:
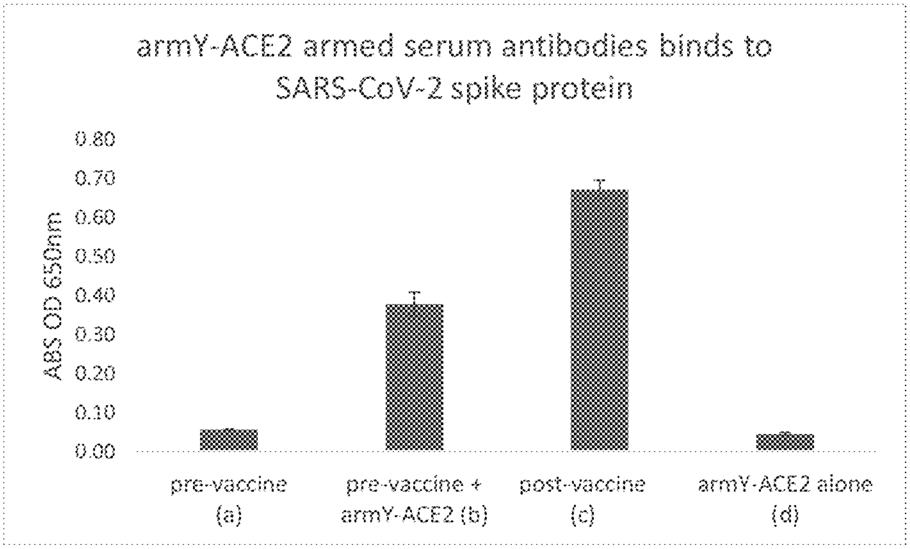
FIG. 14A-C.
Figure 14A:
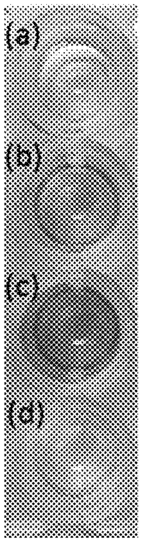
Figure 14B:
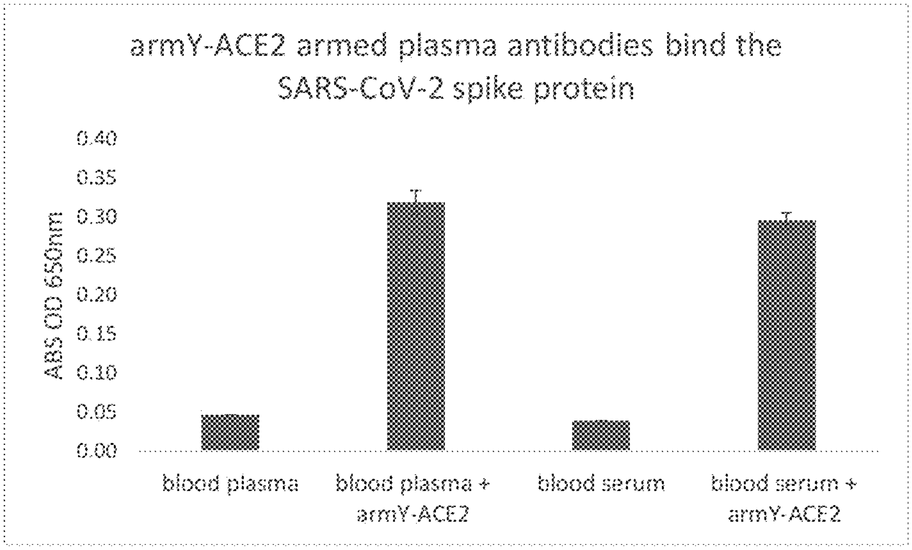
Figure 14C:
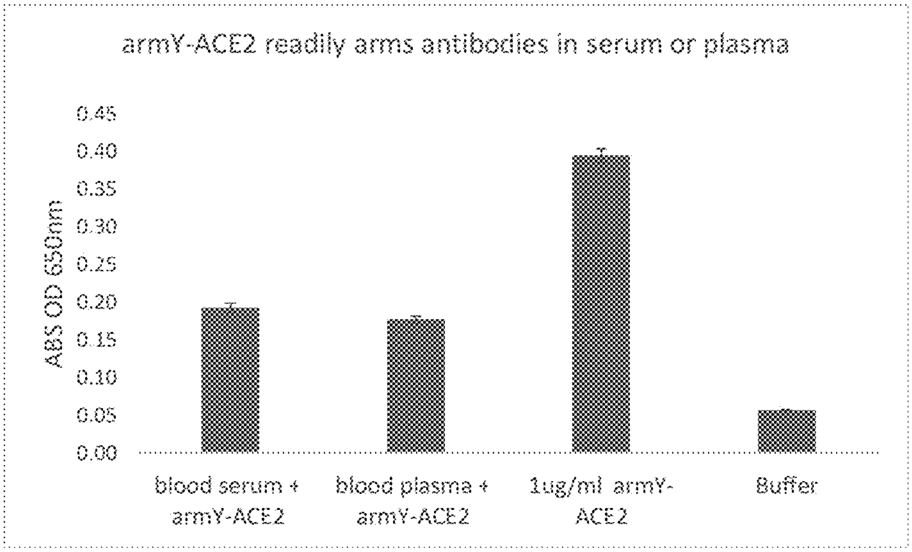

Example 16. Non-Immune Human Serum or Plasma Antibodies Armed with armY-ACE2 Bind to SARS-CoV-2 Spike Protein (FIG. 14A-C)

Binding to SARS-CoV-2 spike protein by armY-ACE2 armed non-immune serum antibodies was demonstrated by measuring the amount of armed antibodies that bind the SARS-CoV-2 spike protein coated on a 96-well plate by an ELISA-based method.

Briefly, 50 ul of 5 ug/ml SARS-CoV-2 spike protein was prepared in ELISA coating buffer (Biolegend, Inc.) and added to a flat bottom 96-well plate (Immulon 2HB). The next day, the wells were washed 2×s with PBS (phosphate buffered saline pH 7.4) (Gibco) and 100 ul 3% BSA in PBS (Boston Bioproducts, Inc.) was added to block unbound sites on the well. [armY-ACE2+antibody] complexes were allowed to form by mixing armY-ACE2 with non-immune serum (pre-vaccine) diluted 1:200 in assay medium for 60 minutes in a 37° C. incubator. Mixtures containing pre-vaccine serum diluted 1:200 in assay medium, post-vaccine (Moderna SARS-CoV-2 spike mRNA vaccine) serum diluted 1:200 in assay medium or armY-ACE2 in assay medium, were included as controls and placed in a 37° C. incubator for 60 minutes. The final concentration of armY-ACE2 was 20 ug/ml. Binding of armY-ACE2 armed non-immune plasma (ACD-A) antibodies to SARS-CoV-2 spike protein was demonstrated following the same procedure described above.

After the incubation period, the samples were added to SARS-CoV-2 spike protein coated wells that had been washed 2×s with PBS+Tween 20 (wash buffer, Pierce), in duplicate. After approximately 120 minutes at room temperature, the wells were washed 4×s and anti-human IgG labeled with HRP (Genscript) was added to the wells and allowed to incubate at room temperature for approximately 25 minutes. After four washes, TMB substrate solution (Biolegend, Inc.) was added to the wells and the blue color absorbance at 650 nm measured using a plate reader (Molecular Devices Thermomax and Softmax Pro software) and a photo taken with a digital camera.

After incubating serum- or plasma-antibodies with armY-ACE2, the amount of free armY-ACE2 was determined by measuring the amount of unengaged armY-ACE2 that can bind to immobilized human IgG. Briefly, serum- or plasma samples incubated with armY-ACE2 as described above, were added to human IgG coated wells, in duplicate. 1 ug/ml of armY-ACE2 alone in assay buffer was added to separate wells as a reference positive control. After approximately 100 minutes at room temperature, the wells were washed and mouse IgG1 anti-myc antibody (clone: 9E10) in assay buffer was added to detect the myc-tagged armY-ACE2 bound to human IgG coated on the wells. After approximately 30 minutes, the wells were washed 3×s and anti-mouse IgG labeled with HRP was added to the wells. After approximately 20 minutes, the wells were washed 4×s and TMB substrate solution (Biolegend, Inc.) was added to the wells and the absorbance at 650 nm measured using a plate reader (Molecular Devices Thermomax and Softmax Pro software).

Figure 15A:
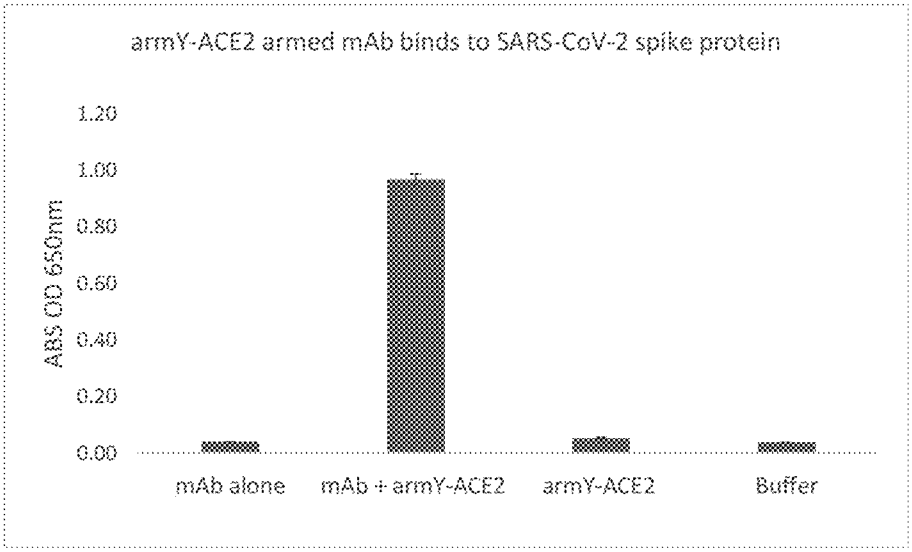
FIG. 15A-B.
Figure 15B:
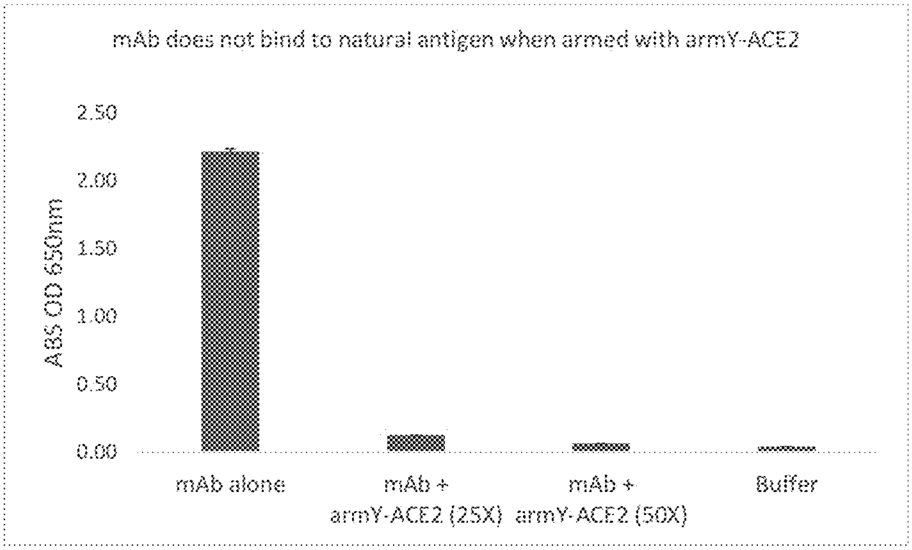

Example 17. Monoclonal Antibody (mAb) Armed with armY-ACE2 Gains the Ability to Bind the SARS-CoV-2 Spike Protein, but is No Longer Able to Bind its Natural Target Antigen (FIG. 15 A-B)

Binding to SARS-CoV-2 spike protein by armY-ACE2 armed mAb (originally anti-selectin) was demonstrated by measuring the amount of armed mAbs that bind to the SARS-CoV-2 spike protein coated on a 96-well plate by an ELISA-based method.

Briefly, 50 ul of 5 ug/ml SARS-CoV-2 spike protein was prepared in ELISA coating buffer (Biolegend, Inc.) and added to a flat bottom 96-well plate (Immulon 2HB). The next day, the wells were washed 2×s with PBS (phosphate buffered saline pH 7.4) (Gibco) and 100 ul 3% BSA in PBS (Boston Bioproducts, Inc.) was added to block unbound sites on the well. [armY-ACE2+mAb] complexes were allowed to form by mixing armY-ACE2 with the mAb in assay medium for 120 minutes in a 37° C. incubator. Mixtures containing mAb in assay medium, armY-ACE2 in assay medium, or assay medium alone were included as controls and placed in a 37° C. incubator for 120 minutes. The final concentration of mAb and armY-ACE2 were 1 ug/ml and 30 ug/ml, respectively.

After the incubation period, the samples were added to SARS-CoV-2 spike protein coated wells, in duplicate, that had been washed 2×s with PBS+Tween 20 (wash buffer, Pierce). After approximately 120 minutes at room temperature, the wells were washed 3×s and anti-human IgG labeled with HRP (Southern Biotech) was added to the wells and allowed to incubate at room temperature for approximately 45 minutes. After four washes, TMB substrate solution (Biolegend, Inc.) was added to the wells and absorbance at 650 nm measured using a plate reader (Molecular Devices Thermomax and Softmax Pro software).

The inability of armY-ACE2 armed mAb (originally anti-selectin) to bind to its natural antigen was demonstrated by measuring the amount of armed mAb that bind to selectin protein coated on a 96-well plate by an ELISA-based method.

Briefly, 100 ul of 2 ug/ml biotinylated selectin protein was prepared in PBS and added to a flat bottom 96-well plate (streptavidin coated wells) after 2 washes with PBS+Tween 20 (wash buffer, Pierce).

[armY-ACE2+mAb] complexes were allowed to form by mixing armY-ACE2 with the mAb in assay medium for 120 minutes in a 37° C. incubator. Mixtures containing mAb in assay medium or assay medium alone were included as controls and placed in a 37° C. incubator for 120 minutes. The final concentration of mAb and armY-ACE2 were 63 ng/ml and 15 ug/ml (50× molar excess) or 7.5 ug/ml (25× molar excess), respectively.

After 2 hours, the selectin-coated wells were washed 2×s with wash buffer and the mixtures added in duplicate wells and allowed to incubate for 1 hour at room temperature. After the incubation period, the wells were washed 3×s. After approximately 60 minutes at room temperature, the wells were washed 3×s and anti-human IgG labeled with HRP (Southern Biotech)+2% mouse serum was added to the wells and allowed to incubate at room temperature for approximately 60 minutes. After four washes, TMB substrate solution (Biolegend, Inc.) was added to the wells and absorbance at 650 nm measured using a plate reader (Molecular Devices Thermomax and Softmax Pro software).

Figure 16:
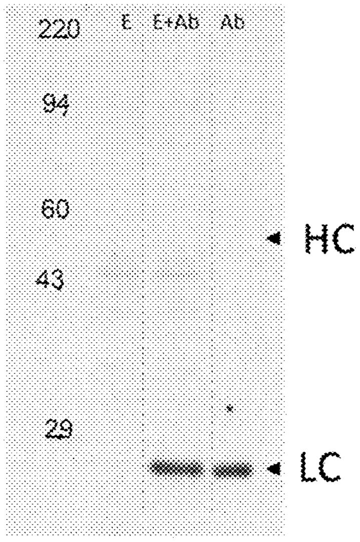
FIG. 16. Specific detection of antibody light-chain (LC, ~25 KDa), but not heavy-chain (HC, ~50 KDa) by mono-biotinylated protein M on 1D gel electrophoresis by Western blot analysis. Antibody sample was loaded alone (right lane, Ab) or in a mixture with *E. coli* lysate (middle lane, E+Ab). *E. coli* lysate alone was also loaded (left lane, E) as control. The molecular weight standard values (KDa, left) are derived from the Coomassie blue stained blots.

Example 18. Biotinylated Protein M Detects the Light-Chain of Antibody, but not the Heavy-Chain on Western Blot (FIG. 16)

Protein M containing an N-terminal biotinylation "Avi-Tag" sequence was mono-biotinylated using the Accelagen TurboBiotinylation kit following the reaction protocol (Accelagen, TurboBiotinylation-protocol). The use of mono-biotinylated protein M fusion as an immunologic research tool for detection of antibody light-chain was demonstrated using a 1D gel electrophoresis Western blot method.

Briefly, the antibody sample was diluted to 1.0 mg/mL with sodium dodecyl sulfate (SDS) boiling buffer and heated to 95° C. for 10 minutes, and further diluted to 0.01 mg/mL. The *E. coli* (K12 MG1655) lysate sample was diluted to 2.5 mg/mL in SDS boiling buffer. SDS slab gel electrophoresis was carried out under reducing conditions according to the method of Laemmli, U. (Nature 227: 680-685, 1970) as modified by O'Farrell (J Biol. Chem. 250: 4007-4021). The samples were loaded in wells in 10% acrylamide slab gels (0.75 mm thick). SDS slab gel electrophoresis was carried out for about 4 hours at 15 mA/gel. The following proteins (Millipore Sigma) were used as molecular weight standards: myosin (220,000), phosphorylase A (94,000), catalase (60,000), actin (43,000), carbonic anhydrase (29,000), and lysozyme (14,000, not shown). After slab gel electrophoresis, the gel for blotting was placed in transfer buffer (10 mM CAPS, pH 11.0, 10% methanol) and transblotted onto PVDF membranes overnight at 145 mA and approximately 100 volts/two gels. The blots were stained with Coomassie Brilliant Blue R-250, cut into pieces at the dark lines and flatbed scanned (not shown).

Western Blot analysis. The membrane sections were destained in 100% MeOH and rinsed briefly in Tween-20 tris buffer saline (TTBS). The blot was blocked for two hours in Superblock with 0.05% Tween-20 (Superblock-T). The blot was then incubated overnight in Superblock-T and rinsed 3×10 minutes in TTBS. The blot was then placed in mono-biotinylated protein M diluted to 1.0 μg/ml in Superblock-T for two hours and rinsed as above. The blot was then placed in poly-HRP streptavidin (ThermoFisher, Cat #N200) diluted 1:500,000 in Superblock-T for two hours, rinsed as above, treated with ThermoFisher Pierce ECL, and exposed to x-ray film for 3 minutes.

Figure 17:
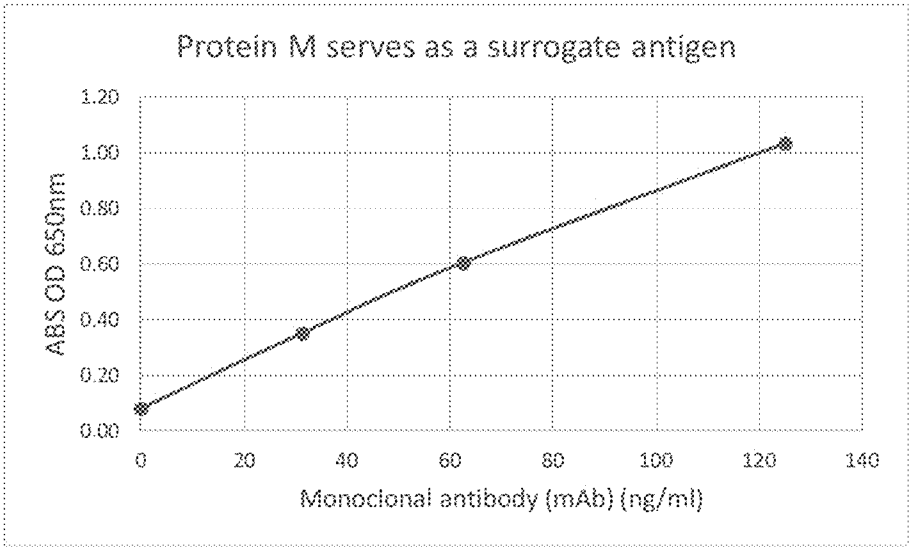
FIG. 17. Biotinylated Protein M is immobilized in streptavidin-coated wells and serves as a surrogate antigen for a monoclonal antibody. Increasing amount of antibody is added to the wells and the level of bound antibody is measured in an ELISA-based method.

Example 19. Protein M Fusion Serves as a Surrogate Antigen and May be Used to Confirm that a) Antigen Binding is Via the Fab Domain of the Antibody and b) the Antibody's Target Antigen and/or Specificity (FIG. 17)

Binding of antibody to antigen is mediated by the Fab arm of the antibody, which contains the variable region where the antigen binding site is found. Protein M binds specifically to the light-chain variable region in the Fab and blocks the antigen binding site. Therefore, protein M may serve as a surrogate antigen and as an immunologic research tool, and used to a) confirm that the antibody binds via its Fab domain and b) confirms its specificity as it loses its antigen binding ability when bound by protein M. A 96-well ELISA-based method was used to demonstrate such protein M uses.

Protein M fusion serves as a surrogate antigen.

Briefly, 100 ul of 2 ug/ml mono-biotinylated protein M was prepared in PBS and added to a flat bottom 96-well plate (streptavidin coated wells) after 2 washes with PBS+Tween 20 (wash buffer, Pierce).

After approximate 2 hours at room temperature, the coated wells were washed 2×s with wash buffer and the varying amounts of monoclonal antibody (originally anti-selectin) were added in duplicate wells and allowed to incubate for approximately 2 hours at room temperature. After the incubation period, the wells were washed 3×s and anti-human IgG labeled with HRP (Southern Biotech) was added to the wells and allowed to incubate at room temperature for approximately 60 minutes. After four washes, TMB substrate solution (Biolegend, Inc.) was added to the wells and absorbance at 650 nm measured using a plate reader (Molecular Devices Thermomax and Softmax Pro software).

Figure 18:
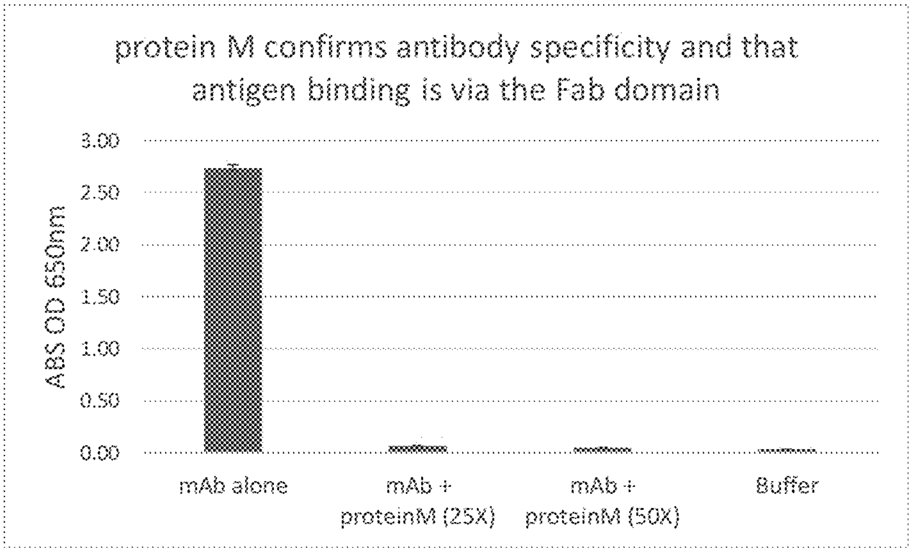
FIG. 18. Protein M fusion blocks the binding of a monoclonal antibody (mAb) to its natural antigen thereby a) shows that antigen binding is Fab dependent and b) confirms the antibody's binding specificity.

Example 20. Protein M is Used to Confirm that a) the Antibody Binds Via its Fab Domain and b) it Loses its Antigen Binding Ability when Bound by Protein M (FIG. 18)

Briefly, 100 ul of 2 ug/ml biotinylated selectin protein was prepared in PBS and added to a flat bottom 96-well plate (streptavidin coated wells) after 2 washes with PBS+Tween 20 (wash buffer, Pierce).

Protein M+monoclonal antibody (mAb) complexes were allowed to form by mixing protein M with the mAb in assay medium for 120 minutes in a 37° C. incubator. Mixtures containing mAb in assay medium or assay medium alone were included as controls and placed in a 37° C. incubator for 120 minutes. The final concentration of mAb and protein M were 125 ng/ml and 3.4 ug/ml (50× molar excess) or 1.7 ug/ml (25× molar excess), respectively.

After 2 hours, the selectin-coated wells were washed 2×s with wash buffer and the mixtures added in duplicate wells and allowed to incubate for approximately 90 minutes at room temperature. After the incubation period, the wells were washed 3×s. After approximately 60 minutes at room temperature, the wells were washed 3×s and anti-human IgG labeled with HRP (Southern Biotech) was added to the wells and allowed to incubate at room temperature for approximately 60 minutes. After four washes, TMB substrate solution (Biolegend, Inc.) was added to the wells and absorbance at 650 nm measured using a plate reader (Molecular Devices Thermomax and Softmax Pro software).

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Specifically intended to be within the scope of the present invention, and incorporated herein by reference in its entirety, is the following publication:

Grover R K, Zhu X, Nieusma T, et al. A structurally distinct human *mycoplasma* protein that generically blocks antigen-antibody union. Science. 2014; 343(6171):656-661.

Blötz C, Singh N, Dumke R, Stülke J. Characterization of an Immunoglobulin Binding Protein (IbpM) From *Mycoplasma pneumoniae*. Front Microbiol. 2020; 11:685. Lei C, Qian K, Li T, et al. Neutralization of SARS-CoV-2 spike pseudotyped virus by recombinant ACE2-Ig. Nat Commun. 2020; 11(1):2070.

Nie J, Li Q, Wu J, et al. Establishment and validation of a pseudovirus neutralization assay for SARS-CoV-2. Emerg Microbes Infect. 2020; 9(1):680-686.

Mccray P B, Pewe L, et al. Lethal infection of K18-hACE2 mice infected with severe acute respiratory syndrome coronavirus. J Virol. 2007; 81(2):813-21.

G. Brett Moreau, Stacey L. Burgess, Jeffrey M. Sturek, Alexandra N. Donlan, William A. Petri Jr., Barbara J. Mann Evaluation of K18-hACE2 mice as a model of SARS-CoV-2 infection. bioRxiv 2020.06.26.171033.

Subbarao K, Mcauliffe J, Vogel L, et al. Prior infection and passive transfer of neutralizing antibody prevent replication of severe acute respiratory syndrome coronavirus in the respiratory tract of mice. J Virol. 2004; 78(7):3572-7.

Mebrahtu E, Zheleznyak A, Hur M A, Laforest R, Lapi S E. Initial characterization of a dually radiolabeled peptide for simultaneous monitoring of protein targets and enzymatic activity. Nucl Med Biol. 2013; 40(2):190-6.

```
SEQUENCE LISTING
1)
Mycoplasma genitalium
The mature protein M sequence
(37-556 amino acid)
                                    SEQ ID NO: 1
TNLVNQSGYALVASGRSGNLGFKLFSTQSPSAEVK

LKSLSLNDGSYQSEIDLSGGANFREKFRNFANELS

EAITNSPKGLDRPVPKTEISGLIKTGDNFITPSFK

AGYYDHVASDGSLLSYYQSTEYFNNRVLMPILQTT

NGTLMANNRGYDDVFRQVPSFSGWSNTKATTVSTS

NNLTYDKWTYFAAKGSPLYDSYPNHFFEDVKTLAI

DAKDISALKTTIDSEKPTYLIIRGLSGNGSQLNEL

QLPESVKKVSLYGDYTGVNVAKQIFANVVELEFYS

TSKANSFGFNPLVLGSKTNVIYDLFASKPFTHIDL

TQVTLQNSDNSAIDANKLKQAVGDIYNYRRFERQF
```

-continued

QGYFAGGYIDKYLVKNVNTNKDSDDDLVYRSLKEL

NLHLEEAYREGDNTYYRVNENYYPGASIYENERAS

RDSEFQNEILKRAEQNGVTFDENIKRITASGKYSV

QFQKLENDTDSSLERMTKAVEGLVTVIGEEKFETV

DITGVSSDTNEVKSLAKELKTNALGVKLKL

2)
*Mycoplasma pneumoniae*
IgG-blocking mature protein M
sequence (36-582 amino acid)

SEQ ID NO: 2

AVLIVNEVLRLQSGETLIASGRSGNLSFQLYSKVN

QNAKSKLNSISLTDGGYRSEIDLGDGSNFREDFRN

FANNLSEAITDAPKDLLRPVPKVEVSGLIKTSSTF

ITPNFKAGYYDQVAADGKTLKYYQSTEYFNNRVVM

PILQTTNGTLTANNRAYDDIFVDQGVPKFPGWFHD

VDKAYYAGSNGQSEYLFKEWNYYVANGSPLYNVYP

NFIHFKQIKTIAFDAPRIKQGNTDGINLNLKQRNP

DYVIINGLTGDGSTLKDLELPESVKKVSIYGDYHS

INVAKQIFKNVLELEFYSTNQDNNFGFNPLVLGDH

TNIIYDLFASKPFNYIDLTSLELKDNQDNIDASKL

KRAVSDIYIRRRFERQMQGYWAGGYIDRYLVKNTN

EKNVNKDNDTVYAALKDINLHLEETYTHGGNTMYR

VNENYYPGASAYEAERATRDSEFQKEIVQRAELIG

VVFEYGVKNLRPGLKYTVKFESPQEQVALKSTDKF

QPVIGSVTDMSKSVTDLIGVLRDNAEILNITNVSK

DETVVAELKEKLDRENVFQEIRT

3)
*Mycoplasma iowae*
IgG-blocking mature protein M
sequence (21-497 amino acid)

SEQ ID NO: 3

VGVYVATTNTQNTSVNVNNNENINYKTNGTVVTGD

KLTFSAVVQQNSNISTQAFINDGTKPVGTYNKEIN

LGKDSITPKYTSGYVETYLESGDTVSRYSSSEYHN

NRTLMPILDTKEHYYTSERTYSEIQKGIYRGWEIS

TKSINYGEQFAYSASPVLKTVFRDLKQETIKAVQF

NLGLSDTSIESINSFLKTNTGIQFVTIKGISQDTD

LSKLVLPESVQKLTLLGQRNTINDLKLPSELQEIE

IYLGSSLKSIDPLIFPKSANIISDVVMNNTSSVFT

EIKLSDSTIDNNSPKLQKAIDDVYTYRIKERAFQG

LVPGGYIASWDLTGTKVTSFNNVNIPPLNDGTGRF

YIAHVEVKTDGNFGNSQNESIGSKPSNDSQINDWF

DWGGGWQKVQEVVVSSSENVSLETATQEIMGFIAK

YPNVKKINIVNVKLTDGSTHEQLKDNVIKAITAKY

GEESQYKDIEFVLPETVPSPVA

-continued

4)
*Mycoplasma tullyi*
IgG-blocking mature protein M
sequence (30-517 amino acid)

SEQ ID NO: 4

IVYTSVKISNTLNQDKQIAGSNLSPTQSNRLIGFQ

TLTKFKIQDLDFELQRKIYSSRLNSAELITKSAVV

LDQSTLQNHDGEVASGQPAPQVPPPVRIPAKEQTG

HTSDFISGYSENNLYYQTPYYYNDRVYMPILDSRK

TYLRNERTTTDIGLNNYEGWITSDHSRVNNRVNVF

NYRPSPELLAKYTDLAADKLIFTMTIDLYQANPEM

INEILKEYSPDFVILSNADSQVMKQLVFPSSVKKL

TIKSNLLDRFDFSLANTEIQELELYTPRLTEYNPF

ALNPNTHLIFDSNYSKPFTSINLYGVPLTHQQVLS

ALEDVFVRRHYERALQGSFSGGYISSLDLSNTGIT

SLSNLMIKNINPYYDSYTMSVKYNSNKNGEIELLK

TNSWKNPNPAPVSTPAASSPTTPTVPSTPGDSTIN

VQDKDLGLLVSSEVKVDPQVLINVVSKYLHNNPRV

NVLDISKVSLKSGSLVDVATNLKAKIDYLNVTI

5)
*Mycoplasma imitans*
IgG-blocking mature protein M
sequence (29-507 amino acid)

SEQ ID NO: 5

GIIYTSVKISSSQFNKQISNPIEVPKRNNTLIGFQ

TLARFKIENLDFELQKNIYSQNENALVNKAAVVQD

NSIINHDGEPTGQNERQVPAPVKILAKEQTGHTSD

FISGYTDNNSYYQSPFYYNDRVFMPILDSHSIYLK

NERTSKEIGLDSYEGWDKIGYSTINSRVSFVQYRA

TDQLIAKFNPSNKQIFAMMINLYQADPAVINNTLR

NYLPDFVILSNADNQIIKRLVFPSSVKKLTIKSNL

LDRFDFSLANSNIQELELYTPNLTEYNPLALNPDT

HLIFDTAYSKPFTSINLYGAKLTTQETQEAFNDIF

VRRYYERYLQGAFVGGYISLLDLSNTGINSVNDYV

VKNINPAYSSYTLSVTYNPGDPGQISILRTTTSIP

SETQPTNPSNNTPSQPTDPNITTQIDAKEKDLKLV

VSSTIQVDTQVVINVVGKYLLNNPRVNNVDISRIQ

LKSGTLVDIANNFKTKMSYLNVSV

6)
Mycoplasma gallisepticum
IgG-blocking mature protein M
sequence (29-417 amino acid)

SEQ ID NO: 6

GIIYTSVKISNSLYQDKLISGQNQPLAPVNRLIGF

QTLAKFRIEGLDFELKKKIYSSTVESVELVNRSAV

LVDDSVLENHDGELTSVQSDPQVPAPVKILAKEQT

GHTSDFVSGYSDDNKYYQSPYYYNDRVYMPILDSP

TIYLKNERTSSDIGLNNYQGWIAVGHARVNSRVSV

-continued

FNYRATDELLAKFNNLPDRLIFTMSIDLYQANPAM

INETLKEYSPDFVILSNADSQTMKQLVFPSSVKKL

TIKSNILDRFDFSLVNSEIQELELYTPNLTEYNPL

ALNPKTHLIFDADYSTRFLSINLYGAQLTNQQALA

ALEDVFVHRYYERALQGSFVDGYISSLVLSDTGIT

SLNNLVIKNINPNYDSYIMSVKYHSNDSGQIELLK

TTAW

7)
*Mycoplasma alvi*
IgG-blocking protein M sequence, signal peptide included (28-540 amino acid)

SEQ ID NO: 7

ISIPFIIQSTHTNNANSTIPNVSKPSGSSLAPINY

SYDNFVNNYDGTLTSNSLVFSASGSKEVKSSLQTR

AITVDGLNDIDSSMGLVDAMSQGLLDNSYDPKYNE

VREVIDMDGAHRKIVTTKCFDNNRKYMPILTYNND

TYYSYSESRTWDDVNRSIYPGWNLNRSNLSSHNQN

KMIGVDILVYTPTEVLKTAYPSVTDKIIGLSISLS

NLISTYGDQTKQVLSQLIDAVNPSLVNFWGVSDSN

LDKLPDLSSNTNIKKISIRGDYSNLNGFVFPSSVL

ELEFSSQNYKAVDPLQIPESAAIIYEQGYSSYFTS

IDLSTHKGMSNEDLQKAVNVVYQQRIHERAFQGDF

AGGYIYSWNLRNTGIYSFNNVTIPMLTDGTGRFYI

AYVAVETDGNQGPIANEVISDNSSKPSNDSQINEW

FDWNQNGWSTITEVKITAKDNVKLNFNNTVQEILG

FINKYPNIKVVDISALQFSNDETLDELIDAVNKAI

ADKYTGMDGTPTVKLDFIKVNYL

8)
*Mycoplasma penetrans*
IgG-blocking mature protein M sequence (31-505 amino acid)

SEQ ID NO: 8

LVTSNNNHENSLNNSSSNNGSNLKVNGSVISTDNL

NIVATGLSSNVSSQVSRQSLSSSSSSESTVDSKYT

AKKKLTTVSGQEKEYLVSTVYENNRKFMPILAYDE

DISYNNYQQSREYKDVVYGNFPGWDKKVAVVHQID

NVDLSKAYASVAEFTPTEILKKHFQVLQTSVKQLY

VALDSKTMTADVITKLVDRYQPDYLRIESVDDTSI

KQLPDMKYFSTVKKVDLGGAFTTIKGVSFPTTTQE

LKISSDNIKSIDPLQIPESAAIITETVHDARFTEI

DLSSHTDLTTDQLQKAVNIVYKDRIKERAFQGNFA

GGYIYSWNLQNTGITSFNDVSIPKLNDGTDRFYIA

YVAVSSGNSNGTANETITGGKEPSNDSQIGEWWDS

SSDGWSKVSKVTVTAKNGASLDYNKTLTEIMGFLA

-continued

KYPNVKTIDISLLKFEDASKTLDGLKTELTNQIKS

KYGEDSSYAKIDFIITSQSN

9)
Artificial armY-ACE2 fusion protein sequence (1,298 amino acids). Including the human IL-2 signal sequence, human myc-peptide epitope tag, linker, human ACE2, linker, *Mycoplasma genitalium* protein M

SEQ ID NO: 9

MYRMQLLSCIALSLALVTNSEQKLISEEDLLRKRG

SPGGAQSTIEEQAKTFLDKFNHEAEDLFYQSSLAS

WNYNTNITEENVQNMNNAGDKWSAFLKEQSTLAQM

YPLQEIQNLTVKLQLQALQQNGSSVLSEDKSKRLN

TILNTMSTIYSTGKVCNPDNPQECLLLEPGLNEIM

ANSLDYNERLWAWESWRSEVGKQLRPLYEEYVVLK

NEMARANHYEDYGDYWRGDYEVNGVDGYDYSRGQL

IEDVEHTFEEIKPLYEHLHAYVRAKLMNAYPSYIS

PIGCLPAHLLGDMWGRFWTNLYSLTVPFGQKPNID

VTDAMVDQAWDAQRIFKEAEKFFVSVGLPNMTQGF

WENSMLTDPGNVQKAVCHPTAWDLGKGDFRILMCT

KVTMDDFLTAHHEMGHIQYDMAYAAQPFLLRNGAN

EGFHEAVGEIMSLSAATPKHLKSIGLLSPDFQEDN

ETEINFLLKQALTIVGTLPFTYMLEKWRWMVFKGE

IPKDQWMKKWWEMKREIVGVVEPVPHDETYCDPAS

LFHVSNDYSFIRYYTRTLYQFQFQEALCQAAKHEG

PLHKCDISNSTEAGQKLFNMLRLGKSEPWTLALEN

VVGAKNMNVRPLLNYFEPLFTWLKDQNKNSFVGWS

TDWSPYADQSIKVRISLKSALGDKAYEWNDNEMYL

FRSSVAYAMRQYFLKVKNQMILFGEEDVRVANLKP

RISFNFFVTAPKNVSDIIPRTEVEKAIRMSRSRIN

DAFRLNDNSLEFLGIQPTLGPPNQPPVSGGGGSGG

GGSGGGGSTNLVNQSGYALVASGRSGNLGFKLFST

QSPSAEVKLKSLSLNDGSYQSEIDLSGGANFREKF

RNFANELSEAITNSPKGLDRPVPKTEISGLIKTGD

NFITPSFKAGYYDHVASDGSLLSYYQSTEYFNNRV

LMPILQTTNGTLMANNRGYDDVFRQVPSFSGWSNT

KATTVSTSNNLTYDKWTYFAAKGSPLYDSYPNHFF

EDVKTLAIDAKDISALKTTIDSEKPTYLIIRGLSG

NGSQLNELQLPESVKKVSLYGDYTGVNVAKQIFAN

VVELEFYSTSKANSFGFNPLVLGSKTNVIYDLFAS

KPFTHIDLTQVTLQNSDNSAIDANKLKQAVGDIYN

YRRFERQFQGYFAGGYIDKYLVKNVNTNKDSDDDL

VYRSLKELNLHLEEAYREGDNTYYRVNENYYPGAS

-continued

IYENERASRDSEFQNEILKRAEQNGVTFDENIKRI

TASGKYSVQFQKLENDTDSSLERMTKAVEGLVTVI

GEEKFETVDITGVSSDTNEVKSLAKELKTNALGVK

LKL

10)
Artificial
Protein M with peptide tags (aka: armY) protein sequence (587 amino acids). Including the human IL-2 signal sequence. Avi-Tag, human myc-peptide epitope tag, linker. *Mycoplasma genitalium* protein M

SEQ ID NO: 10

MYRMQLLSCIALSLALVTNSMAGGLNDIFEAQKIE

WHEGGEQKLISEEDLLRKRAANGGGGSGGGGSTNL

VNQSGYALVASGRSGNLGFKLFSTQSPSAEVKLKS

LSLNDGSYQSEIDLSGGANFREKFRNFANELSEAI

TNSPKGLDRPVPKTEISGLIKTGDNFITPSFKAGY

YDHVASDGSLLSYYQSTEYFNNRVLMPILQTTNGT

LMANNRGYDDVFRQVPSFSGWSNTKATTVSTSNNL

TYDKWTYFAAKGSPLYDSYPNHFFEDVKTLAIDAK

DISALKTTIDSEKPTYLIIRGLSGNGSQLNELQLP

ESVKKVSLYGDYTGVNVAKQIFANVVELEFYSTSK

ANSFGFNPLVLGSKTNVIYDLFASKPFTHIDLTQV

TLQNSDNSAIDANKLKQAVGDIYNYRRFERQFQGY

FAGGYIDKYLVKNVNTNKDSDDDLVYRSLKELNLH

LEEAYREGDNTYYRVNENYYPGASIYENERASRDS

EFQNEILKRAEQNGVTFDENIKRITASGKYSVQFQ

KLENDTDSSLERMTKAVEGLVTVIGEEKFETVDIT

GVSSDTNEVKSLAKELKTNALGVKLKL

11)
Artificial
Protein M horseradish peroxidase (HRP) fusion protein sequence (876 amino acids). Including the human IL-2 signal sequence, human myc-peptide epitope, linker. HRP, linker, *Mycoplasma genitalium* protein M

SEQ ID NO: 11

MYRMQLLSCIALSLALVTNSEQKLISEEDLAANQL

TPTFYDNSCPNVSNIVRDTIVNELRSDPRIAASIL

RLHFHDCFVNGCDASILLDNTTSFRTEKDAFGNAN

SARGFPVIDRMKAAVESACPRTVSCADLLTIAAQQ

SVTLAGGPSWRVPLGRRDSLQAFLDLANANLPAPF

FTLPQLKDSFRNVGLNRSSDLVALSGGHTFGKNQC

RFIMDRLYNFSNTGLPDPTLNTTYLQTLRGLCPLN

GNLSALVDFDLRTPTIFDNKYYVNLEEQKGLIQSD

QELFSSPNATDTIPLVRSFANSTQTFFNAFVEAMD

-continued

RMGNITPLTGTQGQIRLNCRVVNSNSGGGGSGGGG

SGGGGSTNLVNQSGYALVASGRSGNLGFKLFSTQS

PSAEVKLKSLSLNDGSYQSEIDLSGGANFREKFRN

FANELSEAITNSPKGLDRPVPKTEISGLIKTGDNF

ITPSFKAGYYDHVASDGSLLSYYQSTEYFNNRVLM

PILQTTNGTLMANNRGYDDVFRQVPSFSGWSNTKA

TTVSTSNNLTYDKWTYFAAKGSPLYDSYPNHFFED

VKTLAIDAKDISALKTTIDSEKPTYLIIRGLSGNG

SQLNELQLPESVKKVSLYGDYTGVNVAKQIFANVV

ELEFYSTSKANSFGFNPLVLGSKTNVIYDLFASKP

FTHIDLTQVTLQNSDNSAIDANKLKQAVGDIYNYR

RFERQFQGYFAGGYIDKYLVKNVNTNKDSDDDLVY

RSLKELNLHLEEAYREGDNTYYRVNENYYPGASIY

ENERASRDSEFQNEILKRAEQNGVTFDENIKRITA

SGKYSVQFQKLENDTDSSLERMTKAVEGLVTVIGE

EKFETVDITGVSSDTNEVKSLAKELKTNALGVKLK

L

12)
Artificial
Set of three Glycine ($G_4$)-Serine ($S_1$) linker sequence (1-15 amino acid)

SEQ ID NO: 12

GGGGSGGGGSGGGGS

13)
Artificial
Set of two Glycine ($G_4$)-Serine ($S_1$) linker sequence (1-10 amino acid)

SEQ ID NO: 13

GGGGSGGGGS

14)

SEQ ID NO: 14

Artificial
Set of one Glycine ($G_4$)-Serine ($S_1$) linker sequence (1-5 amino acid)
GGGGS

15)

SEQ ID NO: 15

Human

Angiotensin-Converting Enzyme 2 (ACE2) Extracellular Domain Protein Sequence (18-740 Amino Acid)

Essential counter-regulatory carboxypeptidase of the renin-angiotensin hormone system that is a critical regulator of blood volume, systemic vascular resistance, and thus cardiovascular homeostasis. This receptor acts as an attachment receptor for human coronaviruses SARS-CoV and SARS-CoV-2, as well as human coronavirus NL63/HCoV-NL63

16)

SEQ ID NO: 16

QSTIEEQAKTFLDKFNHEAEDLFYQSSLASWNYNT

NITEENVQNMNNAGDKWSAFLKEQSTLAQMYPLQE

-continued

```
IQNLTVKLQLQALQQNGSSVLSEDKSKRLNTILNT

MSTIYSTGKVCNPDNPQECLLLEPGLNEIMANSLD

YNERLWAWESWRSEVGKQLRPLYEEYVVLKNEMAR

ANHYEDYGDYWRGDYEVNGVDGYDYSRGQLIEDVE

HTFEEIKPLYEHLHAYVRAKLMNAYPSYISPIGCL

PAHLLGDMWGRFWTNLYSLTVPFGQKPNIDVTDAM

VDQAWDAQRIFKEAEKFFVSVGLPNMTQGFWENSM

LTDPGNVQKAVCHPTAWDLGKGDFRILMCTKVTMD

DFLTAHHEMGHIQYDMAYAAQPFLLRNGANEGFHE

AVGEIMSLSAATPKHLKSIGLLSPDFQEDNETEIN

FLLKQALTIVGTLPFTYMLEKWRWMVFKGEIPKDQ

WMKKWWEMKREIVGVVEPVPHDETYCDPASLFHVS

NDYSFIRYYTRTLYQFQFQEALCQAAKHEGPLHKC

DISNSTEAGQKLFNMLRLGKSEPWTLALENVVGAK

NMNVRPLLNYFEPLFTWLKDQNKNSFVGWSTDWSP

YADQSIKVRISLKSALGDKAYEWNDNEMYLFRSSV

AYAMRQYFLKVKNQMILFGEEDVRVANLKPRISFN

FFVTAPKNVSDIIPRTEVEKAIRMSRSRINDAFRL

NDNSLEFLGIQPTLGPPNQPPVS
```

Human

CD209 (DC-SIGN) Extracellular Domain Protein Sequence (59-404 Amino Acid).

A pathogen-recognition receptor expressed on the surface of immature dendritic cells (DCs) and involved in initiation of primary immune response. This receptor acts as an attachment receptor for HIV-1, HIV-2, Ebolavirus, Cytomegalovirus, HCV, Dengue virus, Measles virus, Herpes simplex virus 1, Influenza virus, SARS-CoV, Japanese encephalitis virus, Lassa virus, Respiratory syncytial virus, Rift valley fever virus, West-nile virus, Marburg virus, Uukuniemi virus, and *Yersinia Pestis*

```
17)
                                    SEQ ID NO: 17
QVSKVPSSISQEQSRQDAIYQNLTQLKAAVGELSE

KSKLQEIYQELTQLKAAVGELPEKSKLQEIYQELT

RLKAAVGELPEKSKLQEIYQELTWLKAAVGELPEK

SKMQEIYQELTRLKAAVGELPEKSKQQEIYQELTR

LKAAVGELPEKSKQQEIYQELTRLKAAVGELPEKS

KQQEIYQELTQLKAAVERLCHPCPWEWTFFQGNCY

FMSNSQRNWHDSITACKEVGAQLVVIKSAEEQNFL

QLQSSRSNRFTWMGLSDLNQEGTWQWVDGSPLLPS

FKQYWNRGEPNNVGEEDCAEFSGNGWNDDKCNLAK

FWICKKSAASCSRDEEQFLSPAPATPNPPPA
```

Human

C-Type Lectin Domain Family 4 Member M Extracellular Domain Protein Sequence (71-399 Amino Acid).

Probable pathogen-recognition receptor involved in peripheral immune surveillance in liver. This receptor acts as an attachment receptor for Ebolavirus, Hepatitis C virus, HIV-1, Human coronavirus 229E, Human cytomegalovirus/HHV-5, Influenza virus, SARS-CoV, West-nile virus, Japanese encephalitis virus, Marburg virus glycoprotein, and *M. bovis*.

```
18)
                                    SEQ ID NO: 18
QVSKVPSSLSQEQSEQDAIYQNLTQLKAAVGELSE

KSKLQEIYQELTQLKAAVGELPEKSKLQEIYQELT

RLKAAVGELPEKSKLQEIYQELTRLKAAVGELPEK

SKLQEIYQELTRLKAAVGELPEKSKLQEIYQELTE

LKAAVGELPEKSKLQEIYQELTQLKAAVGELPDQS

KQQQIYQELTDLKTAFERLCRHCPKDWTFFQGNCY

FMSNSQRNWHDSVTACQEVRAQLVVIKTAEEQNFL

QLQTSRSNRFSWMGLSDLNQEGTWQWVDGSPLSPS

FQRYWNSGEPNNSGNEDCAEFSGSGWNDNRCDVDN

YWICKKPAACFRDE
```

Human

CD4 Extracellular Domain Protein Sequence (26-396 Amino Acid).

Integral membrane glycoprotein that plays an essential role in the immune response and serves multiple functions in responses against both external and internal offenses. In T-cells, functions primarily as a coreceptor for MHC class II molecule:peptide complex. This coreceptor acts as an attachment receptor for HIV.

```
19)
                                    SEQ ID NO: 19
KKVVLGKKGDTVELTCTASQKKSIQFHWKNSNQIK

ILGNQGSFLTKGPSKLNDRADSRRSLWDQGNFPLI

IKNLKIEDSDTYICEVEDQKEEVQLLVFGLTANSD

THLLQGQSLTLTLESPPGSSPSVQCRSPRGKNIQG

GKTLSVSQLELQDSGTWTCTVLQNQKKVEFKIDIV

VLAFQKASSIVYKKEGEQVEFSFPLAFTVEKLTGS

GELWWQAERASSSKSWITFDLKNKEVSVKRVTQDP

KLQMGKKLPLHLTLPQALPQYAGSGNLTLALEAKT

GKLHQEVNLVVMRATQLQKNLTCEVWGPTSPKLML

SLKLENKEAKVSKREKAVWVLNPEAGMWQCLLSDS

GQVLLESNIKVLPTWSTPVQP
```

Human

Synaptic Vesicle Glycoprotein 2A Extracellular Domain Protein Sequence (469-598 Amino Acid).

Plays a role in the control of regulated secretion in neural and endocrine cells, enhancing selectively low-frequency neurotransmission. This protein acts as an attachment receptor for the *C. botulinum* neurotoxin type A2 (BoNT/A, botA).

20)

SEQ ID NO: 20

PDMIRHLQAVDYASRTKVFPGERVEHVTFNFTLEN

QIHRGGQYFNDKFIGLRLKSVSFEDSLFEECYFED

VTSSNTFFRNCTFINTVFYNTDLFEYKFVNSRLIN

STFLHNKEGCPLDVTGTGEGAYMVY

Human

Synaptic Vesicle Glycoprotein 2B Extracellular Domain Protein Sequence (412-535 Amino Acid).

Probably plays a role in the control of regulated secretion in neural and endocrine cells. This protein acts as an attachment receptor for the *C. botulinum* neurotoxin type A2 (BoNT/A, botA). Probably also serves as a receptor for the closely related *C. botulinum* neurotoxin type A1.

21)

SEQ ID NO: 21

PDMIRYFQDEEYKSKMKVFFGEHVYGATINFTMEN

QIHQHGKLVNDKFTRMYFKHVLFEDTFFDECYFED

VTSTDTYFKNCTIESTIFYNTDLYEHKFINCRFIN

STFLEQKEGCHMDLEQDND

Human

Synaptic Vesicle Glycoprotein 2C Extracellular Domain Protein Sequence (459-578 Amino Acid).

Plays a role in the control of regulated secretion in neural and endocrine cells, enhancing selectively low-frequency neurotransmission. This protein acts as an attachment receptor for *C. botulinum* neurotoxin type A (BoNT/A, botA). Also serves as a receptor for the closely related *C. botulinum* neurotoxin type A2.

22)

SEQ ID NO: 22

KPLQSDEYALLTRNVERDKYANFTINFTMENQIHT

GMEYDNGRFIGVKFKSVTFKDSVFKSCTFEDVTSV

NTYFKNCTFIDTVFDNTDFEPYKFIDSEFKNCSFF

HNKTGCQITFDDDYS

Human

Synaptotagmin I Extracellular Domain Protein Sequence (1-57 Amino Acid).

Calcium sensor that participates in triggering neurotransmitter release at the synapse. This protein acts as an attachment receptor for *C. botulinum* neurotoxin type B (BoNT/B, botB)

23)

SEQ ID NO: 23

MVSESHHEALAAPPVTTVATVLPSNATEPASPGEG

KEDAFSKLKEKFMNELHKIPLP

Human

Synaptotagmin II Extracellular Domain Protein Sequence (1-62 Amino Acid).

Exhibits calcium-dependent phospholipid and inositol polyphosphate binding properties. This protein acts as an attachment receptor for *C. botulinum* neurotoxin type B (BoNT/B, botB)

24) SEQ ID NO: 24

MRNIFKRNQEPIVAPATTTATMPIGPVDNSTESGGAGESQEDMFAKLKE
KLFNEINKIPLPP
Human

HLA Class II Histocompatibility Antigen, DRB1 Beta Chain Extracellular Domain Protein Sequence (30-227 Amino Acid).

A beta chain of antigen-presenting major histocompatibility complex class II (MHCII) molecule. This protein acts as an attachment receptor for Epstein-Barr virus and Staphylococcal enterotoxin A and B.

25) SEQ ID NO: 25

GDTRPRFLWQPKRECHFFNGTERVRFLDRYFYNQEESVRFDSDVGEFRA

VTELGRPDAEYWNSQKDILEQARAAVDTYCRHNYGVVESFTVQRRVQPK

VTVYPSKTQPLQHHNLLVCSVSGFYPGSIEVRWFLNGQEEKAGMVSTGL

IQNGDWTFQTLVMLETVPRSGEVYTCQVEHPSVTSPLTVEWRARSESAQ

SK

Human

Human

HLA Class II Histocompatibility Antigen, DR Alpha Chain Extracellular Domain Protein Sequence (26-216 Amino Acid).

Binds peptides derived from antigens that access the endocytic route of antigen presenting cells (APC) and presents them on the cell surface for recognition by the CD4 T-cells. This protein acts as an attachment receptor for Epstein-Barr virus BZLF2/gp42, *Staphylococcus aureus* enterotoxin A/entA, enterotoxin B/entB, enterotoxin C1/entC1, enterotoxin D/entD, and enterotoxin H/entH.

26) SEQ ID NO: 26

IKEEHVIIQAEFYLNPDQSGEFMFDFDGDEIFHVDMAKKETVWRLEEFG

RFASFEAQGALANIAVDKANLEIMTKRSNYTPITNVPPEVTVLTNSPVE

LREPNVLICFIDKFTPPVVNVTWLRNGKPVTTGVSETVFLPREDHLFRK

FHYLPFLPSTEDVYDCRVEHWGLDEPLLKHWEFDAPSPLPETTE

Human

T Cell Receptor Beta Variable 7-9 Mature Protein Sequence (22-115 Amino Acid).

V region of the variable domain of T cell receptor (TR) beta chain that participates in the antigen recognition. This protein acts as an attachment receptor for *Staphylococcus aureus* enterotoxin A/entA.

27) SEQ ID NO: 27

GVSQNPRHKITKRGQNVTFRCDPISEHNRLYWYRQTLGQGPEFLTYFQN
EAQLEKSRLLSDRFSAERPKGSFSTLEIQRTEQGDSAMYLCASSL

Human

T Cell Receptor Beta Variable 19 Mature Protein Sequence (22-114 Amino Acid).

V region of the variable domain of T cell receptor (TR) beta chain that participates in the antigen recognition. This protein acts as an attachment receptor for *Staphylococcus aureus* enterotoxin B/entB.

28) SEQ ID NO: 28

GITQSPKYLFRKEGQNVTLSCEQNLNHDAMYWYRQDPGQGLRLIYYSQI
VNDFQKGDIAEGYSVSREKKESFPLTVTSAQKNPTAFYLCASSI

Human

Hepatitis a Virus Cellular Receptor 1 Extracellular Domain Protein Sequence (21-364 Amino Acid).

May play a role in T-helper cell development and the regulation of asthma and allergic diseases. This protein acts as an attachment receptor for Hepatitis A virus, Ebola virus, Marburg virus and Dengue virus and *Clostridium perfringens* Epsilon toxin (ETX).

29) SEQ ID NO: 29

SVKVGGEAGPSVTLPCHYSGAVTSMCWNRGSCSLFTCQNGIVWTNGTHV

TYRKDTRYKLLGDLSRRDVSLTIENTAVSDSGVYCCRVEHRGWFNDMKI

TVSLEIVPPKVTTTPIVTTVPTVTTVRTSTTVPTTTTVPMTTVPTTTVP

TTMSIPTTTTVLTTMTVSTTTSVPTTTSIPTTTSVPVTTTVSTFVPPMP

LPRQNHEPVATSPSSPQPAETHPTTLQGAIRREPTSSPLYSYTTDGNDT

VTESSDGLWNNNQTQLFLEHSLLTANTTKGIYAGVCISVLVLLALLGVI

IAKKYFFKKEVQQLSVSFSSLQIKALQNAVEKEVQAEDNIYIENSLYAT

D

Human

Myelin and Lymphocyte Protein Protein Sequence (1-153 Amino Acid).

Could be an important component in vesicular trafficking cycling between the Golgi complex and the apical plasma membrane. This protein acts as an attachment receptor for *Clostridium perfringens* Epsilon toxin (ETX).

30) SEQ ID NO: 30

MAPAAATGGSTLPSGFSVFTTLPDLLFIFEFIFGGLVWILVASSLVPWP

LVQGWVMFVSVFCFVATTTLIILYIIGAHGGETSWVTLDAAYHCTAALF

YLSASVLEALATITMQDGFTYRHYHENIAAVVFSYIATLLYVVHAVFSL

IRWKSS

Human

Complement Factor H Mature Protein Sequence (19-1231 Amino Acid).

Glycoprotein that plays an essential role in maintaining a well-balanced immune response by modulating complement activation. This protein binds to *Streptococcus pneumoniae, Neisseria meningitides, Staphylococcus aureus, Borrelia burgdorferi* and West nile virus.

31) SEQ ID NO: 31

EDCNELPPRRNTEILTGSWSDQTYPEGTQAIYKCRPGYRSLGNVIMVCR

KGEWVALNPLRKCQKRPCGHPGDTPFGTFTLTGGNVFEYGVKAVYTCNE

GYQLLGEINYRECDTDGWTNDIPICEVVKCLPVTAPENGKIVSSAMEPD

REYHFGQAVRFVCNSGYKIEGDEEMHCSDDGFWSKEKPKCVEISCKSPD

VINGSPISQKIIYKENERFQYKCNMGYEYSERGDAVCTESGWRPLPSCE

EKSCDNPYIPNGDYSPLRIKHRTGDEITYQCRNGFYPATRGNTAKCTST

GWIPAPRCTLKPCDYPDIKHGGLYHENMRRPYFPVAVGKYYSYYCDEHF

-continued

ETPSGSYWDHIHCTQDGWSPAVPCLRKCYFPYLENGYNQNYGRKFVQGK

SIDVACHPGYALPKAQTTVTCMENGWSPTPRCIRVKTCSKSSIDIENGF

ISESQYTYALKEKAKYQCKLGYVTADGETSGSITCGKDGWSAQPTCIKS

CDIPVFMNARTKNDFTWFKLNDTLDYECHDGYESNTGSTTGSIVCGYNG

WSDLPICYERECELPKIDVHLVPDRKKDQYKVGEVLKFSCKPGFTIVGP

NSVQCYHFGLSPDLPICKEQVQSCGPPPELLNGNVKEKTKEEYGHSEVV

EYYCNPRFLMKGPNKIQCVDGEWTTLPVCIVEESTCGDIPELEHGWAQL

SSPPYYYGDSVEFNCSESFTMIGHRSITCIHGVWTQLPQCVAIDKLKKC

KSSNLIILEEHLKNKKEFDHNSNIRYRCRGKEGWIHTVCINGRWDPEVN

CSMAQIQLCPPPPQIPNSHNMTTTLNYRDGEKVSVLCQENYLIQEGEEI

TCKDGRWQSIPLCVEKIPCSQPPQIEHGTINSSRSSQESYAHGTKLSYT

CEGGFRISEENETTCYMGKWSSPPQCEGLPCKSPPEISHGVVAHMSDSY

QYGEEVTYKCFEGFGIDGPAIAKCLGEKWSHPPSCIKTDCLSLPSFENA

IPMGEKKDVYKAGEQVTYTCATYYKMDGASNVTCINSRWTGRPTCRDTS

CVNPPTVQNAYIVSRQMSKYPSGERVRYQCRSPYEMFGDEEVMCLNGNW

TEPPQCKDSTGKCGPPPPIDNGDITSFPLSVYAPASSVEYQCQNLYQLE

GNKRITCRNGQWSEPPKCLHPCVISREIMENYNIALRWTAKQKLYSRTG

ESVEFVCKRGYRLSSRSHTLRTTCWDGKLEYPTCAKR

Human

Hepatocyte Growth Factor Receptor Extracellular Domain Protein Sequence (25-932 Amino Acid).

Receptor tyrosine kinase that transduces signals from the extracellular matrix into the cytoplasm by binding to hepatocyte growth factor/HGF ligand. This receptor acts as an attachment receptor for *Listeria monocytogenes* internalin InlB, mediating entry of the pathogen into cells.

32) SEQ ID NO: 32

ECKEALAKSEMNVNMKYQLPNFTAETPIQNVILHEHHIFLGATNYIYVL

NEEDLQKVAEYKTGPVLEHPDCFPCQDCSSKANLSGGVWKDNINMALVV

DTYYDDQLISCGSVNRGTCQRHVFPHNHTADIQSEVHCIFSPQIEEPSQ

CPDCVVSALGAKVLSSVKDRFINFFVGNTINSSYFPDHPLHSISVRRLK

ETKDGFMFLTDQSYIDVLPEFRDSYPIKYVHAFESNNFIYFLTVQRETL

DAQTFHTRIIRFCSINSGLHSYMEMPLECILTEKRKKRSTKKEVFNILQ

AAYVSKPGAQLARQIGASLNDDILFGVFAQSKPDSAEPMDRSAMCAFPI

KYVNDFFNKIVNKNNVRCLQHFYGPNHEHCFNRTLLRNSSGCEARRDEY

RTEFTTALQRVDLFMGQFSEVLLTSISTFIKGDLTIANLGTSEGRFMQV

VVSRSGPSTPHVNFLLDSHPVSPEVIVEHTLNQNGYTLVITGKKITKIP

LNGLGCRHFQSCSQCLSAPPFVQCGWCHDKCVRSEECLSGTWTQQICLP

AIYKVFPNSAPLEGGTRLTICGWDFGFRRNNKFDLKKTRVLLGNESCTL

TLSESTMNTLKCTVGPAMNKHFNMSIIISNGHGTTQYSTFSYVDPVITS

ISPKYGPMAGGTLLTLTGNYLNSGNSRHISIGGKTCTLKSVSNSILECY

TPAQTISTEFAVKLKIDLANRETSIFSYREDPIVYEIHPTKSFISGGST

ITGVGKNLNSVSVPRMVINVHEAGRNFTVACQHRSNSEIICCTTPSLQQ

-continued

LNLQLPLKTKAFFMLDGILSKYFDLIYVHNPVFKPFEKPVMISMGNENV

LEIKGNDIDPEAVKGEVLKVGNKSCENIHLHSEAVLCTVPNDLLKLNSE

LNIEWKQAISSTVLGKVIVQPDQNFT

Human

Membrane Cofactor Protein (CD46) Extracellular Domain Protein Sequence (35-343 Amino Acid).

Acts as a cofactor for complement factor I, a serine protease which protects autologous cells against complement-mediated injury by cleaving C3b and C4b deposited on host tissue. This protein acts as an attachment receptor for Adenovirus subgroup B2 and Ad3, Measles virus, Herpesvirus 6/HHV-6, *Neisseria* and *Streptococcus pyogenes*.

33) SEQ ID NO: 33

CEEPPTFEAMELIGKPKPYYEIGERVDYKCKKGYFYIPPLATHTICDRN

HTWLPVSDDACYRETCPYIRDPLNGQAVPANGTYEFGYQMHFICNEGYY

LIGEEILYCELKGSVAIWSGKPPICEKVLCTPPPKIKNGKHTFSEVEVF

EYLDAVTYSCDPAPGPDPFSLIGESTIYCGDNSVWSRAAPECKVVKCRF

PVVENGKQISGFGKKFYYKATVMFECDKGFYLDGSDTIVCDSNSTWDPP

VPKCLKVLPPSSTKPPALSHSVSTSSTTKSPASSASGPRPTYKPPVSNY

PGYPKPEEGILDSLD

Human

Glycophorin-A Extracellular Domain Protein Sequence (20-91 Amino Acid).

Glycophorin A is the major intrinsic membrane protein of the erythrocyte. This protein acts as an attachment receptor for *Plasmodium falciparum*, Influenza virus, Hepatitis A virus (HAV), *Streptococcus gordonii*.

34) SEQ ID NO: 34

SSTTGVAMHTSTSSSVTKSYISSQTNDTHKRDTYAATPRAHEVSEISVR
TVYPPEEETGERVQLAHHFSEPE

Human

C-Type Lectin Domain Family 4 Member K (Langerin, CD207) Extracellular Domain Protein Sequence (65-328 Amino Acid).

Calcium-dependent lectin displaying mannose-binding specificity. This protein binds to *Candida* species, *Saccharomyces* species, *Malassezia furfur*, human immunodeficiency virus-1 (HIV-1) and *Yesinia pestis*.

35) SEQ ID NO: 35

PRFMGTISDVKTNVQLLKGRVDNISTLDSEIKKNSDGMEAAGVQIQMVN

ESLGYVRSQFLKLKTSVEKANAQIQILTRSWEEVSTLNAQIPELKSDLE

-continued

KASALNTKIRALQGSLENMSKLLKRQNDILQVVSQGWKYFKGNFYYFSL

IPKTWYSAEQFCVSRNSHLTSVTSESEQEFLYKTAGGLWWIGLTKAGME

GDWSWVDDTPFNKVQSVRFWIPGEPNNAGNNEHCGNIKAPSLQAWNDAP

CDKTFLFICKRPYVPSEP

Human

Anthrax Toxin Receptor 1 Mature Protein Sequence (33-564 Amino Acid).

Plays a role in cell attachment and migration. Interacts with extracellular matrix proteins and with the actin cytoskeleton. This protein acts as an attachment receptor for Anthrax toxin.

36) SEQ ID NO: 36

EDGGPACYGGFDLYFILDKSGSVLHHWNEIYYFVEQLAHKFISPQLRMS

FIVFSTRGTTLMKLTEDREQIRQGLEELQKVLPGGDTYMHEGFERASEQ

IYYENRQGYRTASVIIALTDGELHEDLFFYSEREANRSRDLGAIVYCVG

VKDFNETQLARIADSKDHVFPVNDGFQALQGIIHSILKKSCIEILAAEP

STICAGESFQVVVRGNGFRHARNVDRVLCSFKINDSVTLNEKPFSVEDT

YLLCPAPILKEVGMKAALQVSMNDGLSFISSSVIITTTHCSDGSILAIA

LLILFLLLALALLWWFWPLCCTVIIKEVPPPPAEESEEEDDDGLPKKKW

PTVDASYYGGRGVGGIKRMEVRWGEKGSTEEGAKLEKAKNARVKMPEQE

YEFPEPRNLNNNMRRPSSPRKWYSPIKGKLDALWVLLRKGYDRVSVMRP

QPGDTGRCINFTRVKNNQPAKYPLNNAYHTSSPPPAPIYTPPPPAPHCP

PPPPSAPTPPIPSPPSTLPPPPQAPPPNRAPPPSRPPPRPSV

Human

Anthrax Toxin Receptor 2 Extracellular Domain Protein Sequence (34-318 Amino Acid).

Necessary for cellular interactions with laminin and the extracellular matrix. This protein acts as an attachment receptor for Anthrax toxin.

37) SEQ ID NO: 37

QEQPSCRRAFDLYFVLDKSGSVANNWIEIYNFVQQLAERFVSPEMRLSF

IVFSSQATIILPLTGDRGKISKGLEDLKRVSPVGETYIHEGLKLANEQI

QKAGGLKTSSIIIALTDGKLDGLVPSYAEKEAKISRSLGASVYCVGVLD

FEQAQLERIADSKEQVFPVKGGFQALKGIINSILAQSCTEILELQPSSV

CVGEEFQIVLSGRGFMLGSRNGSVLCTYTVNETYTTSVKPVSVQLNSML

CPAPILNKAGETLDVSVSFNGGKSVISGSLIVTATECSNG

38) SEQ ID NO: 38

Artificial
armY-Angiotensin-converting enzyme 2 (ACE2) fusion protein with N-terminal Myc-tag
codon-optimized (for human) nucleotide sequence (3,897 bp)

atgtacaggatgcaactcctgtcttgcattgcactaagtcttgcacttgtcacaaacagtgagcaaaagcttatctctgaagaggacttact aagaaagcggggcagcccaggcggagcgcagagcacaatcgaggaacaggccaagaccttcctggacaagttcaaccacgaagctgaagac ctgttctaccaatctagcctggctagttggaactacaacaccaacattacagaagagaacgtgcagaacatgaacaacgcaggcgacaagtggtcc gccttccttaaagagcagtctacactggcccagatgtaccctctgcaagagattcagaatctgaccgtgaagctgcagctgcaggctctccagcaga atgggtccagcgtgctgtctgaggataagagcaagcggctgaacaccatcctgaatacaatgagcaccatctacagcaccggcaaagtgtgtaac cctgacaacccccaggagtgtctgctgctggaacctggcctgaacgaaatcatggccaactccctggactacaacgagagactgtgggcctggga gagctggcgtagcgaggtgggaaaacagctgcgcccccctgtatgaggagtacgtggtgctgaagaatgagatggccagagccaaccactacga ggactacggcgactattggagaggcgattatgaagtcaacggcgttgacggctacgactacagccggggacagctgatcgaagacgtggaacat acgtagaggagatcaagcctctgtacgagcacctgcacgcctacgtaagagccaaactgatgaatgcctaccccagctacatctcccctatcggct gcctgcccgcccatctgctcggcgacatgtggggcagattctggaccaacctgtattctctgacagtgcctttcggccagaaacctaacatcgacgt gacagatgccatggtggaccaggcctgggatgcccaaagaatcttcaaggaagccgagaaattcttcgtgtccgtggggctgcctaatatgaccca gggcttctgggaaaacagcatgctcaccgatcctggcaacgtgcagaaggcagtgtgccaccccaccgcctgggaccttggaaagggcgacttc cggattctgatgtgcaccaaggtgaccatggacgacttcctgaccgctcaccacgagatgggccacatccagtacgacatggcctacgccgctca gcctttcctcctgagaaacggcgctaatgaaggcttccacgaggccgtgggcgaaatcatgagcctgagcgccgccacccctaagcacctgaagt ctatcggactgctgagccccgactttcaggaggacaacgaaactgagatcaacttcttgctgaaacaggccctgacaatcgttggcaccctgccctt tacctacatgctggaaaagtggagatggatggtctttaagggcgaaatccccaaggaccaatggatgaagaagtggtgggagatgaagcgggaa atcgtgggcgtggtggaacctgtgccccacgacgagacatactgcgatcctgctagcctctttcacgtgagcaatgattactcattcatccggtacta caccagaactctgtaccagttccagttccaggaggccctgtgccaggccgccaagcacgagggccctctgcacaagtgcgacatctctaacagca ccgaggccggccagaagctgttcaacatgctgagactgggcaagagcgaaccttggacactggccctggagaacgtggtcggagccaagaaca tgaacgtgagaccactgctgaactacttcgagcccctgttcacctggctgaaggatcaaaacaagaacagcttcgtgggctggtccacagactgga gcccatacgctgatcagagcatcaaagtgaggatctctctgaagagcgccctgggagataaggcctacgagtggaacgataatgagatgtacctgt tcagaagcagcgtggcctacgccatgcggcagtacttcctgaaagtgaagaaccagatgatcctgtttggcgaggaggatgtgagagtggccaat ctgaaaccaagaatcagctttaactttttcgttaccgctcctaagaacgtgtctgatatcatccctagaaccgaggtggaaaaggccatcagaatgag ccggtccagaatcaacgatgccttccgactgaatgacaactccctggagttcctgggaatccagcccaccctgggccctcctaaccagcctccagt -continued cagcggcggaggaggatctggcggtggaggctctggcggcggcggttcaacaaatctggtgaaccagagcggctacgccctggtggccagcg gcagatccggcaatctgggcttcaagctgttcagcacccagtctccatctgccgaggtgaagctgaagagcctgagccttaacgacggcagctac cagtccgagatcgacctgtcaggcggcgccaacttccgagaaaagttcagaaacttcgccaatgagctgagcgaggccatcacaaacagcccta aaggcctggacagacctgtgcccaagacggaaatcagcggcctgatcaagacaggcgacaactttatcacccctagcttcaaggccggatattat gaccacgtggcctctgatggctccctactgagctactaccagtccaccgagtacttcaacaacagagttctgatgcctatcctgcagacaacaaacg gcactctgatggccaacaaccggggctacgacgacgttttcagacaagtgccctctttcagcggctggagcaacacaaaggccaccactgtgtcc acaagcaacaatctgacatacgataagtggacctatttcgccgccaaaggcagccccctgtacgacagctaccccaaccacttcttcgaggacgtg aagacactggccattgacgctaaggacatcagcgccctgaaaaccaccatcgacagcgagaagcctacctacctgattatccggggactgagcg gaaacggcagccagctgaacgagctgcaactgcctgagtccgtgaaaaaggtgagcctgtacggcgactacaccggcgtgaacgtggctaagc agatcttcgccaacgttgtggaactggaattctacagcaccagcaaggctaactcttttggctttaacccccctggtcctgggatctaaaacgaacgtga tctacgacctgttcgcaagcaagcccttcacccacatcgacctgacacaggtgaccctgcaaaacagcgataattccgccatcgatgccaacaagc tgaagcaagctgtgggcgatatctacaactacaggcggttcgagagacagtttcagggctacttcgccggaggctacatcgacaagtacctggtga agaacgtcaataccaacaaggatagcgatgacgatctggtctaccggagcctgaaagagctgaacctccacctggaggaagcctacagagaagg cgataacacctactacagagtgaatgagaactattaccctggagctagcatctacgagaacgagagagccagcagagacagcgagttccagaac gagatcctgaagcgagccgagcagaacggcgtgacatttgacgagaacatcaaaagaatcacagccagcggcaagtatagcgtgcagttccaaa agctagaaaatgataccgattccagcctggaaagaatgaccaaggccgtggaaggccttgtgaccgtgatcggcgaggaaaagttcgagacagt ggatatcaccggcgtgtctagcgataccaatgaagtgaaaagcctggccaaggaactgaagaccaacgccctgggcgtcaagctgaaactctaa

39) SEQ ID NO: 39

Artificial
Protein M with N-terminal peptide Avi- and Myc-tags (aka: armY) codon-optimized (for human) nucleotide sequence (1,764 bp)

atgtacaggatgcaactcctgtcttgcattgcactaagtcttgcacttgtcacaaacagtatggctggtggcctgaatgacatctttgaggc ccagaagatcgagtggcatgagggaggagagcagaagctgatctccgaggaagatctgctgagaaagcgggccgccaacggcggaggagga tctggcggtggaggctctaccaatctggtgaaccagagcggatacgccctggtggcctctgggagaagcggaaatctgggatttaagctgttcagt acccagtctccaagcgctgaagtgaagctgaaaagcctctccctgaacgacggctcttatcagagcgagatcgacctgagcggcggcgctaactt ccgggagaagttccgcaacttcgctaatgagctgtctgaagccatcacaaacagccctaagggcctggatagacctgtgcccaagacagaaatca gcggcctgatcaagactggagataactttatcacccctagctttaaggccggctactacgaccatgtggctagcgacggttcactgctgtcctactac cagtctacagagtactttaacaaccgggtgctgatgcctatactgcagaccaccaacggcaccctgatggccaataacagaggctacgatgacgtg ttccggcaggtgcccagcttcagcggctggagcaacacaaaggccacaaccgtgagcacctccaacaacctgacctacgacaagtggacctact -continued tcgccgccaagggctctccactgtatgacagctatcctaaccacttcttcgaggacgtgaagacactggccatcgacgccaaggacatctctgccct gaagaccaccatcgacagtgagaaacctacatacctgattatcagaggactgtccggcaacggcagccagctgaacgagcttcagctgcctgaga gcgtgaaaaaggtgagcctgtacggcgactacacaggcgtcaatgtagctaagcaaatcttcgccaacgtggtggaactcgaattctacagcacat ccaaggccaacagcttcggcttcaacccccctggtgctgggcagcaagaccaacgtgatctacgacctgttcgccagcaagcctttcacccacatcg acctgacacaagtgaccctgcagaacagcgataacagcgccattgatgccaacaagctcaaacaggccgtgggcgatatctacaactacagaag attcgagaggcagtttcagggctacttcgccggaggctatatcgataagtacctggtcaagaacgtgaacaccaacaaggactccgacgacgacct ggtgtaccggagcctgaaggaactgaacctgcacctggaagaggcctacagagagggcgataatacctactacagagtgaacgagaactactac cccggagctagcatctacgagaacgagagagcctctagagatagcgagttccagaacgagatcctgaagcgggccgagcagaatggcgtgaca ttcgacgagaacatcaagcggatcaccgccagcggcaagtactccgtgcagttccaaaaactggaaaatgacaccgacagcagcctggaaagaa tgaccaaggctgtggaaggcctggttacagttatcggcgaggagaagtttgaaaccgtggacatcaccggcgtgagctccgataccaatgaggtg aaatctctggccaaagaactgaagacaaatgccctgggcgtcaaattaaaactgtaa

40) SEQ ID NO: 40

Artificial
Protein M horseradish peroxidase (HRP) fusion protein with N-terminal Myc-tag codon-
optimized (for human) nucleotide sequence (2,631 bp)

atgtacaggatgcaactcctgtcttgcattgcactaagtcttgcacttgtcacaaacagtgagcagaaactcatctcagaagaggatctgg cagcaaatcagctgaccccaaccttctacgacaattcttgtccaaacgtctccaacatcgtgcgggacaccattgtgaacgagctgagaagcgacc ctagaatcgccgcttctatcctgagactgcatttccacgactgcttcgtgaatggctgcgacgcctccatcctgctggacaacaccaccagcttccgg acagagaaagacgccttcggaaatgccaacagcgctagaggcttccccgttatcgacagaatgaaggctgccgtggaatctgcctgccctcggac cgtgagctgtgccgacctgctgaccatcgccgcccagcagagcgtgaccctggccggcggtcctagctggcgggtgcctctgggccggagaga tagtctgcaggccttcctggatctggctaatgctaacctccccgctcctttctttaccctgcctcagctgaaggacagctacggaacgtcggcctaaa cagaagcagcgacctggtggccctgtccggaggccacaccttcggcaagaaccagtgcagattcatcatggaccggctgtacaacttcagcaata ccggcctgccagatcctacactgaacacaacctacctgcagacactgagaggcctgtgcccccctcaacgggaatctgagcgccttggtggacttc gacctgagaacccctaccatcttcgacaacaagtactacgtgaacctggaagaacagaagggcctgatccaaagcgatcaggagctgttctcttcc cctaatgccacagacaccatcccccctggtgcggtcattcgccaacagtacccagaccttttttaacgcttttgtggaagccatggatagaatgggcaa catcacccctctgaccggaacacagggacagatcagactgaattgcagagtggtgaacagcaactctggcggaggaggatctggcggtggagg ctctggcggcggcggttcaacaaatctggtgaaccagagcggctacgccctggtggccagcggcagatccggcaatctgggcttcaagctgttca gcacccagtctccatctgccgaggtgaagctgaagagcctgagccttaacgacggcagctaccagtccgagatcgacctgtcaggcggcgccaa cttccgagaaaagttcagaaacttcgccaatgagctgagcgaggccatcacaaacagccctaaaggcctggacagacctgtgcccaagacggaa -continued atcagcggcctgatcaagacaggcgacaactttatcacccctagcttcaaggccggatattatgaccacgtggcctctgatggctccctactgagct actaccagtccaccgagtacttcaacaacagagttctgatgcctatcctgcagacaacaaacggcactctgatggccaacaaccggggctacgac gacgttttcagacaagtgccctctttcagcggctggagcaacacaaaggccaccactgtgtccacaagcaacaatctgacatacgataagtggacc tatttcgccgccaaaggcagcccccctgtacgacagctaccccaaccacttcttcgaggacgtgaagacactggccattgacgctaaggacatcagc gccctgaaaaccaccatcgacagcgagaagcctacctacctgattatccggggactgagcggaaacggcagccagctgaacgagctgcaactg cctgagtccgtgaaaaaggtgagcctgtacggcgactacaccggcgtgaacgtggctaagcagatcttcgccaacgttgtggaactggaattctac agcaccagcaaggctaactcttttggctttaacccccctggtcctgggatctaaaacgaacgtgatctacgacctgttcgcaagcaagcccttcaccca catcgacctgacacaggtgaccctgcaaaacagcgataattccgccatcgatgccaacaagctgaagcaagctgtgggcgatatctacaactaca ggcggttcgagagacagtttcagggctacttcgccggaggctacatcgacaagtacctggtgaagaacgtcaataccaacaaggatagcgatgac gatctggtctaccggagcctgaaagagctgaacctccacctggaggaagcctacagagaaggcgataacacctactacagagtgaatgagaact attaccctggagctagcatctacgagaacgagagagccagcagagacagcgagttccagaacgagatcctgaagcgagccgagcagaacggc gtgacatttgacgagaacatcaaaagaatcacagccagcggcaagtatagcgtgcagttccaaaagctagaaaatgataccgattccagcctggaa agaatgaccaaggccgtggaaggccttgtgaccgtgatcggcgaggaaaagttcgagacagtggatatcaccggcgtgtctagcgataccaatg aagtgaaaagcctggccaaggaactgaagaccaacgccctgggcgtcaagctgaaactctaa

41) SEQ ID NO: 41

Artificial
armY-Angiotensin-converting enzyme 2 (ACE2) fusion protein codon-optimized (for human)
nucleotide sequence (3,837 bp)

atgtacaggatgcaactcctgtcttgcattgcactaagtcttgcacttgtcacaaacagtcagagcacaatcgaggaacaggccaagac cttcctggacaagttcaaccacgaagctgaagacctgttctaccaatctagcctggctagttggaactacaacaccaacattacagaagagaacgtg cagaacatgaacaacgcaggcgacaagtggtccgccttccttaaagagcagtctacactggcccagatgtaccctctgcaagagattcagaatctg accgtgaagctgcagctgcaggctctccagcagaatgggtccagcgtgctgtctgaggataagagcaagcggctgaacaccatcctgaatacaat gagcaccatctacagcaccggcaaagtgtgtaaccctgacaaccccccaggagtgtctgctgctggaacctggcctgaacgaaatcatggccaact ccctggactacaacgagagactgtgggcctgggagagctggcgtagcgaggtgggaaaacagctgcgcccccctgtatgaggagtacgtggtgc tgaagaatgagatggccagagccaaccactacgaggactacggcgactattggagaggcgattatgaagtcaacggcgttgacggctacgacta cagccggggacagctgatcgaagacgtggaacatacgtagaggagatcaagcctctgtacgagcacctgcacgcctacgtaagagccaaactg atgaatgcctaccccagctacatctcccctatcggctgcctgcccgcccatctgctcggcgacatgtggggcagattctggaccaacctgtattctct gacagtgcctacggccagaaacctaacatcgacgtgacagatgccatggtggaccaggcctgggatgcccaaagaatcttcaaggaagccgag aaattcttcgtgtccgtggggctgcctaatatgacccagggcttctgggaaaacagcatgctcaccgatcctggcaacgtgcagaaggcagtgtgc -continued caccccaccgcctgggaccttggaaagggcgacttccggattctgatgtgcaccaaggtgaccatggacgacttcctgaccgctcaccacgagat gggccacatccagtacgacatggcctacgccgctcagcctacctcctgagaaacggcgctaatgaaggcttccacgaggccgtgggcgaaatca tgagcctgagcgccgccacccctaagcacctgaagtctatcggactgctgagccccgactacaggaggacaacgaaactgagatcaacttcttgc tgaaacaggccctgacaatcgttggcaccctgccattacctacatgctggaaaagtggagatggatggtattaagggcgaaatccccaaggacc aatggatgaagaagtggtgggagatgaagcgggaaatcgtgggcgtggtggaacctgtgccccacgacgagacatactgcgatcctgctagcct ctttcacgtgagcaatgattactcattcatccggtactacaccagaactctgtaccagttccagttccaggaggccctgtgccaggccgccaagcacg agggccctctgcacaagtgcgacatctctaacagcaccgaggccggccagaagctgttcaacatgctgagactgggcaagagcgaaccttggac actggccctggagaacgtggtcggagccaagaacatgaacgtgagaccactgctgaactacttcgagcccctgttcacctggctgaaggatcaaa acaagaacagcttcgtgggctggtccacagactggagcccatacgctgatcagagcatcaaagtgaggatctctctgaagagcgccctgggagat aaggcctacgagtggaacgataatgagatgtacctgttcagaagcagcgtggcctacgccatgcggcagtacttcctgaaagtgaagaaccagat gatcctgtttggcgaggaggatgtgagagtggccaatctgaaaccaagaatcagctttaactttttcgttaccgctcctaagaacgtgtctgatatcatc cctagaaccgaggtggaaaaggccatcagaatgagccggtccagaatcaacgatgccttccgactgaatgacaactccctggagttcctgggaat ccagcccaccctgggccctcctaaccagcctccagtcagcggcggaggaggatctggcggtggaggctctggcggcggcggttcaacaaatct ggtgaaccagagcggctacgccctggtggccagcggcagatccggcaatctgggcttcaagctgttcagcacccagtctccatctgccgaggtga agctgaagagcctgagccttaacgacggcagctaccagtccgagatcgacctgtcaggcggcgccaacttccgagaaaagttcagaaacttcgc caatgagctgagcgaggccatcacaaacagccctaaaggcctggacagacctgtgcccaagacggaaatcagcggcctgatcaagacaggcg acaactttatcacccctagcttcaaggccggatattatgaccacgtggcctctgatggctccctactgagctactaccagtccaccgagtacttcaaca acagagttctgatgcctatcctgcagacaacaaacggcactctgatggccaacaaccggggctacgacgacgttttcagacaagtgccctctttcag cggctggagcaacacaaaggccaccactgtgtccacaagcaacaatctgacatacgataagtggacctatttcgccgccaaaggcagccccctgt acgacagctaccccaaccacttcttcgaggacgtgaagacactggccattgacgctaaggacatcagcgccctgaaaaccaccatcgacagcga gaagcctacctacctgattatccggggactgagcggaaacggcagccagctgaacgagctgcaactgcctgagtccgtgaaaaaggtgagcctg tacggcgactacaccggcgtgaacgtggctaagcagatcttcgccaacgttgtggaactggaattctacagcaccagcaaggctaactcttttggct ttaacccccctggtcctgggatctaaaacgaacgtgatctacgacctgttcgcaagcaagcccttcacccacatcgacctgacacaggtgaccctgca aaacagcgataattccgccatcgatgccaacaagctgaagcaagctgtgggcgatatctacaactacaggcggttcgagagacagtttcagggcta cttcgccggaggctacatcgacaagtacctggtgaagaacgtcaataccaacaaggatagcgatgacgatctggtctaccggagcctgaaagagc tgaacctccacctggaggaagcctacagagaaggcgataacacctactacagagtgaatgagaactattaccctggagctagcatctacgagaac gagagagccagcagagacagcgagttccagaacgagatcctgaagcgagccgagcagaacggcgtgacatttgacgagaacatcaaaagaat -continued cacagccagcggcaagtatagcgtgcagttccaaaagctagaaaatgataccgattccagcctggaaagaatgaccaaggccgtggaaggcctt gtgaccgtgatcggcgaggaaaagttcgagacagtggatatcaccggcgtgtctagcgataccaatgaagtgaaaagcctggccaaggaactga agaccaacgccctgggcgtcaagctgaaactctaa

42) SEQ ID NO: 42

Artificial
armY-CD209 (DC-SIGN) fusion protein codon-optimized (for human) nucleotide sequence
(2,706 bp)

atgtaccgaatgcagctgctgtcttgtattgccctgtccctggccctggttaccaattctcaagtgagcaaggtgcccagcagcatctctc aggagcagagcagacaggacgccatctaccagaacctgactcaactgaaggcggctgtgggcgaactgagcgagaagtctaagctgcaggag atctatcaggaactgacacaactgaaggctgccgtgggggaattacccgagaagagcaagctgcaggaaatctaccaggagctgaccagactca aagccgccgtgggcgagctgccagagaagtctaaactgcaggaaatctaccaggaattgacatggctgaaggcagctgttggcgagctgcctga gaaaagcaagatgcaggagatttaccaggagctcacacggctgaaggccgccgtcggcgaactccccgagaaaagcaagcagcaggagatct accaggagcttacaagacttaaggccgctgtgggagagctgcctgagaagtccaaacaacaggaaatctaccaagaactgaccagactgaaagc cgccgtgggagaactgccagaaaaaagcaagcagcaggagatctaccaagaactgacacagcttaaagcagctgttgagcggctgtgtcaccca tgcccttgggagtggacattcttccagggcaactgctacttcatgagcaatagccaaaggaactggcacgacagcatcacagcctgcaaggaagt gggggcccagctggtggtgatcaagtccgccgaagaacaaaatttcctgcagctgcagtcctccagaagcaacagattcacatggatgggcctgt cagacctgaaccaagaaggcacctggcagtgggtcgatggcagcccccctgctgccctattcaagcagtactggaaccgcggcgagcctaacaa tgtgggcgaggaagattgcgccgagtttagcggcaacggctggaatgacgacaagtgcaacctcgccaagttctggatctgtaaaaagtccgccg cctcctgcagccgcgacgaggagcagtttctgtcccctgcccccgccacccctaatcctcctcccgccggcggtggcggaagcggcggcggcg gcagcggaggaggcggcagcaccaacctggtgaatcagagcggctacgccctggtggcctctggtagatctggcaacctgggattcaagctgtt cagcacacagtctcctagtgccgaagtgaagctgaagtcactgagcctgaacgacggcagctaccagagcgaaatcgacctgtctggcggtgcta acttcagagagaagttccggaacttcgccaacgagctgtccgaggccattaccaacagtcccaagggcctggaccggcctgtgcctaagaccga gatcagcggcctgatcaagaccggcgacaacttcatcacccctagattaaggctggctactacgaccacgtggcctccgatggctctctgctgtcc tattatcagagcacagagtacttcaacaatagagtgctgatgcctatcctgcaaacaaccaacggcaccctgatggccaataataggggatacgac gacgtattcggcaggtgcctagcttctccggctggagcaacaccaaggccacaaccgtgtctacaagcaacaacctgacatacgacaagtggac ctactttgccgccaaggggagccctctgtacgactcttatcctaatcatttcttcgaggacgtgaagaccctggccatcgatgccaaggatatcagcg ccctgaagaccaccatcgacagcgaaaaacccacctacctgatcatccggggcctgagcggcaatggcagccagctgaacgaactgcagctgc cagaaagcgtgaagaaggtgtctctgtacggcgactacaccggcgtgaacgtggctaagcagatcttcgccaatgttgttgagcttgagttctacag cacgagcaaggccaactcattcggatcaacccccctggtgctgggaagtaagacaaacgtgatctatgacctgtttgccagcaaacctttcacccac -continued atcgacctgacccaggtgaccctgcagaacagcgacaacagcgccattgatgctaacaagctgaaacaggccgtgggagacatctacaactacc ggagattcgagagacagttccaaggctacttcgccggcggctatatcgataagtacctggtgaaaaacgtgaacaccaacaaggatagcgatgac gacctggtgtacagaagcctgaaggaactgaacctgcacctggaggaagcctacagagaaggcgataacacatactacagagtgaacgagaact actaccctggagccagcatctacgagaacgagagagcctctcgggactccgagttccagaacgaaatcctgaaacgggccgagcagaacggcg tgacatttgatgaaaacatcaagagaatcaccgctagcggcaagtacagcgtgcagtttcagaagctggagaacgacactgattctagcctggaaa gaatgaccaaggcggtcgagggcctggtgaccgtgatcggcgaggagaagttcgaaaccgtggacatcaccggcgtgtccagcgacaccaatg aggtgaaatctctggccaaagagctgaagaccaacgccctcggagtgaagctgaagctgtaa

43) SEQ ID NO: 43

Artificial
armY-C-type lectin domain family 4 member M fusion protein codon-optimized (for human)
nucleotide sequence (2,655 bp)

atgtaccggatgcagctgctgtcttgtatcgccctgagcctggccctggtcaccaattctcaggtgtctaaggtgccttctagcctgagcc aggagcagtctgagcaggacgctatctaccagaacctgacacagcttaaggccgctgtgggcgaactgtcagaaaagtctaagctccaagagatc taccaggagcttacacagctgaaagccgccgtgggcgagctgcctgagaagtccaagttgcaagagatctaccaggagctgacccggctgaaag ccgccgtgggagagctgcccgagaagagcaaactgcaggaaatctatcaggagctgaccagactgaaggccgccgtgggagagctgcccgag aaatccaagctacaggagatctaccaggagctgacaagactgaaggccgcagtgggcgagctgccagaaaagagcaagctgcaggagatctac caggaactgacagagctgaaggccgccgttggagaactgcctgaaaagtccaaactgcaggaaatctatcaggagctgacacagctgaaggctg ccgtgggcgaactccctgaccagtccaagcagcagcagatttaccaggaactgaccgacctgaaaacagccttcgagagactgtgtagacactgc cctaaggactggacattcttccagggcaactgctacttcatgagcaacagccagcggaactggcacgacagcgtgaccgcctgtcaggaggtgc gggcccagctggtggtcatcaagaccgccgaagagcaaaacttcctgcagctgcaaacaagcagaagcaacagattcagctggatgggcctga gcgatctgaaccaggagggcacctggcagtgggtggatggaagccctctgtctccaagcttccaaagatactggaacagcggagagcctaacaa ctctggaaatgaggactgcgccgagttcagcggttctggctggaatgacaacagatgcgacgtggacaactactggatctgcaagaaacccgccg cctgcttccgagatgagggcggtggcggaagcggcggcggaggcagcggaggcggcgggagtaccaacctggtgaatcagagcggctacgc cctggtcgcctcgggcagatccggcaatctgggcttcaagctgttcagcacacaaagcccttctgctgaagtgaaactgaagagcctgagcctgaa tgatggctcttaccagagcgagatcgacttatccgggggagccaactttcgggaaaaattcagaaacttcgctaacgagctgagcgaggccatcac caactcccccaagggcctggatagacctgtgcccaagacagagatcagcggcctgatcaagaccggcgataacttcatcacccctagctttaagg ccggatactacgaccacgtggcttccgatggcagcctgctgagctactaccagagcaccgagtacttcaacaacagagtactgatgcctatcctgc agacaacaaatggcaccctgatggccaacaataggggctacgatgacgtgttcagacaggttccttcattcagcggctggagcaatacgaaggct acaaccgtgtcgaccagcaacaacctgacctatgacaagtggacctacttcgccgctaagggcagccctctgtacgacagctaccccaaccacttc -continued ttcgaggatgtgaaaaccctggccattgacgccaaggacatcagcgccctgaaaaccaccatcgacagcgagaagcctacatacctgatcatcag aggcctgtcaggcaacggctcccagctgaacgaactgcaactgccagagagtgttaagaaggtgagcctgtacggcgactatacaggagtgaac gtggctaagcagatcttcgctaatgtggtggaactggaattctacagcaccagcaaagccaacagcttcggctttaacccccctggtgctgggcagca agaccaacgtgatctacgaccttttcgccagcaagcccttcacccacatcgacctgacccaggtgaccctgcagaatagcgacaattctgccattga cgccaacaagctgaaacaggccgtgggcgatatctacaactacaggcggttcgaaagacagttccaaggctattttgccggcggctacatcgaca agtacctggtcaagaacgtgaacaccaacaaggattccgacgacgatctagtgtaccggagcttgaaggaactcaacctgcatctggaagaggcc tacagagaaggcgacaacacatactaccgcgtgaacgagaactactaccctggcgccagcatctacgagaacgaacgggcttctagagatagcg agtttcagaatgaaatcctgaagagagccgaacagaacggcgtgaccttcgacgagaacattaagcggatcacagcctctggcaagtacagcgtg cagtttcagaagctggaaaacgacaccgacagctctctcgagagaatgaccaaggccgttgagggcctggtgacagtgatcggcgaggaaaagt tcgaaaccgtggacatcaccggcgtgtcctctgataccaacgaggtgaagagcctggcaaaggaactgaagaccaacgccctgggcgtgaagct gaagctgtaa

44) SEQ ID NO: 44

Artificial
armY-CD4 fusion protein codon-optimized (for human) nucleotide sequence (2,781 bp)

atgtacagaatgcagctgctgagctgcatcgccctgtccctggccctggttacaaacagcaagaaggtggtgctgggaaaaaagggc gacaccgtggaactgacctgcaccgctagccagaagaagagcatccaatttcactggaagaacagcaaccagatcaaaatcctggggaaccagg gctctttcctgacaaagggcccctctaagctgaatgatagagccgacagccggagatcgctgtgggaccagggcaacttcccccctgatcatcaaga acctgaagatcgaggatagtgacacatacatctgcgaggtggaagatcagaaggaagaggtgcaactgctggtgttcggactgaccgccaacag cgacactcacctgctgcagggccagtctctcacactaaccctggaaagccctcctggaagctctccaagcgtccagtgtagatctcctagaggcaa gaacatccagggcggcaagaccctactgtgtctcagctggagctgcaggactcaggcacctggacatgtaccgtactgcaaaatcagaaaaagg tggaattcaagatcgacatcgttgtgctggccttccagaaggccagcagcatcgtgtacaagaaggaaggagagcaggtggagttttctttccctct cgcctttaccgtggaaaaactgaccggttcaggcgagctgtggtggcaggccgagcgcgcaagctccagcaagagctggatcacattcgacctta agaacaaagaggtgagcgtgaagagagtgacccaggaccccaagctgcagatgggcaagaagctgcccctgcacctgaccctcccgcaagcc ctgcctcagtacgccggatccggcaacctgacactggccctcgaagccaaaaccggaaagctgcaccaggaggtgaacctggtggtgatgaga gccacccagctgcagaaaaatctgacctgcgaagtgtggggccctacaagccctaagctcatgctgagtcttaaactggagaacaaggaggctaa agtgagcaagcgggaaaaggccgtgtgggtgctgaatcctgaggccggcatgtggcagtgcctgctgtctgacagcgggcaagtgctgctggaa tctaacatcaaggtcctgcccacctggtccacccctgtgcagccaggcggcggaggatctggcggcggcggcagcggaggcggcggctccac caacctggtgaatcagagcggctacgccctggtggctagcggtagatccggcaatctgggattcaagcttttctccacacagagccctagcgccga agtgaagttgaaatctctgagcctgaacgacggctcctaccagtccgagatcgacctgagcggcggcgctaatttcagagagaagtacggaactt -continued cgccaatgagctgtctgaagctatcaccaacagccctaaaggacttgatcgcccagtgcccaagaccgagattagcggcctgatcaagacaggcg ataactttatcacccctagtttcaaggctggctattatgaccacgtggccagcgacggaagcctgctgagctactaccagagcacagagtacttcaac aaccgggtgctgatgcctatcctgcagaccaccaacggcacgctgatggccaacaacagaggctacgacgacgtgttccggcaggtgcctagctt tagcggatggagcaacaccaaggctacaactgtgagcaccagcaacaacctgacctacgataagtggacctacttcgccgccaaaggcagccct ctgtacgatagctaccctaaccacttcttcgaggacgtgaagacactggctatcgacgccaaggacattagcgccctgaaaaccacaattgactctg aaaagcccacctacctgatcatcagaggactgagcggcaacggcagccagctgaacgagctgcagctgcctgaatctgtgaaaaaagtcagcctt tacggcgactacaccggcgtgaacgtggccaagcagatcttcgccaatgtggtggaactggagttctacagcacctctaaagccaacagtacggc ttcaacccccctggtgctgggctctaaaaccaatgtaatttatgacctcttcgctagcaagcctacacacacatcgatctgacccaggtgacactgcag aactctgacaacagcgccatcgatgccaataagctgaagcaggccgtgggcgacatctacaactaccggagattcgagagacagtacagggcta ctttgccggcggctacatcgataagtacctggttaagaacgtgaataccaacaaggactctgatgacgacctggtgtacagaagcctgaaggaact gaacctgcatctggaagaggcctacagagaaggcgacaacacctactatcgggtgaatgagaactactatcccggcgcttctatctacgagaatga gcgggccagcagagatagtgagttccaaaatgagatcctgaagcgggcagagcaaaacggcgtgaccttcgacgagaacatcaagagaatcac cgcctccggcaaatacagcgtgcagttccagaaactggaaaacgacactgatagcagcctggaacggatgaccaaggccgtagagggcctggt caccgtgatcggcgaggagaagtttgagacagtggacatcacaggcgtgagctccgataccaacgaggtgaagagcctggccaaggaactgaa gaccaacgccctgggagtgaagctgaagctataa

45) SEQ ID NO: 45

Artificial
armY-Synaptic vesicle glycoprotein 2A fusion protein codon-optimized (for human)
nucleotide sequence (2,058 bp)

atgtacagaatgcagctgctgtcatgcatcgccctctccctcgccctggtgaccaacagccccgacatgatcagacacctgcaggccg tcgactacgccagcagaaccaaagtgttccccggagaacgggtggaacacgtgacatttaacttcaccctggaaaaccagatccacagaggcgg ccagtacttcaacgacaagttcatcggcctgagactgaagtccgtgtccttcgaggatagcctgtagaggaatgctactagaggacgtgacatcta gcaataccttttttccggaactgcacattcatcaacaccgtgttctacaacaccgatctgtttgaatacaagttcgtgaacagcagactgatcaacagca cctactgcacaacaaggagggctgtcctttagatgtgaccggaacgggcgagggcgcctacatggtgtacggcggcggaggctccggcggcg gtggcagcggtggaggaggcagcaccaatctggtcaaccaatctggctatgccctggtcgccagtggcagaagcgggaacctgggcttcaagct gttcagcacacagagccctagcgctgaagtgaaactgaagagcctgtctctgaacgacggctcttatcagagcgagatcgacctgtccggaggcg ccaatttcagagagaagttcaggaacttcgccaacgagctgagcgaggccatcaccaattcccctaagggactggatagacctgtgccaaaaacc gagattagcggcctgattaagaccggagataatttcatcacacccagctttaaggccggatattacgaccacgtggcctctgacggcagcctgctga gctactaccagagcaccgagtacttcaacaaccgggtgctgatgcctatcctgcaaacaacaaatggcacactgatggccaacaaccggggatat -continued gacgacgtgttccgccaggtgcccagcttcagcggctggagcaacacaaaggctacaaccgtgtctaccagcaacaacctgacctacgataagtg gacctacttcgccgctaaaggcagccctctgtacgacagctaccccaaccacttcttcgaggacgtcaagaccctggcgatagacgccaaagaca tcagcgctctgaagaccaccatcgacagcgaaaagccaacatacctgatcatcagaggcctgagcggcaacggctcacagctgaacgagctgca gctgcctgagagcgtgaaaaaggtgtcactgtacggcgattacaccggcgtgaacgtggccaagcagatcttcgcaaacgttgtggaactggaatt ctactctacaagcaaggccaacagcttcggctttaatcctctggtgctggggtctaagacaaacgtgatctacgacctgttcgccagtaagcctacac ccacatcgacctgacccaggttacactgcagaactccgacaacagcgccatcgacgccaacaagctgaaacaggccgtgggcgacatctacaac tacaggagattcgaaagacagttccagggctattttgccggcggctacatcgacaagtacctggtgaagaacgtgaataccaacaaggactctgat gacgatctcgtgtaccggagcctgaaggaactgaatctgcatctggaagaagcttaccgggaaggcgacaatacctactacagagtgaacgagaa ctactaccctggcgctagcatctacgagaacgaacgggccagcagagattctgagttccaaaacgagatcctgaagcgggccgagcagaatggc gtcaccttcgacgagaacatcaagagaatcaccgcctctggcaaatacagcgtgcagttccaaaaactggaaaacgatactgatagctcccttgag agaatgaccaaggccgtggaaggactggtgaccgtgatcggcgaagagaagttcgagacagtggacatcacaggcgtgtccagcgataccaat gaggtgaagagcctggccaaggagctgaaaaccaacgccctcggcgtgaagctgaagctgtaa

46) SEQ ID NO: 46

Artificial
armY-Synaptic vesicle glycoprotein 2B fusion protein codon-optimized (for human)
nucleotide sequence (2,040 bp)

atgtacagaatgcagttgctgtcttgtatcgccctcagcctggctctggtgacgaatagcccagacatgatccgctacttccaggacgag gaatacaagagcaagatgaaggtgttctaggcgagcatgtgtacggcgccaccatcaacttcaccatggaaaaccagatccaccagcacggcaa gctggttaatgacaagtttacaagaatgtactttaagcacgtgctgttcgaggatacctttttttgatgagtgctacttcgaggacgtgacaagcaccgac acatacttcaagaactgcaccatcgagagcaccatcttctacaacaccgacctgtatgagcacaagttcatcaactgcagatttatcaacagcaccttc ctggaacagaaagagggctgccacatggacctggaacaagacaatgatggaggcggaggaagcggcggcggaggcagcggcggcggggg aagcaccaatctggtgaatcaaagcggctacgccctggtggctagcggcagaagcggcaacctgggcttcaagctgtttagcacacagagcccta gcgctgaagtgaagctgaagtctctctctctgaatgacggctcctaccagtctgagatcgacctcagcggaggcgccaacttcagggaaaagttcc ggaacttcgccaacgagctgagcgaggccattacaaacagccctaagggcctggacagacctgtgcccaagaccgagatcagcggcctgatca agactggagataattttattacccctagcttcaaggcaggctactacgaccacgtggcctccgatggctctctgctgtcctattatcagagcacagagt actttaacaacagagtgctgatgcctatcctgcagaccacaaacggcaccctgatggccaacaatagaggctatgatgatgtgttcagacaggtgcc ttctttcagcggatggtccaacacaaaggccacaacagtttctacaagcaacaacctgacctacgataagtggacatacttcgccgccaagggctct ccactgtacgacagctaccctaaccacttcttcgaagatgtgaagaccctggccatcgacgccaaggacatcagcgcccttaaaacaaccattgac agcgagaagcctacctacctgatcatcagaggactgagcggaaacggctcccagctgaacgaactgcaactgcctgagtctgtgaaaaaggtga -continued gcctgtacggcgattacaccggcgttaacgtggctaaacagatcttcgccaacgtggtggaactggagttctacagcaccagcaaggccaatagct tcgggttcaacccccctggtccttggctccaaaaccaacgtcatctacgacctgttcgcttctaagcccttcacacacatcgacctgacccaggttaccc tgcagaactcagacaacagtgctatcgacgccaacaaactgaagcaggccgtgggcgatatctataactaccggagattcgagcggcagttccaa ggctacttcgccggcggatatatcgacaagtacctggtcaagaacgtgaacaccaacaaggacagcgatgacgacctggtgtaccggagcctga aggaactgaacctgcacctggaagaagcctaccgggaaggcgacaacacctactaccgggtgaacgagaattactaccccggcgctagcatcta cgagaacgagagagcctccagagattcagagttccagaacgagatcctgaaaagagccgagcagaatggcgtgaccttcgacgagaacatcaa gcggatcacagcctctggcaaatacagcgtgcagttccagaagctggaaaatgataccgatagcagcctggaaagaatgaccaaggcggtggaa ggcttggtcaccgtgatcggcgaggagaagttcgagacagtggacatcaccggcgtgtccagcgacaccaacgaggtgaaaagcctggccaag gaactgaagaccaacgccctgggcgtgaagctgaagctgtaa

47) SEQ ID NO: 47

Artificial
armY-Synaptic vesicle glycoprotein 2C fusion protein codon-optimized (for human)
nucleotide sequence (2,028 bp)

atgtaccgcatgcagctgctgagctgcatcgccctgagcctggctctggtgacaaacagcaaacctctgcagagcgacgagtacgcc ctgctgacaagaaacgtcgagcgggacaagtacgccaattttaccatcaactttaccatggaaaaccagatccacaccggaatggaatacgataat ggcagattcattggcgttaagttcaaaagcgtgacattcaaagatagcgtgttcaagagctgtacattcgaagatgtgaccagcgtaaatacctacttc aaaaactgcaccttcatcgacaccgtgttcgacaacaccgatttcgagccttacaagttcatcgacagcgagttcaagaactgcagctttttccacaac aaaaccggatgtcagatcaccttcgacgacgactacagcggcggcggcggctcgggcggaggaggctctggtggcggcggcagcacaaacct ggtcaaccagagcgggtatgccctggtggccagcggcagaagcggcaatctgggcttcaagctgttcagcacacagtccccaagcgctgaggtg aagctcaaatctctgtcccttaacgacggcagttaccaaagcgagatcgacctgagcggcggagccaacttccgggaaaagttcagaaatttcgct aatgaactgagcgaggccatcacgaatagccctaagggcctggatagacccgtgcccaagactgagatcagcggcctgattaagacaggagata acttcatcacacctagcttcaaggccggctattacgaccacgtggcctcagacggctccctgctgagctactaccagagcacagagtacttcaacaa ccgggtgctgatgcctatcctgcagaccaccaacggaacactgatggccaacaacagaggctatgacgatgtgtttagacaggtcccctcttttagc ggatggtccaacaccaaggctacaacagtgtccaccagcaacaacctgacctacgacaagtggacatatttcgccgccaagggaagccctctgta cgacagctacccaaaccacttcttcgaggacgtgaagaccctggccattgacgccaaagacatcagcgccctgaagaccacaatcgattctgaga aacctacctatctgatcatcagaggactctctggcaacggcagccagctgaacgagctgcagctgcctgagagcgtgaaaaaggtgtccctgtac ggcgattacaccggcgtgaacgtggccaagcagatcttcgccaacgtggtggaacttgagttctacagcaccagcaaggccaattctttcggcttca acccccctggtcctgggcagcaagacaaatgtgatctacgacctgttcgcctctaagcctttcacccacatcgacctgacccaggtgacactgcaaaa ttccgataacagcgccatcgacgctaacaagctgaagcaggccgtgggcgacatctacaactaccggcggtttgagcggcagtttcagggctactt -continued tgctggcggatacatcgacaagtacctggtgaagaacgtgaacacaaacaaggactctgatgacgacctggtttaccggtctctgaaggaactgaa cctccatctggaagaagcctacagagaaggcgacaacacctactacagggtgaacgagaactactaccccggcgctagcatctacgagaacgaa agagcctctagagatagcgaatttcagaacgagatcctgaagagagctgaacagaatggcgtgacctttgatgagaacatcaagcggatcaccgc ctccggcaagtacagcgtgcagttccaaaagctggagaatgataccgactccagcctggaaagaatgaccaaggcagtggagggcctggtgacc gtgatcggcgaggaaaagttcgagacagtggacatcaccggcgttagcagcgacaccaacgaggtgaagtctctggccaaggaactgaagacc aacgccctgggagtgaaactgaagctgtaa

48) SEQ ID NO: 48

Artificial
armY-Synaptotagmin I fusion protein codon-optimized (for human) nucleotide sequence
(1,839 bp)

atgtacagaatgcagctgctgagctgcatcgccctgagcctggccctggttacaaacagcatggtgtccgagagccaccacgaggcc ttagcagctcctcctgtgaccaccgtggctacagtgctgcccagcaatgccaccgagcctgccagccctggagagggaaaagaggacgcctttag caagctgaaggagaagttcatgaacgagctgcataagatccctctgcctggaggtggcggcagcggaggaggtggctccggcggcggcggctc caccaacctggtgaaccagagcggctacgccctggtggccagcggaagaagcggcaacctgggcttcaagctgttttctacgcagagccccagc gccgaagtgaagctgaagagcctgtcactgaacgacggcagctatcagtctgagatcgacctgtctggcggggccaatttcagagagaaatttag aaacttcgctaatgagctgagcgaggccatcaccaactcgcccaagggcctggacagacctgtgcccaagaccgaaatcagcggcctgattaaa acaggcgataacttcatcacccccttcttttaaggctggctactacgaccacgtggccagcgatggcagcctgctgtcttactaccagagcacagagt actttaacaacagagtgctgatgcctatcctgcagaccaccaacggaacactgatggccaacaaccggggctacgacgacgtcttcagacaggtg cctagcttctctggctggtccaacaccaaggcgacaaccgtgtccaccagcaacaatctgacatacgataagtggacctacttcgctgccaagggc tccccactgtacgactcttatccaaaccacttcttcgaggatgtgaaaactctggctatcgacgccaaggacatcagcgctctgaagaccacaatcga cagcgaaaagcccacctacctgatcatcagaggactgagcggaaatggctcacagctgaacgaactgcagctgcctgagtctgtgaagaaggtgt ccctctacggcgactacaccggcgtcaacgtggccaagcaaatcttcgccaatgtggtggaactggaattctacagcaccagcaaggccaacagc ttcggcttcaacccccctggtgctggggagcaaaacaaacgtgatctatgacctgttcgccagcaagcctttcacccacatcgatctgacccaagtga ccctgcagaacagcgataatagcgccatcgacgccaacaagctcaagcaggccgtgggcgatatctacaactacaggcggttcgagagacagtt tcagggctacttcgccggcggctacatcgacaaatacctggtcaagaacgtgaacaccaacaaagactctgatgacgacctggtctaccggagcc tgaaagagcttaatctgcacctggaagaggcctaccgggaaggcgacaacacatactacagagtgaacgagaactactacccaggcgccagtatt tacgagaacgaacgcgcctctagagatagcgagttccaaaatgagattttaaaaagagccgagcagaacggcgtgacattcgacgagaacatcaa -continued gcggatcaccgcctccggcaagtacagcgtgcagttccagaagctggaaaatgataccgacagcagcctggaacggatgaccaaggccgtgga aggcctggtgaccgtgatcggcgaggaaaagttcgaaaccgtcgacatcacaggcgtgtctagcgacaccaatgaggtgaagagccttgctaag gaactgaagacaaacgccctgggcgtgaaactgaagctgtaa

49) SEQ ID NO: 49

Artificial
armY-Synaptotagmin II fusion protein codon-optimized (for human) nucleotide sequence
(1,854 bp)

atgtaccggatgcagctgctgagctgcatcgccctgtccctggccctggtgacaaacagcatgagaaacattttcaagagaaaccagg agcctatcgtggcccctgctacaaccacagccacaatgcctatcggccctgtggataattcgactgaaagcggcggagccggcgagtcccaaga agatatgttcgccaagctgaaagagaaactgttcaacgagatcaacaagatccccctgcctccaggcggcggcggcagcggaggaggcggcag cggtggcggcggcagcacaaatctggtaaaccagagcggctacgccctggttgcctccggaagaagcggaaacctgggatttaagctgttcagc acccagtccccatctgctgaagtgaaactgaagagcctgagcctgaatgacggctcttaccagagcgagatcgacctgagtggaggcgccaattt cagagagaaattccgcaacttcgccaatgagctgagcgaggccatcaccaacagccctaagggcctggacagacctgtgcccaagaccgaaatc agcggactgatcaagaccggcgacaacttcatcacccccttcttttaaggctggatattacgaccacgtggcctctgacggatctctgctgagctacta ccagtctaccgagtacttcaacaaccgggtgctgatgccaattcttcagacaaccaacggcaccctgatggccaacaatagaggctacgacgatgt gttccggcaagtgcctagcttttctggctggagcaacaccaaggccaccaccgtgtccaccagcaacaacctcacctatgataagtggacctacttt gctgctaaaggcagcccccctgtacgactcttatcctaaccacttcttcgaagatgtgaagaccctggctatcgatgccaaggacatcagcgccctga aaaccaccatcgacagcgagaagcccacctacctgatcatcagaggcctatctggcaacggcagccagctgaacgagctgcagctccctgagag cgtgaagaaggtgtctctgtacggcgattacaccggcgttaatgtggctaaacagatcttcgccaacgtggtggaactggaattctacagcacatcta aagcaaacagttttggcttcaatcctctggtgctgggcagcaagaccaacgtgatctacgacctgtttgctagcaagcccttcacacacatcgatctg acccaggtgaccctgcaaaactccgataatagcgccattgacgccaacaaactcaagcaggccgtgggcgatatctacaactacaggcggttcga gagacagttccagggctacttcgccggcggatatatcgacaagtacctggtcaagaacgtcaacacaaacaaggacagcgatgacgacctggtct accggagcctgaaggaactgaacctgcatctggaggaagcctacagagaaggcgacaacacctactacagagtgaacgagaactactaccccg gcgccagcatctacgagaatgaaagagcctcaagagattccgagttccagaacgagatcctgaagcgggccgagcagaacggcgtgacattcg acgagaacatcaagcggatcaccgccagcggcaagtacagcgtgcagtttcagaagctggaaaacgacaccgactcaagcctggaaagaatga caaaggccgtggaaggcctggtgactgtgatcggcgaagagaagttcgagacagtggacatcacaggcgtgtctagcgacaccaacgaggtga aaagcctggccaaggaactgaagacaaacgccctgggcgtgaagctgaagctataa -continued

50) SEQ ID NO: 50

Artificial
armY-HLA class II histocompatibility antigen, DRB1 beta chain fusion protein codon-optimized (for human) nucleotide sequence (2,262 bp)

atgtaccggatgcagctgctgagctgcatcgccctgtctcttgccctggtgaccaactctggagacaccagacctagattcctgtggca gcccaagagggaatgtcacttttttcaacggtacagagcgggtgagattcctggaccggtacttctacaaccaggaggaaagcgtgcggtttgatag cgacgtgggcgagttccgggctgtgactgaactgggccggcccgatgccgagtactggaacagccagaaggatatcctggagcaggccagag ccgcagtggacacctactgcagacacaactacggcgttgtggaaagcttcaccgtgcaaagaagagtgcagcctaaagtgaccgtgtacccatct aaaacacagcctctgcagcaccacaatctgctggtatgcagcgtgtccggcttctaccctggcagcatcgaggtgcggtggttcctgaacggccag gaggaaaaagccggcatggtgtctaccggcctgatccagaatggcgactggaccttccagaccctggtgatgctggaaacagtgcctagatccgg cgaggtgtacacctgccaggtggagcaccccagcgtcaccagcccactgaccgtggaatggcgggccagatctgagagcgctcagagcaagg gcggcggcggaagcggcggcggaggaagcggcggcggcggcagcacaaatctggtcaaccagagcggctacgccctggtggccagtggca gaagcgggaacctgggctttaagctgtttagcacccagagccccagcgccgaagtgaagctgaaaagcctgtccctgaacgacggcagctacca gagcgagatcgacctgtccggcggagccaacttcagagagaagttcagaaactttgccaacgagctgagcgaggccattacaaatagccctaag ggcctggatagaccagtgcctaagaccgagattagcggcctgatcaagaccggcgataacttcatcacaccttcctttaaggccggttactatgacc acgtggccagcgacggctccctcctgagctactatcagtctaccgagtacttcaacaaccgggtgctgatgcctatcctgcaaacaacaaacggca ccctgatggccaacaacagaggctacgacgatgtgttcagacaagtgccctctttcagcggatggagcaacaccaaggctacaaccgtctccacta gcaacaacctcacctacgacaagtggacctattttgccgccaagggcagccctctgtacgacagctaccctaaccacttcttcgaggacgtgaaga ccctggccatcgacgctaaggacatcagcgcccttaagaccacaatcgattctgagaagcctacctacctgatcatccggggcttatctggcaacg gctctcagctgaatgagctgcagctgccggaaagcgtgaagaaggtgtccctctacggcgactacacaggcgtgaatgttgccaagcagatcttc gccaacgtggtggaactagaattctactccaccagcaaggctaacagctttggcttcaatcctctggtgctgggcagcaaaaccaatgtgatctatga tctgttcgcttctaagcccttcacccacatcgatctgacacaggtgaccctgcagaacagcgacaatagcgccatcgacgctaacaagctgaaaca ggctgtgggcgacatctacaactaccggagattcgagagacaattccagggctacttcgccggaggatatatcgacaagtacctggtgaaaaacgt gaacaccaacaaggattctgatgacgacctggtttacaggagcctgaaggaactgaaccttcatctggaagaagcctacagagagggcgacaata catactacagagtgaacgagaattactaccccggcgccagcatctacgagaacgaaagagcctctagagacagcgagttccaaaacgaaatcctc aagcgcgctgagcagaacggagtgacattcgacgagaacattaagcggatcaccgccagcggcaagtacagcgtccagttccagaaactggaa aacgacaccgattctagcctggaaaggatgaccaaggccgtggaaggcctggtaacagtgatcggagaggagaaattcgagacagttgacatca ccggggtgagcagcgatacaaatgaggtgaagtctctggccaaggaactgaaaaccaacgccctgggagtcaagctgaagctgtaa Artificial -continued armY-HLA class II histocompatibility antigen, DR alpha chain fusion protein codon-optimized (for human) nucleotide sequence (2,241 bp)

51) SEQ ID NO: 51 atgtaccggatgcagctgctgtcatgcatcgccctgagcctcgctctggttaccaatagcatcaaggaagagcacgtgatcatccaggc cgagttctacctgaatcctgatcagagcggagagttcatgttcgacttcgacggcgatgagatctacatgtggacatggccaaaaaggaaaccgtgt ggcggctggaagagtaggccggttcgcctccttcgaggcccagggagctaggccaatatcgccgtggacaaggccaatctggagatcatgacc aagcggagcaactacacccctatcaccaacgtgccacctgaggtgacagtgctgaccaatagccccgtggagctgcgggaacctaacgttctgat ctgcttcatcgacaagtttacacccccccgtggtgaatgttacatggctgagaaacgggaagcctgtgaccacaggagtgtccgagacagtgttcctg cctagagaagaccacctgttccggaagttccactacctgcccttcctgccttccaccgaggacgtgtacgattgtagagtggaacactggggcctgg acgagcctctcctgaagcactgggagtttgacgcaccatcccctctgcctgagacaaccgaaggcggaggcggctccggcggcggaggtagcg gaggcggcggcagcaccaacctggtcaaccagtccggatacgccctggtggccagcggcagatctggcaatctcggcttcaagcttttcagcac gcagtcccctagcgccgaagtgaaactgaaatctctgtctctgaacgacggcagctaccagagcgagatcgacctgagcggcggcgccaatttca gagagaagtttcggaacttcgccaacgagctgtccgaggctattaccaacagtccaaagggactggatagacctgtgcccaagaccgagatcagc ggcctgatcaagacaggcgacaacttcatcacccctagcttcaaggccggctactacgaccacgtggcttctgatggctctctactgagctactacc agagcacagaatactttaacaatagagtgctgatgcctatcctgcagaccactaacggcaccctgatggccaacaacagaggctacgacgacgtgt tcagacaagtgccttcttttagcggatggtccaacacgaaggccaccacagtgtctacatctaacaacctgacatatgacaagtggacctacttcgcc gccaagggcagccctctgtacgacagctatcctaatcacttcttcgaggatgtgaaaacactggctatcgacgcgaaagacattagcgccctgaag accaccatcgatagcgaaaagcccacctacctgatcatcagaggcctctctggcaacggctctcagctgaacgagctgcaacttccggagagcgt gaagaaagtgtccctgtacggcgactacaccggcgtgaacgtcgctaaacagatctttgccaacgtcgtggaactggaattctatagcaccagcaa ggccaacagcttcggcttcaacccccctggtgctgggaagcaagaccaacgtgatctatgacctctttgcttctaaacctttcacccacatcgacctga cccaggtcacactgcagaacagcgacaacagcgccatcgacgccaacaagctgaagcaggctgtgggcgatatctacaactaccgtagattcga gcgccagttccagggctatttcgccggcggctacatcgacaagtacctggtgaagaacgtgaacacaaacaaggacagcgacgatgatctggtct acagaagcctgaaggagctgaacctgcacctggaagaagcctacagagagggcgataacacctactacagggttaatgagaattactaccccgg cgctagcatctacgagaacgagcgcgccagcagagattctgaattccaaaacgagatcctgaaaagagccgaacagaacggcgtgacattcgat gagaacatcaagcggatcacagccagcggcaagtacagtgtgcagtttcagaaactggaaaacgacaccgacagcagcctggagagaatgacc aaggccgtggaaggcctggtgaccgtgatcggcgaggaaaagttcgaaaccgttgacattaccggcgtgtctagcgataccaacgaggtgaaga gcctggccaaggagctgaagacaaacgccctgggggtgaagctgaagttataa -continued Artificial
armY-T cell receptor beta variable 7-9 fusion protein codon-optimized (for human) nucleotide sequence (1,950 bp)

52) SEQ ID NO: 52 atgtaccgcatgcagctgctgagctgcatcgccctgagcctcgccctggtgaccaacagcggcgttagccagaacccccggcacaa gattaccaagoggggccagaacgtgaccttcagatgtgaccccatcagcgaacacaaccggctgtactggtacagacagacactgggccaagga cctgagttcctgacctacttccagaacgaagcccagctggagaaatctagactgctttccgatagattcagcgccgagaggcctaagggctcttttag cacactggagatccagagaacagagcagggcgatagcgcaatgtacctgtgcgccagcagcctgggcggcggcggcagcggcggaggcgg ctccggcggcggcggatctaccaacctggtgaaccagtctggctacgccctggtggcctctggtagaagcggcaacctgggctttaagctgtttag cacacagagtccctctgccgaggtgaagctgaagagcctgtccctgaacgacggcagctatcagtccgagatcgatctgagtggcggagctaact tccgggaaaagttcagaaacttcgccaatgagctgtctgaagccatcaccaatagccctaagggcctggacagacctgtgcctaagaccgagattt ctggcctgatcaagacaggtgataatttcatcacccctagctttaaggctggctactacgaccacgtggccagcgatggaagcctgctgagctacta ccagtccaccgagtacttcaacaacagagtgctcatgcctatcctgcaaaccacaaacggaacactgatggccaacaacagaggatatgatgacgt gttcagacaggtgccatctttttccggctggagcaacaccaaggccaccaccgtgtctacaagcaacaacctgacatatgacaagtggacctacttc gccgccaagggctccccactgtacgacagctaccctaaccacttcttcgaggacgtaaagacactggctatcgatgccaaagacatcagcgcctta aagaccaccatcgacagcgagaagcccacctacctgatcatcagaggactgagtggcaacggcagccagctgaatgaactgcagctgcctgaat ctgtgaagaaggtgtccctgtacggcgactacaccggagtgaacgtggccaagcagatcttcgctaatgtggtcgagctggaattctacagcacca gcaaggccaatagcttcggcttcaaccctctggtcctcggctctaagaccaacgtcatctacgacctattcgctagcaagcctttcacccacatcgac ctgacccaggtgaccctgcagaacagtgacaatagcgccatcgacgccaacaagctgaagcaagccgtgggggacatctacaactaccggaga tttgagcggcagttccagggctatttcgctggcggatacatcgacaagtacctggtgaaaaacgtgaatacaaacaaggacagcgacgacgatctg gtgtaccgctctctgaaggaactgaacctgcatctggaagaggcctacagagagggcgataatacctactaccgggtgaacgagaactactaccc cggcgcctccatctacgagaacgaacgggccagccgggacagcgaattccaaaacgagatcctgaaaagagctgaacagaatggcgtgacctt cgacgagaacatcaagagaatcaccgcctccggcaagtacagcgtgcagttccagaagctggaaaatgacactgattctagcttggaaagaatga caaaagccgtggaaggcctggtcacagtgatcggcgaggaaaagttcgagacagtggacatcacaggcgtgagcagcgataccaacgaggtg aaaagcctggctaaagagctgaagaccaacgccctgggcgttaaactgaaactgtaa Artificial
armY-T cell receptor beta variable 19 fusion protein codon-optimized (for human) nucleotide sequence (1,947 bp)

53) SEQ ID NO: 53 atgtatagaatgcagctgctgtcctgcatagccctgtctctggctctggtgaccaactctgggatcacccagtccccaaagtacttgtttag aaaggagggccagaacgtcaccctgtcttgtgaacagaacctcaaccacgacgccatgtactggtaccggcaggaccctggacagggcctgag -continued actgatctactacagccaaatcgttaatgatttccaaaagggagatattgctgagggctacagcgtgtccagagaaaagaaagaaagcttccctctg accgtgaccagcgcccagaagaaccctaccgccttctacctgtgcgcctccagcattggcggcggcggcagcggaggcggaggcagcggagg cggcggctcaacaaacctggttaaccagtccggctacgccctggtcgcctccggaagaagcggcaacctcggcttcaagctgttcagcacccag agcccttccgccgaggtgaagctgaagagcctgagcctgaacgacggcagctaccagagcgagatcgacctgtctggcggagctaatttccgcg agaagttcagaaacttcgccaacgagctgagcgaggccatcacaaacagccctaagggcctggacagacctgtgcctaagacagagatcagcg gcctgatcaagaccggcgataatttcatcacaccatcttttaaggccggatattacgaccacgtggccagcgatggcagcctgctgagctactacca gtctaccgagtactttaacaacagggtccttatgccaatcctgcaaacaacaaacggcacactgatggccaacaatcggggctatgatgatgtgttca gacaggtgccctctttcagcggatggtccaacaccaaggccaccacagtgtctaccagcaacaacctgacctacgataagtggacttacttcgccg ccaagggctcacccctgtacgacagctaccctaaccatttcttcgaagatgtgaagacgctggccatcgacgcaaaggacatcagcgccctgaag accaccatcgacagcgaaaaacccacctacctgatcatccggggcctaagcgggaatggtagccagctgaacgagctgcagctgcctgagagc gtgaaaaaggtgagcctgtacggcgactacacaggcgtgaacgtggccaaacagatcttcgctaatgtggtggaactggaattctattctacatcca aggccaacagcttcggcttcaacccccctggtgctgggctctaaaacaaacgtgatctacgacctgttcgctagcaagcctttcacccacatcgacct gacccaagtgaccctgcagaatagcgataacagcgctatcgacgccaacaagctgaagcaggccgtgggagacatctacaattacagaagatttg aaagacagttccagggctacttcgccggcggctacatcgacaaatacctggtgaagaacgtgaataccaacaaggattctgacgacgacctggtct accggtctctgaaagagctgaacctgcacctggaagaggcctaccgggagggagataacacctattaccgggtgaacgagaattactaccccgg cgcctccatctatgagaacgagagagccagcagagacagcgagttccagaacgagatcctgaaaagagccgagcagaacggcgtgaccttcga cgagaacatcaagcggatcaccgccagtggcaagtacagcgtgcagtttcaaaagctagaaaacgacacagatagcagcctggaaagaatgac caaggctgtggaaggcctggtgaccgtgatcggcgaggaaaagtttgagacagtggacatcaccggcgtgagctctgacaccaatgaggtcaaa agcctggctaaggaactgaagaccaacgccctgggcgtgaagctgaaactctaa

54) SEQ ID NO: 54

Artificial
armY-Hepatitis A virus cellular receptor 1 fusion protein codon-optimized (for human)
nucleotide sequence (2,700 bp)

atgtaccgcatgcagcttctgtcttgtatcgccctgagcctggcgctggtcaccaacagcagcgtgaaagttggcggagaggccggtc ctagcgtcaccctgccttgccactactctggcgctgtgaccagcatgtgctggaaccggggcagctgtagcctgttcacctgccagaatggcatcgt gtggacaaacggtacacacgtgacatacagaaaggacacaagatacaagctgctgggcgacctgtcaagacgggatgtgtctctgaccatcgag aacaccgctgtaccgacagcggcgtgtactgctgcagagtggagcacagaggctggttcaatgacatgaagatcaccgtgagcctggagatcgt gcctccaaaggtgaccaccacgcctatcgtgacaaccgtacctacagtgaccaccgtgcggaccagcacaaccgtgcctaccaccaccaccgtg cccatgaccacggtgcccaccacaaccgtgccaaccaccatgagcatccccaccacgacaacagtgctgacaaccatgaccgtactacaacaac -continued atcagtgcctaccacaacaagcattcccacaaccacaagcgtgcctgtcacaacaaccgtgtccacattcgtgcctcctatgcccctgcctagacag aatcacgagcctgtggctacctctcctagctcccctcagcctgccgagacacaccctactaccctgcagggcgccatccggagagaacccaccag cagccctctgtatagttacaccaccgacggcaatgataccgtgaccgaaagcagcgatggactgtggaacaacaaccaaacacagctgttcctgg aacattccctgctgacagccaatacaaccaagggcatctacgccggagtgtgcatctccgtgctggtcctgctggcactgctgggagttatcatcgc caagaagtactttttcaagaaggaagtgcagcagctgagcgtgagcttctccagcctgcagatcaaagattgcagaacgccgtggaaaaggaagt gcaagccgaagataacatctacatcgagaactccctgtacgccaccgatggcggcggaggctccggcggcggaggaagcggcggcggcggc tccacaaatctggtgaaccagagcgggtacgccctggtggccagcggcagaagcggaaatctgggcttcaagctgtttagcacccagagcccttc tgccgaggtgaaactgaaaagcctgtccctcaacgacggcagctaccagagcgagattgacctgagcggcggagccaatttcagagagaagttc cgcaacttcgctaacgagctgtctgaagcaatcacaaactcccctaagggactggatagacccgtgcctaaaaccgagatcagcggcctgatcaa gactggagacaatttcatcacccctagctttaaggccggctactatgaccacgttgcctccgacggcagcctgctgagctactaccagtctacagag tactttaacaacagagtgctgatgcctattctgcagacaactaacggcacactgatggccaacaatcggggctacgatgacgtgttcagacaagtgc ccagctttagcggctggagcaacaccaaggctactaccgtgtctaccagcaacaacctgacctacgacaagtggacctacttcgccgctaagggct ccccactgtatgacagttaccccaaccacttcttcgaggacgtaaagaccctggccattgacgccaaggatatcagcgccctgaaaaccaccatcg acagtgagaagcccacctacctgatcatccggggcctgagcggcaacggctctcagcttaacgagctgcagctgcctgagagcgtgaaaaaggt gagtctatacggcgactacaccggcgtgaacgtggccaaacagatcttcgccaacgtggtggagctggaattctacagcaccagcaaggccaact ctttcggcttcaacccccctcgtgctgggctccaagacaaacgtgatctacgacctgtttgcttctaaacctttcacccacatcgacctcacccaggtga ccctgcaaaatagcgataacagcgccatcgacgccaacaagctgaagcaggctgttggagatatctataactaccggagattcgaaagacagttcc aaggctatttcgccggcggctacatcgacaaatacctggtgaaaaacgtgaataccaacaaggacagcgacgatgacctggtgtacagatctctga aggagctgaacctgcacctggaagaggcctacagagaaggcgacaacacatactacagagtgaacgagaactactacccaggagcttctatcta cgagaatgaaagagccagcagagactctgagttccagaacgagatcctgaagcgggccgagcagaacggcgtgaccttcgacgagaatatcaa gagaatcaccgcctccggcaagtacagcgtgcagtttcagaagctggaaaacgatacagactccagcctggaacggatgacaaaggccgtgga gggcctggtgaccgtgatcggcgaggaaaaattcgaaaccgtggacatcaccggcgtctccagcgataccaacgaggtgaagagcctggccaa ggaactgaagaccaacgccctgggagtgaagctgaagctataa

55) SEQ ID NO: 55

Artificial
armY-Myelin and lymphocyte protein fusion protein codon-optimized (for human) nucleotide
sequence (2,127 bp)

atgtacagaatgcagctgctgagctgcatcgccctgtccctggccctggtgaccaatagcatggcccctgccgccgctaccggcggta gcacactgcctagcggcttcagcgtgtttacaacactgcctgacctgctctttatcttcgagttcatcttcggcggcctggtgtggatcctggtggcctc -continued tagcctggtcccttggcccctggtgcagggctgggtcatgttcgtgtccgtgttctgcttcgtggcaacaaccacactgatcatcctgtacattatcgg cgcccacggtggcgagacaagctgggtgacactggacgccgcttatcattgtaccgccgctctgttttacctgtcagcaagcgtgctggaagccctt gccaccatcaccatgcaggatggctttacctacaggcactaccacgagaacatcgccgccgtggtgttctcctacatcgccacactgctgtatgtcgt gcacgccgtgttcagcctgattagatggaagtccagcggcggcggcggatctggcggaggcggaagcggcggcggaggctctaccaacctgg tgaaccagagcggatacgccctggtggcctctggcagaagcggaaacctgggcttcaaactgttcagcacccagtccccaagcgccgaggtgaa actgaagagcctgagcctgaatgacggcagctaccagagcgagattgacctctctggtggagccaatttcagagagaagttccggaacttcgcca acgaactgtctgaagccatcaccaacagcccaaaaggcctcgatagaccagtgcccaagaccgaaatcagcggactgatcaagaccggcgata atttcattacccctagctttaaggctggctattacgaccacgtggcttctgacggcagcctgctgagctactaccagagcaccgagtactttaacaata gagtgctgatgcctatcctgcagaccaccaacggcaccctgatggccaacaacagaggttacgacgacgtgttcagacaggtgcctagcttcagc ggctggtccaacaccaaggcgactaccgtctccacaagcaacaacctgacctacgataagtggacctacttcgccgcaaagggctctcctctgtac gacagctaccccaaccacttcttcgaagatgtgaagaccctggctatcgatgctaaagatatcagtgccctgaagacaacaatcgacagcgagaaa cctacctacctgatcatcagaggcctgagcggaaatggctcgcagctgaacgagctgcagctgcctgagtccgtgaaaaaggtgtccctctacgg cgactataccggcgtgaacgttgccaagcagatctttgctaatgtggttgagctggagttctacagcacctctaaggccaattcttttggcttcaacccc ctggtgctgggcagcaagaccaacgtgatctacgacctgttcgccagcaagcccttcacccacatcgatctcacccaagtgacactgcaaaactcc gacaacagcgccatcgacgccaacaagctgaagcaggccgtgggcgatatctacaactacagacggttcgagagacagttccagggatatttcg ccggcggctacatcgacaagtacctggtcaagaacgtgaacacgaacaaggatagcgatgacgacctggtgtaccggagcctgaaggaactga acctgcacctggaagaggcttaccgggaaggcgacaacacctactaccgcgtgaatgaaaactactaccctggcgccagcatctacgagaacga gcgggcctcccgggacagcgaattccagaatgaaatcctgaaaagagccgagcagaacggggtgaccttcgacgagaacatcaagcggatcac cgccagcggcaagtactccgtgcagttccaaaagctggaaaacgataccgacagcagcctggaaagaatgactaaggccgtcgagggcctggtt acagtgatcggcgaggaaaaatttgagacagtggacatcacaggcgtcagcagcgacacaaacgaggtgaagtctctggccaaggagctgaag accaacgcccttggagttaagctgaagttataa

56) SEQ ID NO: 56

Artificial
armY-Complement factor H fusion protein codon-optimized (for human) nucleotide sequence
(5,307 bp)

atgtacagaatgcagctgctgtcctgcatcgccctgtctctggccctggttaccaattcagaagattgcaacgagctgcctcctcggcgg aacaccgaaatcctgaccggatcctggagcgaccagacataccccgagggcacccaggccatttacaagtgtcggcctggctacaggtcactgg ggaacgttatcatggtgtgccggaaaggcgagtgggtggccctgaaccctctgcggaagtgccagaaacggccatgtggccaccctggcgaca cccctttcggaaccttcaccctcacaggtggcaacgtctttgagtacggcgtgaaagccgtttacacatgcaatgagggataccagctgctcggaga -continued gatcaactacagagagtgtgataccgacggatggaccaacgacatccccatctgtgaagtggtgaagtgcctccctgtcacagcccctgaaaacg gcaagatcgtgtcttctgctatggagcctgatagagaatatcactttggccaggccgtgagattcgtgtgcaactctgggtacaaaatcgagggagat gaggaaatgcactgctctgatgacggcttctggagcaaggaaaagcctaagtgcgtggagatcagctgcaagagtcctgacgtgatcaacggctc ccctatctcacagaagatcatttacaaggagaacgaaagattccagtacaaatgtaacatgggatacgagtactctgaaagaggtgatgccgtttgta ctgaatccggctggcggcctctgcctagctgcgaggagaagagctgtgacaatccttacatccccaatggagattacagccctctcagaatcaagc accgcaccggcgacgagatcacctaccagtgtcgcaacggattttaccccgctacccggggcaacaccgccaagtgtacctccacaggctggat ccctgcccccagatgcaccctgaaaccctgcgactaccctgatatcaagcacggcggcctgtatcacgagaacatgagaagaccttacttccctgt ggccgtgggcaagtactactcttattactgcgatgaacactttgaaacccctagcggcagctactgggatcacatccactgtacccaggatggctgg tctccagctgtgccatgtctgcgcaagtgctacttcccctacctggaaaacggctacaaccagaactacggtagaaagttcgtgcagggcaagtcta tcgacgtggcatgccaccccggctacgccctacctaaggctcagaccacagtgacctgtatggaaaacggttggtctcccaccccacgctgcatcc gggtgaagacctgctccaagtcttctatcgatattgaaaacggcttcatctctgaatcccaatacacctatgctctgaaggaaaaggccaagtaccag tgtaagctgggatacgtgaccgccgacggcgagacatctggctccatcacctgtggcaaggacggctggagcgcacagcccacatgcattaagt cttgcgacatcccggtgttcatgaacgccagaaccaagaacgatttcacctggttcaagctgaacgacacactggattacgagtgtcacgacggata tgaaagcaataccggcagcaccaccggcagcatagtgtgcggctacaacggctggagcgatctgcccatctgctacgaaagagaatgcgagctg cctaagatcgatgtgcacctggtgcccgatcggaagaaggaccagtacaaggtgggcgaagtgctgaagtttagctgcaagcccggattcacaat cgtgggaccaaattctgtgcagtgctaccacttcggcctgagccccgacctgcccatctgcaaggaacaagtgcagagctgtggacctcctcctga gctgctgaacggaaacgtgaaagagaagacaaaggaggagtacggccattctgaggtggtcgagtactactgtaaccctagattcctgatgaagg gccctaacaagatccaatgcgtggacggagagtggaccaccctgcccgtttgcatagtggaggaaagcacctgtggcgacatcccggaactgga acacggctgggcccagctgagcagccctccctactactacggcgattctgtcgaatttaactgtagcgagtcattcaccatgatcggccatagaagc attacttgcatccacggagtgtggactcagttacctcagtgcgttgccatcgacaagctgaagaagtgtaaatctagcaacctgatcattctggaaga acacctgaagaacaagaaagaattcgaccacaattcaaacatcagatacagatgccggggcaaagagggctggatccacaccgtgtgcatcaac ggcagatgggaccccgaggtgaactgcagcatggcccagatccagctgtgtcctcctcccccccagatcccaaacagccacaacatgaccacca cgctgaactaccgagacggcgagaaggtgagcgtgctgtgccaggagaactacctgatccaggagggcgaagagatcacatgtaaggacggtc gttggcagagcatcccccctgtgcgttgaaaagatcccctgcagccagcctcctcaaatcgagcacggcaccatcaacagctccagatcctcccag gagtcctacgcccacggcacaaaactgagctacacatgcgaaggcggattccggatttctgaagagaacgagaccacctgctacatgggcaagt ggagctctccccctcaatgtgagggcctgccttgcaagagccctcctgagatcagccacggcgtggttgcccacatgtctgatagctaccaatacg gcgaggaagtgacttataagtgcttcgaggggtttgggatcgatggtcccgccattgccaagtgcctgggagaaaaatggtctcatccaccatcatg -continued tatcaagaccgactgcctgagtttgcctagctttgagaatgctatccctatgggcgagaagaaggacgtatacaaagccggcgagcaggtgacata cacatgtgccacctactacaaaatggacggcgccagcaatgtaacgtgtataaatagcagatggacaggcagacctacctgcagagatacaagct gcgtgaatcctcccacagtccaaaatgcttatatcgtgagtcggcagatgagcaagtaccctagcggcgagagagtgagataccagtgcaggtcc ccctacgagatgttcggcgacgaggaggtgatgtgcctaaacggcaactggacggaacctcctcagtgcaaagacagcaccggaaaatgcggc cctcctcctcctattgacaacggcgatatcaccagattccactgagcgtgtacgctcctgcttcatctgtcgagtaccaatgccagaatctgtaccag ctggaaggtaataagagaatcacctgcagaaacggacagtggagcgaacctcctaagtgcctgcacccttgcgtgatctccagagagatcatgga aaactacaacatcgccctgagatggaccgccaaacagaagctgtacagccggaccggcgagagcgtcgagttcgtgtgtaagagaggttaccga ctgtcctctagaagccataccctgcggaccacctgctgggacggcaaactagagtaccctacgtgcgccaagcggggcggaggtggctcagga ggcggcggctctggcggcggcggctctacaaacctggtgaaccagagcggttatgccctggtggccagcggcaggtctggaaatctgggcttta agctgttttcaacgcagagcccttccgccgaagttaagctgaaatcactgagcctgaatgacggctcctaccagagcgagatcgacctgtctggag gagctaactttagagagaagttcaggaacttcgctaacgagctgagcgaagccatcaccaatagccctaaaggcttggacagacctgtgcccaag actgagatcagcggcttgatcaagaccggcgacaacttcatcaccccatcttttaaggccggctactacgaccacgtggcctctgacggaagcctg ctatcctactatcagtctactgagtacttcaacaacagagtgctgatgcctatcttgcagaccaccaatggcaccctgatggccaacaaccggggata tgacgatgtgttcagacaggtgcctagcttcagcggatggagcaacaccaaggcgacaaccgtgagcacatccaacaacctgacatacgacaagt ggacatattttgcggccaagggctctccactgtatgatagctaccccaatcacttcttcgaggacgtgaagaccctggccatcgacgccaaagacat cagcgcccttaagacaacgatcgattccgagaagcctacctacctgatcattagaggcctgagcggcaacggcagccagctgaacgagctgcag ctgccagagtccgtgaagaaagtgtccctgtatggcgactacacaggcgtcaacgtggccaagcaaatcttcgctaatgtggtggaacttgagttct acagcacatcgaaggctaactctacggcttcaacccccctggtgctgggcagcaagaccaatgtgatttacgacctgttcgccagcaagcccttcac acacatcgacctgacccaagtgacactgcaaaacagcgataacagcgccatcgacgccaacaagctgaagcaggctgtgggcgacatctacaa ctaccggagattcgagagacagttccagggctacttcgccggcggctacatcgataagtacctggtgaagaacgtgaataccaacaaagactctga tgacgacctggtgtacagaagcctgaaagagctgaacctgcatctggaagaagcctaccgggagggcgataacacctactaccgggtgaacgaa aactactatcctggcgctagcatctacgagaacgaacgagccagcagggattctgaattccagaacgagatcctgaagcgggccgagcagaacg gagtgacatttgatgagaacatcaaacggatcaccgccagcggcaaatactccgttcagttccaaaaactggaaaatgatacagacagcagcctgg agagaatgaccaaggccgtggaaggcctggtgacggtgatcggcgaagagaaattcgagaccgtggacatcaccggcgtaagctctgacacca acgaagtgaagagcctggctaaggaactgaagaccaacgccctgggggtcaagctgaagctgtaa -continued Artificial
armY-Hepatocyte growth factor receptor fusion protein codon-optimized (for human)
nucleotide sequence (4,392 bp)

57) SEQ ID NO: 57 atgtaccggatgcaactgctgagctgcatagccttatctctggcactggtgaccaacagcgagtgcaaggaagccctcgccaagagtg aaatgaacgtgaatatgaaataccagctgcctaacttcaccgccgaaacccctatccagaacgtcatcctgcatgagcaccacatcttcctgggcgc tacaaattacatctacgtgctgaatgaggaggacttgcagaaagtcgccgaatacaagaccggacccgtgctggagcacccggactgcttcccatg tcaggattgcagttctaaggccaacctgagtggtggcgtttggaaggacaacatcaacatggccctggtggtcgacacatattacgacgatcagctg attagctgtggcagcgtgaaccggggcacctgccagagacacgtgttccctcacaaccacactgccgacatccagagcgaagtgcactgcatctt cagcccccagatcgaggagcctagccagtgtcctgactgcgtggtgtcagccctgggtgctaaggtactgtccagcgttaaggacagattcatcaa ctttttcgtgggtaacacaatcaacagcagctacttccccgatcaccctctgcacagcatatccgtgcggagactcaaggaaacaaaggacggcttc atgttcctgacagaccagagctatatcgatgtgctgcctgagttcagagattcttaccccatcaagtacgtgcacgccttcgagagcaacaattttatct atttcctgacagtccaaagggagacactcgatgcccagaccttccacaccagaatcatccggttctgcagcattaacagtggactgcactcttatatg gaaatgcccctggaatgtatcctcacagagaaaaggaagaaaagaagcactaagaaggaggtgttcaacattctgcaggctgcttacgtgtccaag cctggcgctcagctggccagacagatcggcgccagcctgaacgatgacatcctgttcggcgtcttcgcccaatctaagcctgacagcgccgagcc catggacagatctgctatgtgcgctttccccatcaagtacgtgaatgacttcttcaacaagatcgtgaacaagaacaacgtgcggtgcctgcaacact tctacggccctaaccacgagcactgttttaatagaaccctactgcggaactcctctggttgtgaagctagaagagacgaataccggaccgagttcac caccgccctgcagagggtggacctgttcatgggccaattcagcgaggtcctgctgacatctataagcaccttcatcaagggagatctgacaatcgc caacctgggcaccagtgagggcagattcatgcaggtggtggtgagtagatccggccctagtacaccccatgttaacttcctgctggactcacaccc cgtgtcccctgaggtgatcgtggaacatacactgaaccagaatggctatacactggtgatcaccggaaagaagattaccaagattcctctgaacgg cctgggctgcagacacttccagagctgtagccagtgcctgagcgcccctccttttgtgcagtgcggctggtgccacgacaagtgcgtgcgcagcg aggagtgcctgagcggcacctggacacagcagatctgtctgcctgccatctacaaggtctttccaaacagcgccccattggaaggcggaactcgg ctgacaatctgcggctgggacttcggctttcggcggaacaacaagtttgacctgaagaagacccgggtgctgctgggcaacgagagctgtaccct gaccctgagcgaaagcaccatgaacacgctgaaatgcaccgtgggcccagccatgaacaaacacttcaacatgtctatcatcatcagcaatggcc acggcacaacccagtacagcacgttcagctacgtggaccctgtgatcaccagcatctcaccgaagtacggccctatggccggcggcacattgctg accctgaccggaaattatctgaactcgggcaacagccgtcacatctccataggcggaaagacatgcacgctgaagtcggtgtctaacagcatcctg gagtgctacacaccagcccagaccatctcgacagaattcgctgtaaagctgaagatcgatctcgctaatcgagagacaagcatcttttcttacagag aggatcctatcgtgtacgagatccaccctacaaagtctttcatcagcggcggcagcaccatcacaggcgtgggaaaaaacctgaactctgtgtctgt gccgagaatggtgatcaacgtgcacgaggctggcagaaacttcacagtggcctgccagcatagaagcaacagcgaaatcatctgctgcaccacc -continued ccctcgctgcagcagcttaatctgcagctgcccctgaaaacgaaggccttcttcatgctggatgggatcctgtctaagtacttcgatctcatctacgtg cacaatcctgtgtttaagccattcgagaagcccgtcatgatctctatgggcaacgagaacgtgctcgagatcaagggcaatgatatcgaccctgagg ccgtgaaaggcgaggtgctgaaagtgggcaacaaaagctgcgaaaacatccacctgcacagcgaagccgtgctgtgcaccgtgcctaacgactt gctgaagctgaactccgagctgaatatcgagtggaagcaggccatcagctctaccgtcctgggcaaggtgattgtgcaacctgaccagaacttcac cggcggtggcggtagtggaggcggcgggagcggaggcggaggaagcaccaacctggtgaaccagagcgggtacgccctggtagctagcgg cagaagcggcaacctgggctttaagctgttttctacccagagccctagcgccgaagtgaagctgaagagcctgagcctgaacgacggcagttacc aatccgagatcgacctgtctggcggcgccaacttcagagagaagttcagaaacttcgctaatgagctgtctgaggccatcaccaacagccctaagg gcctggatagacctgtgccaaagaccgagatctccggcctgatcaaaaccggcgataactttatcacacctagctttaaggccggctactacgacc acgtggcctccgacggctccctgctgtcctactaccagagcacagaatacttcaacaacagagtgctgatgcctatcctgcaaaccacaaacggca ccctgatggccaacaacagaggctacgacgatgtgttccggcaggtgcctagcttctccggctggagcaacaccaaggccactaccgtttctacca gtaacaacctgacctacgataagtggacctactttgccgccaagggcagcccccctgtacgactcataccccaatcacttctttgaagatgtgaagac cctggccatcgatgccaaagatatcagcgctctgaaaacaaccatcgactccgagaagcccacctaccttattatcagaggcctgtccggcaacgg ctctcagctgaatgagctgcagctcccagaaagcgtgaagaaggtgtcgctgtacggcgactacaccggcgtcaatgtggccaaacagatatttgc caacgtagtagaattggaattctactctacaagcaaagccaactcttttggatttaaccccttagtgctaggatctaagacaaacgtgatctacgacctg ttcgccagcaaacctttcacccacatcgacctgacccaagtgaccctgcagaacagcgacaacagcgctatcgacgccaacaagctgaagcagg ccgtcggcgatatatacaattaccggcggttcgagagacagttccagggctacttcgccggaggatacatcgacaagtacctggtgaagaacgtga acactaataaggacagcgacgacgacctcgtgtacagaagcctgaaagaactgaatctgcacctggaagaagcctaccgggaaggagacaaca cctactacagagtgaacgaaaactactaccctggcgccagcatctatgagaacgagagagccagcagagattctgaattccagaacgagattctga aacgggccgagcagaatggcgtgaccttcgacgagaatattaagcgcatcaccgccagcggcaaatattccgtccagtttcagaagctcgagaac gacaccgacagcagcctggaaagaatgaccaaggccgtggaaggcctggtgaccgtgatcggcgaggaaaaattcgagaccgtggatatcacc ggcgtgagcagcgacacaaacgaagtgaagagcctggccaaggaactgaagaccaacgccctgggagtgaagctcaagctgtaa

58) SEQ ID NO: 58

Artificial
armY-Membrane cofactor protein (CD46) fusion protein codon-optimized (for human)
nucleotide sequence (2,595 bp)

atgtaccgcatgcagctgctgagctgcatcgccctgtctctggctctggtgaccaacagctgcgaggaacctccaaccttcgaggccat ggaactgatcggcaagccaaagccctactatgagattggcgaaagagtggattacaaatgcaagaaaggctacttttacatcccccccctggccac ccacaccatctgtgatagaaaccacacatggctgcctgtctccgacgacgcctgttaccgggagacatgcccttacatccgagaccctctcaatgga caggccgtgcctgctaatggcacatatgagttcggataccaaatgcacttcatctgcaacgagggctactacctgatcggcgaagaaatcctgtact -continued

```
gcgagctgaaaggctcggtggctatttggtccggcaaacctcctatctgtgaaaaggtgctgtgcacccctcctcctaagatcaaaaacggcaagc
acacctttagcgaggtggaagtgttcgagtacctggatgccgtgacatatagctgtgaccccgcccctggccctgatcccttcagcctgattggcga
gagcaccatctattgcggcgataactctgtgtggagccgggccgcccctgaatgcaaggtggtgaagtgcagattccctgtggtggaaaacggaa
agcagatctccggctttggcaaaaagttctactataaggctaccgtgatgttcgagtgcgacaagggattctacctggacggctctgatacaatcgtg
tgcgacagcaactctacgtgggaccctccagtgcctaagtgtctgaaagttctgcctcctagctctacaaagccccccgccctgagccacagcgtgt
ccaccagcagcacaaccaagtccccagccagcagcgccagcggacctagacccacctacaagcctcctgtgtccaactaccctggctaccccaa
gcctgaggaaggcatcctggatagcctggatggcggcggcggctccggcggtggaggatctggcggcggaggaagcacattatctggtgaatc
agagcggctacgccctggttgccagcggcagaagcggcaacctgggcttcaagctgtttagcacacagagccccagcgccgaggtgaagctga
agagcttgtcgctaaatgatggctcctaccagtctgagatcgatctgagcgggggcgccaattttagagagaagttccggaacttcgcaaacgagct
gtctgaagccatcaccaacagccctaaggggctggacagacctgtgccaaagaccgagattagcggcctcatcaagacaggcgacaatttcatca
cacctagcttcaaggccggatactatgaccacgtggcctccgacggcagcctgctgagctactaccagagcacagagtacttcaacaacagagtg
ctgatgcctatcctgcagaccaccaacggcaccctcatggccaacaatcggggctatgacgacgtgttcaggcaggtgcctagcttcagcggctg
gagcaacaccaaggccaccactgtgtctacctccaacaacctgacctacgacaagtggacctacttcgcagctaaaggctctccactgtacgatag
ctacccaaaccacttcttcgaggacgtgaagaccctggctattgacgccaaggacatctctgccctgaagaccacaatcgacagcgagaagccta
cctacctgatcatccggggcctgagcggaaacggcagccagctgaacgagctgcagctgcccgagtccgtgaaaaaagtgtccctgtacggcga
ctacaccggcgtgaacgtggccaagcagatcttcgctaatgtggtggaacttgagttctactctaccagtaaggccaactcctttggatttaacccccct
ggtgctgggcagcaagaccaacgtgatctacgacctgttcgcctctaaacctttcacccatatcgacctgacccaggttacactgcaaaacagcgat
aactctgccatcgatgccaacaagctgaagcaagccgtgggcgacatctacaactaccgcagatttgaacggcagttccagggctacttcgccgg
cggctacatcgacaagtacttggtcaagaacgtgaataccaacaaggatagcgacgatgacctggtctaccggagcctgaaggaactgaacctgc
acctggaagaagcctacagagaaggtgacaatacctactatagagtgaacgagaactactacccgggagccagtatctacgagaacgaaagagc
ctctagagatagcgagttccaaaacgagatcctgaaaagagctgaacagaacggcgtgaccttcgacgagaacatcaagagaatcaccgccagc
ggcaagtacagcgtgcagtttcagaagctggaaaacgacaccgacagctccctggaacggatgaccaaggctgttgagggcctggtcacagtga
tcggagaggaaaagttcgaaacagtggatatcacgggcgttagcagcgacaccaacgaggtcaagagcctggccaaagagctgaagacaaac
gccctgggcgtgaagctgaagctgtaa
```

-continued

| | |
|---|---|
| 59) SEQ ID NO: 59 | Artificial<br>armY-Glycophorin-A fusion protein codon-optimized (for human) nucleotide sequence<br>(1,884 bp) |

atgtaccgtatgcagctgctgtcttgcatcgccctcagcctggctctggtgaccaacagctctagcacaacaggcgttgccatgcacac cagcaccagctctagcgtgaccaagagttacatctcttctcagaccaacgatacccacaagagagacacgtacgccgccaccccaagagcccatg aggtgtctgaaatcagcgtgcggaccgtgtacccccccgaggaagaaaccggcgagcgggtgcagctggcccaccacttttctgagcctgaggg aggtggaggcagcggcggcggcggcagcggcggaggcggcagcaccaacctggttaaccagtccggctatgccctggtggctagcggcaga tccggcaacctgggctttaagctgttcagcacccagagccccagcgccgaggtgaaactgaagagtctgagcctgaatgacggctcttatcagag cgagatcgacctgagcggcggcgccaatttcagagagaagtttcggaacttcgccaatgaactgtccgaagccatcaccaacagcccaaagggc ctggacagacccgtgcctaaaacagaaatcagcggactgatcaagaccggcgataatttcatcacacctagcttcaaggccggctactacgacca cgtggccagcgacggctccctcctgagctactaccaaagcacagagtacttcaacaaccgggtgctgatgcctatcctgcagaccacaaatggca ccctcatggccaataacagaggctatgatgacgtgttccggcaggtgcccagctttagcggatggagcaacaccaaggccacaaccgtgtccaca tccaacaacctgacctacgacaagtggacctacttcgctgctaagggcagccctctgtacgactcttaccctaaccacttcttcgaggatgtgaagac gctggctatcgacgccaaggacatctcggccctgaagaccacaatcgacagcgagaagcctacatacctgatcatcagaggactgagcggcaac ggcagccaactgaatgagctgcagctgcctgagagcgtgaaaaaggtgagcctgtacggcgactataccggcgtgaatgtggctaagcagatctt cgccaacgtcgtggaactggaattctacagcaccagcaaggctaactccttcggctttaacccccctggtgctgggctccaaaacaaacgtgatctac gacctgttcgcctccaaacctttcacccacatcgacctgacacaagtgacactgcaaaatagcgataacagcgccatcgacgccaacaagcttaag caggccgtgggcgacatctacaactacagaagattcgagagacagtttcagggctatttcgccggaggctatattgataaatacctggtgaagaac gtgaacaccaacaaagatagcgacgacgatctggtgtacagatctctgaaagagctgaacctgcacctggaagaggcctaccgggaaggagata acacctactacagggtcaacgagaactactaccctggagccagcatctacgagaacgagagagcttctagagatagcgagttccagaatgaaatc ctgaagcgggccgaacagaacggagtgacattcgacgagaacattaagcggatcaccgcctctgggaagtacagcgtgcagttccagaagctg gagaacgacaccgattcttctctggaaagaatgaccaaggcagtcgagggcctggtgaccgtgatcggagaggaaaagttcgagacagtcgaca tcactggcgtgagctcggacaccaacgaggtaaagagcctggccaaggaactgaagaccaacgccctgggcgtgaagctcaaactgtaa

| | |
|---|---|
| 60) SEQ ID NO: 60 | Artificial<br>armY-C-type lectin domain family 4 member K (Langerin, CD207) fusion protein codon-<br>optimized (for human) nucleotide sequence (2,460 bp) |

atgtatcggatgcagctgctgagctgcatcgccttatccctggctctggtgacaaactcccctagattcatgggcaccatcagcgacgtg aaaacgaacgtgcagctgctgaagggaagagtggacaacatctctaccctggattctgagatcaaaaagaactccgatggcatggaagctgctgg cgtgcaaatccagatggtgaatgagagcctgggctacgtgcggtcccagttcctgaagctgaagaccagcgtggaaaaggccaacgcccagatt -continued cagatcctgacaagaagctgggaggaagtgtctacactgaatgctcagatccccgagctgaaaagcgatctcgagaaggctagcgccctgaaca ccaagatccgggccttgcaaggctctctggaaaacatgagcaagctgctgaagagacagaacgatatcctgcaggtcgtgtctcagggctggaag tacttcaagggcaacttctactacctctgatccctaagacctggtactctgccgagcagttctgcgtgtccagaaacagccacctgaccagcgtta ccagtgagagcgagcaggagttcctgtataagacagccggaggcctgatctattggatcggcctgaccaaggccggcatggagggcgattggag ctgggtcgacgacacccctacaacaaagtgcagagcgtgcggttaggatccccggcgagcctaacaacgccggcaacaacgagcactgcggc aatatcaaagcccctagcctgcaggcctggaacgatgccccgtgcgacaagacatactgttcatctgtaaaaggccttacgtgcccagcgaaccc ggcggcggcggcagcggaggcggcggctctggcggaggaggaagcaccaacctggtgaaccagagcggctacgccctggtcgccagcggc agaagcggaaatctgggcttcaagctgtttagcacacagagcccatctgcagaggtgaaactgaagagcctgagcctgaacgacggcagctacc agtctgagatcgacctgtctggcggggccaatttccgggaaaagttccggaacttcgctaacgagctgtctgaagccatcaccaatagtccaaagg gcctggaccggcctgtgcctaagactgagatactggccttatcaagacaggcgacaacttcatcacccctagattaaggccggctactacgacca cgtggccagcgatgggtctctgctgagctactaccagagcacagagtacttcaacaatagagtgctgatgccaatcctgcaaacaacaaatggcac actgatggccaacaaccggggctacgacgatgtgttcagacaggttcctagcttcagcggctggtccaacaccaaggccaccaccgtgagcaca agcaacaacctgacatatgataagtggacctacttcgccgctaagggcagccctctgtacgacagctaccctaaccatacttcgaggacgtgaaga cgctggccattgacgccaaagacatctcggccctgaagaccaccatcgacagcgaaaaacctacctacctgatcatcagaggcctgagcggcaa cggatctcagctgaacgagctgcagctgcccgagagcgtgaagaaggtgagcctctacggcgactacaccggcgtgaacgtggccaagcagat tttcgcaaacgtggtggaactggaattttacagcacctccaaggctaacagcttcggctttaacccccctggtgctgggatctaagaccaatgtgatcta cgacctcttcgcttccaagccctttacccacatcgacctgacccaggtgaccctgcaaaattcagataatagcgccatcgacgccaacaagctgaaa caagccgtgggcgacatctacaactacagaagattcgagcgccagttccagggctattttgctggcggttacatcgacaagtacctggtgaaaaac gtgaacaccaacaaggacagcgacgatgacctggtgtacagatccctgaaagagctgaacctgcacctggaagaggcctacagagagggcgat aatacctactatagagtgaatgagaactactaccctggcgccagtatctacgagaacgaaagagctagcagagacagcgagttccagaacgagat cctgaagcgggccgagcagaatggcgtgaccttcgacgagaacatcaagcggatcacagccagcggcaagtacagcgtgcagttccagaaact ggaaaacgacacagatagcagcctcgagagaatgaccaaggccgtggaaggactggtgaccgtcatcggcgaagaaaagttcgaaacggtgg acatcaccggagtgtcctccgacaccaatgaggtgaagtccctggccaaggaactgaagaccaatgccctcggagtgaagctgaagctataa

61) SEQ ID NO: 61

Artificial
armY-Anthrax toxin receptor 1 fusion protein codon-optimized (for human) nucleotide
sequence (3,264 bp)

atgtacagaatgcagctgttgagctgtatcgccctgagcctggccctggtgaccaacagcgaggacggtggccctgcctgctacggc gggtagacctgtacttcatcctggataagtccggttctgtgctgcaccactggaacgaaatctactacttcgtggaacagctggcccacaagtttatct -continued ccccctcagctgcggatgagcttcatcgtgttctccacaagaggcaccaccctgatgaagctgaccgaggatcgcgagcagatcagacagggactg gaagagctgcagaaagtgctgcctggcggcgatacatacatgcacgagggatttgagagagcctccgagcagatctattacgagaacagacagg gctaccgcaccgccagcgtgatcattgccctgacagacggcgagctgcatgaagatctgttcttctacagcgagcgcgaggccaacagaagccg ggacctgggcgccatcgtgtactgtgtgggcgtgaaggacttcaacgaaacccagctggccagaatcgccgatagcaaggatcacgtgttccctg tgaacgacggattccaggccctgcagggcatcatccacagcattctaaagaagtcctgcatcgagatcctggctgctgaacccagcaccatctgcg ccggcgagagcttccaggtggtggtgcggggcaacggcttccggcacgccagaaacgtggacagagttctgtgcagctttaagatcaatgatagc gtgacacttaacgagaagcccttcagcgtggaagatacctacctgctgtgtcctgctccaatcttaaaagaggtgggaatgaaagccgccctgcaa gtgtccatgaacgatggcctctcttttatcagttccagcgtgatcatcaccacaacccactgttctgatggtagcatcctggccatcgccctgctcatcc tgtttctgctgctggccttggccctgctgtggtggttctggcctctgtgctgcaccgtgatcatcaaagaagtgcctcctcctcccgctgaagagagcg aagaggaggacgacgacggcctgcctaagaaaaagtggcccacagtcgatgcttcttactacggcggcagaggcgttggcgggatcaagcgga tggaagtgcggtggggagaaaagggcagtaccgaggaaggagctaagctggaaaaggccaagaatgccagagtgaagatgcctgagcagga gtacgagttccccgagcctcggaacctgaacaacaacatgagacggccctcctctccaagaaagtggtacagccctatcaagggcaagctggac gccctctgggtcctgctgagaaagggctacgacagagtgagcgtgatgcggccccagcctggcgacactggcagatgcatcaactttaccaggg tgaagaacaaccagcctgccaagtacccccctgaacaacgcctaccacacaagctctcctcctcccgctcccatctacactccgcccccccagcc ccacactgccctcccccaccaccctctgcccctacccctcccatccccagccccccttcaaccctgcctcccccctccgcaagcccctccaccaaac agagcacctccacctagcagacccccctcctagaccttctgtgggcggcggcggcagcggcggaggcggcagcggcggaggcgggagcacca acctggtgaaccagagcggctacgccctggtggcctccggcagaagcggcaacctgggcttcaagctgttctcgacccagagcccttctgccga ggtgaagctgaaaagcctgtcactgaatgacggctcttaccagagcgagatcgacctgagcggcggagctaacttcagagaaaagttccggaact tcgccaacgagctgtctgaggccatcaccaacagccctaagggcctggacagacccgtacccaagaccgagatcagcggactgattaagacgg gcgacaacttcatcacaccttccttcaaggctggatactacgatcatgtggccagcgacggcagcctgctgagctactaccagtccacagagtactt caacaacagagtcctgatgcctatcctccagaccaccaatggcaccctgatggccaacaatagaggctacgacgacgtgttcaggcaggttccttc tttctccggctggagcaacacaaaggccaccacagtgagcacaagcaataacctcacctacgacaaatggacctacttcgctgccaagggcagcc ccctctacgactcttatcctaaccactttttcgaggatgtgaaaacactggctatcgatgccaaggacatcagcgcccttaaaacaacaatcgactccg agaaacctacctacctgatcatcagaggcctgtccggcaatggcagccagctgaacgagctgcaactgcctgaaagcgtgaaaaaagtgagcct gtatggggactacaccggcgtgaacgtggccaagcagatcttcgccaatgtggtggaactggagttctacagcactagcaaggccaattctttcgg ctttaacccccctggtgctgggcagcaagacaaacgtgatctacgatctgttcgccagcaagcctttcacccacatcgacctgacacaggtgacgctg cagaacagcgacaacagcgccatcgacgccaacaagctgaagcaggccgtgggcgacatttacaactaccggagattcgagagacaatttcag -continued ggctatttcgccggcggatacatcgacaagtatctggtcaaaaatgtgaataccaacaaggatagcgacgacgacctggtataccggtccctgaaa gaactgaacctgcacttggaggaagcctacagagagggcgacaatacctactatagagtcaacgagaactactaccctggcgcctccatctacga aaatgaacgggcctctagagactctgagttccaaaacgagatcctgaaaagagcagagcagaatggcgtcaccttcgacgagaacatcaagcgc attaccgccagcggaaagtactccgtgcagttccagaagctggagaacgataccgacagctctctggaacggatgaccaaggccgtggagggac tggtcaccgtgatcggcgaagagaagttcgaaaccgtggacatcaccggcgtgtcttctgacacaaacgaagtgaaaagcctggctaaagagctg aagacaaacgccctgggagtgaagctgaagctgtaa

62) SEQ ID NO: 62

Artificial
armY-Anthrax toxin receptor 2 fusion protein codon-optimized (for human) nucleotide
sequence (2,523 bp)

atgtacagaatgcagctgctctcttgcattgccctgagcctggccctggtgaccaatagccaggagcaacctagctgcagaagagcctt cgacctctacttcgtgctggataagtccggcagcgtcgccaacaattggatcgagatctacaacttcgtacagcagctggccgaacgcttcgtgagc cccgagatgagactgagcttcatcgtgttctcttcccaggccaccatcatcctgcctctgaccggcgacagaggcaaaatctcaaagggcctggaa gatctgaaaagagtgtcccccgtcggcgagacatacatccacgagggcctgaagctggccaatgaacagatccagaaggccggcggactgaag accagcagcatcatcattgccctgaccgacggcaaactggacggcctggtccctagctacgccgagaaggaagccaagatcagccggagcctg ggcgcttctgtgtactgcgtgggagtgctggacttcgagcaggctcaactggagaggatcgctgatagcaaggagcaggttttcccagtgaaagg cggctttcaagccctgaaaggcatcatcaacagcatcctggcccagagctgtacagagatcctggaactccagcctagcagcgtgtgcgtcggcg aagagttccagatcgtgttaagcggcagaggcttcatgctgggcagcagaaacggcagcgtgctgtgcacatacaccgtcaatgagacctacaca acaagcgtgaagcccgtgtccgtgcagctgaatagcatgctgtgtcctgcccctatcctcaacaaggccggcgaaaccctggacgtgtccgtgtctt tcaatggcggcaagagcgtaatctccggctctctgatcgtgacagccaccgagtgcagcaacggaggcggaggcggatctggtggcggaggat cgggcggtggcggtagcaccaacctggtgaaccagtcaggctacgcccttgtggccagcggaagatccggcaacctgggctttaagctgttttcta cacagagcccatctgctgaagtgaagctgaagtctctcagcctgaacgacggctcttatcagtccgagatcgatctgagcggaggagccaatttcc gggagaagttcagaaactttgctaatgagctgagcgaagccatcacaaacagccctaagggcctggatagacctgtgcccaagaccgagatcag cggactgatcaagacaggcgacaacttcatcaccccaagcttcaaggctggctactatgaccacgtggcctctgatggatccctgctgtcttattacc agagcacagaatacttcaacaacagagtgctgatgcctatcctgcaaaccaccaatggaacgctgatggccaacaaccggggctacgatgacgtg ttcagacaggtgcctagcttcagcggatggagcaacaccaaggccacaacagtcagcacctctaacaacctgacctacgacaagtggacctacttt gccgctaagggctctccactgtacgatagctaccccaaccacttctttgaggacgtgaagacactggccatcgatgccaaagacatatctgcgctga agaccaccatcgacagcgagaagcctacatatctgatcatcagaggcttgagcggcaacgggtctcagctgaacgagcttcagctgcctgagagc gtgaaaaaggtgagcctgtacggcgactacaccggcgtgaacgtggccaagcagatcttcgctaacgtggtggaattagagttctacagcaccag -continued caaggccaacagcttcggcttcaacccctggtgctgggctctaagacaaacgtgatctacgatctgttcgccagcaaacccttcacccacatcgat ctgacccaggtgaccctgcagaactccgacaacagcgccatcgacgccaacaagctgaaacaggccgtgggcgacatctacaattaccggagat tcgagcggcaattccagggctactttgcgggcggctacatcgacaagtacctggtgaagaacgtgaacacgaacaaggacagcgacgacgacct ggtgtaccggagccttaaggagctgaacctgcatctggaagaagcctaccgggagggcgataacacatattaccgggtgaatgagaactactacc ctggcgccagcatctacgagaacgagagagccagcagagatagcgaattccaaaacgaaatcctgaagcgggccgagcagaacggcgtgactt tcgacgagaatattaagagaatcaccgcctccggaaagtacagcgtgcagtttcagaaactggaaaacgatacagactcaagcttggagcgcatg accaaggccgtggaaggcctggtgaccgtaatcggcgaggaaaaattcgaaaccgtggacattaccggcgtgtcttctgacaccaacgaggtga agagcctggctaaagagctgaagaccaacgccctgggcgtcaagctgaagctgtaa

63) SEQ ID NO: 63

Artificial
Protein M with radiolabel peptide tag (KGRPLVY) protein sequence (555 amino acids).
Including the human IL-2 signal sequence, radiolabel tag, linker, Mycoplasma genitalium
protein M

MYRMQLLSCIALSLALVTNSKGRPLVYGGSGGGGSTNLVNQSGYALVASGRSGNLG

FKLFSTQSPSAEVKLKSLSLNDGSYQSEIDLSGGANFREKFRNFANELSEAITNSPKGLDRPVP

KTEISGLIKTGDNFITPSFKAGYYDHVASDGSLLSYYQSTEYFNNRVLMPILQTTNGTLMANN

RGYDDVFRQVPSFSGWSNTKATTVSTSNNLTYDKWTYFAAKGSPLYDSYPNHFFEDVKTLAI

DAKDISALKTTIDSEKPTYLIIRGLSGNGSQLNELQLPESVKKVSLYGDYTGVNVAKQIFANV

VELEFYSTSKANSFGFNPLVLGSKTNVIYDLFASKPFTHIDLTQVTLQNSDNSAIDANKLKQA

VGDIYNYRRFERQFQGYFAGGYIDKYLVKNVNTNKDSDDDLVYRSLKELNLHLEEAYREGD

NTYYRVNENYYPGASIYENERASRDSEFQNEILKRAEQNGVTFDENIKRITASGKYSVQFQKL

ENDTDSSLERMTKAVEGLVTVIGEEKFETVDITGVSSDTNEVKSLAKELKTNALGVKLKL

64) SEQ ID NO: 64

Substitution #1: Alanine mutagenesis (underlined “A”) of a) 494-507 amino acid (highlighted
in green) and b) 527-540 amino acid (highlighted in green) predicted to be immunogenic in
Protein M (469-556 amino acid). See SEQ ID NO: 1 for the original sequence (37-556 amino acids).

TNLVNQSGYALVASGRSGNLGFKLFSTQSPSAEVKLKSLSLNDGSYQSEIDLSGGANF

REKFRNFANELSEAITNSPKGLDRPVPKTEISGLIKTGDNFITPSFKAGYYDHVASDGSLLSYY

QSTEYFNNRVLMPILQTTNGTLMANNRGYDDVFRQVPSFSGWSNTKATTVSTSNNLTYDKW

TYFAAKGSPLYDSYPNHFFEDVKTLAIDAKDISALKTTIDSEKPTYLIIRGLSGNGSQLNELQLP

ESVKKVSLYGDYTGVNVAKQIFANVVELEFYSTSKANSFGFNPLVLGSKTNVIYDLFASKPFT

-continued

HIDLTQVTLQNSDNSAIDANKLKQAVGDIYNYRRFERQFQGYFAGGYIDKYLVKNVNTNKD

SDDDLVYRSLKELNLHLEEAYREGDNTYYRVNENYYPGASIYENERASRDSEFQNEILKRAE

QNGVTFDENIKRITASGKYSVQFQALANATASALAAMTKAVEGLVTVIGEEKFETVAIAGVA

SATNAVASLAKELKTNALGVKLKL

Substitution #2: Alanine mutagenesis (underlined "A") of a) 494-507 amino acid (highlighted in green) and b) 527-540 amino acid (highlighted in green) predicted to be immunogenic in Protein M (469-556 amino acid). See SEQ ID NO: 1 for the original sequence (37-556 amino acids).

65) SEQ ID NO: 65

TNLVNQSGYALVASGRSGNLGFKLFSTQSPSAEVKLKSLSLNDGSYQSEIDLSGGANF

REKFRNFANELSEAITNSPKGLDRPVPKTEISGLIKTGDNFITPSFKAGYYDHVASDGSLLSYY

QSTEYFNNRVLMPILQTTNGTLMANNRGYDDVFRQVPSFSGWSNTKATTVSTSNNLTYDKW

TYFAAKGSPLYDSYPNHFFEDVKTLAIDAKDISALKTTIDSEKPTYLIIRGLSGNGSQLNELQLP

ESVKKVSLYGDYTGVNVAKQIFANVVELEFYSTSKANSFGFNPLVLGSKTNVIYDLFASKPFT

HIDLTQVTLQNSDNSAIDANKLKQAVGDIYNYRRFERQFQGYFAGGYIDKYLVKNVNTNKD

SDDDLVYRSLKELNLHLEEAYREGDNTYYRVNENYYPGASIYENERASRDSEFQNEILKRAE

QNGVTFDENIKRITASGKYSVQFAKLANATASALARMTKAVEGLVTVIGEEKFETVAIAGVA

SATNAVKSLAKELKTNALGVKLKL

Substitution #3: Alanine mutagenesis (underlined "A") of a) 494-507 amino acid (highlighted in green) and b) 527-540 amino acid (highlighted in green) predicted to be immunogenic in Protein M (469-556 amino acid). See SEQ ID NO: 1 for the original sequence (37-556 amino acids).

66) SEQ ID NO: 66

TNLVNQSGYALVASGRSGNLGFKLFSTQSPSAEVKLKSLSLNDGSYQSEIDLSGGANF

REKFRNFANELSEAITNSPKGLDRPVPKTEISGLIKTGDNFITPSFKAGYYDHVASDGSLLSYY

QSTEYFNNRVLMPILQTTNGTLMANNRGYDDVFRQVPSFSGWSNTKATTVSTSNNLTYDKW

TYFAAKGSPLYDSYPNHFFEDVKTLAIDAKDISALKTTIDSEKPTYLIIRGLSGNGSQLNELQLP

ESVKKVSLYGDYTGVNVAKQIFANVVELEFYSTSKANSFGFNPLVLGSKTNVIYDLFASKPFT

HIDLTQVTLQNSDNSAIDANKLKQAVGDIYNYRRFERQFQGYFAGGYIDKYLVKNVNTNKD

SDDDLVYRSLKELNLHLEEAYREGDNTYYRVNENYYPGASIYENERASRDSEFQNEILKRAE

QNGVTFDENIKRITASGKYSVQFQALEADADSALEAMTKAVEGLVTVIGEEKFETVDIAGVS

ADTAEVASLAKELKTNALGVKLKL

-continued

Substitution #4: Alanine mutagenesis (underlined “A”) of a) 494-507 amino acid (highlighted in green) and b) 527-540 amino acid (highlighted in green) predicted to be immunogenic in Protein M (469-556 amino acid). See SEQ ID NO: 1 for the original sequence (37-556 amino acids).

67) SEQ ID NO: 67

TNLVNQSGYALVASGRSGNLGFKLFSTQSPSAEVKLKSLSLNDGSYQSEIDLSGGANF

REKFRNFANELSEAITNSPKGLDRPVPKTEISGLIKTGDNFITPSFKAGYYDHVASDGSLLSYY

QSTEYFNNRVLMPILQTTNGTLMANNRGYDDVFRQVPSFSGWSNTKATTVSTSNNLTYDKW

TYFAAKGSPLYDSYPNHFFEDVKTLAIDAKDISALKTTIDSEKPTYLIIRGLSGNGSQLNELQLP

ESVKKVSLYGDYTGVNVAKQIFANVVELEFYSTSKANSFGFNPLVLGSKTNVIYDLFASKPFT

HIDLTQVTLQNSDNSAIDANKLKQAVGDIYNYRRFERQFQGYFAGGYIDKYLVKNVNTNKD

SDDDLVYRSLKELNLHLEEAYREGDNTYYRVNENYYPGASIYENERASRDSEFQNEILKRAE

QNGVTFDENIKRITASGKYSVQFAKLANDTASSAERATKAVEGLVTVIGEEKFETVAITGASS

ATNAVKALAKELKTNALGVKLKL

*Armoracia rusticana*
Horseradish peroxidase mature protein sequence (31-338 amino acids).

68) SEQ ID NO: 68

QLTPTFYDNSCPNVSNIVRDTIVNELRSDPRIAASILRLHFHDCFVNGCDASILLDNTTS

FRTEKDAFGNANSARGFPVIDRMKAAVESACPRTVSCADLLTIAAQQSVTLAGGPSWRVPLG

RRDSLQAFLDLANANLPAPFFTLPQLKDSFRNVGLNRSSDLVALSGGHTFGKNQCRFIMDRL

YNFSNTGLPDPTLNTTYLQTLRGLCPLNGNLSALVDFDLRTPTIFDNKYYVNLEEQKGLIQSD

QELFSSPNATDTIPLVRSFANSTQTFFNAFVEAMDRMGNITPLTGTQGQIRLNCRVVNSNS

*Escherichia coli*
Alkaline phosphatase mature protein sequence (22-471 amino acids).

69) SEQ ID NO: 69

RTPEMPVLENRAAQGDITAPGGARRLTGDQTAALRDSLSDKPAKNIILLIGDGMGDS

EITAARNYAEGAGGFFKGIDALPLTGQYTHYALNKKTGKPDYVTDSAASATAWSTGVKTYN

GALGVDIHEKDHPTILEMAKAAGLATGNVSTAELQDATPAALVAHVTSRKCYGPSATSEKCP

GNALEKGGKGSITEQLLNARADVTLGGGAKTFAETATAGEWQGKTLREQAQARGYQLVSD

AASLNSVTEANQQKPLLGLFADGNMPVRWLGPKATYHGNIDKPAVTCTPNPQRNDSVPTLA

QMTDKAIELLSKNEKGFFLQVEGASIDKQDHAANPCGQIGETVDLDEAVQRALEFAKKEGNT

LVIVTADHAHASQIVAPDTKAPGLTQALNTKDGAVMVMSYGNSEEDSQEHTGSQLRIAAYG

PHAANVVGLTDQTDLFYTMKAALGLK

-continued

*Photinus pyralis*
Luciferase protein sequence (1-550 amino acid).
70) SEQ ID NO: 70

MEDAKNIKKGPAPFYPLEDGTAGEQLHKAMKRYALVPGTIAFTDAHIEVNITYAEYF

EMSVRLAEAMKRYGLNTNHRIVVCSENSLQFFMPVLGALFIGVAVAPANDIYNERELLNSM

NISQPTVVFVSKKGLQKILNVQKKLPIIQKIIIMDSKTDYQGFQSMYTFVTSHLPPGFNEYDFV

PESFDRDKTIALIMNSSGSTGLPKGVALPHRTACVRFSHARDPIFGNQIIPDTAILSVVPFHEIGF

GMFTTLGYLICGFRVVLMYRFEEELFLRSLQDYKIQSALLVPTLFSFFAKSTLIDKYDLSNLHE

IASGGAPLSKEVGEAVAKRFHLPGIRQGYGLTETTSAILITPEGDDKPGAVGKVVPFFEAKVV

DLDTGKTLGVNQRGELCVRGPMIMSGYVNNPEATNALIDKDGWLHSGDIAYWDEDEHFFIV

DRLKSLIKYKGYQVAPAELESILLQHPNIFDAGVAGLPDDDAGELPAAVVVLEHGKTMTEKE

IVDYVASQVTTAKKLRGGVVFVDEVPKGLTGKLDARKIREILIKAKKGGKSKL

Artificial
Xpress tag, a peptide recognized by an antibody
71) SEQ ID NO: 71

DLYDDDDK

Artificial
E-tag, a peptide recognized by an antibody (13 amino acid)
72) SEQ ID NO: 72

GAPVPYPDPLEPR

Artificial
FLAG-tag, a peptide recognized by an antibody (8 amino acid)
73) SEQ ID NO: 73

DYKDDDDK

Artificial
HA-tag, a peptide recognized by an antibody (9 amino acid)
74) SEQ ID NO: 74

YPYDVPDYA

Artificial
HA-tag, a peptide recognized by an antibody (9 amino acid)
75) SEQ ID NO: 75

YPYDVPDYA

Artificial
His-tag, 5-10 histidines bound by a nickel or cobalt chelate or antibody (6 amino acid)
76) SEQ ID NO: 76

HHHHHH

-continued

Artificial
Myc-tag, a short peptide recognized by an antibody (14 amino acid)

77) SEQ ID NO: 77

EQKLISEEDLLRKR

Artificial
S-tag, a short peptide recognized by an antibody (15 amino acid)

78) SEQ ID NO: 78

KETAAAKFERQHMDS

Artificial
Softag 1, for mammalian expression, a short peptide recognized by an antibody (13 amino acid)

79) SEQ ID NO: 79

SLAELLNAGLGGS

Artificial
VSV-tag, a peptide recognized by an antibody (11 amino acid)

80) SEQ ID NO: 80

YTDIEMNRLGK

Artificial
Softag 3, for prokaryotic expression, a short peptide recognized by an antibody (8 amino acid)

81) SEQ ID NO: 81

TQDPSRVG

Artificial
VS tag, a peptide recognized by an antibody (14 amino acid)

82) SEQ ID NO: 82

GKPIPNPLLGLDST

Artificial
Avi-Tag, a peptide allowing biotinylation by the enzyme BirA and so the protein can be isolated by streptavidin and/or avidin (20 amino acid)

83) SEQ ID NO: 83

MAGGLNDIFEAQKIEWHEGG

Artificial
SBP-tag, a peptide which binds to streptavidin (38 amino acid)

84) SEQ ID NO: 84

MDEKTTGWRGGHVVEGLAGELEQLRARLEHHPQGQREP

Artificial
Strep-tag (Strep-tag II), a peptide which binds to streptavidin or the modified streptavidin called streptactin (8 amino acid)

85) SEQ ID NO: 85

WSHPQFEK

*Escherichia coli*
BCCP (Biotin Carboxyl Carrier Protein), a protein domain biotinylated by BirA enabling recognition by streptavidin (73-156 amino acids)

86) SEQ ID NO: 86

PAAAEISGHIVRSPMVGTFYRTPSPDAKAFIEVGQKVNVGDTLCIVEAMKMMNQIEA

-continued

DKSGTVKAILVESGQPVEFDEPLVVIE

87) SEQ ID NO: 87

Artificial
TC tag, a tetracysteine tag that is recognized by FlAsH and ReAsH biarsenical compounds (6 amino acid)

CCPGCC

88) SEQ ID NO: 88

Artificial
Calmodulin-tag, a peptide bound by the protein calmodulin (26 amino acid)

KRRWKKNFIAVSAANRFKKISSSGAL

89) SEQ ID NO: 89

Artificial
Polyglutamate tag, a peptide binding efficiently to anion-exchange resin such as Mono-Q (6 amino acids)

EEEEEE

90) SEQ ID NO: 90

*Rhodococcus* sp./Artificial
Halo-tag, a mutated hydrolase that covalently attaches to the HaloLin Resin (297 amino acid)

MAEIGTGFPFDPHYVEVLGERMHYVDVGPRDGTPVLFLHGNPTSSYVWRNIIPHVAP

THRCIAPDLIGMGKSDKPDLGYFFDDHVRFMDAFIEALGLEEVVLVIHDWGSALGFHWAKR

NPERVKGIAFMEFIRPIPTWDEWPEFARETFQAFRTTDVGRKLIIDQNVFIEGTLPMGVVRPLT

EVEMDHYREPFLNPVDREPLWRFPNELPIAGEPANIVALVEEYMDWLHQSPVPKLLFWGTPG

VLIPPAEAARLAKSLPNCKAVDIGPGLNLLQEDNPDLIGSEIARWLSTLEISG

91) SEQ ID NO: 91

*Escherichia coli*
Maltose binding protein-tag, a protein which binds to amylose agarose (27-396 amino acid)

KIEEGKLVIWINGDKGYNGLAEVGKKFEKDTGIKVTVEHPDKLEEKFPQVAATGDGP

DIIFWAHDRFGGYAQSGLLAEITPDKAFQDKLYPFTWDAVRYNGKLIAYPIAVEALSLIYNKD

LLPNPPKTWEEIPALDKELKAKGKSALMFNLQEPYFTWPLIAADGGYAFKYENGKYDIKDVG

VDNAGAKAGLTFLVDLIKNKHMNADTDYSIAEAAFNKGETAMTINGPWAWSNIDTSKVNY

GVTVLPTFKGQPSKPFVGVLSAGINAASPNKELAKEFLENYLLTDEGLEAVNKDKPLGAVAL

KSYEEELAKDPRIAATMENAQKGEIMPNIPQMSAFWYAVRTAVINAASGRQTVDEALKDAQ

TRITK

92) SEQ ID NO: 92

*Escherichia coli*
Nus-tag, recognized by an antibody (1-495)

MNKEILAVVEAVSNEKALPREKIFEALESALATATKKKYEQEIDVRVQIDRKSGDFDT

FRRWLVVDEVTQPTKEITLEAARYEDESLNLGDYVEDQIESVTFDRITTQTAKQVIVQKVREA

-continued

ERAMVVDQFREHEGEIITGVVKKVNRDNISLDLGNNAEAVILREDMLPRENFRPGDRVRGVL

YSVRPEARGAQLFVTRSKPEMLIELFRIEVPEIGEEVIEIKAAARDPGSRAKIAVKTNDKRIDPV

GACVGMRGARVQAVSTELGGERIDIVLWDDNPAQFVINAMAPADVASIVVDEDKHTMDIAV

EAGNLAQAIGRNGQNVRLASQLSGWELNVMTVDDLQAKHQAEAHAAIDTFTKYLDIDEDF

ATVLVEEGFSTLEELAYVPMKELLEIEGLDEPTVEALRERAKNALATIAQAQEESLGDNKPAD

DLLNLEGVDRDLAFKLAARGVCTLEDLAEQGIDDLADIEGLTDEKAGALIMAARNICWFGDE

A

93) SEQ ID NO: 93

*Escherichia coli*
Thioredoxin-tag is commonly used in expression and purification of recombinant proteins. It improves the solubility of that protein of interest. Recognized by an antibody (2-109 amino acid)

SDKIIHLTDDSFDTDVLKADGAILVDFWAEWCGPCKMIAPILDEIADEYQGKLTVAKL
NIDQNPGTAPKYGIRGIPTLLLFKNGEVAATKVGALSKGQLKEFLDANLA

94) SEQ ID NO: 94

Artificial
Isopeptag, a peptide which binds covalently to pilin-C protein (16 amino acid)

TDKDMTITFTNKKDAE

95) SEQ ID NO: 95

Artificial
SpyTag, a peptide which binds covalently to SpyCatcher protein (13 amino acids)

AHIVMVDAYKPTK

96) SEQ ID NO: 96

*Aequorea victoria*
Green fluorescent protein-tag, a protein which is spontaneously fluorescent and can be bound by antibodies (1-238 amino acid)

MSKGEELFTGVVPILVELDGDVNGHKFSVSGEGEGDATYGKLTLKFICTTGKLPVPW

PTLVTTFSYGVQCFSRYPDHMKQHDFFKSAMPEGYVQERTIFFKDDGNYKTRAEVKFEGDTL

VNRIELKGIDFKEDGNILGHKLEYNYNSHNVYIMADKQKNGIKVNFKIRHNIEDGSVQLADH

YQQNTPIGDGPVLLPDNHYLSTQSALSKDPNEKRDHMVLLEFVTAAGITHGMDELYK

97) SEQ ID NO: 97

Artificial
Allows for cleavage by TEV protease between the Gln and Ser residues (7 amino acid)

ENLYFQS

-continued

Artificial
Allows for cleavage by Thrombin protease between Arg and Gly residues (6 amino acid)

98) SEQ ID NO: 98

LVPRGS

Artificial
Allows for cleavage by PreScission protease between the Gln and Gly residues (8 amino acid)

99) SEQ ID NO: 99

LEVLFQGP

Human
C1q A-chain mature amino acid sequence (23-245amino acid)

100) SEQ ID NO: 100

EDLCRAPDGKKGEAGRPGRRGRPGLKGEQGEPGAPGIRTGIQGLKGDQGEPGPSGNP

GKVGYPGPSGPLGARGIPGIKGTKGSPGNIKDQPRPAFSAIRRNPPMGGNVVIFDTVITNQEEP

YQNHSGRFVCTVPGYYYFTFQVLSQWEICLSIVSSSRGQVRRSLGFCDTTNKGLFQVVSGGM

VLQLQQGDQVWVEKDPKKGHIYQGSEADSVFSGFLIFPSA

Human
C1q B-chain mature amino acid sequence (28-253 amino acid)

101) SEQ ID NO: 101

QLSCTGPPAIPGIPGIPGTPGPDGQPGTPGIKGEKGLPGLAGDHGEFGEKGDPGIPGNP

GKVGPKGPMGPKGGPGAPGAPGPKGESGDYKATQKIAFSATRTINVPLRRDQTIRFDHVITN

MNNNYEPRSGKFTCKVPGLYYFTYHASSRGNLCVNLMRGRERAQKVVTFCDYAYNTFQVT

TGGMVLKLEQGENVFLQATDKNSLLGMEGANSIFSGFLLFPDMEA

Human
C1q C-chain mature amino acid sequence (29-245 amino acid)
NTGCYGIPGMPGLPGAPGKDGYDGLPGPKGEPGIPAIPGIRGPKGQKGEPGLPGHPGK

NGPMGPPGMPGVPGPMGIPGEPGEEGRYKQKFQSVFTVTRQTHQPPAPNSLIRFNAVLTNPQ

GDYDTSTGKFTCKVPGLYYFVYHASHTANLCVLLYRSGVKVVTFCGHTSKTNQVNSGGVLL

RLQVGEEVWLAVNDYYDMVGIQGSDSVFSGFLLFPD

What is claimed is:

1. A conjugate comprising: a first polypeptide having a specific binding affinity for an immunoglobulin molecule, wherein the first polypeptide has at least 99% identity over its entire length to one of SEQ ID NOS: 1, 2, and 63-66; conjugated to a second polypeptide having a specific binding affinity for a pathogen, a toxin or a cancer cell.

2. The conjugate of claim 1, wherein the second polypeptide is a protein fragment of a cellular receptor.

3. The conjugate of claim 2, wherein the second polypeptide has at least 95% identity over its entire length to one of SEQ ID NOS: 15-36.

4. The conjugate of claim 3, wherein the pathogen is SARS-CoV-2 virus and the second polypeptide comprises the sequence of SEQ ID NO: 15.

5. The conjugate of claim 1, wherein the second polypeptide is a single-domain antibody.

6. The conjugate of claim 1, further comprising a spacer between the first polypeptide and the second polypeptide.

7. The conjugate of claim 6, wherein the spacer is a cleavable peptide having a sequence of one of SEQ ID NOS: 96-98.

8. The conjugate of claim 1, wherein the conjugate protein bound to an immunoglobulin is capable of recruiting the C1q complement component.

9. A fusion protein comprising:

a first polypeptide having a specific binding affinity for an immunoglobulin molecule, wherein the first polypeptide has at least 99% identity over its entire length to one of SEQ ID NOS: 1, 2, and 63-66; genetically fused to a second polypeptide having a specific binding affinity for a pathogen, a toxin or a cancer cell.

10. The fusion protein of claim 9, wherein the second polypeptide is a protein fragment of a cellular receptor.

11. The fusion protein of claim 10, wherein the second polypeptide has at least 95% identity over its entire length to one of SEQ ID NOS: 15-36.

12. The fusion protein of claim 11, wherein the pathogen is SARS-CoV-2 virus and the second polypeptide comprises the sequence of SEQ ID NO: 15.

13. The fusion protein of claim 9, wherein the second polypeptide is a single-domain antibody.

14. The fusion protein of any one of claim 9, further comprising a spacer between the first polypeptide and the second polypeptide.

15. The fusion protein of claim 14, wherein the spacer is a cleavable peptide having a sequence of one of SEQ ID NOS: 96-98.

16. The fusion protein of claim 9, wherein the fusion protein bound to an immunoglobulin is capable of recruiting the C1q complement component.

17. A method for inactivating, eliminating or eradicating a bloodborne pathogen or cancer cell in a subject, comprising:

obtaining a sample of blood, serum or plasma from the subject or from a donor compatible with the subject, wherein the sample comprises immunoglobulins;

adding the conjugate of claim 1 or the fusion protein of claim 9 to the sample, wherein the first polypeptide binds to the immunoglobulins present in the sample, and wherein the second polypeptide has a specific binding affinity for the pathogen or cancer cell; and administrating the sample comprising the conjugate or fusion protein bound to the immunoglobulins to the subject;

thereby inactivating, eliminating or eradicating the bloodborne pathogen or cancer cell in the subject.

18. The method of claim 17, wherein the second polypeptide is a protein fragment of a cellular receptor.

19. The method of claim 18, wherein the second polypeptide has at least 95% identity over its entire length to one of SEQ ID NOS: 15-18, 24-25, 28, and 30-34.

20. The method of claim 19, wherein the pathogen is SARS-CoV-2 virus and the second polypeptide comprises the sequence of SEQ ID NO: 15.

21. The method of claim 17, wherein the second polypeptide is a single-domain antibody.

22. The method of claim 17, the fusion protein comprises a spacer between the first polypeptide and the second polypeptide.

23. The method of claim 22, wherein the spacer is a cleavable peptide having a sequence of one of SEQ ID NOS: 96-98.

24. The method of claim 17, wherein the conjugate or fusion protein bound to the immunoglobulins inactivates, eliminates or eradicates the bloodborne pathogen or cancer cell via recruitment of the C1q complement component.

25. A method for neutralizing a toxin in a subject, comprising:

obtaining a sample of blood, serum or plasma from the subject or from a donor compatible with the subject, wherein the sample comprises immunoglobulins;

adding the conjugate of claim 1 or the fusion protein of claim 9 to the sample, wherein the first polypeptide binds to the immunoglobulins present in the sample, and wherein the second polypeptide has a specific binding affinity for the toxin; and administrating the sample comprising the conjugate or fusion protein bound to the immunoglobulins to the subject;

thereby neutralizing the toxin in the subject.

26. The method of claim 25, wherein the second polypeptide is a protein fragment of a cellular receptor.

27. The method of claim 26, wherein the second polypeptide has at least 95% identity over its entire length to one of SEQ ID NOS: 19-29 and 35-36.

28. The method of claim 25, wherein the second polypeptide is a single-domain antibody.

29. The method of claim 25, the fusion protein comprises a spacer between the first polypeptide and the second polypeptide.

30. The method of claim 29, wherein the spacer is a cleavable peptide having a sequence of one of SEQ ID NOS: 96-98.

* * * * *